United States Patent
Kumar et al.

(10) Patent No.: US 9,422,569 B2
(45) Date of Patent: Aug. 23, 2016

(54) CONSTRUCT AND METHOD FOR SYNTHETIC BIDIRECTIONAL PLANT PROMOTER UBI1

(71) Applicant: Dow AgroSciences LLC, Indianapolis, IN (US)

(72) Inventors: Sandeep Kumar, Carmel, IN (US); Diaa Alabed, Carmel, IN (US); Terry Wright, Carmel, IN (US); Manju Gupta, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 271 days.

(21) Appl. No.: 13/674,606

(22) Filed: Nov. 12, 2012

(65) Prior Publication Data
US 2013/0254943 A1    Sep. 26, 2013

Related U.S. Application Data

(60) Provisional application No. 61/582,138, filed on Dec. 30, 2011, provisional application No. 61/617,252, filed on Mar. 29, 2012.

(51) Int. Cl.
*C12N 15/82* (2006.01)

(52) U.S. Cl.
CPC ........ *C12N 15/8216* (2013.01); *C12N 15/8222* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 6,388,170 | B1 | 5/2002 | Gan et al. |
| 7,235,652 | B2 | 6/2007 | Tuli et al. |
| 7,557,203 | B2 | 7/2009 | Linemann et al. |
| 2005/0188432 | A1 | 8/2005 | Li et al. |
| 2006/0150282 | A1 | 7/2006 | Linemann et al. |
| 2007/0033677 | A1 | 2/2007 | Lin |
| 2009/0038025 | A1* | 2/2009 | Lai et al. ............... 800/268 |
| 2011/0041208 | A1 | 2/2011 | Pennell et al. |
| 2011/0177228 | A1 | 7/2011 | Alexandrov et al. |
| 2011/0252504 | A1 | 10/2011 | Fu et al. |

FOREIGN PATENT DOCUMENTS

| | | |
|---|---|---|
| CN | 101001951 | 7/2007 |
| EP | 1862552 A2 | 12/2007 |
| WO | 2006013072 | 2/2006 |
| WO | 2010069950 A1 | 6/2010 |
| WO | 2011022469 | 2/2011 |

OTHER PUBLICATIONS

Christensen__594464__polyubiquitin__maize__genomic__1992.*
Xie__Nature Biotech__19__677__2001.*
Christensen__Transgen Res__5__213__1996.*
Christensen__Plant Mol Biol__18__675__1992.*
Potenza__In Vitro Cell Dev Biol Plant__40__1__2004.*
Donald__EMBO J__9__1717__1990.*
Kim__Plant Mol Biol__24__105__1994.*
Dolferus__Plant Phys__105__1075__1994.*
Xie et al., Nat Biotech 19:677-79 (2001).*
Christensen et al., Transgenic Res 5:213-18 (1996).*
Potenza et al., In Vitro Cell Dev Biol Plant 40:1-22 (2004).*
Kim et al., Plant Mol Biol 24:105-17 (1994).*
Donald & Cashmore, EMBO J 9:1717-26 (1990).*
Dolferus et al., Plant Physiol 105:1075-87 (1994).*
Barfield, D G., et al., "Gene-Transfer in Plants of Brassrca-Juncea Usrng Agrobacterium Tumefacriens-Mediated Transformation" Plant Cell Rep., 1991, pp. 308-314, vol. 10.
Bhullar, S. S., et al., "Strategies for development of functionally equivalent promoters with minimum sequence homology for transgene expression in plants: cis-elements in a novel DNA context versus domarn swappin" 2003, Plant Physiol. pp. 132988-132998.
Christensen, AH, et al., "Maize Polyubiquitin Genes: Structure, Thermal Perturbation of Expression and Transcript Splicing, and Promoter Activity Following Transfer to Protoplasts by Electroporation," 1992, Plant Mol Biology, pp. 675-689, vol. 18.
Langridge, W.H.R. et al., "Dual Promoter of Agrobacterium-Tumefaciens Mannopine Synthase Genes is Regulated by Plant-Growth Honmones," 1989, P Nat/ Acad Sci USA pp. 3219-3223, vol. 86.
Mourrain, P., et al., "A single transgene locus triggers both transcriptional and post•transcriptional silencing through double-stranded RNA production," 2007, Planta. pp. 365-379, vol. 225.
Velten, J, L., et al. "Isolation of a Dual Plant Promoter Fragment from the Ti Plasmid of Agrobacterium• Tumefaciens," 1984,. EMBO J, p. 2723-2730, vol. 3.
Xie, M.T.,et al., "Bidirectionalization of polar promoters in plants," 2001, Nat Biotechnol. pp. 19677-19679.
Christensen et al.; Polyubiquity [maize, Genomic, 3841 nt]; GenBank S94464.1; 1993.
International Search Report and written Opinion for International Application No. PCT/US2012/064683, dated Mar. 28, 2013.

* cited by examiner

*Primary Examiner* — Medina A Ibrahim
*Assistant Examiner* — Russell Boggs
(74) *Attorney, Agent, or Firm* — Yung H. Lee; Magleby Cataxinos & Greenwood

(57) ABSTRACT

Provided are constructs and methods for expressing multiple genes in plant cells and/or plant tissues. The constructs provided comprise at least one bidirectional promoter link to multiple gene expression cassettes. In some embodiments, the constructs and methods provided employ a bidirectional promoter based on a minimal core promoter element from a *Zea mays* Ubiquitin-1 gene, or a functional equivalent thereof. In some embodiments, the constructs and methods provided allow expression of genes between three and twenty.

1 Claim, 74 Drawing Sheets maize Ubi1 promoter synthetic bidirectional Ubi1 promoter bidirectional GUS and yfp expression cassettes SEQ ID NO: 1 shows a 215 bp region of a *Zea mays* Ubi1 minimal core promoter (minUbi1P):

CTGGACCCCTCTCGAGAGTTCCGCTCCACCGTTGGACTTGCTCCGCTGTCGGCATCCAG
AAATTGCGTGGCGGAGCGGCAGACGTGAGCCGGCACGGCAGGCGGCCTCCTCCTCCT
CTCACGGCACCGGCAGCTACGGGGGATTCCTTTCCCACCGCTCCTTCGCTTTCCCTTCC
TCGCCCGCCGTAATAAATAGACACCCCCTCCACACCCTCT

FIG. 7A

SEQ ID NO: 2 shows a *Z. mays* Ubi1 intron:

GTACCTCCCCAACCTCGTGTTGTTCGGAGCGCACACACACACAACCAGATCTCCCCCA
AATCCACCCGTCGGCACCTCCGCTTCAAGGTACGCCGCTCGTCCTCCCCCCCCCCCCCC
TCTCTACCTTCTCTAGATCGGCGTTCCGGTCCATGCATGGTTAGGGCCCGGTAGTTCTA
CTTCTGTTCATGTTTGTGTTAGATCCGTGTTTGTGTTAGATCCGTGCTGCTAGCGTTCGT
ACACGGATGCGACCTGTACGTCAGACACGTTCTGATTGCTAACTTGCCAGTGTTTCTCT
TTGGGGAATCCTGGGATGGCTCTAGCCGTTCCGCAGACGGGATCGATTTCATGATTTTT
TTTGTTTCGTTGCATAGGGTTTGGTTTGCCCTTTTCCTTTATTTCAATATATGCCGTGCA
CTTGTTTGTCGGGTCATCTTTTCATGCTTTTTTTGTCTTGGTTGTGATGATGTGGTCTG
GTTGGGCGGTCGTTCTAGATCGGAGTAGAATTCTGTTTCAAACTACCTGGTGGATTTAT
TAATTTTGGATCTGTATGTGTGTGCCATACATATTCATAGTTACGAATTGAAGATGATG
GATGGAAATATCGATCTAGGATAGGTATACATGTTGATGCGGGTTTTACTGATGCATA
TACAGAGATGCTTTTTGTTCGCTTGGTTGTGATGATGTGGTGTGGTTGGGCGGTCGTTC
ATTCGTTCTAGATCGGAGTAGAATACTGTTTCAAACTACCTGGTGTATTTATTAATTTT
GGAACTGTATGTGTGTGTCATACATCTTCATAGTTACGAGTTTAAGATGGATGGAAAT
ATCGATCTAGGATAGGTATACATGTTGATGTGGGTTTTACTGATGCATATACATGATG
GCATATGCAGCATCTATTCATATGCTCTAACCTTGAGTACCTATCTATTATAATAAACA
AGTATGTTTTATAATTATTTCGATCTTGATATACTTGGATGATGGCATATGCAGCAGCT
ATATGTGGATTTTTTTAGCCCTGCCTTCATACGCTATTTATTTGCTTGGTACTGTTTCTT
TTGTCGATGCTCACCCTGTTGTTTGGTGTTACTTCTGCAG

FIG. 7B

SEQ ID NO: 3 shows the reverse complement of a polynucleotide comprising a Z. mays minUbi1P minimal core promoter (underlined); a Z. mays Ubi1 leader (ZmUbi1 exon; bold font); and a Z. mays Ubi1 intron (lower case):

ctgcagaagtaacaccaaacaacagggtgagcatcgacaaaagaaacagtaccaagcaaataaatagcgtatgaaggcagggctaaaaaat
ccacatatagctgctgcatatgccatcatccaagtatatcaagatcgaaataattataaaacatacttgtttattataatagataggtactcaaggttag
agcatatgaatagatgctgcatatgccatcatgtatatgcatcagtaaaacccacatcaacatgtatacctatcctagatcgatatttccatccatctta
aactcgtaactatgaagatgtatgacacacacatacagttccaaaattaataaatacaccaggtagtttgaaacagtattctactccgatctagaacg
aatgaacgaccgcccaaccacaccacatcatcacaaccaagcgaacaaaaagcatctctgtatatgcatcagtaaaacccgcatcaacatgtata
cctatcctagatcgatatttccatccatcatcttcaattcgtaactatgaatatgtatggcacacacatacagatccaaaattaataaatccaccaggta
gtttgaaacagaattctactccgatctagaacgaccgcccaaccagaccacatcatcacaaccaagacaaaaaaaagcatgaaaagatgaccc
gacaaacaagtgcacggcatatattgaaataaaggaaaagggcaaaccaaaccctatgcaacgaaacaaaaaaaatcatgaaatcgatcccgt
ctgcggaacggctagagccatcccaggattccccaaagagaaacactggcaagttagcaatcagaacgtgtctgacgtacaggtcgcatccgt
gtacgaacgctagcagcacggatctaacacaaacacggatctaacacaaacatgaacagaagtagaactaccgggccctaaccatgcatgga
ccggaacgccgatctagagaaggtagagagggggggggggggggaggacgagcggcgtac**CTTGAAGCGGAGGTGCC
GACGGGTGGATTTGGGGGAGATCTGGTTGTGTGTGTGCGCTCCGAACAACAC
GAGGTTGGGGAGGTACCA**<u>AGAGGGTGTGGAGGGGGTGTCTATTTATTACGGCGGGC
GAGGAAGGGAAAGCGAAGGAGCGGTGGGAAAGGAATCCCCCGTAGCTGCCGGTGCC
GTGAGAGGAGGAGGAGGCCGCCTGCCGTGCCGGCTCACGTCTGCCGCTCCGCCACGC
AATTTCTGGATGCCGACAGCGGAGCAAGTCCAACGGTGGAGCGGAACTCTCGAGAGG
GGTCCAG</u>

FIG. 8A

SEQ ID NO: 4 shows a segment of a Z. mays Ubi1 upstream element, which element (and/or its reverse complement) may be located in a synthetic Ubi1 promoter with a minUbi1P element adjacent to its 5' or 3' end:

GTGCAGCGTGACCCGGTCGTGCCCCTCTCTAGAGATAATGAGCATTGCATGTCTAAGT
TATAAAAAATTACCACATATTTTTTTTGTCACACTTGTTTGAAGTGCAGTTTATCTATCT
TTATACATATATTTAAACTTTACTCTACGAATAATATAATCTATAGTACTACAATAATA
TCAGTGTTTTAGAGAATCATATAAATGAACAGTTAGACATGGTCTAAAGGACAATTGA
GTATTTTGACAACAGGACTCTACAGTTTTATCTTTTTAGTGTGCATGTGTTCTCCTTTTT
TTTTGCAAATAGCTTCACCTATATAATACTTCATCCATTTTATTAGTACATCCATTTAG
GGTTTAGGGTTAATGGTTTTATAGACTAATTTTTTAGTACATCTATTTTATTCTATTT
TAGCCTCTAAATTAAGAAAACTAAAACTCTATTTTAGTTTTTTTATTTAATAGTTTAGA
TATAAAATAGAATAAAATAAAGTGACTAAAAATTAAACAAATACCCTTTAAGAAATT
AAAAAAACTAAGGAAACATTTTTCTTGTTTCGAGTAGATAATGCCAGCCTGTTAAACG
CCGTCGACGAGTCTAACGGACACCAACCAGCGAACCAGCAGCGTCGCGTCGGGCCAA
GCGAAGCAGACGGCACGGCATCTCTGTCGCTGCCT

FIG. 8B

SEQ ID NO: 5 shows an exemplary synthetic Ubi1 bidirectional promoter, wherein the reverse complement of a first minUbi1P, and a second minUbi1P, are underlined:

CTGCAGAAGTAACACCAAACAACAGGGTGAGCATCGACAAAAGAAACAGTACCAAG
CAAATAAATAGCGTATGAAGGCAGGGCTAAAAAAATCCACATATAGCTGCTGCATAT
GCCATCATCCAAGTATATCAAGATCGAAATAATTATAAAACATACTTGTTTATTATAA
TAGATAGGTACTCAAGGTTAGAGCATATGAATAGATGCTGCATATGCCATCATGTATA
TGCATCAGTAAAACCCACATCAACATGTATACCTATCCTAGATCGATATTTCCATCCAT
CTTAAACTCGTAACTATGAAGATGTATGACACACATACAGTTCCAAAATTAATAAA
TACACCAGGTAGTTTGAAACAGTATTCTACTCCGATCTAGAACGAATGAACGACCGCC
CAACCACACCACATCATCACAACCAAGCGAACAAAAAGCATCTCTGTATATGCATCAG
TAAAACCCGCATCAACATGTATACCTATCCTAGATCGATATTTCCATCCATCATCTTCA
ATTCGTAACTATGAATATGTATGGCACACACATACAGATCCAAAATTAATAAATCCAC
CAGGTAGTTTGAAACAGAATTCTACTCCGATCTAGAACGACCGCCCAACCAGACCACA
TCATCACAACCAAGACAAAAAAAGCATGAAAGATGACCCGACAAACAAGTGCAC
GGCATATATTGAAATAAAGGAAAAGGGCAAACCAAACCCTATGCAACGAAACAAAAA
AAATCATGAAATCGATCCCGTCTGCGGAACGGCTAGAGCCATCCCAGGATTCCCCAAA
GAGAAACACTGGCAAGTTAGCAATCAGAACGTGTCTGACGTACAGGTCGCATCCGTGT
ACGAACGCTAGCAGCACGGATCTAACACAAACACGGATCTAACACAAACATGAACAG
AAGTAGAACTACCGGGCCCTAACCATGCATGGACCGGAACGCCGATCTAGAGAAGGT
AGAGAGGGGGGGGGGGGAGGACGAGCGGCGTACCTTGAAGCGGAGGTGCCGACG
GGTGGATTTGGGGGAGATCTGGTTGTGTGTGTGCGCTCCGAACAACACGAGGTTGG
GGAGGTACCA<u>AGAGGGTGTGGAGGGGGTGTCTATTTATTACGGCGGGCGAGGAAGGG</u>
<u>AAAGCGAAGGAGCGGTGGGAAAGGAATCCCCCGTAGCTGCCGGTGCCGTGAGAGGA</u>
<u>GGAGGAGGCCGCCTGCCGTGCCGGCTCACGTCTGCCGCTCCGCCACGCAATTCTGGA</u>
<u>TGCCGACAGCGGAGCAAGTCCAACGGTGGAGCGGAACTCTCGAGAGGGTCCAGCCG</u>
CGGAGTGTGCAGCGTGACCCGGTCGTGCCCCTCTCTAGAGATAATGAGCATTGCATGT
CTAAGTTATAAAAAATTACCACATATTTTTTTGTCACACTTGTTTGAAGTGCAGTTTA
TCTATCTTTATACATATATTTAAACTTTACTCTACGAATAATATAATCTATAGTACTAC
AATAATATCAGTGTTTTAGAGAATCATATAAATGAACAGTTAGACATGGTCTAAAGGA
CAATTGAGTATTTTGACAACAGGACTCTACAGTTTTATCTTTTTAGTGTGCATGTGTTC
TCCTTTTTTTTTGCAAATAGCTTCACCTATATAATACTTCATCCATTTTATTAGTACATC
CATTTAGGGTTTAGGGTTAATGGTTTTTATAGACTAATTTTTTTAGTACATCTATTTTAT
TCTATTTTAGCCTCTAAATTAAGAAAACTAAAACTCTATTTTAGTTTTTTTATTTAATAG
TTTAGATATAAAATAGAATAAAATAAAGTGACTAAAAATTAAACAAATACCCTTTAAG
AAATTAAAAAAACTAAGGAAACATTTTCTTGTTTCGAGTAGATAATGCCAGCCTGTT
AAACGCCGTCGACGAGTCTAACGGACACCAACCAGCGAACCAGCAGCGTCGCGTCGG
GCCAAGCGAAGCAGACGGCACGGCATCTCTGTCGCTGCCT<u>CTGGACCCCTCTCGAGAG</u>
<u>TTCCGCTCCACCGTTGGACTTGCTCCGCTGTCGGCATCCAGAAATTGCGTGGCGGAGC</u>
<u>GGCAGACGTGAGCCGGCACGGCAGGCGGCCTCCTCCTCCTCTCACGGCACCGGCAGCT</u>
<u>ACGGGGGATTCCTTTCCCACCGCTCCTTCGCTTTCCCTTCCTCGCCCGCCGTAATAAAT</u>
<u>AGACACCCCTCCACACCCTCTTTCCCCAACCTCGTGTTGTTC</u>

FIG. 9A

```
GGAGCGCACACACACACAACCAGATCTCCCCCAAATCCACCCGTCGGCACCTCCGCTT
CAAGGTACGCCGCTCGTCCTCCCCCCCCCCCCCCTCTCTACCTTCTCTAGATCGGCGT
TCCGGTCCATGCATGGTTAGGGCCCGGTAGTTCTACTTCTGTTCATGTTTGTGTTAGAT
CCGTGTTTGTGTTAGATCCGTGCTGCTAGCGTTCGTACACGGATGCGACCTGTACGTCA
GACACGTTCTGATTGCTAACTTGCCAGTGTTTCTCTTTGGGGAATCCTGGGATGGCTCT
AGCCGTTCGCAGACGGGATCGATTTCATGATTTTTTTGTTTCGTTGCATAGGGTTTG
GTTTGCCCTTTTCCTTTATTTCAATATATGCCGTGCACTTGTTTGTCGGGTCATCTTTTC
ATGCTTTTTTTGTCTTGGTTGTGATGATGTGGTCTGGTTGGGCGGTCGTTCTAGATCG
GAGTAGAATTCTGTTTCAAACTACCTGGTGGATTTATTAATTTTGGATCTGTATGTGTG
TGCCATACATATTCATAGTTACGAATTGAAGATGATGGATGGAAATATCGATCTAGGA
TAGGTATACATGTTGATGCGGGTTTTACTGATGCATATACAGAGATGCTTTTTGTTCGC
TTGGTTGTGATGATGTGGTGTGGTTGGGCGGTCGTTCATTCGTTCTAGATCGGAGTAGA
ATACTGTTTCAAACTACCTGGTGTATTTATTAATTTTGGAACTGTATGTGTGTGTCATA
CATCTTCATAGTTACGAGTTTAAGATGGATGGAAATATCGATCTAGGATAGGTATACA
TGTTGATGTGGGTTTTACTGATGCATATACATGATGGCATATGCAGCATCTATTCATAT
GCTCTAACCTTGAGTACCTATCTATTATAATAAACAAGTATGTTTTATAATTATTTCGA
TCTTGATATACTTGGATGATGGCATATGCAGCAGCTATATGTGGATTTTTTTAGCCCTG
CCTTCATACGCTATTTATTTGCTTGGTACTGTTTCTTTTGTCGATGCTCACCCTGTTGTT
TGGTGTTACTTCTGCAG
```

FIG. 9B

SEQ ID NO: 6 shows an exemplary nucleic acid comprising *yfp* and *GUS* gene expression cassettes driven by a synthetic Ubi1 bidirectional promoter.

```
AGCACTTAAAGATCTTTAGAAGAAAGCAAAGCATTTATTAATACATAACAATGTCCAG
GTAGCCCAGCTGAATTACAATACGCAACTGCTCATAATAATTCAACAAACCCAAGTAG
TACACAACATCCAGAAGCAAATAAAGCCCATACGTACCAAAGCCTACACAAGCAGCA
ACACTCACTGCCAGTGCCGGTGGGTCTTTAAAGCACACGGGCCTTGACCACGCGATCC
ACCTTGAAACAAACTTGGTAAAATTAAAGCAAACCAGAAGCACACACACGCCAACGC
AACGCTTCTGATCGCGCGCCCAAGGCCCGGCCGGCCAGAACGTACGACGGACACGCA
CACGCTGCGACCGAGCTCTAGGTGATTAAGCTAACTACTCAAAGGTAGGTCTTGCGAC
AGTCAACAGCTCTGACAGTTTCTTTCAAGGACATGTTGTCTCTGTGGTCTGTCACATCT
TTGGAAAGTTTCACATGGTAAGACATGTGATGATACTCTGGAACATGAACTGGACCTC
CACCAATGGGAGTGTTCATCTGGGTGTGGTCAGCCACTATGAAGTCGCCTTTGCTGCC
AGTAATCTCATGACAGATCTTGAAGGCTGACTTGAGACCGTGGTTGGCTTGGTCACCC
CAGATGTAGAGGCAGTGGGGAGTGAAGTTGAACTCCAAGTTCTTTCCCAACACATGAC
CATCTTTCTTGAAGCCTTGACCATTGAGTTTGACCCTATTGTAGACAGACCCATTCTA
AAGGTGACTTCAGCCCTAGTCTTGAAGTTGCCATCTCCTTCAAAGGTGATTGTGCGCTC
TTGCACATAGCCATCTGGCATACAGGACTTGTAGAAGTCCTTCAACTCTGGACCATAC
TTGGCAAAGCACTGTGCTCCATAGGTGAGAGTGGTGACAAGTGTGCTCCAAGGCACA
GGAACATCACCAGTTGTGCAGATGAACTGTGCATCAACCTTTCCCACTGAGGCATCTC
CGTAGCCTTTCCCACGTATGCTAAAGGTGTGGCCATCAACATTCCCTTCCATCTCCACA
ACGTAAGGAATCTTCCCATGAAAGAGAAGTGCTCCAGATGCCATGGTGTCGTGTGGAT
CCGGTACACACGTGCCTAGGACCGGTTCAACTAACTACTGCAGAAGTAACACCAAAC
AACAGGGTGAGCATCGACAAAAGAAACAGTACCAAGCAAATAAATAGCGTATGAAG
GCAGGGCTAAAAAAATCCACATATAGCTGCTGCATATGCCATCATCCAAGTATATCAA
GATCGAAATAATTATAAAACATACTTGTTTATTATAATAGATAGGTACTCAAGGTTAG
AGCATATGAATAGATGCTGCATATGCCATCATGTATATGCATCAGTAAAACCCACATC
AACATGTATACCTATCCTAGATCGATATTTCCATCCATCTTAAACTCGTAACTATGAAG
ATGTATGACACACACATACAGTTCCAAAATTAATAAATACACCAGGTAGTTTGAAACA
GTATTCTACTCCGATCTAGAACGAATGAACGACCGCCCAACCACACCACATCATCACA
ACCAAGCGAACAAAAAGCATCTCTGTATATGCATCAGTAAAACCCGCATCAACATGTA
TACCTATCCTAGATCGATATTTCCATCCATCATCTTCAATTCGTAACTATGAATATGTA
TGGCACACACATACAGATCCAAAATTAATAAATCCACCAGGTAGTTTGAAACAGAATT
CTACTCCGATCTAGAACGACCGCCCAACCAGACCACATCATCACAACCAAGACAAAA
AAAAGCATGAAAAGATGACCCGACAAACAAGTGCACGGCATATATTGAAATAAAGGA
AAAGGGCAAACCAAACCCTATGCAACGAAACAAAAAAAATCATGAAATCGATCCCGT
CTGCGGAACGGCTAGAGCCATCCCAGGATTCCCCAAAGAGAAACACTGGCAAGTTAG
CAATCAGAACGTGTCTGACGTACAGGTCGCATCCGTGTACGAACGCTAGCAGCACGG
ATCTAACACAAACACGGATCTAACACAAACATGAACAGAAGTAGAACTACCGGGCCC
TAACCATGCATGGACCGGAACGCCGATCTAGAGAAGGTAGAGAGGGGGGGGGGGGG
GAGGACGAGCGGCGTACCTTGAAGCGGAGGTGCCGACGGGTGGATTTGGGGGAGATC
TGGTTGTGTGTGTGTGCGCTCCGAACAACACGAGGTTGGGGAGGTACCAAGAGGGTGT
GGAGGGGGTGTCTATTTATTACGGCGGGCGAGGAAGGGAAAGCGAAGGAGCGGTGGG
AAAGGAATCCCCCGTAGCTGCCGGTGCCGTGAGAGGAGGAGGAGGCCGCCTGCCGTG
CCGGCTCACGTCTGCCGCTCCGCCACGCAATTTCTGGATGCCGACAGCGGAGCAAGTC
CAACGGTGGAGCGGAACTCTCGAGAGGGGTCCAGCCGCGGAGTGTGCAGCGTGACCC
GGTCGTGCCCTCTCTAGAGATAATGAGCATTGCATGTCTAAGTTATAAAAAATTACC
ACATATTTTTTTTGTCACACTTGTTTGAAGTGCAG
```

FIG. 10A

```
TTTATCTATCTTTATACATATATTTAAACTTTACTCTACGAATAATATAATCTATAGTAC
TACAATAATATCAGTGTTTTAGAGAATCATATAAATGAACAGTTAGACATGGTCTAAA
GGACAATTGAGTATTTTGACAACAGGACTCTACAGTTTTATCTTTTTAGTGTGCATGTG
TTCTCCTTTTTTTTGCAAATAGCTTCACCTATATAATACTTCATCCATTTTATTAGTAC
ATCCATTTAGGGTTTAGGGTTAATGGTTTTTATAGACTAATTTTTTAGTACATCTATTT
TATTCTATTTTAGCCTCTAAATTAAGAAAACTAAAACTCTATTTTAGTTTTTTTATTTAA
TAGTTTAGATATAAAATAGAATAAAATAAAGTGACTAAAAATTAAACAAATACCCTTT
AAGAAATTAAAAAAACTAAGGAAACATTTTTCTTGTTTCGAGTAGATAATGCCAGCCT
GTTAAACGCCGTCGACGAGTCTAACGGACACCAACCAGCGAACCAGCAGCGTCGCGT
CGGGCCAAGCGAAGCAGACGGCACGGCATCTCTGTCGCTGCCTCTGGACCCCTCTCGA
GAGTTCCGCTCCACCGTTGGACTTGCTCCGCTGTCGGCATCCAGAAATTGCGTGGCGG
AGCGGCAGACGTGAGCCGGCACGGCAGGCGGCCTCCTCCTCCTCTCACGGCACCGGC
AGCTACGGGGATTCCTTTCCCACCGCTCCTTCGCTTTCCCTTCCTCGCCCGCCGTAAT
AAATAGACACCCCCTCCACACCCTCTTTCCCCAACCTCGTGTTGTTCGGAGCGCACAC
ACACACAACCAGATCTCCCCCAAATCCACCCGTCGGCACCTCCGCTTCAAGGTACGCC
GCTCGTCCTCCCCCCCCCCCCCCCTCTCTACCTTCTCTAGATCGGCGTTCCGGTCCATG
CATGGTTAGGGCCCGGTAGTTCTACTTCTGTTCATGTTTGTGTTAGATCCGTGTTTGTG
TTAGATCCGTGCTGCTAGCGTTCGTACACGGATGCGACCTGTACGTCAGACACGTTCT
GATTGCTAACTTGCCAGTGTTTCTCTTTGGGGAATCCTGGGATGGCTCTAGCCGTTCCG
CAGACGGGATCGATTTCATGATTTTTTTGTTTCGTTGCATAGGGTTTGGTTTGCCCTTT
TCCTTTATTTCAATATATGCCGTGCACTTGTTTGTCGGGTCATCTTTTCATGCTTTTTTT
GTCTTGGTTGTGATGATGTGGTCTGGTTGGGCGGTCGTTCTAGATCGGAGTAGAATTCT
GTTTCAAACTACCTGGTGGATTTATTAATTTTGGATCTGTATGTGTGTGCCATACATAT
TCATAGTTACGAATTGAAGATGATGGATGGAAATATCGATCTAGGATAGGTATACATG
TTGATGCGGGTTTTACTGATGCATATACAGAGATGCTTTTTGTTCGCTTGGTTGTGATG
ATGTGGTGTGGTTGGGCGGTCGTTCATTCGTTCTAGATCGGAGTAGAATACTGTTTCAA
ACTACCTGGTGTATTTATTAATTTTGGAACTGTATGTGTGTGTCATACATCTTCATAGT
TACGAGTTTAAGATGGATGGAAATATCGATCTAGGATAGGTATACATGTTGATGTGGG
TTTTACTGATGCATATACATGATGGCATATGCAGCATCTATTCATATGCTCTAACCTTG
AGTACCTATCTATTATAATAAACAAGTATGTTTTATAATTATTTCGATCTTGATATACT
TGGATGATGGCATATGCAGCAGCTATATGTGGATTTTTTAGCCCTGCCTTCATACGCT
ATTTATTTGCTTGGTACTGTTTCTTTTGTCGATGCTCACCCTGTTGTTTGGTGTTACTTCT
GCAGGTACAGTAGTTAGTTGAGGTACAGCGGCCGCAGGGCACCATGGTCCGTCCTGTA
GAAACCCCAACCCGTGAAATCAAAAACTCGACGGCCTGTGGGCATTCAGTCTGGATC
GCGAAAACTGTGGAATTGATCAGCGTTGGTGGGAAAGCGCGTTACAAGAAAGCCGGG
CAATTGCTGTGCCAGGCAGTTTTAACGATCAGTTCGCCGATGCAGATATTCGTAATTAT
GCGGGCAACGTCTGGTATCAGCGCGAAGTCTTTATACCGAAAGGTTGGGCAGGCCAG
CGTATCGTGCTGCGTTTCGATGCGGTCACTCATTACGGCAAAGTGTGGGTCAATAATC
AGGAAGTGATGGAGCATCAGGGCGGCTATACGCCATTTGAAGCCGATGTCACGCCGT
ATGTTATTGCCGGGAAAAGTGTACGTATCACCGTTTGTGTGAACAACGAACTGAACTG
GCAGACTATCCCGCCGGGAATGGTGATTACCGACGAAAACGGCAAGAAAAAGCAGTC
TTACTTCCATGATTTCTTTAACTATGCCGGAATCCATCGCAGCGTAATGCTCTACACCA
CGCCGAACACCTGGGTGGACGATATCACCGTGGTGACGCATGTCGCGCAAGACTGTA
ACCACGCGTCTGTTGACTGGCAGGTGGTGGCCAATGGTGATGTCAGCGTTGAACTGCG
TGATGCGGATCAACAGGTGGTTGCAACTGGACAAGGCACTAGCGGGACTTTGCAAGT
GGTGAAT
```

FIG. 10B

CCGCACCTCTGGCAACCGGGTGAAGGTTATCTCTATGAACTGTGCGTCACAGCCAAAA
GCCAGACAGAGTGTGATATCTACCCGCTTCGCGTCGGCATCCGGTCAGTGGCAGTGAA
GGGCGAACAGTTCCTGATTAACCACAAACCGTTCTACTTTACTGGCTTTGGTCGTCATG
AAGATGCGGACTTGCGTGGCAAAGGATTCGATAACGTGCTGATGGTGCACGACCACG
CATTAATGGACTGGATTGGGGCCAACTCCTACCGTACCTCGCATTACCCTTACGCTGA
AGAGATGCTCGACTGGGCAGATGAACATGGCATCGTGGTGATTGATGAAACTGCTGCT
GTCGGCTTTAACCTCTCTTTAGGCATTGGTTTCGAAGCGGGCAACAAGCCGAAAGAAC
TGTACAGCGAAGAGGCAGTCAACGGGGAAACTCAGCAAGCGCACTTACAGGCGATTA
AAGAGCTGATAGCGCGTGACAAAAACCACCCAAGCGTGGTGATGTGGAGTATTGCCA
ACGAACCGGATACCCGTCCGCAAGGTGCACGGGAATATTTCGCGCCACTGGCGGAAG
CAACGCGTAAACTCGACCCGACGCGTCCGATCACCTGCGTCAATGTAATGTTCTGCGA
CGCTCACACCGATACCATCAGCGATCTCTTTGATGTGCTGTGCCTGAACCGTTATTACG
GATGGTATGTCCAAAGCGGCGATTTGGAAACGGCAGAGAAGGTACTGGAAAAAGAAC
TTCTGGCCTGGCAGGAGAAACTGCATCAGCCGATTATCATCACCGAATACGGCGTGGA
TACGTTAGCCGGGCTGCACTCAATGTACACCGACATGTGGAGTGAAGAGTATCAGTGT
GCATGGCTGGATATGTATCACCGCGTCTTTGATCGCGTCAGCGCCGTCGTCGGTGAAC
AGGTATGGAATTTCGCCGATTTTGCGACCTCGCAAGGCATATTGCGCGTTGGCGGTAA
CAAGAAAGGGATCTTCACTCGCGACCGCAAACCGAAGTCGGCGGCTTTTCTGCTGCAA
AAACGCTGGACTGGCATGAACTTCGGTGAAAAACCGCAGCAGGGAGGCAAACAATGA
GACGTCCGGTAACCTTTAAACTGAGGGCACTGAAGTCGCTTGATGTGCTGAATTGTTT
GTGATGTTGGTGGCGTATTTTGTTTAAATAAGTAAGCATGGCTGTGATTTTATCATATG
ATCGATCTTTGGGGTTTTATTTAACACATTGTAAAATGTGTATCTATTAATAACTCAAT
GTATAAGATGTGTTCATTCTTCGGTTGCCATAGATCTGCTTATTTGACCTGTGATGTTTT
GACTCCAAAAACCAAAATCACAACTCAATAAACTCATGGAATATGTCCACCTGTTTCT
TGAAGAGTTCATCTACCATTCCAGTTGGCATTTATCAGTGTTGCAGCGGCGCTGTGCTT
TGTAACATAACAATTGTTACGGCATATATCCAA

FIG. 10C

```
   1    AATTACAACG GTATATATCC TGCCAGTCAG CATCATCACA CCAAAAGTTA GGCCCGAATA
  61    GTTTGAAATT AGAAAGCTCG CAATTGAGGT CTACAGGCCA AATTCGCTCT TAGCCGTACA
 121    ATATTACTCA CCAGATCCTA ACCGGTGTGA TCATGGGCCG CGATTAAAAA TCTCAATTAT
 181    ATTTGGTCTA ATTTAGTTTG GTATTGAGTA AAACAAATTC GGCGCCATGC CCGGGCAAGC
 241    GGCCGCACAA GTTTGTACAA AAAAGCAGGC TGAGTATTCA CTACAGTAGT GCATCGATGG
 301    AGTCATCACG CAGACTATCT CAGCATGTGC GTAGCACGTC TAGACCTAGG TAGGTTAATT
 361    AAGCTTGCAT GCCGGAGGAA ATATGAATTC AGCACTTAAA GATCTTTAGA AGAAAGCAAA
                                                 ~~~~~~~~~~~~~~~~~~~~~~~~~~~
                                                        ZmLip 3' UTR v1
 421    GCATTTATTA ATACATAACA ATGTCCAGGT AGCCCAGCTG AATTACAATA CGCAACTGCT
        ~~~~~~~~~~~~~~~~~~~~~~~~~~~~~~~~~~~~~~~~~~~~~~~~~~~~~~~~~~~~~~~
                                    ZmLip 3' UTR v1
 481    CATAATAATT CAACAAACCC AAGTAGTACA CAACATCCAG AAGCAAATAA AGCCCATACG
        ~~~~~~~~~~~~~~~~~~~~~~~~~~~~~~~~~~~~~~~~~~~~~~~~~~~~~~~~~~~~~~~
                                    ZmLip 3' UTR v1
 541    TACCAAAGCC TACACAAGCA GCAACACTCA CTGCCAGTGC CGGTGGGTCT TTAAAGCACA
        ~~~~~~~~~~~~~~~~~~~~~~~~~~~~~~~~~~~~~~~~~~~~~~~~~~~~~~~~~~~~~~~
                                    ZmLip 3' UTR v1
 601    CGGGCCTTGA CCACGCGATC CACCTTGAAA CAAACTTGGT AAAATTAAAG CAAACCAGAA
        ~~~~~~~~~~~~~~~~~~~~~~~~~~~~~~~~~~~~~~~~~~~~~~~~~~~~~~~~~~~~~~~
                                    ZmLip 3' UTR v1
 661    GCACACACAC GCCAACGCAA CGCTTCTGAT CGCGCGCCCA AGGCCCGGCC GGCCAGAACG
        ~~~~~~~~~~~~~~~~~~~~~~~~~~~~~~~~~~~~~~~~~~~~~~~~~~~~~~~~~~~~~~~
                                    ZmLip 3' UTR v1
 721    TACGACGGAC ACGCACACGC TGCGACCGAG CTCTCAAAGG TAGGTCTTGC GACAGTCAAC
        ~~~~~~~~~~~~~~~~~~~~~~~~~~~~~~        ~~~~~~~~~~~~~~~~~~~~~~~~~~
             ZmLip 3' UTR v1                       PhiYFP v3 (with intron)
 781    AGCTCTGACA GTTTCTTTCA AGCTCATGTT GTCTCTGTGG TCTGTCACAT CTTTGGAAAG
        ~~~~~~~~~~~~~~~~~~~~~~~~~~~~~~~~~~~~~~~~~~~~~~~~~~~~~~~~~~~~~~~
                                    PhiYFP v3 (with intron)
 841    TTTCACATGG TAAGACATAT GATGATACTC TGGAACATGA ACTGGACCTC CACCAATGGG
        ~~~~~~~~~~~~~~~~~~~~~~~~~~~~~~~~~~~~~~~~~~~~~~~~~~~~~~~~~~~~~~~
                                    PhiYFP v3 (with intron)
 901    AGTGTTCATC TGGGTGTGGT CAGCCACTAT GAAGTCGCCT TTGCTGCCAG TAATCTCATG
        ~~~~~~~~~~~~~~~~~~~~~~~~~~~~~~~~~~~~~~~~~~~~~~~~~~~~~~~~~~~~~~~
                                    PhiYFP v3 (with intron)
 961    ACATATCTTG AAGGCTGACT TGAGACCGTG GTTGGCTTGG TCTCCCCAGA TGTAGAGGCA
        ~~~~~~~~~~~~~~~~~~~~~~~~~~~~~~~~~~~~~~~~~~~~~~~~~~~~~~~~~~~~~~~
                                    PhiYFP v3 (with intron)
1021    GTGGGGAGTG AAGTTGAACT CCAAGTTCTT TCCCAACACG TGACCATCTT TCTTGAAGCC
        ~~~~~~~~~~~~~~~~~~~~~~~~~~~~~~~~~~~~~~~~~~~~~~~~~~~~~~~~~~~~~~~
                                    PhiYFP v3 (with intron)
1081    TTGACCATTG AGTTTGACCC TATTGTAGAC AGACCCATTC TCAAAGGTGA CTTCAGCCCT
        ~~~~~~~~~~~~~~~~~~~~~~~~~~~~~~~~~~~~~~~~~~~~~~~~~~~~~~~~~~~~~~~
                                    PhiYFP v3 (with intron)
1141    AGTCTTGAAG TTGCCATCTC CTTCAAAGGT GATTGTGCGC TCTTGCACAT AGCCATCTGG
        ~~~~~~~~~~~~~~~~~~~~~~~~~~~~~~~~~~~~~~~~~~~~~~~~~~~~~~~~~~~~~~~
                                    PhiYFP v3 (with intron)
1201    CATACAGGAC TTGTAGAAGT CCTTCAACTC TGGACCATAC TTGGCAAAGC ACTGTGCTCC
        ~~~~~~~~~~~~~~~~~~~~~~~~~~~~~~~~~~~~~~~~~~~~~~~~~~~~~~~~~~~~~~~
                                    PhiYFP v3 (with intron)
```

FIG. 23A

```
1261  ATAGGTGAGA GTGGTGACAA GTGTGCTCCA AGGCACAGGA ACATCTCCGG TAGTACAGAT
                    PhiYFP v3 (with intron)
1321  GAATTGTGCA TCAACCTGCA CATCACCATG TTTTGGTCAT ATATTAGAAA AGTTATAAAT
                    PhiYFP v3 (with intron)
                         ST-LS1 intron v2
1381  TAAAATATAC ACACTTATAA ACTACAGAAA AGCAATAGCT ATATACTACA TTCTTTTATT
                    PhiYFP v3 (with intron)
                       ST-LS1 intron v2
1441  TTGAAAAAAA TACTTGAAAT ACTATATTAC TACTAATTAG TGATAATTAT TATATATATA
                    PhiYFP v3 (with intron)
                       ST-LS1 intron v2
1501  TCAAAGGTAG AAGCAGAAAC ATACCTTTCC CACTGAGGCA TCTCCGTAGC CTTTCCCACG
                    PhiYFP v3 (with intron)
     ST-LS1 intron v2
1561  TATGCTAAAG GTGTGGCCAT CAACATTCCC TTCCATCTCC ACAACGTAAG GAATCTTCCC
                    PhiYFP v3 (with intron)
1621  ATGAAAGAGA AGTGCTCCAG ATGACATAGG GCCGGGATTC TCCTCCACGT CACCGCATGT
                                                   2A
      PhiYFP v3 (with intron)
1681  TAGAAGACTT CCTCTGCCCT CGCGGGCAGG CCTAACTCCA CCAACTGTGG TGCGAGTCAA
           2A
                               AAD-1 v3 (no stop)
1741  GTATCTGAAC TTGCCAGCAT AGTCAGGAAC AGCACGGTGC ATGGTGCACA AGTTGTCCCA
                         AAD-1 v3 (no stop)
1801  GACAAGGACT TGGTCTTTCT TCCACCTCAC ACGGCAAGTG AAGTCAAATC TGCTGGCATG
                       AAD-1 v3 (no stop)
1861  CTCATAGAGG AACTGAAGCA ATGGCTTTGA TTCTGCATCT GTCATGCCCT CAATTCTCTG
                       AAD-1 v3 (no stop)
1921  ACAGTAGACT TGATTCACAT AAAGGCCTTT CCTTCCAGAG CCAGGATGAG TCACAACCAA
                       AAD-1 v3 (no stop)
1981  GGGATGGACT GTCTCTCTGT CACCAGCATC AACATCCATC ACCTTGACTG AGGTGTTGCT
                       AAD-1 v3 (no stop)
```

FIG. 23B

```
2041  GAAGCGACGG TTCTGTGCTT GGTAGAGGGA ACCGAACACA CGTGTGGCAG AGTGCACAAC
                                  AAD-1 v3 (no stop)
2101  GTTGAGCCCT TCGATGGTGG CTTGCATGGT TGGAGACAAG GTCTCCCAAG CTGTGTACAT
                                  AAD-1 v3 (no stop)
2161  TGAAAGGAAC CCAGTGTCTC CGCCATGCTC AGGAACATCT ATGGCCCTCA TCACAACAGC
                                  AAD-1 v3 (no stop)
2221  AGCTGGAGGT GCATCAAGGA AAGTGGAGTC TGTGTGCCAG TCATCACCAA TCACCCTTCC
                                  AAD-1 v3 (no stop)
2281  AGACTCATTG GCTTCTCTGC GGATCATCTG AACCTCTGGA TAGCCTTCAA TGCTCTTGAG
                                  AAD-1 v3 (no stop)
2341  AAGAGGCACT GGATCAACTG GTCCAAACCT TCTTGAGAAT GCAATGTGCT GCTCATTGGT
                                  AAD-1 v3 (no stop)
2401  GATTGCTTGG CCAGGAAAGT AGATGACTTG GTAAGTGTGG AAGGCATCCA ATATCTCATT
                                  AAD-1 v3 (no stop)
2461  CCAGGTGCTG TCATCAAGTG GTTCCCTCAA GTCCACTCCA GTGATCTCAG CACCAAGGAC
                                  AAD-1 v3 (no stop)
2521  ACCAGTGAGT GGCTGGACAG CTATTCTCTC AAAGCGTTGG GAGAGAGGGC TGAGGGCAGC
                                  AAD-1 v3 (no stop)
2581  ATGAGCCATG GTGTCGTGTG GATCCGGTAC ACACGTGCCT AGGACCGGTT CAACTAACTA 2641  CTGCAGAAGT AACACCAAAC AACAGGGTGA GCATCGACAA AGAAACAGT ACCAAGCAAA
                                  ZmUbi1 Intron v3
2701  TAAATAGCGT ATGAAGGCAG GGCTAAAAAA ATCCACATAT AGCTGCTGCA TATGCCATCA
                                  ZmUbi1 Intron v3
2761  TCCAAGTATA TCAAGATCGA ATAATTATA AAACATACTT GTTTATTATA ATAGATAGGT
                                  ZmUbi1 Intron v3
2821  ACTCAAGGTT AGAGCATATG AATAGATGCT GCATATGCCA TCATGTATAT GCATCAGTAA
                                  ZmUbi1 Intron v3
2881  AACCCACATC AACATGTATA CCTATCCTAG ATCGATATTT CCATCCATCT TAAACTCGTA
                                  ZmUbi1 Intron v3
2941  ACTATGAAGA TGTATGACAC ACACATACAG TTCCAAAATT AATAAATACA CCAGGTAGTT
                                  ZmUbi1 Intron v3
3001  TGAAACAGTA TTCTACTCCG ATCTAGAACG AATGAACGAC CGCCCAACCA CACCACATCA
                                  ZmUbi1 Intron v3
```

FIG. 23C

```
3061   TCACAACCAA GCGAACAAAA AGCATCTCTG TATATGCATC AGTAAAACCC GCATCAACAT
                                    ZmUbi1 Intron v3
3121   GTATACCTAT CCTAGATCGA TATTTCCATC CATCATCTTC AATTCGTAAC TATGAATATG
                                    ZmUbi1 Intron v3
3181   TATGGCACAC ACATACAGAT CCAAAATTAA TAAATCCACC AGGTAGTTTG AAACAGAATT
                                    ZmUbi1 Intron v3
3241   CTACTCCGAT CTAGAACGAC CGCCCAACCA GACCACATCA TCACAACCAA GACAAAAAAA
                                    ZmUbi1 Intron v3
3301   AGCATGAAAA GATGACCCGA CAAACAAGTG CACGGCATAT ATTGAAATAA AGGAAAAGGG
                                    ZmUbi1 Intron v3
3361   CAAACCAAAC CCTATGCAAC GAAACAAAAA AAATCATGAA ATCGATCCCG TCTGCGGAAC
                                    ZmUbi1 Intron v3
3421   GGCTAGAGCC ATCCCAGGAT TCCCCAAAGA GAAACACTGG CAAGTTAGCA ATCAGAACGT
                                    ZmUbi1 Intron v3
3481   GTCTGACGTA CAGGTCGCAT CCGTGTACGA ACGCTAGCAG CACGGATCTA ACACAAACAC
                                    ZmUbi1 Intron v3
3541   GGATCTAACA CAAACATGAA CAGAAGTAGA ACTACCGGGC CCTAACCATG CATGGACCGG
                                    ZmUbi1 Intron v3
3601   AACGCCGATC TAGAGAAGGT AGAGAGGGGG GGGGGGGGGA GGACGAGCGG CGTACCTTGA
                                                                      ZmUbi1 leader v1
                                    ZmUbi1 Intron v3
3661   AGCGGAGGTG CCGACGGGTG GATTTGGGGG AGATCTGGTT GTGTGTGTGT GCGCTCCGAA
       ZmUbi1 leader v1
3721   CAACACGAGG TTGGGGAGGT ACCAAGAGGG TGTGGAGGGG GTGTCTATTT ATTACGGCGG
                                                MinUbi1P
3781   GCGAGGAAGG GAAAGCGAAG GAGCGGTGGG AAAGGAATCC CCCGTAGCTG CCGGTGCCGT
                                                MinUbi1P
3841   GAGAGGAGGA GGAGGCCGCC TGCCGTGCCG GCTCACGTCT GCCGCTCCGC CACGCAATTT
                                                MinUbi1P
3901   CTGGATGCCG ACAGCGGAGC AAGTCCAACG GTGGAGCGGA ACTCTCGAGA GGGGTCCAGC
                                                MinUbi1P
                                                ZmUbi1 promoter v2
3961   CGCGGAGTGT GCAGCGTGAC CCGGTCGTGC CCCTCTCTAG AGATAATGAG CATTGCATGT
                    ZmUbi1 promoter v2
```

FIG. 23D

```
4021   CTAAGTTATA AAAAATTACC ACATATTTTT TTTGTCACAC TTGTTTGAAG TGCAGTTTAT
                            ZmUbi1 promoter v2

4081   CTATCTTTAT ACATATATTT AAACTTTACT CTACGAATAA TATAATCTAT AGTACTACAA
                            ZmUbi1 promoter v2

4141   TAATATCAGT GTTTTAGAGA ATCATATAAA TGAACAGTTA GACATGGTCT AAAGGACAAT
                            ZmUbi1 promoter v2

4201   TGAGTATTTT GACAACAGGA CTCTACAGTT TTATCTTTTT AGTGTGCATG TGTTCTCCTT
                            ZmUbi1 promoter v2

4261   TTTTTTTGCA AATAGCTTCA CCTATATAAT ACTTCATCCA TTTTATTAGT ACATCCATTT
                            ZmUbi1 promoter v2

4321   AGGGTTTAGG GTTAATGGTT TTTATAGACT AATTTTTTTA GTACATCTAT TTTATTCTAT
                            ZmUbi1 promoter v2

4381   TTTAGCCTCT AAATTAAGAA AACTAAAACT CTATTTTAGT TTTTTTATTT AATAGTTTAG
                            ZmUbi1 promoter v2

4441   ATATAAAATA GAATAAAATA AAGTGACTAA AAATTAAACA AATACCCTTT AAGAAATTAA
                            ZmUbi1 promoter v2

4501   AAAAACTAAG GAAACATTTT TCTTGTTTCG AGTAGATAAT GCCAGCCTGT TAAACGCCGT
                            ZmUbi1 promoter v2

4561   CGACGAGTCT AACGGACACC AACCAGCGAA CCAGCAGCGT CGCGTCGGGC CAAGCGAAGC
                            ZmUbi1 promoter v2

4621   AGACGGCACG GCATCTCTGT CGCTGCCTCT GGACCCCTCT CGAGAGTTCC GCTCCACCGT
                            ZmUbi1 promoter v2

4681   TGGACTTGCT CCGCTGTCGG CATCCAGAAA TTGCGTGGCG GAGCGGCAGA CGTGAGCCGG
                            ZmUbi1 promoter v2

4741   CACGGCAGGC GGCCTCCTCC TCCTCTCACG GCACCGGCAG CTACGGGGGA TTCCTTTCCC
                            ZmUbi1 promoter v2

4801   ACCGCTCCTT CGCTTTCCCT TCCTCGCCCG CCGTAATAAA TAGACACCCC CTCCACACCC
                            ZmUbi1 promoter v2
                                        ZmUbi1 leader v1

4861   TCTTTCCCCA ACCTCGTGTT GTTCGGAGCG CACACACACA CAACCAGATC TCCCCCAAAT
                                                                        ZmUbi1 intron v2
                                           ZmUbi1 promoter v2
           ZmUbi1 leader v1
```

FIG. 23E

```
4921    CCACCCGTCG GCACCTCCGC TTCAAGGTAC GCCGCTCGTC CTCCCCCCCC CCCCCCCTCT
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
4981    CTACCTTCTC TAGATCGGCG TTCCGGTCCA TGCATGGTTA GGGCCCGGTA GTTCTACTTC
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5041    TGTTCATGTT TGTGTTAGAT CCGTGTTTGT GTTAGATCCG TGCTGCTAGC GTTCGTACAC
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5101    GGATGCGACC TGTACGTCAG ACACGTTCTG ATTGCTAACT TGCCAGTGTT TCTCTTTGGG
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5161    GAATCCTGGG ATGGCTCTAG CCGTTCCGCA GACGGGATCG ATTTCATGAT TTTTTTTGTT
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5221    TCGTTGCATA GGGTTTGGTT TGCCCTTTTC CTTTATTTCA ATATATGCCG TGCACTTGTT
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5281    TGTCGGGTCA TCTTTTCATG CTTTTTTTTG TCTTGGTTGT GATGATGTGG TCTGGTTGGG
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5341    CGGTCGTTCT AGATCGGAGT AGAATTCTGT TTCAAACTAC CTGGTGGATT TATTAATTTT
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5401    GGATCTGTAT GTGTGTGCCA TACATATTCA TAGTTACGAA TTGAAGATGA TGGATGGAAA
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
5461    TATCGATCTA GGATAGGTAT ACATGTTGAT GCGGGTTTTA CTGATGCATA TACAGAGATG
                    ZmUbi1 promoter v2
                ~~~~~~~~~~~~~~~~~~~~~~~~~~~~~~~~~~~~~~~~~~~~~~~~~~~~~~~~~~
                                 ZmUbi1 intron v2
                ~~~~~~~~~~~~~~~~~~~~~~~~~~~~~~~~~~~~~~~~~~~~~~~~~~~~~~~~~~
```

FIG. 23F

```
5521    CTTTTTGTTC GCTTGGTTGT GATGATGTGG TGTGGTTGGG CGGTCGTTCA TTCGTTCTAG
                          ZmUbi1 promoter v2
        ~~~~~~~~~~~~~~~~~~~~~~~~~~~~~~~~~~~~~~~~~~~~~~~~~~~~~~~~~~~~~~
                           ZmUbi1 intron v2
        ~~~~~~~~~~~~~~~~~~~~~~~~~~~~~~~~~~~~~~~~~~~~~~~~~~~~~~~~~~~~~~
5581    ATCGGAGTAG AATACTGTTT CAAACTACCT GGTGTATTTA TTAATTTTGG AACTGTATGT
                          ZmUbi1 promoter v2
        ~~~~~~~~~~~~~~~~~~~~~~~~~~~~~~~~~~~~~~~~~~~~~~~~~~~~~~~~~~~~~~
                           ZmUbi1 intron v2
        ~~~~~~~~~~~~~~~~~~~~~~~~~~~~~~~~~~~~~~~~~~~~~~~~~~~~~~~~~~~~~~
5641    GTGTGTCATA CATCTTCATA GTTACGAGTT TAAGATGGAT GGAAATATCG ATCTAGGATA
                          ZmUbi1 promoter v2
        ~~~~~~~~~~~~~~~~~~~~~~~~~~~~~~~~~~~~~~~~~~~~~~~~~~~~~~~~~~~~~~
                           ZmUbi1 intron v2
        ~~~~~~~~~~~~~~~~~~~~~~~~~~~~~~~~~~~~~~~~~~~~~~~~~~~~~~~~~~~~~~
5701    GGTATACATG TTGATGTGGG TTTTACTGAT GCATATACAT GATGGCATAT GCAGCATCTA
                          ZmUbi1 promoter v2
        ~~~~~~~~~~~~~~~~~~~~~~~~~~~~~~~~~~~~~~~~~~~~~~~~~~~~~~~~~~~~~~
                           ZmUbi1 intron v2
        ~~~~~~~~~~~~~~~~~~~~~~~~~~~~~~~~~~~~~~~~~~~~~~~~~~~~~~~~~~~~~~
5761    TTCATATGCT CTAACCTTGA GTACCTATCT ATTATAATAA ACAAGTATGT TTTATAATTA
                          ZmUbi1 promoter v2
        ~~~~~~~~~~~~~~~~~~~~~~~~~~~~~~~~~~~~~~~~~~~~~~~~~~~~~~~~~~~~~~
                           ZmUbi1 intron v2
        ~~~~~~~~~~~~~~~~~~~~~~~~~~~~~~~~~~~~~~~~~~~~~~~~~~~~~~~~~~~~~~
5821    TTTCGATCTT GATATACTTG GATGATGGCA TATGCAGCAG CTATATGTGG ATTTTTTTAG
                          ZmUbi1 promoter v2
        ~~~~~~~~~~~~~~~~~~~~~~~~~~~~~~~~~~~~~~~~~~~~~~~~~~~~~~~~~~~~~~
                           ZmUbi1 intron v2
        ~~~~~~~~~~~~~~~~~~~~~~~~~~~~~~~~~~~~~~~~~~~~~~~~~~~~~~~~~~~~~~
5881    CCCTGCCTTC ATACGCTATT TATTTGCTTG GTACTGTTTC TTTTGTCGAT GCTCACCCTG
        ZmUbi1 promoter v2
        ~~~~~~~~~~~~~~~~~~~~~~~
        ZmUbi1 intron v2
        ~~~~~~~~~~~~~~~~~~~~~~~
5941    TTGTTTGGTG TTACTTCTGC AGGTACAGTA GTTAGTTGAG GTACAGCGGC CGCACACGAC
                                      8V6 (no stop)
                 ~~~~~~~~~~~~~~~~~~~~~~~~~~~~~~~~~~~~~~~~~~~~~~~~~~~~~~~~
6001    ACCATGTCCG CCCGCGAGGT GCACATCGAC GTGAACAACA AGACCGGCCA CACCCTCCAG
                                      8V6 (no stop)
                 ~~~~~~~~~~~~~~~~~~~~~~~~~~~~~~~~~~~~~~~~~~~~~~~~~~~~~~~~
6061    CTGGAGGACA AGACCAAGCT CGACGGCGGC AGGTGGCGCA CCTCCCCGAC CAACGTGGCC
                                      8V6 (no stop)
                 ~~~~~~~~~~~~~~~~~~~~~~~~~~~~~~~~~~~~~~~~~~~~~~~~~~~~~~~~
6121    AACGACCAGA TCAAGACCTT CGTGGCCGAA TCCAACGGCT TCATGACCGG CACCGAGGGC
                                      8V6 (no stop)
                 ~~~~~~~~~~~~~~~~~~~~~~~~~~~~~~~~~~~~~~~~~~~~~~~~~~~~~~~~
6181    ACCATCTACT ACTCCATCAA CGGCGAGGCC GAGATCAGCC TCTACTTCGA CAACCCGTTC
                                      8V6 (no stop)
                 ~~~~~~~~~~~~~~~~~~~~~~~~~~~~~~~~~~~~~~~~~~~~~~~~~~~~~~~~
```

FIG. 23G

```
6241   GCCGGCTCCA ACAAATACGA CGGCCACTCC AACAAGTCCC AGTACGAGAT CATCACCCAG
                        8V6 (no stop)
       ~~~~~~~~~~~~~~~~~~~~~~~~~~~~~~~~~~~~~~~~~~~~~~~~~~~~~~~~~~~~~~~~
6301   GGCGGCTCCG GCAACCAGTC CCACGTGACC TACACCATCC AGACCACCTC CTCCCGCTAC
                                        2A
                                        ~~~~~~~~~~~~~~~~~~~~~~~~~~~~~~~
       8V6 (no stop)
       ~~~~~~~~~~~~~~
6361   GGCCACAAGT CCGAGGGCAG AGGAAGTCTT CTAACATGCG GTGACGTGGA GGAGAATCCC
       2A
       ~~~~~~
                                      Cry35Ab1 v5
                         ~~~~~~~~~~~~~~~~~~~~~~~~~~~~~~~~~~~~~~~~~~~~~~~
6421   GGCCCTATGC TCGACACCAA CAAGGTGTAC GAGATCAGCA ACCACGCCAA CGGCCTCTAC
                                       Cry35Ab1 v5
       ~~~~~~~~~~~~~~~~~~~~~~~~~~~~~~~~~~~~~~~~~~~~~~~~~~~~~~~~~~~~~~~~
6481   GCCGCCACCT ACCTCTCCCT CGACGACTCC GGCGTGTCCC TCATGAACAA GAACGACGAC
                                       Cry35Ab1 v5
       ~~~~~~~~~~~~~~~~~~~~~~~~~~~~~~~~~~~~~~~~~~~~~~~~~~~~~~~~~~~~~~~~
6541   GACATCGACG ACTACAACCT CAAGTGGTTC CTCTTCCCGA TCGACGACGA CCAGTACATC
                                       Cry35Ab1 v5
       ~~~~~~~~~~~~~~~~~~~~~~~~~~~~~~~~~~~~~~~~~~~~~~~~~~~~~~~~~~~~~~~~
6601   ATCACCTCCT ACGCCGCCAA CAACTGCAAG GTGTGGAACG TGAACAACGA CAAGATCAAC
                                       Cry35Ab1 v5
       ~~~~~~~~~~~~~~~~~~~~~~~~~~~~~~~~~~~~~~~~~~~~~~~~~~~~~~~~~~~~~~~~
6661   GTGTCCACCT ACTCCTCCAC CAACTCCATC CAGAAGTGGC AGATCAAGGC CAACGGCTCC
                                       Cry35Ab1 v5
       ~~~~~~~~~~~~~~~~~~~~~~~~~~~~~~~~~~~~~~~~~~~~~~~~~~~~~~~~~~~~~~~~
6721   TCCTACGTGA TCCAGTCCGA CAACGGCAAG GTGCTCACCG CCGGCACCGG CCAGGCCCTC
                                       Cry35Ab1 v5
       ~~~~~~~~~~~~~~~~~~~~~~~~~~~~~~~~~~~~~~~~~~~~~~~~~~~~~~~~~~~~~~~~
6781   GGCCTCATCC GCCTCACCGA CGAGTCCTCC AACAACCCGA ACCAGCAGTG GAACCTGACG
                                       Cry35Ab1 v5
       ~~~~~~~~~~~~~~~~~~~~~~~~~~~~~~~~~~~~~~~~~~~~~~~~~~~~~~~~~~~~~~~~
6841   TCCGTGCAGA CCATCCAGCT CCCGCAGAAG CCGATCATCG ACACCAAGCT CAAGGACTAC
                                       Cry35Ab1 v5
       ~~~~~~~~~~~~~~~~~~~~~~~~~~~~~~~~~~~~~~~~~~~~~~~~~~~~~~~~~~~~~~~~
6901   CCGAAGTACT CCCCGACCGG CAACATCGAC AACGGCACCT CCCCGCAGCT CATGGGCTGG
                                       Cry35Ab1 v5
       ~~~~~~~~~~~~~~~~~~~~~~~~~~~~~~~~~~~~~~~~~~~~~~~~~~~~~~~~~~~~~~~~
6961   ACCCTCGTGC CGTGCATCAT GGTGAACGAC CCGAACATCG ACAAGAACAC CCAGATCAAG
                                       Cry35Ab1 v5
       ~~~~~~~~~~~~~~~~~~~~~~~~~~~~~~~~~~~~~~~~~~~~~~~~~~~~~~~~~~~~~~~~
7021   ACCACCCCGT ACTACATCCT CAAGAAGTAC CAGTACTGGC AGAGGGCCGT GGGCTCCAAC
                                       Cry35Ab1 v5
       ~~~~~~~~~~~~~~~~~~~~~~~~~~~~~~~~~~~~~~~~~~~~~~~~~~~~~~~~~~~~~~~~
7081   GTCGCGCTCC GCCCGCACGA GAAGAAGTCC TACACCTACG AGTGGGGCAC CGAGATCGAC
                                       Cry35Ab1 v5
       ~~~~~~~~~~~~~~~~~~~~~~~~~~~~~~~~~~~~~~~~~~~~~~~~~~~~~~~~~~~~~~~~
7141   CAGAAGACCA CCATCATCAA CACCCTCGGC TTCCAGATCA ACATCGACAG CGGCATGAAG
                                       Cry35Ab1 v5
       ~~~~~~~~~~~~~~~~~~~~~~~~~~~~~~~~~~~~~~~~~~~~~~~~~~~~~~~~~~~~~~~~
```

FIG. 23H

```
7201    TTCGACATCC CGGAGGTGGG CGGCGGTACC GACGAGATCA AGACCCAGCT CAACGAGGAG
                             Cry35Ab1 v5

7261    CTCAAGATCG AGTACTCCCA CGAGACGAAG ATCATGGAGA AGTACCAGGA GCAGTCCGAG
                             Cry35Ab1 v5

7321    ATCGACAACC CGACCGACCA GTCCATGAAC TCCATCGGCT TCCTCACCAT CACCTCCCTG
                             Cry35Ab1 v5

7381    GAGCTCTACC GCTACAACGG CTCCGAGATC CGCATCATGC AGATCCAGAC CTCCGACAAC
                             Cry35Ab1 v5

7441    GACACCTACA ACGTGACCTC CTACCCGAAC CACCAGCAGG CCCTGCTGTG AGTAGTTAGC
                             StPinII 3' UTR v2

7501    TTAATCACCT AGAACCTAGA CTTGTCCATC TTCTGGATTG GCCAACTTAA TTAATGTATG
                             StPinII 3' UTR v2

7561    AAATAAAAGG ATGCACACAT AGTGACATGC TAATCACTAT AATGTGGGCA TCAAAGTTGT
                             StPinII 3' UTR v2

7621    GTGTTATGTG TAATTACTAG TTATCTGAAT AAAAGAGAAA GAGATCATCC ATATTTCTTA
                             StPinII 3' UTR v2

7681    TCCTAAATGA ATGTCACGTG TCTTTATAAT TCTTTGATGA ACCAGATGCA TTTCATTAAC
                             StPinII 3' UTR v2

7741    CAAATCCATA TACATATAAA TATTAATCAT ATATAATTAA TATCAATTGG GTTAGCAAAA
        StPinII 3' UTR v2

7801    CAAATCTAGT CTAGGTGTGT TTTGCTCTAG TGCTAGCCTC GAGGTCGACT CTGATCATGG
7861    ATGCTACGTC ACGGCAGTAC AGGACTATCA TCTTGAAAGT CGATTGAGCA TCGAAACCCA
7921    GCTTTCTTGT ACAAAGTGGT TGCGGCCGCT TAATTAAATT TAAATGTTTG GGGATCCTCT
                             ZmUbi1 promoter v2

7981    AGAGTCGACC TGCAGTGCAG CGTGACCCGG TCGTGCCCCT CTCTAGAGAT AATGAGCATT
                             ZmUbi1 promoter v2

8041    GCATGTCTAA GTTATAAAAA ATTACCACAT ATTTTTTTTG TCACACTTGT TTGAAGTGCA
                             ZmUbi1 promoter v2

8101    GTTTATCTAT CTTTATACAT ATATTTAAAC TTACTCTAC GAATAATATA ATCTATAGTA
                             ZmUbi1 promoter v2

8161    CTACAATAAT ATCAGTGTTT TAGAGAATCA TATAAATGAA CAGTTAGACA TGGTCTAAAG
                             ZmUbi1 promoter v2

8221    GACAATTGAG TATTTTGACA ACAGGACTCT ACAGTTTTAT CTTTTTAGTG TGCATGTGTT
                             ZmUbi1 promoter v2
```

FIG. 23I

```
8281    CTCCTTTTTT TTTGCAAATA GCTTCACCTA TATAATACTT CATCCATTTT ATTAGTACAT
                   ZmUbi1 promoter v2

8341    CCATTTAGGG TTTAGGGTTA ATGGTTTTTA TAGACTAATT TTTTAGTAC ATCTATTTTA
                   ZmUbi1 promoter v2

8401    TTCTATTTTA GCCTCTAAAT TAAGAAAACT AAAACTCTAT TTTAGTTTTT TTATTTAATA
                   ZmUbi1 promoter v2

8461    GTTTAGATAT AAAATAGAAT AAAATAAAGT GACTAAAAAT TAAACAAATA CCCTTTAAGA
                   ZmUbi1 promoter v2

8521    AATTAAAAAA ACTAAGGAAA CATTTTTCTT GTTTCGAGTA GATAATGCCA GCCTGTTAAA
                   ZmUbi1 promoter v2

8581    CGCCGTCGAC GAGTCTAACG GACACCAACC AGCGAACCAG CAGCGTCGCG TCGGGCCAAG
                   ZmUbi1 promoter v2

8641    CGAAGCAGAC GGCACGGCAT CTCTGTCGCT GCCTCTGGAC CCCTCTCGAG AGTTCCGCTC
                   ZmUbi1 promoter v2

8701    CACCGTTGGA CTTGCTCCGC TGTCGGCATC CAGAAATTGC GTGGCGGAGC GGCAGACGTG
                   ZmUbi1 promoter v2

8761    AGCCGGCACG GCAGGCGGCC TCCTCCTCCT CTCACGGCAC CGGCAGCTAC GGGGGATTCC
                   ZmUbi1 promoter v2

8821    TTTCCCACCG CTCCTTCGCT TTCCCTTCCT CGCCCGCCGT AATAAATAGA CACCCCCTCC
                   ZmUbi1 promoter v2

8881    ACACCCTCTT TCCCCAACCT CGTGTTGTTC GGAGCGCACA CACACACAAC CAGATCTCCC
                   ZmUbi1 promoter v2
                                                                 ZmUbi1 intron v2

8941    CCAAATCCAC CGTCGGCAC CTCCGCTTCA AGGTACGCCG CTCGTCCTCC CCCCCCCCCC
                   ZmUbi1 promoter v2
                   ZmUbi1 intron v2

9001    CCCTCTCTAC CTTCTCTAGA TCGGCGTTCC GGTCCATGCA TGGTTAGGGC CCGGTAGTTC
                   ZmUbi1 promoter v2
                   ZmUbi1 intron v2

9061    TACTTCTGTT CATGTTTGTG TTAGATCCGT GTTTGTGTTA GATCCGTGCT GCTAGCGTTC
                   ZmUbi1 promoter v2
                   ZmUbi1 intron v2
```

FIG. 23J

```
9121    GTACACGGAT GCGACCTGTA CGTCAGACAC GTTCTGATTG CTAACTTGCC AGTGTTTCTC
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9181    TTTGGGGAAT CCTGGGATGG CTCTAGCCGT TCCGCAGACG GGATCGATTT CATGATTTTT
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9241    TTTGTTTCGT TGCATAGGGT TTGGTTTGCC CTTTTCCTTT ATTTCAATAT ATGCCGTGCA
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9301    CTTGTTTGTC GGGTCATCTT TTCATGCTTT TTTTTGTCTT GGTTGTGATG ATGTGGTCTG
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9361    GTTGGGCGGT CGTTCTAGAT CGGAGTAGAA TTCTGTTTCA AACTACCTGG TGGATTTATT
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9421    AATTTTGGAT CTGTATGTGT GTGCCATACA TATTCATAGT TACGAATTGA AGATGATGGA
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9481    TGGAAATATC GATCTAGGAT AGGTATACAT GTTGATGCGG GTTTTACTGA TGCATATACA
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9541    GAGATGCTTT TTGTTCGCTT GGTTGTGATG ATGTGGTGTG GTTGGGCGGT CGTTCATTCG
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9601    TTCTAGATCG GAGTAGAATA CTGTTTCAAA CTACCTGGTG TATTTATTAA TTTTGGAACT
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
9661    GTATGTGTGT GTCATACATC TTCATAGTTA CGAGTTTAAG ATGGATGGAA ATATCGATCT
                   ZmUbi1 promoter v2
                   ~~~~~~~~~~~~~~~~~~~~~~~~~~~~~~~~~~~~~~~~~~~~~~~~~~~~~~~
                                 ZmUbi1 intron v2
                   ~~~~~~~~~~~~~~~~~~~~~~~~~~~~~~~~~~~~~~~~~~~~~~~~~~~~~~~
```

FIG. 23K

```
9721   AGGATAGGTA TACATGTTGA TGTGGGTTTT ACTGATGCAT ATACATGATG GCATATGCAG
              ZmUbi1 promoter v2
              ~~~~~~~~~~~~~~~~~~~~~~~~~~~~~~~~~~~~~~~~~~~~~~~~~~~~~~~~~
                       ZmUbi1 intron v2
              ~~~~~~~~~~~~~~~~~~~~~~~~~~~~~~~~~~~~~~~~~~~~~~~~~~~~~~~~~
9781   CATCTATTCA TATGCTCTAA CCTTGAGTAC CTATCTATTA TAATAAACAA GTATGTTTTA
              ZmUbi1 promoter v2
              ~~~~~~~~~~~~~~~~~~~~~~~~~~~~~~~~~~~~~~~~~~~~~~~~~~~~~~~~~
                       ZmUbi1 intron v2
              ~~~~~~~~~~~~~~~~~~~~~~~~~~~~~~~~~~~~~~~~~~~~~~~~~~~~~~~~~
9841   TAATTATTTC GATCTTGATA TACTTGGATG ATGGCATATG CAGCAGCTAT ATGTGGATTT
              ZmUbi1 promoter v2
              ~~~~~~~~~~~~~~~~~~~~~~~~~~~~~~~~~~~~~~~~~~~~~~~~~~~~~~~~~
                       ZmUbi1 intron v2
              ~~~~~~~~~~~~~~~~~~~~~~~~~~~~~~~~~~~~~~~~~~~~~~~~~~~~~~~~~
9901   TTTTAGCCCT GCCTTCATAC GCTATTTATT TGCTTGGTAC TGTTTCTTTT GTCGATGCTC
       ZmUbi1 promoter v2
       ~~~~~~~~~~~~~~~~~~~~~~~~~~~
          ZmUbi1 intron v2                                      PAT v9
       ~~~~~~~~~~~~~~~~~~~~~~~~~~~                              ~~~~~
9961   ACCCTGTTGT TTGGTGTTAC TTCTGCAGGG TACAGTAGTT AGTTGACACG ACACCATGTC
                                   PAT v9
              ~~~~~~~~~~~~~~~~~~~~~~~~~~~~~~~~~~~~~~~~~~~~~~~~~~~~~~~~~
10021  TCCGGAGAGG AGACCAGTTG AGATTAGGCC AGCTACAGCA GCTGATATGG CCGCGGTTTG
                                   PAT v9
              ~~~~~~~~~~~~~~~~~~~~~~~~~~~~~~~~~~~~~~~~~~~~~~~~~~~~~~~~~
10081  TGATATCGTT AACCATTACA TTGAGACGTC TACAGTGAAC TTTAGGACAG AGCCACAAAC
                                   PAT v9
              ~~~~~~~~~~~~~~~~~~~~~~~~~~~~~~~~~~~~~~~~~~~~~~~~~~~~~~~~~
10141  ACCACAAGAG TGGATTGATG ATCTAGAGAG GTTGCAAGAT AGATACCCTT GGTTGGTTGC
                                   PAT v9
              ~~~~~~~~~~~~~~~~~~~~~~~~~~~~~~~~~~~~~~~~~~~~~~~~~~~~~~~~~
10201  TGAGGTTGAG GGTGTTGTGG CTGGTATTGC TTACGCTGGG CCCTGGAAGG CTAGGAACGC
                                   PAT v9
              ~~~~~~~~~~~~~~~~~~~~~~~~~~~~~~~~~~~~~~~~~~~~~~~~~~~~~~~~~
10261  TTACGATTGG ACAGTTGAGA GTACTGTTTA CGTGTCACAT AGGCATCAAA GGTTGGGCCT
                                   PAT v9
              ~~~~~~~~~~~~~~~~~~~~~~~~~~~~~~~~~~~~~~~~~~~~~~~~~~~~~~~~~
10321  AGGATCCACA TTGTACACAC ATTTGCTTAA GTCTATGGAG GCGCAAGGTT TTAAGTCTGT
                                   PAT v9
              ~~~~~~~~~~~~~~~~~~~~~~~~~~~~~~~~~~~~~~~~~~~~~~~~~~~~~~~~~
10381  GGTTGCTGTT ATAGGCCTTC CAAACGATCC ATCTGTTAGG TTGCATGAGG CTTTGGGATA
                                   PAT v9
              ~~~~~~~~~~~~~~~~~~~~~~~~~~~~~~~~~~~~~~~~~~~~~~~~~~~~~~~~~
10441  CACAGCCCGT GGTACATTGC GCGCAGCTGG ATACAAGCAT GGTGGATGGC ATGATGTTGG
                                   PAT v9
              ~~~~~~~~~~~~~~~~~~~~~~~~~~~~~~~~~~~~~~~~~~~~~~~~~~~~~~~~~
10501  TTTTTGGCAA AGGGATTTTG AGTTGCCAGC TCCTCCAAGG CCAGTTAGGC CAGTTACCCA
       PAT v9                                                ZmLip 3' UTR v1
       ~~~~~~~                                               ~~~~~~~~~~~~~~
```

FIG. 23L

```
10561    GATCTGACTG AGCTTGAGCT TATGAGCTTA TGAGCTTAGA GCTCGGTCGC AGCGTGTGCG
                    ZmLip 3' UTR v1
10621    TGTCCGTCGT ACGTTCTGGC CGGCCGGGCC TTGGGCGCGC GATCAGAAGC GTTGCGTTGG
                    ZmLip 3' UTR v1
10681    CGTGTGTGTG CTTCTGGTTT GCTTTAATTT TACCAAGTTT GTTTCAAGGT GGATCGCGTG
                    ZmLip 3' UTR v1
10741    GTCAAGGCCC GTGTGCTTTA AAGACCCACC GGCACTGGCA GTGAGTGTTG CTGCTTGTGT
                    ZmLip 3' UTR v1
10801    AGGCTTTGGT ACGTATGGGC TTTATTTGCT TCTGGATGTT GTGTACTACT TGGGTTTGTT
                    ZmLip 3' UTR v1
10861    GAATTATTAT GAGCAGTTGC GTATTGTAAT TCAGCTGGGC TACCTGGACA TTGTTATGTA
                    ZmLip 3' UTR v1
10921    TTAATAAATG CTTTGCTTTC TTCTAAAGAT CTTTAAGTGC TTCTAGAGCA TGCACATAGA
10981    CACACACATC ATCTCATTGA TGCTTGGTAA TAATTGTCAT TAGATTGTTT TTATGCATAG
11041    ATGCACTCGA AATCAGCCAA TTTTAGACAA GTATCAAACG GATGTGACTT CAGTACATTA
11101    AAAACGTCCG CAATGTGTTA TTAAGTTGTC TAAGCGTCAA TTTGATTTAC AATTGAATAT
11161    ATCCTGCCCC AGCCAGCCAA CAGCTCGATT TACAATTGAA TATATCCTGC CGGCCGGCCC
11221    ACGCGTGTCG AGGAATTCTG ATCTGGCCCC CATTTGGACG TGAATGTAGA CACGTCGAAA
11281    TAAAGATTTC CGAATTAGAA TAATTTGTTT ATTGCTTTCG CCTATAAATA CGACGGATCG
11341    TAATTTGTCG TTTTATCAAA ATGTACTTTC ATTTTATAAT AACGCTGCGG ACATCTACAT
11401    TTTTGAATTG AAAAAAAATT GGTAATTACT CTTTCTTTTT CTCCATATTG ACCATCATAC
11461    TCATTGCTGA TCCATGTAGA TTTCCCGGAC ATGAAGCCAT TTACAATTGA ATATATCCTG
11521    CC
```

FIG. 23M

SEQ ID NO: 15
CTGGACCCCTCTCGAGTGTTCCGCTTCACCGTTGGACTTGCTACGCTGTCAGCATCGA
GATGTTGCGTGGCGGAGCGGCAGACTTGAGCCGTCACGGCAGGCGGCCTCCTCCTCC
TCTCACGGCATCTGTAGCTACGGGGGATTCCTTTCGCACCGCTCGTTCGCTTTCCCTT
CCTCGTCTGCCGAAATAATGTTACACCCCTCCACAGCCTCT

SEQ ID NO: 16
CTGGACCCCTCTCGAGAGTTCCGCTCCACCGTTGGACTAGCTCTGCTGTCGGCATCCA
GAAAATGCTTGGCAGTGCGGCAGACGTGAGCCGGCACGGCAGGGGGCCTCCTCCTG
CTCTCACGGCACATGAAGCTACGGGTGATAGCTTGCCCACCGCTCCAACGCTTTCCC
TTACTCTCACGCCGTAATAAATAGACACCCCTTCCACAACCTCT

SEQ ID NO: 17
CTGGACCTCTCTCGAGAGTTGCGCTCCACCGATGGACTTGCTCCGCTGTCGGCGTCC
ATAATTTGCGTGGCGGAGCGGCAGACGGGAGCCGGCACGGCAGGGAGCCTCGTCCT
CCTCTCACGGCACCTGCAACTACGGGGGATTCCTATCCCACCGCTCCTTCGCTTTCAC
TTCTTCGCCCTCCTTAATAAGTAGACACCCCATCCGAGCCCTCT

SEQ ID NO: 18
CAAGACCCCTCTCGAGAGTTCCGCACCACCGTTGGACGTGCTCCGCTATCTGCATCC
AGAAATTGCGTGGCGGAACGGTAAACGTGAGCCGTCACGGCAGGCGGCCTCCTCCT
CCTCTCACGACACCGGCAGCTACGGGGGATACCTGTCACACAGCTCCTTCGCTTTTCT
TTCCTCGCCCGCCGTAATATGTATACACTCCCTCCGCACCCTCT

SEQ ID NO: 19
CTGGACCCCTCTCGAGGGTTCCGTTCCACCGTTGGTCTTGGTCCGCTGTCGGGATCCA
GAAATAGCGTGGCGGAGCGGCAGACGTGATCCGGCACGGCATGCGGCCTCCTAGTC
CTATCACAGCACCGGCAGCTATGGGAGATTCCATTCCCACCGCTCCTGCGCTTTCACT
GGCTGGCCCGCCGTGATAGATAGACACCCCCTCCACACCCTCT

FIG. 24A

SEQ ID NO: 20
GTTGGCTTCTCTTGTGAGTTCTGCTTCACGGATGGACTTGGTCAACGGACGGCATCCA
GAATTTGCGTGGCGTAGCGGCGGACGTGATCCGGCGCGGCAGGCGGCTTCCTCCTCC
TCTCACTTAAGCGACAGCTACAGGGGATTCCTTTCCCACCGCTCCTTCGCTTGCCGTA
CCTCGCCCGCCGTAATAAATAGACACCCCTTCCACTCCCTCT

SEQ ID NO: 21
CTGGATCCCTCTCGAGAGTGCGGCTCCGACGTTGGACTTGCTCCGAAGTCGGCATCC
AAAAATTGCGTGGTGGAGAGGCAGACTTGAGCCGGCACGGCAGGAGGCCTCGTCCT
ACTCGCACGGTATCGGCAGCAACGGGAGAATCCTTGCACTCTGCTCCTTCGCTGTAC
CTTCCTCGCCCGCTGATATTGATAGACACCCCCTGCATACCCTCT

SEQ ID NO: 22
ATGGACCCTTCTCGAGTGTTCGGCTCCACCGTTAGACTTGCTCCACGATCGACATCA
AGAAATTGCGAGACGGAGCTACAAACGTAAGAAATCTCGGTAGGGGGCCTCCTCCT
CCTCTCACGGCACCGGCAGCTACGGGGGATTCCTGTCCCACCTCTCCTTCACGTTCCC
TACCTCGCCCGCCATAATTAATAAGCACCCCTCCGCACCCTCT

SEQ ID NO: 23
CTGGACCCCTCTAAAGAGTTCCACGCCACCGTTATAATGGCTCCGCTGTCGGCATCC
AGAAATTACTTGGCGGATCAGCAGACGTGAGCCAGCATGGCTGGCGGCCTCCTCCTC
CTCTCACGATGCCGTCAGCTACGGGGGATTCCTTTCCCAACGCTCCTTCGCTTTCCTA
TGCGCGCCTGCCGGATTAAATAGGCAGCTTCTCGTCACCCTCT

SEQ ID NO: 24
CAAGACACCTCTCGATTGTTCCGCTTCACCGTTGGACTTTCTCCTCAGTCGGCATACA
GAAATTGCTTGGCGAAGCGGCAGACATGAGCCGGCACGACATGCGTCCTCATTCTCC
TCTCATGGCACCGGCAGTTACTGGTGAATCCTATCGCACCGCTCCTTCGCTGTCCCTT
AATCGCCCGCCGAAAATAATTGACACCCCATCCACACCCTCT

FIG. 24B

SEQ ID NO: 25
GAGGACCCCTCTCGTGTGTATCGCTCCACCTTTGGAGTTGGTCCACTATCGGCGTACA
GAAAATTCGTTGCGAAGCGGCAGACGTGAGCCTACACGGCAGTCGGCCTCTACCTCC
TGACAAGGCACGTGCAGCTACAGATGATGCCTTTCCCACCACTCCTTCGCGTTCCTTT
CCTCGCCATCAGTAATGAATGGACACGTCCTCCAGACTCTCT

SEQ ID NO: 26
CTGAACCCATCTCGAGTATGCCGCACGATCGATTGACATGCTCCACTGGCAGCATCC
AGAAATTGCATTGGGGAGCATCAGGCGTGAGCCTGCACGGCAGGCGGACTATTCCT
CCTCGCGCGGCACCGGCAACTACGGGGGATGCTTGACCGACCGCTCCATCGATTTCC
CAATCTCGCTTGCCGTATTAAATAGATAACCCCTTCACACCCTCT

SEQ ID NO: 27
CTGGACTCCTTACGGGAGATCCGCTCCACCGTTGGACTAGCTCCGTTTTCGGCTTCAA
TAAAGGGCGTGGGGGAGCGGCAGTCGGGGGCAGGCACGGCAGTGGTCCTCATCCAT
ATCTCACGGGGCCGGCAGTTGAGGGGGATTCCTGTCCCACCTCACCTACTCTTTCCCT
ACCTCGTCTGCCATATTAAATAGTCACCCCCTCCACAACCTTT

SEQ ID NO: 28
TTGGACCCCTCTCGAAAGTTAGGCTCCGCCGTTGGACTGGTTTCGCGGTCATCAATC
AGGAATTGCGGGGCGGAGGGTCAGACGTGTGCCGGCACAGCAGGTGGCCTCCTCAT
CGTCACAAGGCACTGGCAACTACGGGTGATTCATTTCCTTCAGCACCTACGCTTACC
CTGCCACGCCCTCCGTATTATAATGACACCCCCTCCACACCTTAT

SEQ ID NO: 29
CTGGACCCCACGCGGGGTTTTCGTTCCTCCGTTGGGATAGCTCCGGTGTCAGCATAC
AGAGAATATATGTCGGAGCGGAAGACGTGAGCCGACACGGCGGGCTGCCGCCTCCT
CCTGTCACGACACCGGCAGGTACGGGGGATTCCGTTCCCGCCGCACAGTCACTTTCG
CTTCCTTGCCGGTCGTATTAAATAGACACCGTGTCCACAGCCTCT

FIG. 24C

SEQ ID NO: 30
CTTGAGCCCACTCTAGAGTTCCGTTTCACCGAATGACTAGCTCCGCTGTCGGTATCCA
TTAAGTGGGAGGCAGAACGTCATATGAGAGTCGGCACGGGAGGCGTTCGCCACGTC
CGCGCACTACAGCGGGAGCTGCGGAATATACCTGTCCCAATGCTGCTACGCTTTCCC
TTCCGCGCCCACCGTAGAAAAATGACAGTCCCTTCACACCCTCT

SEQ ID NO: 31
TAGGAGGCCTCTCGAAAGGTCCGGAACTCCGTAGGACGTGCTCCGCTGACAGCATCC
AGGAATATCATGGGGGAGCTGCAGACGAGAGCCTGGACGACAAGGGGTCACCTCGG
CCGCTGACAGCTGCGGCAGCAACGGAGTATGCTTTTCTCACCGCTCCGGCGCTTTCC
CTTCGACGCAGGCCAGAATAAGTAGACATCAGCGCCACACCCTCT

SEQ ID NO: 32
CTTGTCTCCACTCTGATGTTCCGCTCCAACATTTGATTTGCTCCTCTGTAGGCATACA
GTTATTGGGGGACTGATCGGCAGACGTGAGCCAGCACTGCAAACGGCCAACTCCTCC
TCTCTCGACTAAGGGATTAATTAAGGATACCTTACCCGCGGCTCCTTCTCTTTCCCTA
CCTAGCCCGCCTTATTAAATAGAGACCGCCTCCACAGCCGCT

SEQ ID NO: 33
CTGTACCCTTCACAAGGGTTACACGCTACCGATGGACTTGCACCACTGTGGGGTTCC
AATAATTGCGTGGCTGGGCGTCAGACATATTCCGGCATGGCAAGCGGCCTGCTCCTC
CTCTGGGAGCACCGGCAACAATGGGGGATTCCAAGCCCGCAGGTCCTTCGTTTTACC
GTCCTCGCCCGCCGTAGTATGTAGGCATCCAGAGACTACCTCT

SEQ ID NO: 34
CAGGAACCCTAACGAGGGTTCCGCACGACCAAATGACTTGATCTTCTGTCGGCATCC
AGAAATGGGGTGTCAGAGCGGCATGCGTGAGCCGGCGGGGCGTGCGGCCTCATGCT
GCTCTCGCGGGACTAGGAGTTACGGGGGATACCTGTATTGCCGCTCCGACACTGTAC
CATCCTCTCCCGCCGGAGTATAGAGACACCCCCTCGACGCCATAT

FIG. 24D

SEQ ID NO: 35
CTGTGCTCCTGTATGGGGTTCAACTCCACCGTGAAATTTGCGCCTCTGTCGTCATCCA
GAAATTGCGTGGTTGATCTGCTGACGTTAAAGGGCTCTGCAGGCGGCTTCCTTCGGC
TATGAAGGTACTGGCGTCTGCAAGTGATGCTTTTGCTAACTCGCCTTCGATGTCCCTT
CCTCGCGTGCTTTAATAGGTTGTCAGCCGCTCCAGACCATTT

SEQ ID NO: 36
CTGGTCCCATCGCTAGTGGTACGCTCCACCGGTGGAGTAGCTCAGATGTCTGAAGGG
TGGAATTTAGAGGTGGAGAGACAGACGTGAGCTAGAGCGGCATGGGACCTGGTCCA
CCGCTCGAGGCAATGGCAACGACTGTTGAAACCTTGCCCACCACTCCTGCAATTTTC
CATCCTCACCGGCCGGAATGAATTAAAACCCACGTCACAACCTCT

SEQ ID NO: 37
CGTGACAGGGCTCGGGTGTTCGGCTCCATCGTAGTGCATGCGCCGATGTAAGTATAC
AAGAAGTACGTGGCTTGGCGTCTGACGAGGGCCGTCAAGGCAGGCGGCCTCCTTCTA
AGCTTACGGCGCCGGCAGGTTCGTAGGTTACCTTACACTCAACTCATAGTCTATCTAT
TACTCGTACTGCGTTATAAATTGTCACCCCCTCCACACCCTCT

SEQ ID NO: 38
AGGAACGCTTCTCGATGGTTGCGCACATAGGAGGGACTTGATAGTCGGTGGAAATCT
AAGAATTGCATATCAGATCTGCAGACGTTAGCCGACATGGCTAGCAGACTACTCCGC
TTCACACGTCAGCGAAAGCGACGGAGGATTTCTTGCCAACGGCGCCTTCGCGAACCC
TTCCTCGCCCGTCGGAAGAAAGATACTCCCCTTGCACACCCTCT

SEQ ID NO: 39
CTTGACTTGGCTCGAGAGTTCTGCGCTTCCATTGTAGTTGCAGCGATGTCGGAGTCCG
AGGGTTGCGTGGCGGTGCGGCAGACGTGGGCAGATACGACTGTATGCCAGCACCTA
AACATACGGTACCAGAAGCTGCGGTGGATACCTTTCCCGACGCATATACGTTTTCCG
TGCCTCTCACGCCGTAGTAAATAAACTCCCCCTCCTGTTCCTTT

FIG. 24E

SEQ ID NO: 50: yellow fluorescent protein from *Phialidium sp.* SL-2003 (Phiyfp; 234 a.a.; GenBank: AAR85349.1):
MSSGALLFHG KIPYVVEMEG NVDGHTFSIR GKGYGDASVG KVDAQFICTT
GDVPVPWSTL VTTLTYGAQC FAKYGPELKD FYKSCMPEGY VQERTITFEG
DGVFKTRAEV TFENGSVYNR VKLNGQGFKK DGHVLGKNLE FNFTPHCLYI
WGDQANHGLK SAFKIMHEIT GSKEDFIVAD HTQMNTPIGG GPVHVPEYHH
ITYHVTLSKD VTDHRDNMSL VETVRAVDCR KTYL SEQ ID NO: 51: Phiyfpv3; 234 a.a.

MSSGALLFHG KIPYVVEMEG NVDGHTFSIR GKGYGDASVG KVDAQFICTT
GDVPVPWSTL VTTLTYGAQC FAKYGPELKD FYKSCMPDGY VQERTITFEG
DGNFKTRAEV TFENGSVYNR VKLNGQGFKK DGHVLGKNLE FNFTPHCLYI
WGDQANHGLK SAFKICHEIT GSKGDFIVAD HTQMNTPIGG GPVHVPEYHH
MSYHVKLSKD VTDHRDNMSL KETVRAVDCR KTYL

FIG. 25

CONSTRUCT AND METHOD FOR SYNTHETIC BIDIRECTIONAL PLANT PROMOTER UBI1

CROSS-REFERENCE TO RELATED APPLICATIONS

This application claims priority under 35 U.S.C. §119 of U.S. provisional patent application Ser. No. 61/582,138 filed Dec. 30, 2011, which application is hereby incorporated by reference in its entirety. This application also claims priority of U.S. provisional patent application Ser. No. 61/617,252 filed Mar. 29, 2012, which application is hereby incorporated by reference in its entirety.

TECHNICAL FIELD

This invention is generally related to the field of plant molecular biology, and more specifically the field of stable expression of multiple genes in transgenic plants.

BACKGROUND

Many plant species are capable of being transformed with transgenes from other species to introduce agronomically desirable traits or characteristics, for example, improving nutritional value quality, increasing yield, conferring pest or disease resistance, increasing drought and stress tolerance, improving horticultural qualities (such as pigmentation and growth), imparting herbicide resistance, enabling the production of industrially useful compounds and/or materials from the plant, and/or enabling the production of pharmaceuticals. The introduction of transgenes into plant cells and the subsequent recovery of fertile transgenic plants that contain a stably integrated copy of the transgene can be used to produce transgenic plants that possess the desirable traits.

Control and regulation of gene expression can occur through numerous mechanisms. Transcription initiation of a gene is a predominant controlling mechanism of gene expression. Initiation of transcription is generally controlled by polynucleotide sequences located in the 5'-flanking or upstream region of the transcribed gene. These sequences are collectively referred to as promoters. Promoters generally contain signals for RNA polymerase to begin transcription so that messenger RNA (mRNA) can be produced. Mature mRNA is translated by ribosome, thereby synthesizing proteins. DNA-binding proteins interact specifically with promoter DNA sequences to promote the formation of a transcriptional complex and initiate the gene expression process. There are a variety of eukaryotic promoters isolated and characterized from plants that are functional for driving the expression of a transgene in plants. Promoters that affect gene expression in response to environmental stimuli, nutrient availability, or adverse conditions including heat shock, anaerobiosis, or the presence of heavy metals have been isolated and characterized. There are also promoters that control gene expression during development or in a tissue, or organ specific fashion. In addition, prokaryotic promoters isolated from bacteria and virus have been isolated and characterized that are functional for driving the expression of a transgene in plants.

A typical eukaryotic promoter consists of a minimal promoter and other cis-elements. The minimal promoter is essentially a TATA box region where RNA polymerase II (polII), TATA-binding protein (TBP), and TBP-associated factors (TAFs) may bind to initiate transcription. However in most instances, sequence elements other than the TATA motif are required for accurate transcription. Such sequence elements (e.g., enhancers) have been found to elevate the overall level of expression of the nearby genes, often in a position- and/or orientation-independent manner. Other sequences near the transcription start site (e.g., INR sequences) of some polII genes may provide an alternate binding site for factors that also contribute to transcriptional activation, even alternatively providing the core promoter binding sites for transcription in promoters that lack functional TATA elements. See e.g., Zenzie-Gregory et al. (1992) J. Biol. Chem. 267: 2823-30.

Other gene regulatory elements include sequences that interact with specific DNA-binding factors. These sequence motifs are sometimes referred to as cis-elements, and are usually position- and orientation-dependent, though they may be found 5' or 3' to a gene's coding sequence, or in an intron. Such cis-elements, to which tissue-specific or development-specific transcription factors bind, individually or in combination, may determine the spatiotemporal expression pattern of a promoter at the transcriptional level. The arrangement of upstream cis-elements, followed by a minimal promoter, typically establishes the polarity of a particular promoter. Promoters in plants that have been cloned and widely used for both basic research and biotechnological application are generally unidirectional, directing only one gene that has been fused at its 3' end (i.e., downstream). See, for example, Xie et al. (2001) Nat. Biotechnol. 19(7):677-9; U.S. Pat. No. 6,388,170.

Many cis-elements (or "upstream regulatory sequences") have been identified in plant promoters. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al. (1989) Proc. Natl. Acad. Sci. USA 86:3219-23. The type of control of specific promoter elements is typically an intrinsic quality of the promoter; i.e., a heterologous gene under the control of such a promoter is likely to be expressed according to the control of the native gene from which the promoter element was isolated. These elements also typically may be exchanged with other elements and maintain their characteristic intrinsic control over gene expression.

It is often necessary to introduce multiple genes into plants for metabolic engineering and trait stacking, which genes are frequently controlled by identical or homologous promoters. However, homology-based gene silencing (HBGS) is likely to arise when multiple introduced transgenes have homologous promoters driving them. See e.g., Mol et al. (1989) Plant Mol. Biol. 13:287-94. HBGS has been reported to occur extensively in transgenic plants. See e.g., Vaucheret and Fagard (2001) Trends Genet. 17:29-35. Several mechanisms have been suggested to explain the phenomena of HBGS, all of which include the feature that sequence homology in the promoter triggers cellular recognition mechanisms that result in silencing of the repeated genes. See e.g., Matzke and Matzke (1995) Plant Physiol. 107:679-85; Meyer and Saedler (1996) Ann. Rev. Plant Physiol. Plant Mol. Biol. 47:23-48; Fire (1999) Trends Genet. 15:358-63; Hamilton and Baulcombe (1999) Science 286:950-2; and Steimer et al. (2000) Plant Cell 12:1165-78.

Strategies to avoid HBGS in transgenic plants frequently involve the development of synthetic promoters that are functionally equivalent but have minimal sequence homology. When such synthetic promoters are used for expressing transgenes in crop plants, they may aid in avoiding or reducing HBGS. See e.g., Mourrain et al. (2007) Planta 225(2):365-79; Bhullar et al. (2003) Plant Physiol. 132:988-98. Such promoters can be generated by introducing known cis-elements in a novel or synthetic stretch of DNA, or alternatively by "domain swapping," wherein domains of one promoter are replaced with functionally equivalent domains from other heterologous promoters.

Thus, there remains a need for constructs and methods for stable expression of multiple transgenes effectively with minimum risk for recombination or loss of transgenes through breeding or multiple generations in transgenic plants.

Disclosure

Described herein are methods for converting an Ubi1 polar promoter into synthetic bidirectional promoters, such that one synthetic promoter can direct the expression of two genes flanking the promoter. In some embodiments, a method for converting an Ubi1 polar promoter into a synthetic bidirectional promoter may comprise, for example and without limitation, identifying the minimal promoter element nucleotide sequence of an Ubi1 promoter; and/or providing a nucleic acid comprising two minimal Ubi1 promoter element nucleotide sequences oriented in opposite directions. In particular embodiments, a nucleic acid may comprise two minimal Ubi1 promoter element nucleotide sequences oriented in opposite directions, such that the end of each minimal promoter element that is closest to the corresponding native Ubi1 gene is further from the other minimal promoter element than an end of the nucleic acid that is proximate to a coding sequence operably linked to the promoter element. In some examples, the minimal Ubi1 promoter element is isolated from maize. Additional elements of a native Ubi1 promoter that may be engineered to be included in a synthetic bidirectional promoter include Ubi1 introns, Ubi1 exons, and/or all or part of an Ubi1 upstream promoter region. In some examples, a synthetic bidirectional promoter may comprise more than one of any of the foregoing.

Also described herein are Ubi1 minimal promoters that may be useful in constructing synthetic promoters (e.g., synthetic bidirectional promoters), and particular synthetic promoters produced by the foregoing methods. In some embodiments, a synthetic bidirectional promoter is a promoter that is able to control transcription of an operably linked nucleotide sequence in a plant cell. For example, a synthetic bidirectional promoter may be able in particular embodiments to control transcription in a plant cell of two operably linked nucleotide sequences that flank the promoter.

Particular embodiments of the invention include cells (e.g., plant cells) comprising an Ubi1 minimal promoter or functional equivalent thereof. For example, specific embodiments include a cell comprising a synthetic promoter (e.g., a synthetic bidirectional promoter) that includes an Ubi1 minimal promoter or functional equivalent thereof. Plant cells according to particular embodiments may be present in a cell culture, a tissue, a plant part, and/or a whole plant. Thus, a plant (e.g., a monocot or dicot) comprising a cell comprising an Ubi1 minimal promoter or functional equivalent thereof is included in some embodiments.

Some embodiments of the invention include a means for initiating transcription in a direction-independent manner. Means for initiating transcription in a direction-independent manner include the Ubi1 minimal promoter of SEQ ID NO: 1. Some embodiments of the invention include a means for initiating transcription of two operably linked nucleotide sequences of interest. Means for initiating transcription of two operably linked nucleotide sequences of interest include the synthetic bidirectional Ubi1 promoter of SEQ ID NO: 5.

The foregoing and other features will become more apparent from the following detailed description of several embodiments, which proceeds with reference to the accompanying figures.

Also provided are constructs and methods for expressing multiple genes in plant cells and/or plant tissues. The constructs provided comprise at least one bidirectional promoter link to multiple gene expression cassettes. In some embodiments, the constructs and methods provided employ a bidirectional promoter based on a minimal core promoter element from a *Zea mays* Ubiquitin-1 gene, or a functional equivalent thereof. In some embodiments, the constructs and methods provided allow expression of genes between three and twenty.

In one aspect, provided is a synthetic polynucleotide comprising a minimal core promoter element from an Ubiquitin-1 gene of *Zea mays* or *Zea luxurians*. In one embodiment, the minimal core promoter element comprises a polynucleotide sequence that is at least 65%, 70%, 75%, 80%, 85%, 90%, 95%, or 100% identical to SEQ ID NO: 1 or its complement. In a further or alternative embodiment, the minimal core promoter element comprises a polynucleotide sequence selected from the group consisting of SEQ ID NOs: 1 and 15-39. In a further embodiment, the minimal core promoter element comprising SEQ ID NO: 1 or its complement. In a further embodiment, the minimal core promoter element consists essentially of SEQ ID NO: 1 or its complement. In another embodiment, the synthetic polynucleotide further comprises an exon from an Ubiquitin-1 gene and an intron from an Ubiquitin-1 gene. In a further embodiment, the exon or intron is from an Ubiquitin-1 gene of *Zea mays* or *Zea luxurians*.

In another embodiment, the synthetic polynucleotide further comprises an upstream regulatory sequence from an Ubiquitin-1 gene. In a further embodiment, wherein the upstream regulatory sequence comprises a polynucleotide sequence that is at least 65%, 70%, 75%, 80%, 85%, 90%, 95%, or 100% identical to SEQ ID NO: 4 or its complement. In a further embodiment, wherein the upstream regulatory sequence comprises SEQ ID NO: 4 or its complement. In a further embodiment, wherein the upstream regulatory sequence consists essentially of SEQ ID NO: 4 or its complement.

In another embodiment, the synthetic polynucleotide further comprises at least one element selected from a list comprising an upstream regulatory sequence (URS), an enhancer element, an exon, an intron, a transcription start site, a TATA box, and a heat shock consensus element. In another embodiment, the synthetic polynucleotide further comprises a nucleotide sequence of interest operably linked to the minimal core promoter element. In another embodiment, the synthetic polynucleotide further comprises an element selected from the group consisting of an upstream regulatory sequence (URS), an enhancer element, an exon, an intron, a transcription start site, a TATA box, a heat shock consensus element, and combinations thereof. In another embodiment, the synthetic polynucleotide further comprises a nucleotide sequence of interest operably linked to the minimal core promoter element.

In another embodiment, the synthetic polynucleotide further comprises a second minimal core promoter element from *Zea mays* or *Zea luxurians*, wherein the two minimal core promoter elements are in reverse complimentary orientation with respect to each other in the polynucleotide. In a further or alternative embodiment, the synthetic polynucleotide further comprises an exon from an Ubiquitin-1 gene and an intron from an Ubiquitin-1 gene. In a further embodiment, the synthetic polynucleotide comprises a polynucleotide sequence that is at least 65%, 70%, 75%, 80%, 85%, 90%, 95%, or 100% identical to SEQ ID NO: 3 or its complement. In a further embodiment, the synthetic polynucleotide comprises SEQ ID NO: 3 or its complement. In a further embodiment, the synthetic polynucleotide consists essentially of SEQ ID NO: 3 or its complement.

In a further or alternative embodiment, the synthetic polynucleotide further comprises an upstream regulatory sequence from an Ubiquitin-1 gene. In a further embodiment, wherein the upstream regulatory sequence comprises a polynucleotide sequence that is at least 65%, 70%, 75%, 80%, 85%, 90%, 95%, or 100% identical to SEQ ID NO: 4 or its complement. In a further embodiment, the upstream regulatory sequence comprises SEQ ID NO: 4 or its complement. In a further embodiment, the upstream regulatory sequence consists essentially of SEQ ID NO: 4 or its complement.

In another embodiment, the synthetic polynucleotide comprising two minimal core promoter elements further comprises at least one element selected from a list comprising an upstream regulatory sequence (URS), an exon, an intron, a transcription start site, a TATA box, a heat shock consensus element, and a translational START and/or STOP nucleotide sequence. In a further or alternative embodiment, the synthetic polynucleotide comprising two minimal core promoter elements further comprises an element selected from the group consisting of an upstream regulatory sequence (URS), an exon, an intron, a transcription start site, a TATA box, a heat shock consensus element, a translational START and/or STOP nucleotide sequence, and combinations thereof. In a further embodiment, the synthetic polynucleotide comprises SEQ ID NO: 5 or its complement. In a further embodiment, the synthetic polynucleotide consists essentially of SEQ ID NO: 5 or its complement.

In another embodiment, the synthetic polynucleotide comprising two minimal core promoter elements comprises a first nucleotide sequence of interest operably linked to one of the minimal core promoter elements. In a further embodiment, the synthetic polynucleotide comprises a second nucleotide sequence of interest operably linked to the minimal core promoter element that is not operably linked to the first nucleotide sequence of interest.

In one embodiment of the synthetic polynucleotide provided, the exon is from an Ubiquitin-1 gene of a Zea spp. In one embodiment of the synthetic polynucleotide provided, the exon is from an Ubiquitin-1 gene of Zea mays or Zea luxurians. In another embodiment, the intron is from an Ubiquitin-1 gene of a Zea spp. In another embodiment, the intron is from an Ubiquitin-1 gene of Zea mays or Zea luxurians. In a further or alternative embodiment, the Zea spp. is Zea mays. In another embodiment, the Zea spp. is Zea luxurians.

In another aspect, provided is a method for producing a transgene cell. The methods comprise transforming the cell with the synthetic polynucleotide described herein. In one embodiment, the cell is a plant cell. In another aspect, provided is a plant cell comprising the synthetic polynucleotide described herein. In another aspect, provided is a plant comprising a plant cell comprising the synthetic polynucleotide described herein.

In another aspect, provided is a method for expressing a nucleotide sequence of interest in a plant cell. The method comprises introducing into the plant cell the nucleotide sequence of interest operably linked to a means for initiating transcription in a direction-independent manner. In another aspect, provided is a method for expressing a nucleotide sequence of interest in a plant cell. The method comprises introducing into the plant cell the nucleotide sequence of interest operably linked to a means for initiating transcription of two operably linked nucleotide sequences of interest. In a further embodiment, the method comprising introducing into the plant cell a nucleic acid comprising: (a) the nucleotide sequence of interest operably linked to the means for initiating transcription of two operably linked nucleotide sequences of interest; and (b) a second nucleotide sequence of interest operably linked to the means for initiating transcription of two operably linked nucleotide sequences of interest.

In a further or alternative embodiment, the means for initiating transcription of two operably linked nucleotide sequences of interest comprises SEQ ID NO: 5 or its complement. In a further or alternative embodiment, the means for initiating transcription of two operably linked nucleotide sequences of interest comprises SEQ ID NO: 5. In another embodiment, the means for initiating transcription of two operably linked nucleotide sequences of interest comprises complement of SEQ ID NO: 5. In another embodiment, the nucleic acid is introduced into the plant cell so as to target to a predetermined site in the DNA of the plant cell the nucleotide sequence of interest operably linked to the means for initiating transcription of two operably linked nucleotide sequences of interest. In a further or alternative embodiment, the nucleotide sequence of interest operably linked to the means for initiating transcription of two operably linked nucleotide sequences of interest is targeted to the predetermined site utilizing Zinc finger nuclease-mediated recombination.

In another aspect, provided is a nucleic acid construct for expressing multiple genes in plant cells and/or tissues. The nucleic acid construct comprises (a) a bidirectional promoter; and (b) two gene expression cassettes on opposite ends of the bidirectional promoter; wherein at least one of the gene expression cassettes comprises two or more genes linked via a translation switch.

In one embodiment, the nucleic acid construct does not comprise a viral sequence. In another embodiment, the bidirectional promoter does not comprise a viral sequence. In another embodiment, the bidirectional promoter comprises at least one enhancer. In another embodiment, the bidirectional promoter does not comprise an enhancer. In another embodiment, the nucleic acid construct comprises a binary vector for *Agrobacterium*-mediated transformation.

In one embodiment, the bidirectional promoter comprises an element selected from the group consisting of a cis-element or upstream regulatory sequence (URS), an enhancer element, an exon, an intron, a transcription start site, a TATA box, a heat shock consensus element, and combinations thereof. In a further or alternative embodiment, the bidirectional promoter comprises an upstream regulatory sequence (URS) from an Ubiquitin gene. In a further embodiment, the bidirectional promoter comprises (i) a promoter different from a promoter of an Ubiquitin gene and (ii) an upstream regulatory sequence (URS) from an Ubiquitin gene.

In another embodiment, the bidirectional promoter comprises a minimal core promoter element from an Ubiquitin-1 gene of Zea mays or Zea luxurians. In another embodiment, the bidirectional promoter further comprises a second minimal core promoter from Zea mays or Zea luxurians, wherein the two minimal core promoter elements are in reverse complimentary orientation with respect to each other. In a further embodiment, the minimal core promoter element comprises a polynucleotide sequence at least 65%, 70%, 75%, 80%, 85%, 90%, 95%, or 100% identical to SEQ ID NO:1 or its complement. In a further or alternative embodiment, the minimal core promoter element comprises a polynucleotide sequence selected from the group consisting of SEQ ID NOs: 1 and 15-39. In a further embodiment, the minimal core promoter element comprises a polynucleotide sequence selected from the group consisting of SEQ ID NOs: 1 and 15-34. In a further embodiment, the minimal core promoter element comprises a polynucleotide sequence selected from the group consisting of SEQ ID NOs: 1 and 15-29. In a further embodiment, the minimal core promoter element comprises a polynucleotide sequence selected from the group consisting of SEQ ID NOs: 1 and 15-24. In a further embodiment, the minimal core promoter element comprises a polynucleotide sequence selected from the group consisting of SEQ ID NOs: 1 and 15-19. In a further embodiment, the minimal core promoter element comprises a polynucleotide sequence of SEQ ID NO: 1.

In a further or alternative embodiment, the bidirectional promoter comprises an exon from an Ubiquitin-1 gene and/or an intron from an Ubiquitin gene. In a further embodiment, the bidirectional promoter comprises a polynucleotide of at least 75%, 80%, 85%, 90%, 95% or 100% identical to SEQ ID NO: 3 or its complement. In a further embodiment, the bidirectional promoter comprises a polynucleotide of SEQ ID NO: 3 or its complement. In another embodiment, the bidirectional promoter comprises an intron from an alcohol dehydrogenase gene. In one embodiment, the nucleic acid construct is stably transformed into transgenic plants. In one embodiment, the plants are monocotyledons plants. In another embodiment, the plants are dicotyledons plants. In another embodiment, the plants are not monocotyledons plants. In another embodiment, the plants are not dicotyledons plants.

In a further or alternative embodiment, the bidirectional promoter comprises an upstream regulatory sequence from an Ubiquitin gene. In a further embodiment, the upstream regulatory sequence from an Ubiquitin gene comprises a polynucleotide of sequence at least 75%, 80%, 85%, 90%, 95%, or 100% identical to SEQ ID NO: 4 or its complement. In a further embodiment, the upstream regulatory sequence from an Ubiquitin gene comprises a polynucleotide of SEQ ID NO: 4 or its complement. In another embodiment, the bidirectional promoter comprises a polynucleotide of at least 75%, 80%, 85%, 90%, 95%, or 100% identical to SEQ ID NO: 5 or its complement. In another embodiment, the bidirectional promoter comprises a polynucleotide of SEQ ID NO: 5 or its complement.

In one embodiment, both the gene expression cassettes comprise two or more genes linked via a translation switch. In a further or alternative embodiment, the translation switch is selected from the group consisting of an internal ribosome entry site (IRES), an alternative splicing site, a ribozyme cleavage site, a polynucleotide sequence coding a 2A peptide, a polynucleotide sequence coding a 2A-like peptide, a polynucleotide sequence coding an intern, a polynucleotide sequence coding a protease cleavage site, and combinations thereof. In a further or alternative embodiment, the translation switch comprises a cis-acting hydrolase element (CHYSEL). In a further embodiment, the CHYSEL is a 2A or 2A-like peptide sequence. In another embodiment, a gene upstream of the translational switch does not comprise a translation stop codon. In another embodiment, the nucleic acid construct enables or allows expression of at least four genes. In a further embodiment, all four genes are transgenes. In another embodiment, the nucleic acid construct enables expression of genes between three and twenty. In another embodiment, the nucleic acid construct enables expression of genes between four and eight. In a further or alternative embodiment, the genes are transgenes. In another embodiment, at least one gene expression cassette comprises a polynucleotide sequence encoding a fusion protein. In a further embodiment, the fusion protein comprises three to five genes.

In some embodiments, expression of genes from the bidirectional promoter is at least four-fold higher as compared to a unidirectional promoter. In some embodiments, expression of genes from the bidirectional promoter is from three to ten folds higher as compared to a unidirectional promoter. In some embodiments, expression of genes from the bidirectional promoter is from four to eight folds higher as compared to a unidirectional promoter. In some embodiments, a selection marker gene is placed at far end from the promoter (i.e., at the 3' end of a gene expression cassette downstream of another gene).

In another aspect, provided is a method for generating a transgenic plant, comprising transforming a plant cell with the nucleic acid construct provided herein. In another aspect, provided is a method for generating a transgenic cell, comprising transforming the cell with the nucleic acid construct provided herein. In another aspect, provided is a plant cell comprising the nucleic acid construct provided herein. In a further or alternative embodiment, the nucleic acid construct is stably transformed into the plant cell. In another aspect, provided is a transgenic plant comprising the nucleic acid construct provided herein. In a further or alternative embodiment, the nucleic acid construct is stably transformed into cells of the transgenic plant. In another aspect, provide is a method for expressing multiple genes in plant cells and/or tissues, comprising introducing into the plant cells and/or tissues the nucleic acid construct provided herein. In a further or alternative embodiment, the plant cells and/or tissues are stably transformed with the nucleic acid construct provided herein. In another aspect, provided is a binary vector for *Agrobacterium*-mediated transformation. In one embodiment, the binary vector comprises the nucleic acid construct provided herein. In another embodiment, the binary vector comprises the synthetic polynucleotide provided herein. In another aspect, provided is the use of the bidirectional promoter provided herein for multiple-transgenes expression in plants.

BRIEF DESCRIPTION OF THE DRAWINGS AND SEQUENCES

FIG. 1 shows an exemplary (not to scale) maize Ubi1 (ZmUbi1) promoter, which comprises an approximately 900 bp Upstream Element located 5' of the transcription start site (TSS). The upstream element contains a TATA box (located approximately −30 bp of the TSS), and two overlapping heat shock consensus elements (located approximately −200 bp of the TSS). This promoter also comprises about 1100 bp 3' of the TSS region. This 3' region contains an adjacent leader sequence (ZmUbi1 exon), and an intron.

FIG. 7A shows SEQ ID NO: 1, which comprises a 215 bp region of a *Zea mays* Ubi1 minimal core promoter (minUbi1P). FIG. 7B shows SEQ ID NO:2, which comprises a *Z. mays* Ubi1 intron.

FIG. 8A shows SEQ ID NO: 3, which comprises the reverse complement of a polynucleotide comprising a *Z. mays* minUbi1P minimal core promoter (underlined); a *Z. mays* Ubi1 leader (ZmUbi1 exon; bold font); and a *Z. mays* Ubi1 intron (lower case). FIG. 8B shows SEQ ID NO: 4, which comprises a segment of a *Z. mays* Ubi1 upstream element, where element (and/or its reverse complement) may be located in a synthetic Ubi1 promoter with a minUbi1P element adjacent to its 5' or 3' end.

FIGS. 9A and 9B show SEQ ID NO: 5, which comprises an exemplary synthetic Ubi1 bidirectional promoter, wherein the reverse complement of a first minUbi1P, and a second minUbi1P, are underlined. FIGS. 10A-10C show SEQ ID NO: 6, which comprises an exemplary nucleic acid comprising yfp and GUS gene expression cassettes driven by a synthetic Ubi1 bidirectional promoter.

SEQ ID NO: 7 comprises a YFP Forward Primer: 5'-GATGCCTCAGTGGGAAAGG-3'. SEQ ID NO: 8 comprises a YFP Reverse Primer: 5'-CCATAGGTGAGAGTGGTGAC AA-3'. SEQ ID NO: 9 comprises an Invertase Forward Primer: 5'-TGGCGGACGA CGACTTGT-3'. SEQ ID NO: 10 comprises an Invertase Reverse Primer: 5'-AAAGTTTGGA GGCTGCCGT-3'. SEQ ID NO: 11 comprises an Invertase Probe: 5'-CGAGCAGACC GCCGTGTACT TCTACC-3'. SEQ ID NO: 12 comprises an AAD1 Forward Primer: 5'-TGTTCGGTTC CCTCTACCAA-3'. SEQ ID NO: 13 comprises an AAD1 Reverse Primer: 5'-CAACATCCAT CACCTTGACT GA-3'. SEQ ID NO: 14 comprises an AAD1 Probe: 5'-CACAGAACCG TCGCTTCAGC AACA-3' (see also Table 7).

Figure 11:
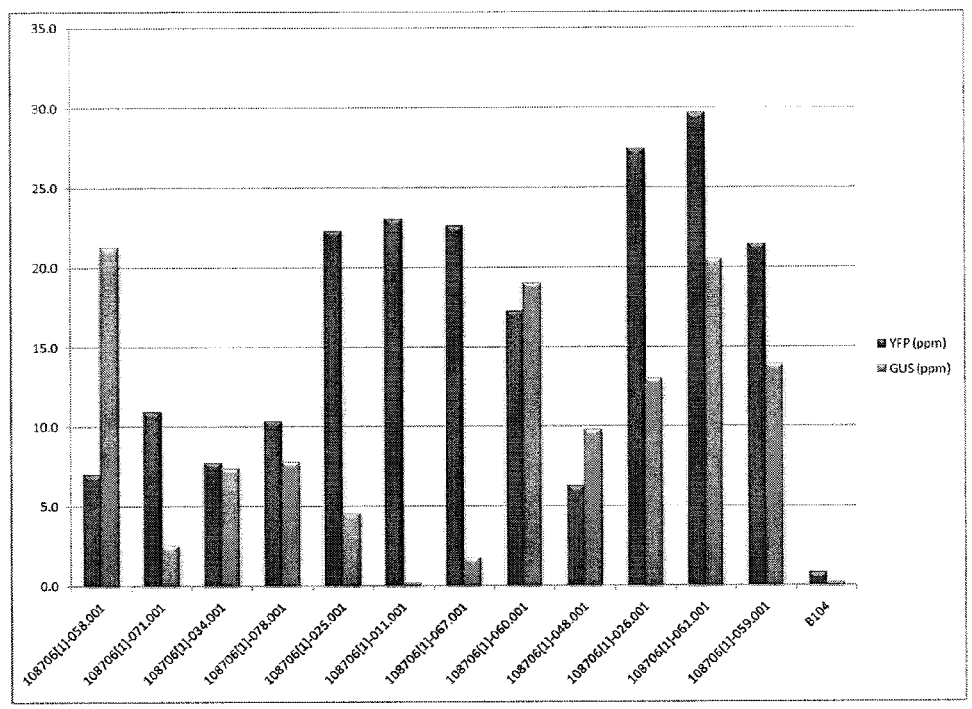

FIG. 11 shows a representative Western blot analysis confirming stable YFP and GUS expression driven by a bidirectional *Z. mays* Ubiquitin1 Promoter construct (pDAB108706) in maize $T_0$ plants. Representative plants showed stable YFP expression in leaf driven by the Min-UbiP1 minimal core promoter element. The amount of protein which was produced is indicated as parts per million (ppm).

Figure 12:
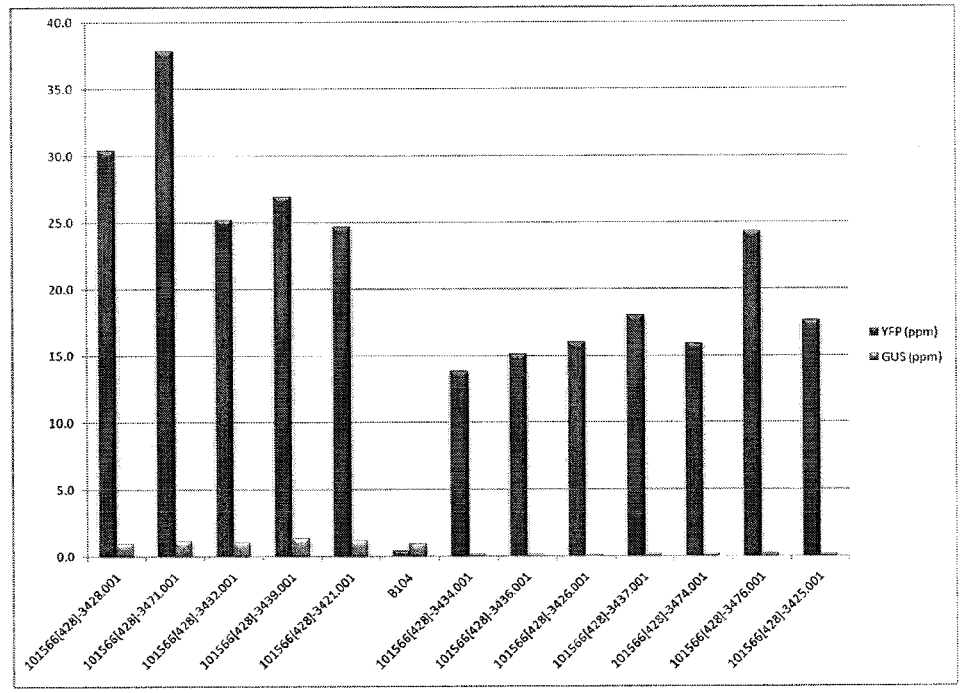

FIG. 12 shows a representative Western blot analysis showing stable YFP and GUS expression from the control construct containing a ZmUbi1 promoter that only drives expression of YFP (pDAB101556); a GUS coding sequence is not contained in this construct. The amount of protein which was produced is indicated as parts per million (ppm).

Figure 13A:
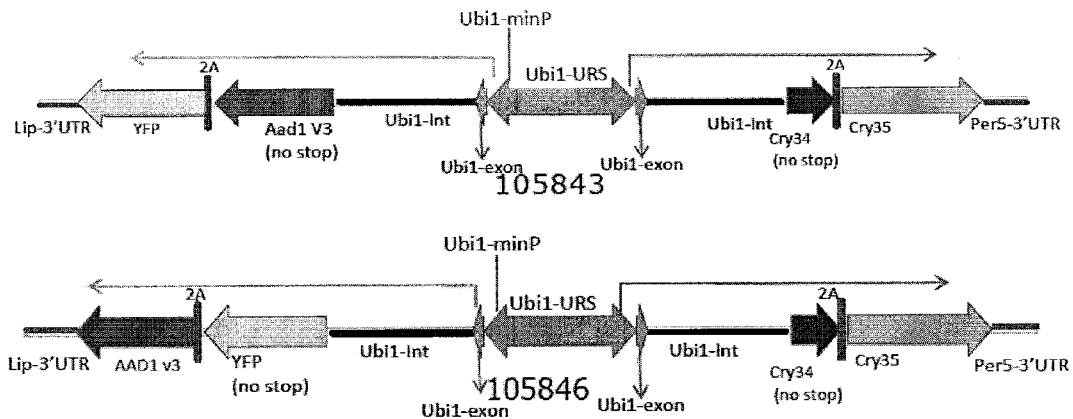
Figure 13B:
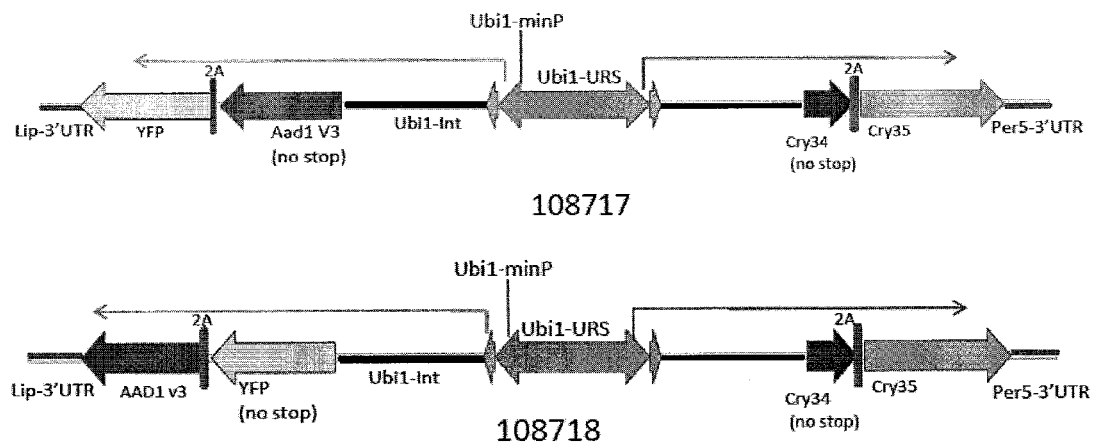

FIG. 13A shows exemplary constructs of four-gene cassette stacks pDAB105843 [showing two cassettes of AAD1-2A-YFP (or Phiyfp) plus Cry34-2A-Cry35] and pDAB105846 [showing two cassettes of YFP (or Phiyfp)-2A-AAD1 plus Cry34-2A-Cry35]. Shaded arrows indicate direction of transcription from the bidirectional promoter. Ubi1-minP comprises 200nt sequence upstream of transcriptional start site of maize Ubi1 promoter. Ubi1-URS comprises maize Ubi1 promoter upstream regulatory region consisting of sequence upstream of transcription start site excluding the 200nt minimal promoter (shown as arrow). Ubi1-Int comprises an intron of maize Ubi1 promoter. FIG. 13B shows additional exemplary binary constructs of four-gene cassette stacks from pDAB108717 and pDAB108718.

Figure 14:
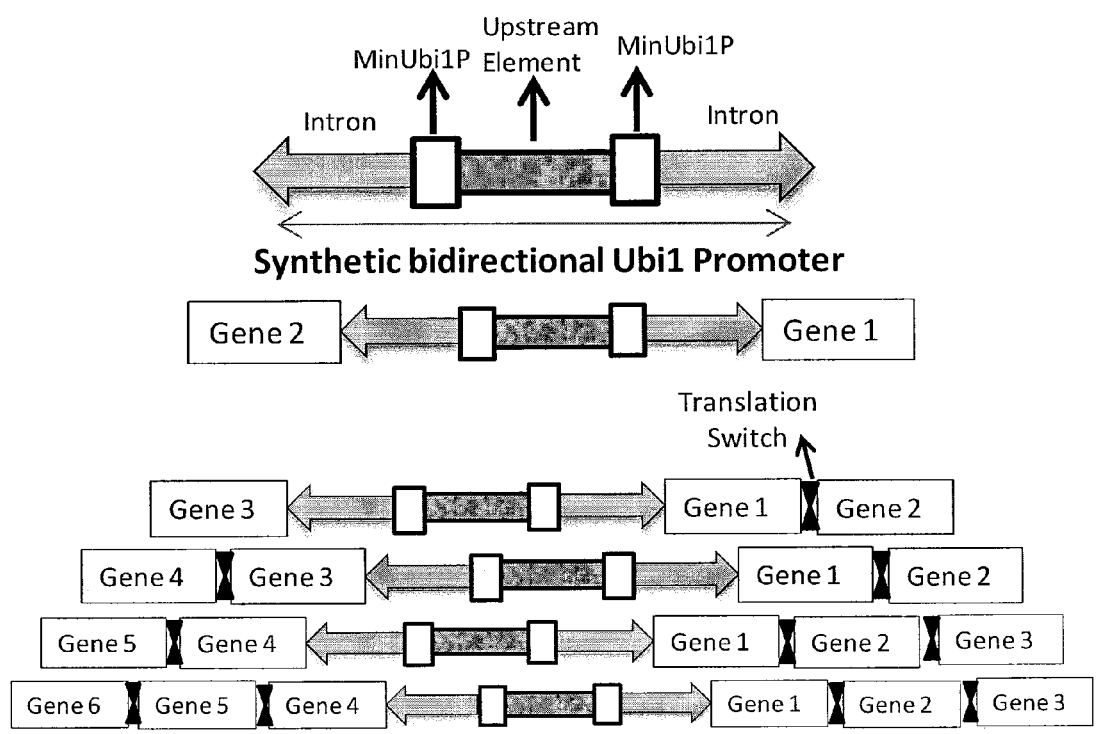

FIG. 14 shows exemplary schematic presentations of multi-gene constructs provided herein. Translation switches are shown using a special symbol.

Figure 15A:
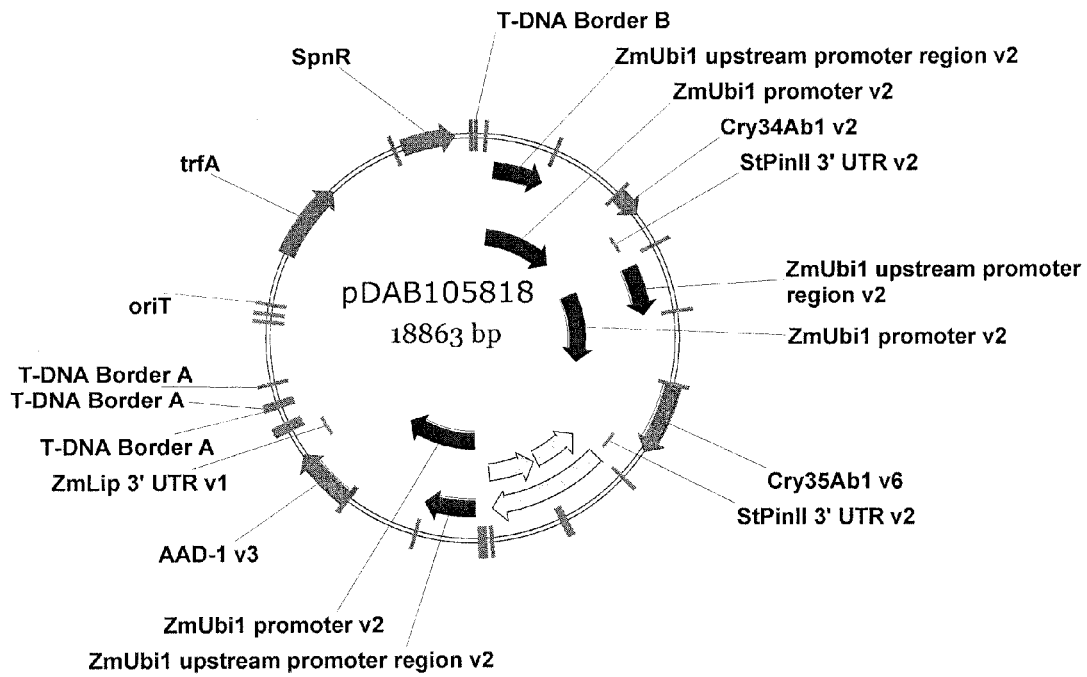
Figure 15B:
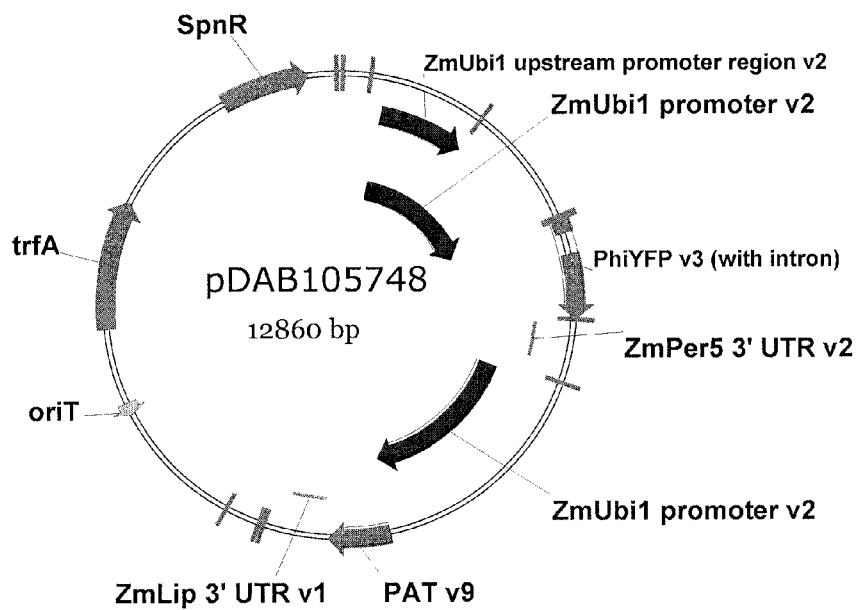

FIGS. 15A and 15B show representative maps for plasmids pDAB105818 and pDAB105748, respectively.

Figure 16A:
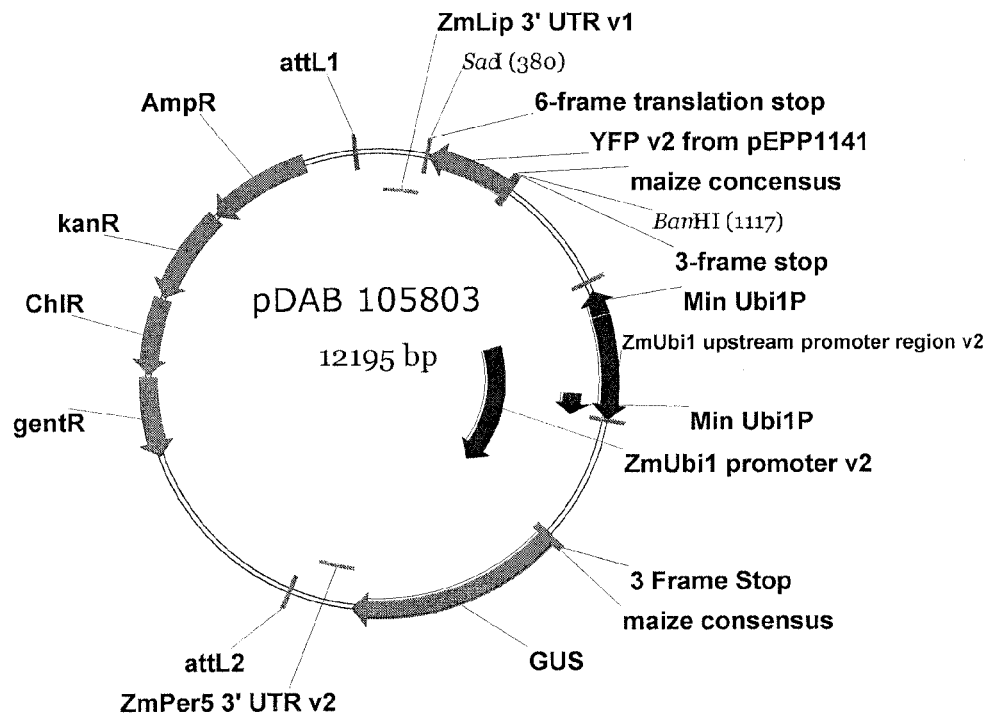
Figure 16B:
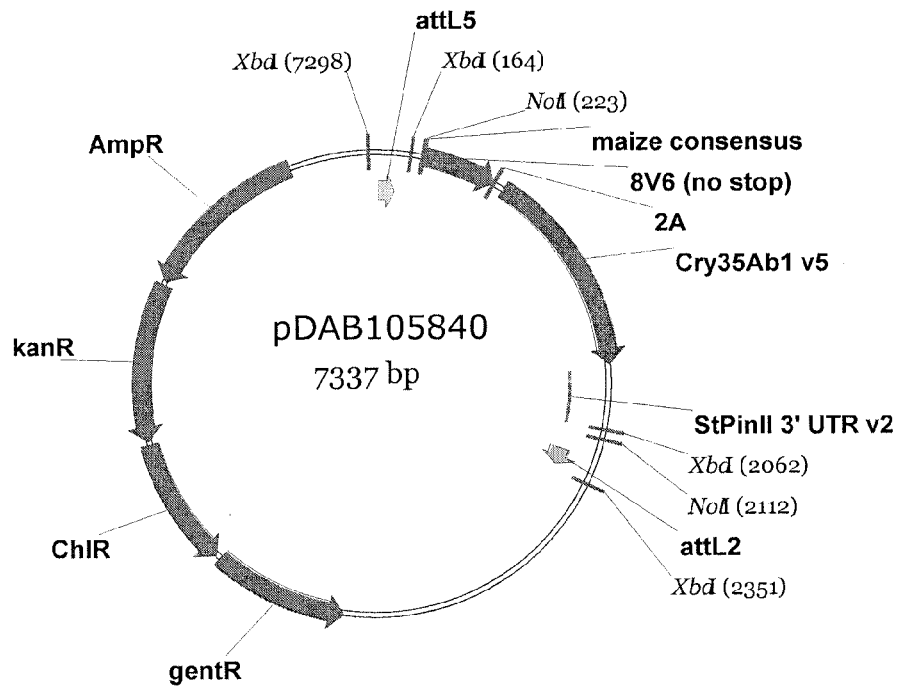

FIGS. 16A and 16B show representative maps of plasmids pDAB105803 and pDAB105840, respectively.

Figure 17A:
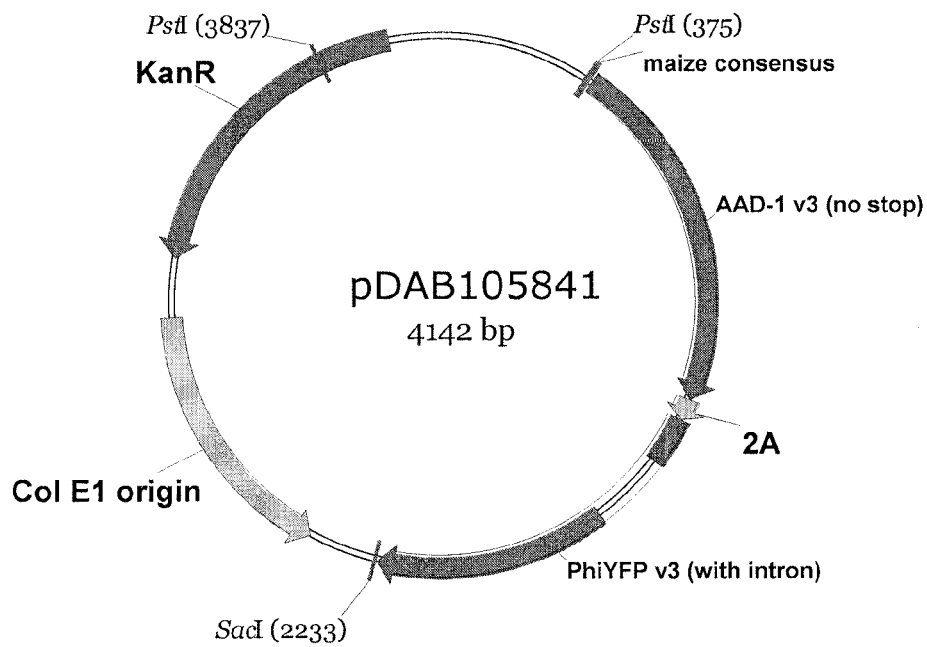
Figure 17B:
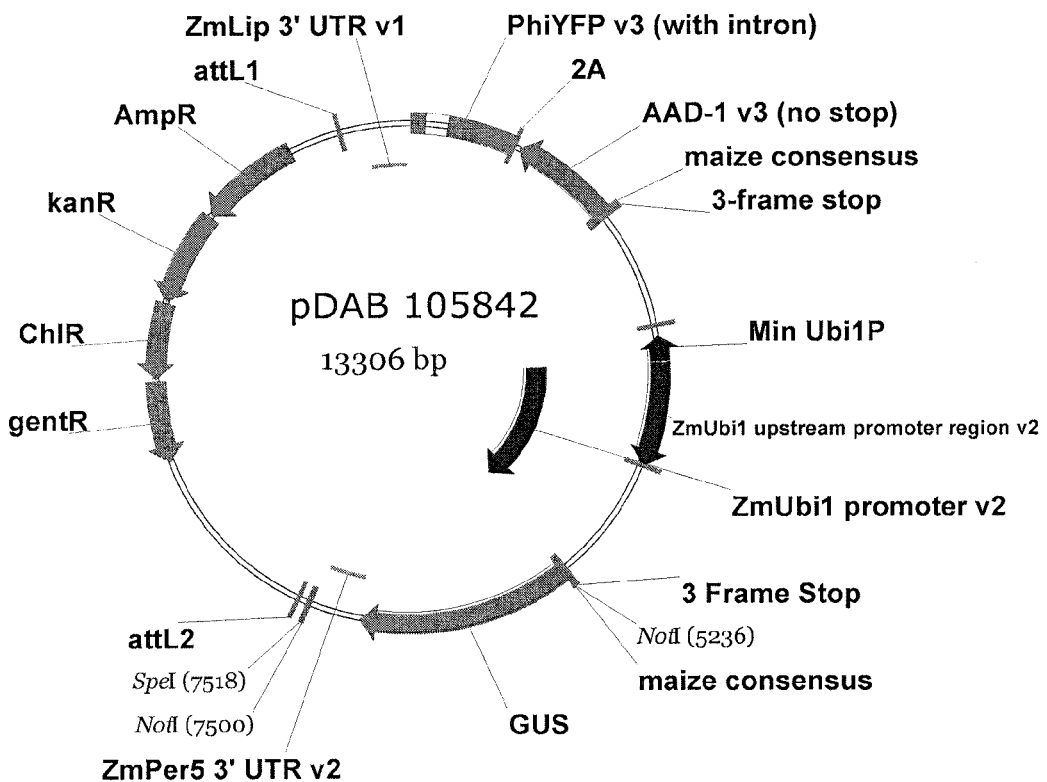

FIGS. 17A and 17B show representative maps for plasmids pDAB105841 and pDAB105842, respectively.

Figure 18A:
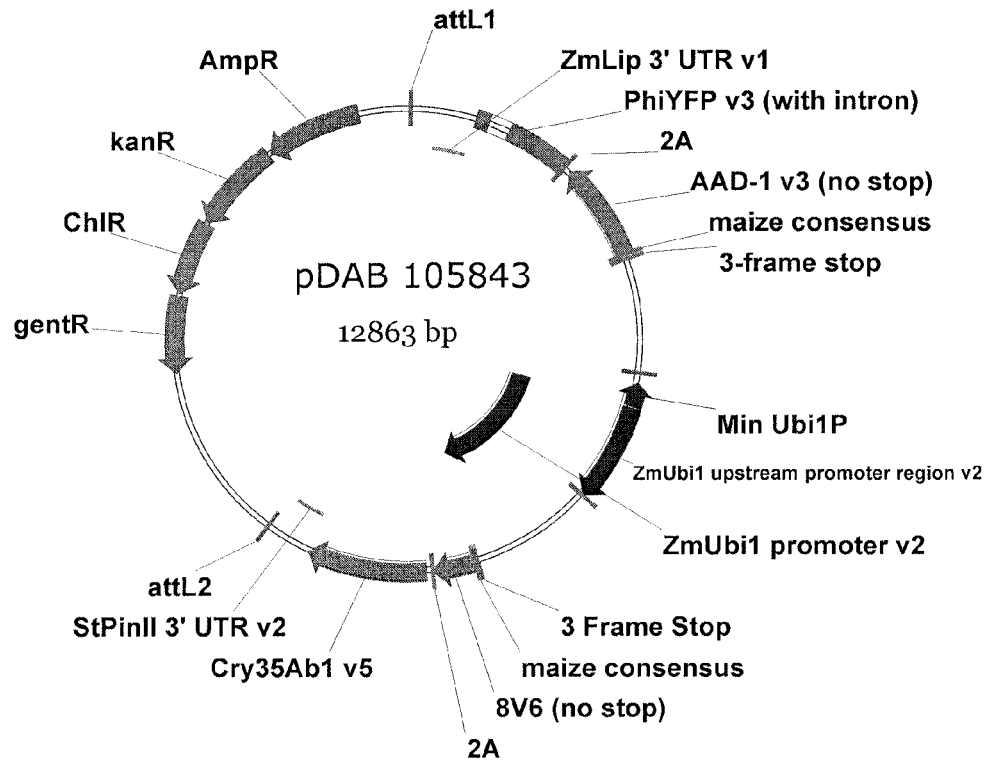
Figure 18B:
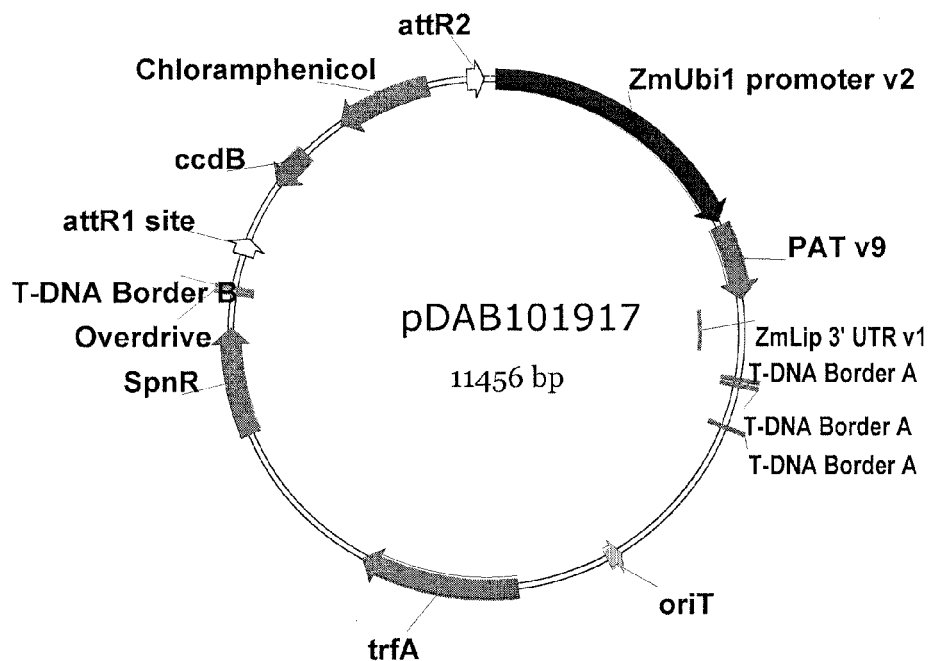

FIGS. 18A and 18B show representative maps of plasmids pDAB105843 and pDAB101917, respectively.

Figure 19:
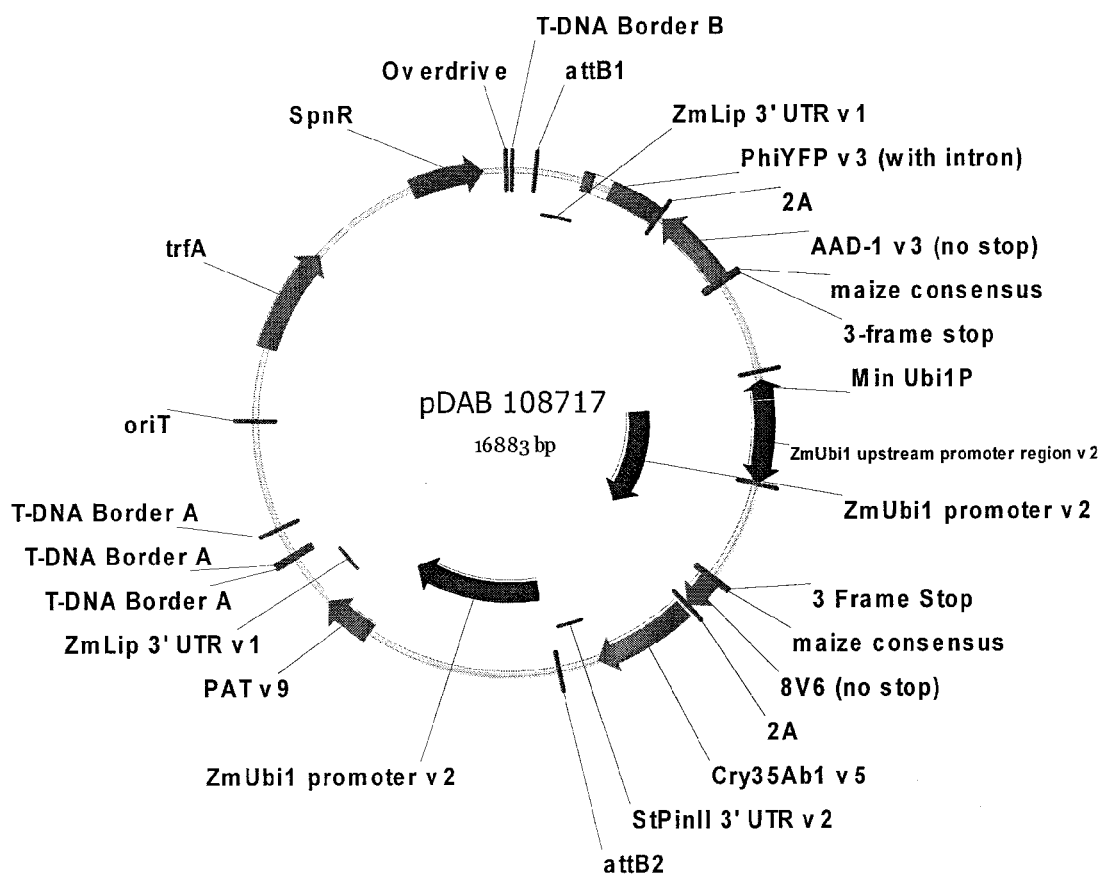

FIG. 19 shows a representative map of plasmid pDAB108717.

Figure 20A:
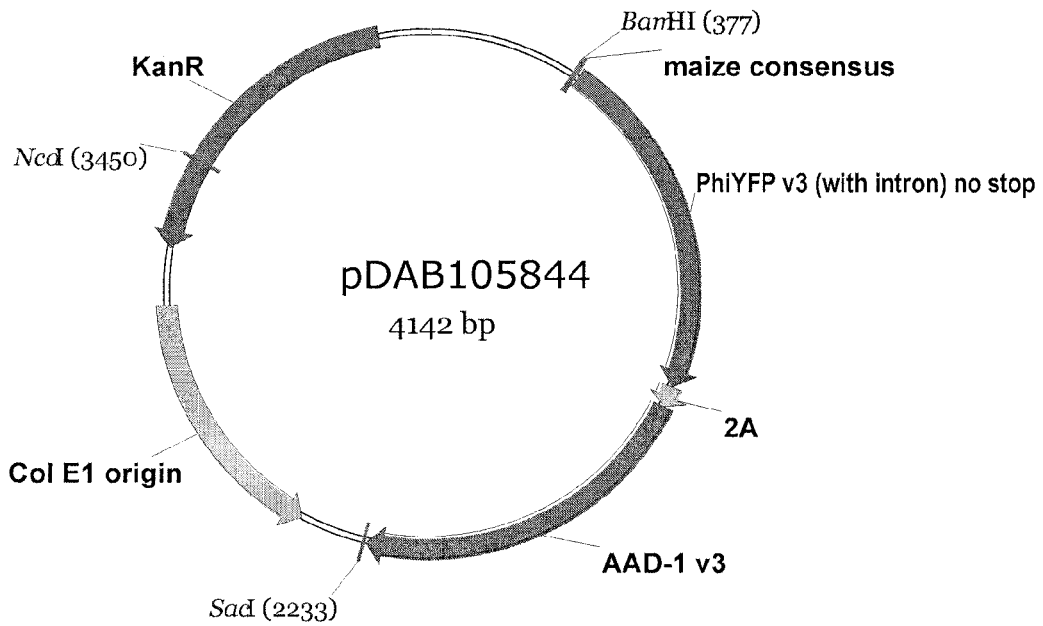
Figure 20B:
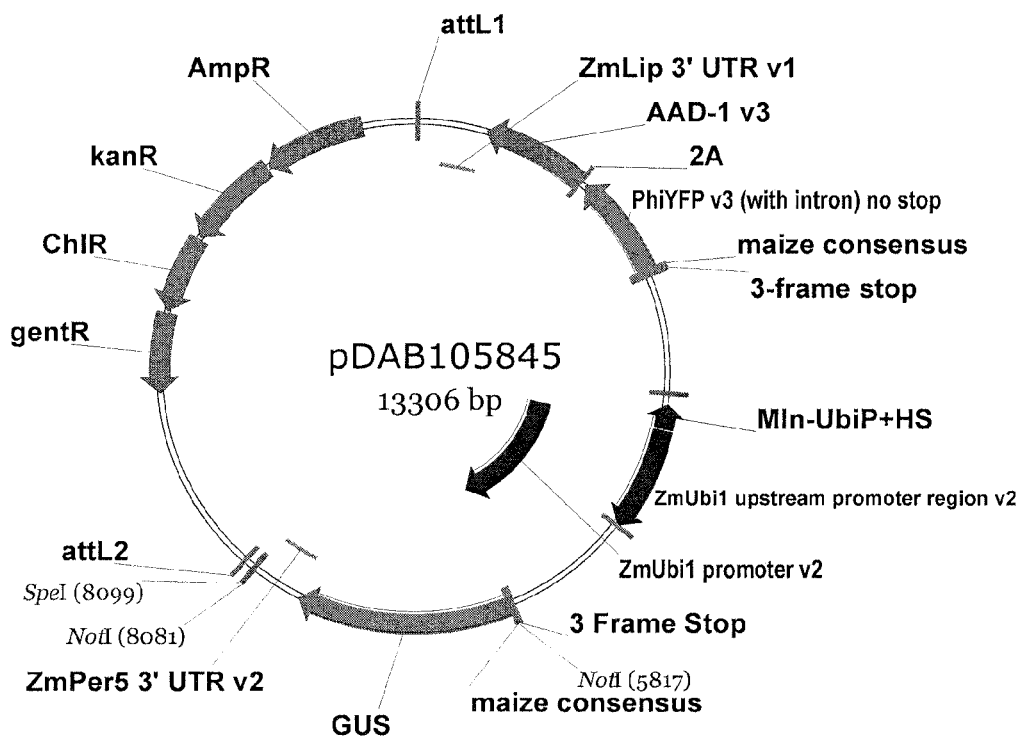

FIGS. 20A and 20B show representative maps for plasmids pDAB105844 and pDAB105845, respectively.

Figure 21A:
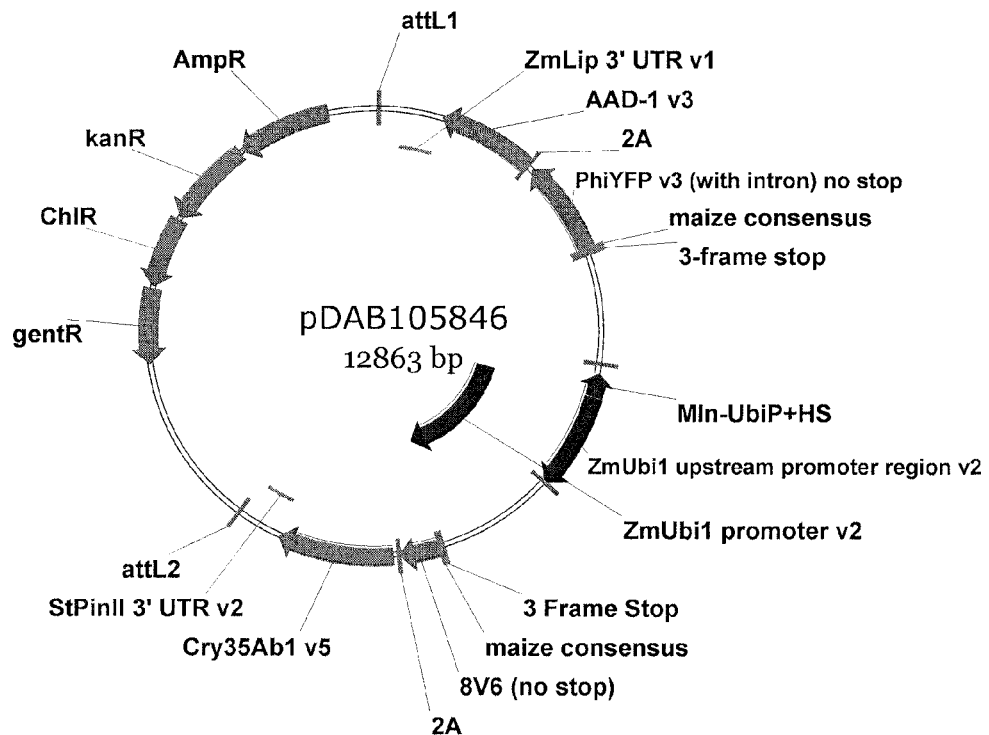
Figure 21B:
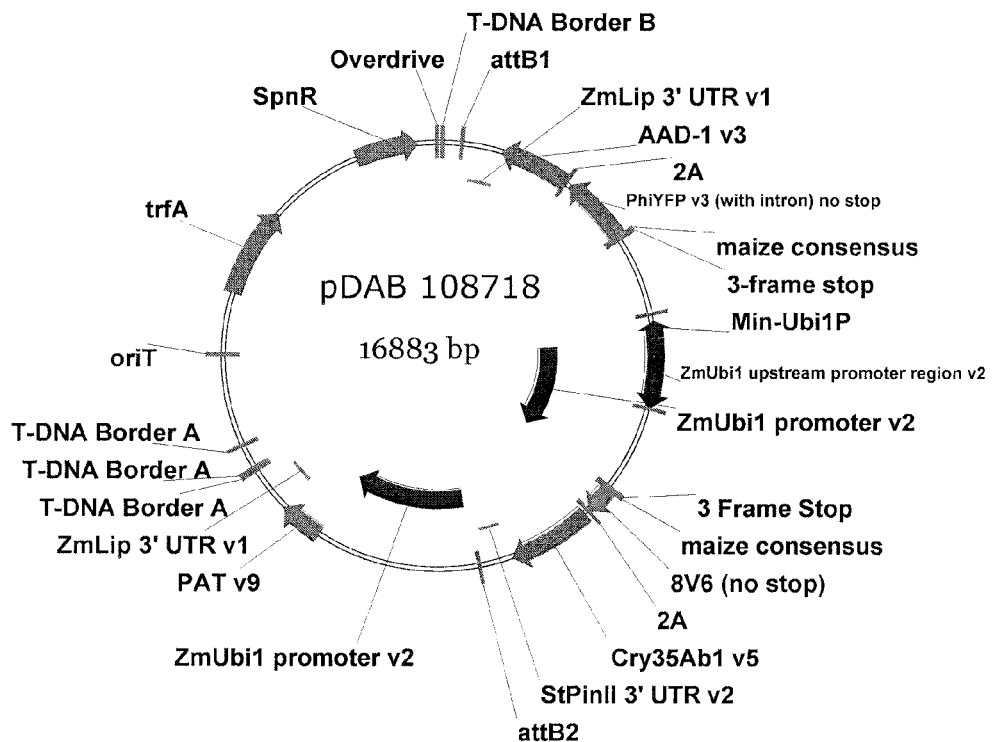

FIGS. 21A and 21B show representative maps of plasmids pDAB105846 and pDAB108718, respectively.

Figure 22A:
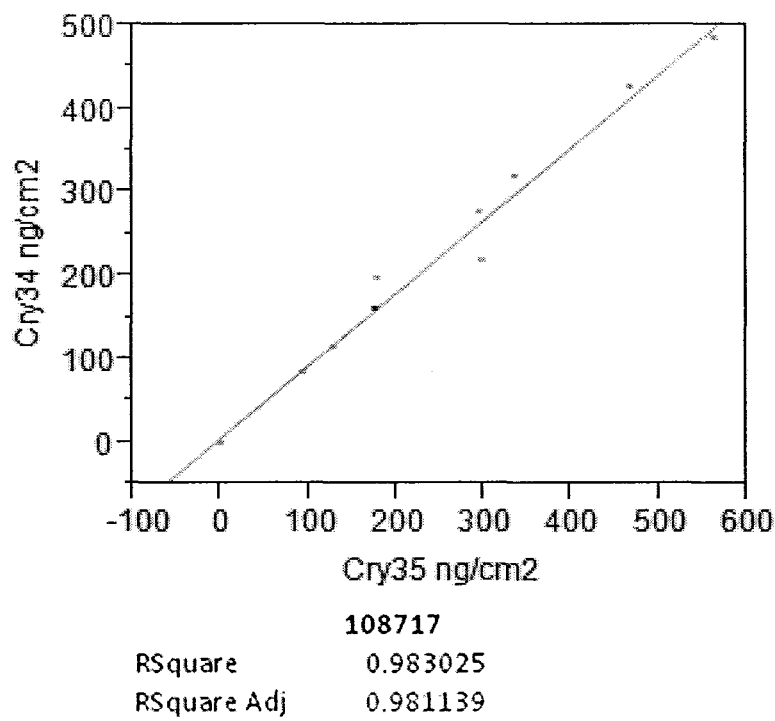
Figure 22B:
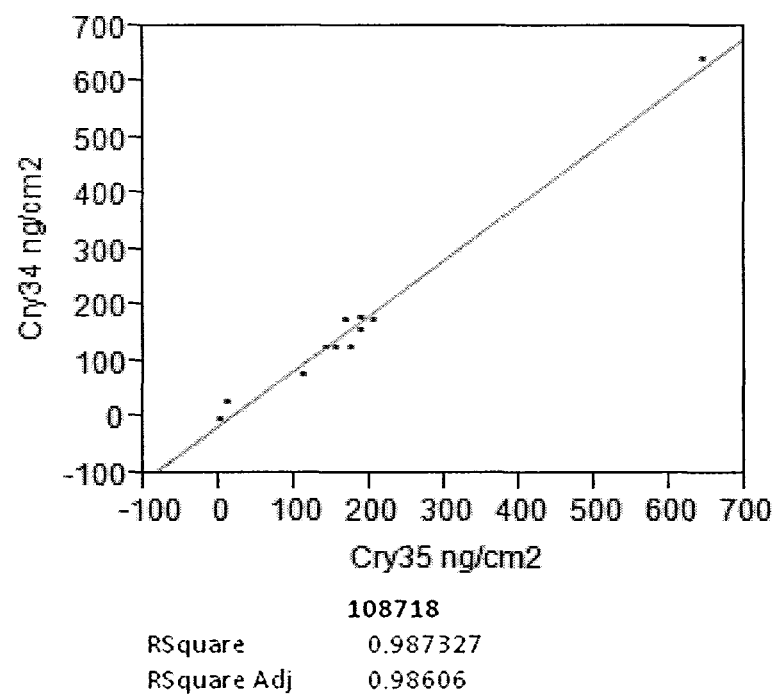

FIG. 22 shows exemplary protein expression data for Cry35 of pDAB108717 (FIG. 22A) and pDAB108718 (FIG. 22B).

FIGS. 23A-M show a nucleic acid sequence (SEQ ID NO:52) for gene expression cassettes of pDAB108717, where each gene and element is illustrated.

FIGS. 24 A-E shows additional minimal core promoters (min-Ubi1P or Ubi1-minP) of SEQ ID NOs: 15-39.

FIG. 25 shows two exemplary sequences for yellow fluorescent proteins from *Phialidium* sp. SL-2003 (Phiyfp, SEQ ID NO: 50; and Phiyfpv3, SEQ ID NO: 51).

Figure 26:
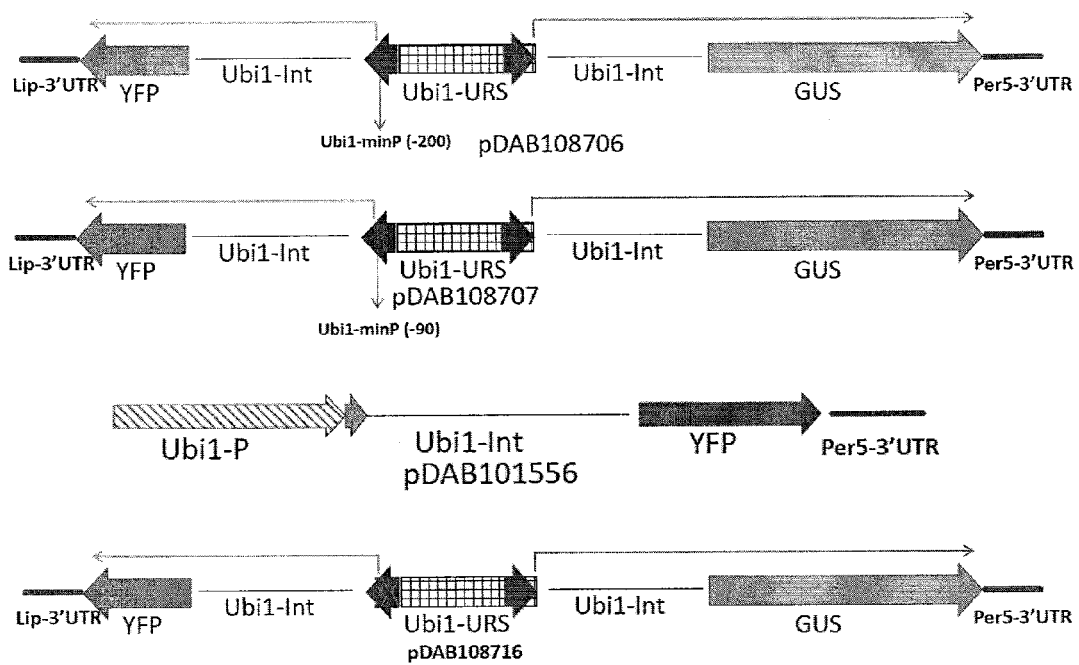

FIG. 26 shows exemplary embodiments of the synthetic Ubi1 bidirectional promoter and constructs provided, including pDAB108706 (ZMUbi bidirectional (−200)) and pDAB108707 (ZMUbi bidirectional (−90)). pDAB101556 (ZmUbi1-YFP control) and pDAB108716 (ZMUbi1 without minimal promoter) serve as control constructs with unidirectional promoters.

Figure 27A:
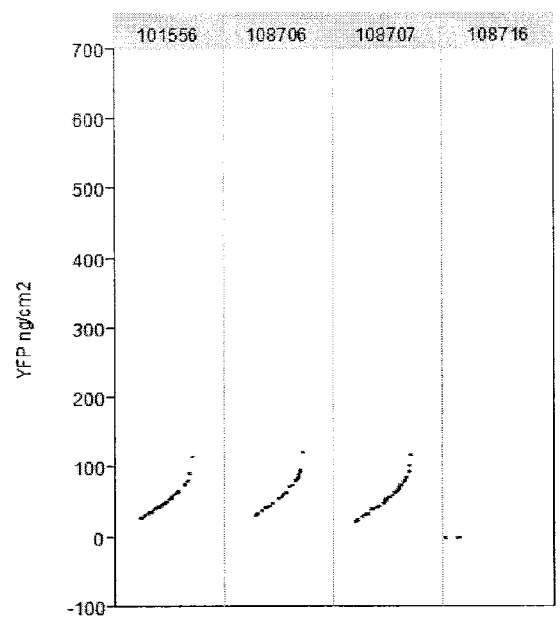
Figure 27B:
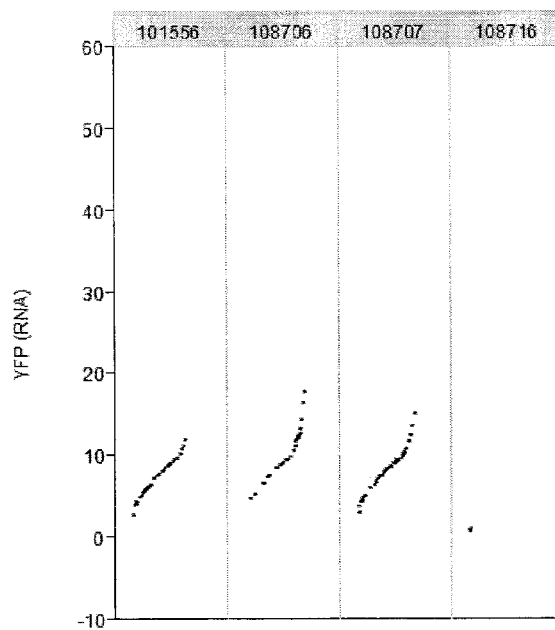

FIG. 27A shows exemplary expression results (V6) from the four constructs shown in FIG. 26 for YFP protein (LCMS) in ng/cm2. FIG. 27B shows exemplary relative expression results (V6) from the four constructs shown in FIG. 26 for YFP RNA.

Figure 28A:
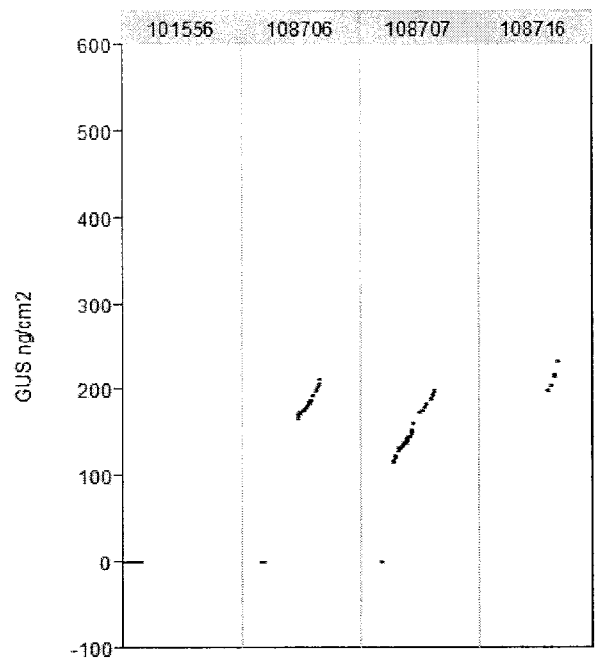
Figure 28B:
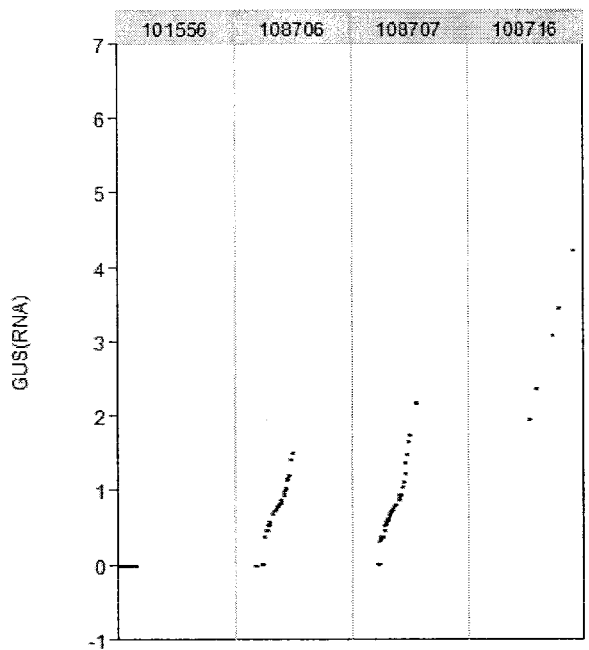

FIG. 28A shows exemplary expression results (V6) from the four constructs shown in FIG. 26 for GUS protein (LCMS) in ng/cm2. FIG. 28B shows exemplary relative expression results (V6) from the four constructs shown in FIG. 26 for GUS RNA.

Figure 29A:
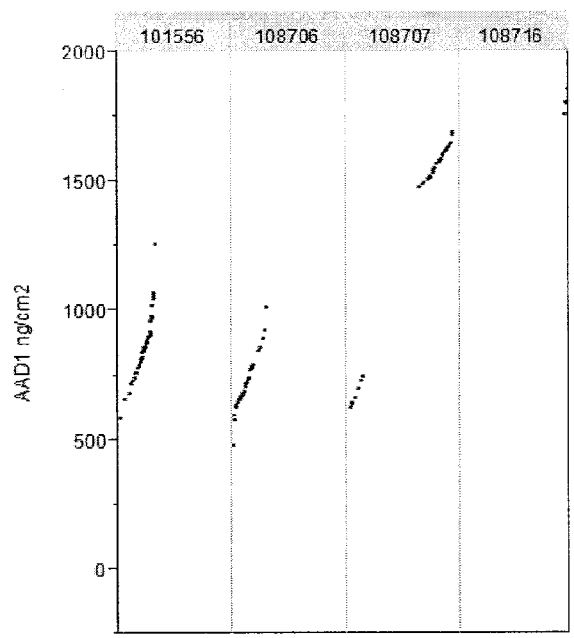
Figure 29B:
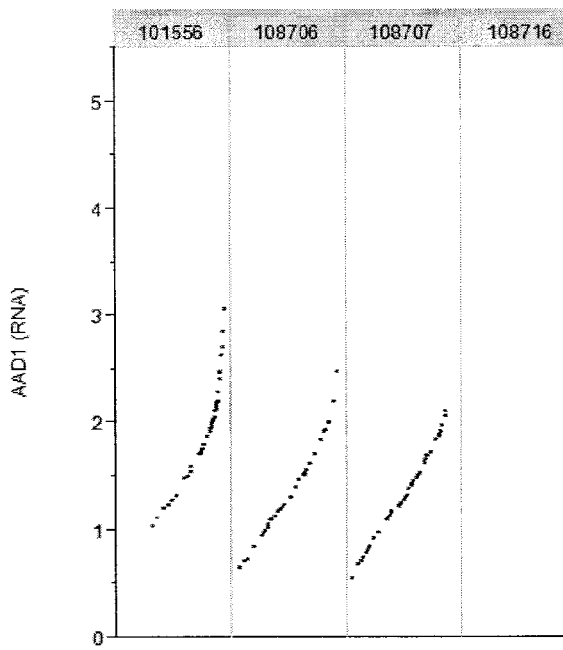

FIG. 29A shows exemplary expression results (V6) from the four constructs shown in FIG. 26 for AAD1 protein (LCMS) in ng/cm2. FIG. 29B shows exemplary relative expression results (V6) from the four constructs shown in FIG. 26 for AAD1 RNA.

Figure 30A:
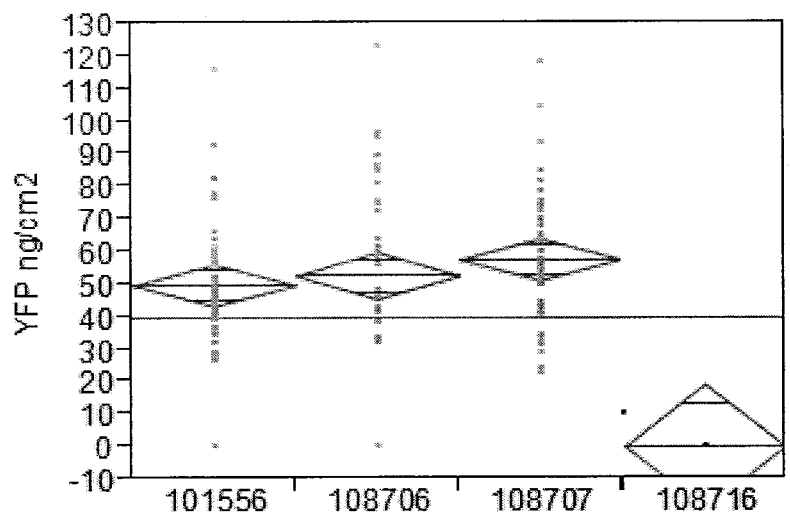
Figure 30B:
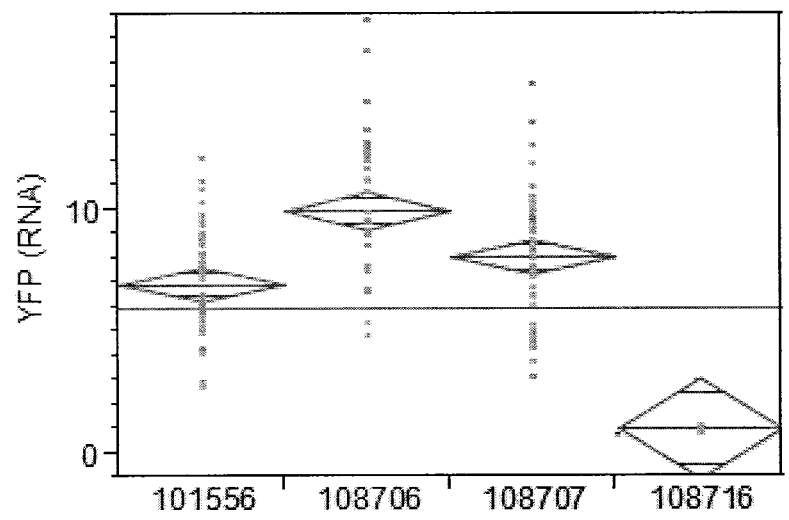

FIG. 30A shows a statistical analysis of expression results (V6) from the four constructs shown in FIG. 26 for YFP protein (LCMS) in ng/cm2. The mean values for pDAB108707, pDAB108706, pDAB101556, and pDAB108716 are 57.63, 52.66, 49.75, and 0 respectively. FIG. 30B shows a statistical analysis of relative expression results (V6) from the four constructs shown in FIG. 26 for YFP RNA. The mean values for pDAB108706, pDAB108707, pDAB101556, and pDAB108716 are 9.96, 8.07, 6.95, and 1.01 respectively.

Figure 31A:
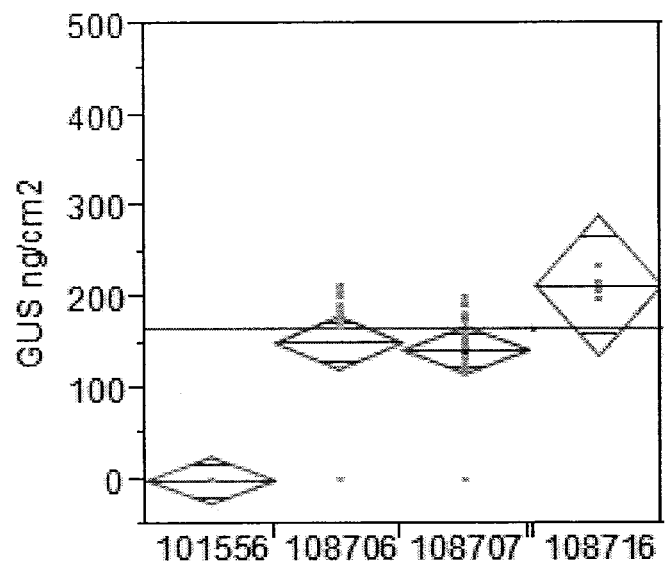
Figure 31B:
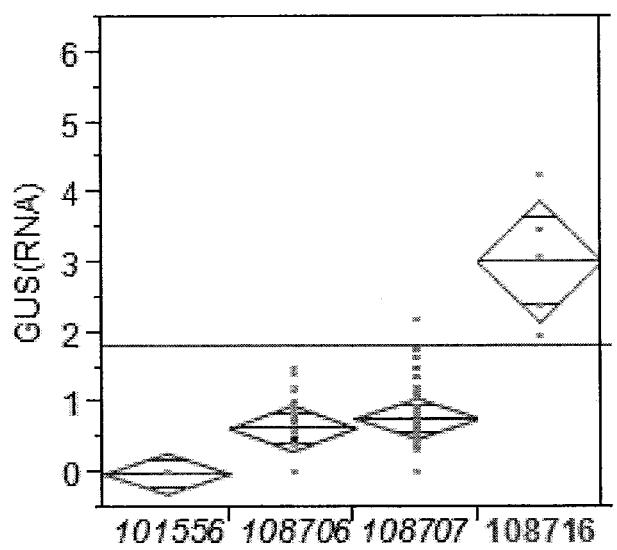

FIG. 31A shows a statistical analysis of expression results (V6) from the four constructs shown in FIG. 26 for GUS protein (LCMS) in ng/cm2. The mean values for pDAB108706, pDAB108707, pDAB101556, and pDAB108716 are 151.27, 143.22, 0, and 213.17 respectively. FIG. 31B shows a statistical analysis of relative expression results (V6) from the four constructs shown in FIG. 26 for GUS RNA. The mean values for pDAB108706, pDAB108707, pDAB101556, and pDAB108716 are 0.65, 0.78, 0, and 3.03 respectively.

Figure 32A:
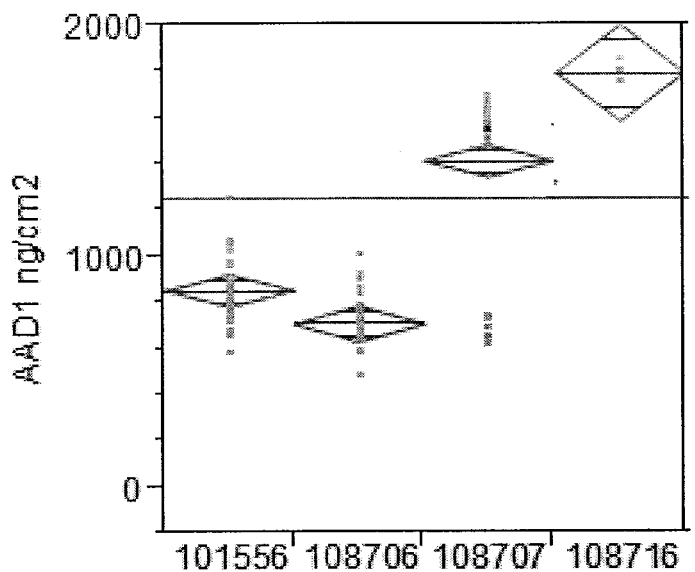
Figure 32B:
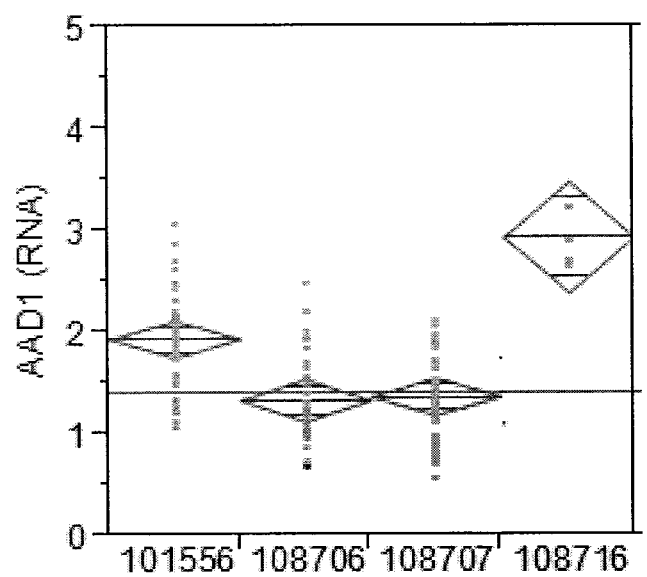

FIG. 32A shows a statistical analysis of expression results (V6) from the four constructs shown in FIG. 26 for AAD1 protein (LCMS) in ng/cm2. The mean values for pDAB108706, pDAB108707, pDAB101556, and pDAB108716 are 710.88, 1417.01, 856.58, and 1795.43 respectively. FIG. 32B shows a statistical analysis of relative expression results (V6) from the four constructs shown in FIG. 26 for AAD1 RNA. The mean values for pDAB108706, pDAB108707, pDAB101556, and pDAB108716 are 1.33, 1.37, 1.93, and 2.93 respectively.

Figure 33A:
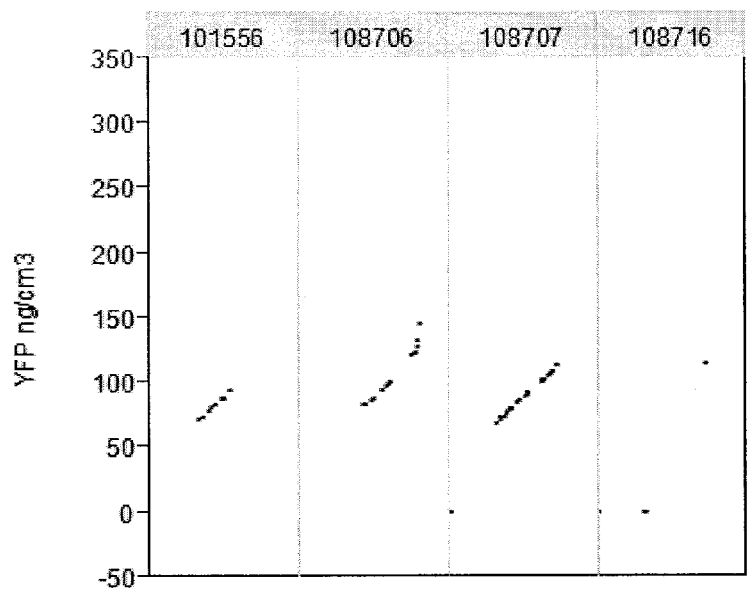
Figure 33B:
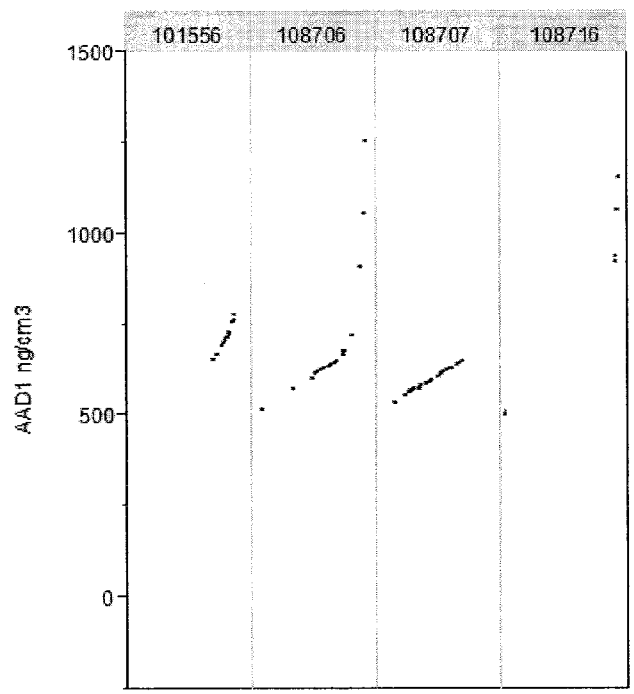
Figure 33C:
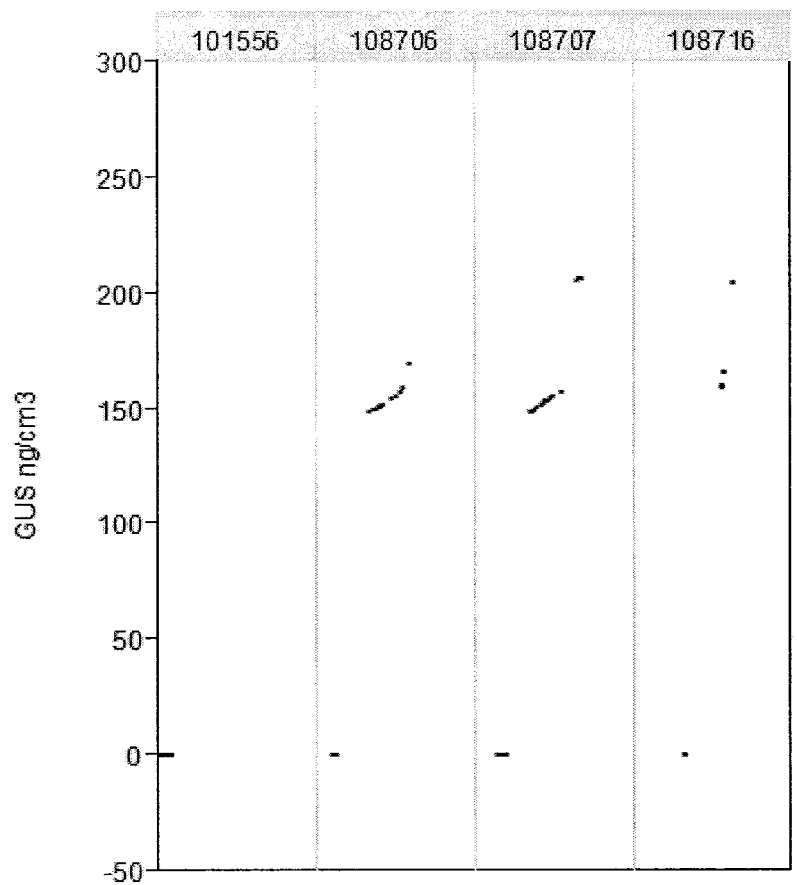

FIGS. 33A, 33B, and 33C show exemplary expression results (V10) from the four constructs shown in FIG. 26 for YFP, AAD1, and GUS protein (LCMS) in ng/cm2 respectively.

Figure 34A:
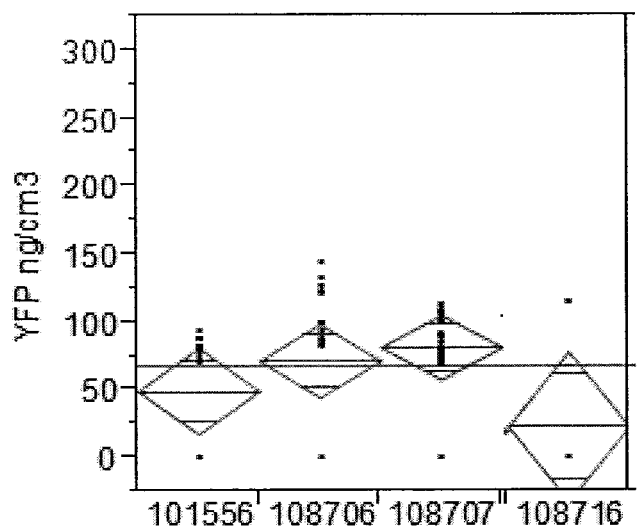
Figure 34B:
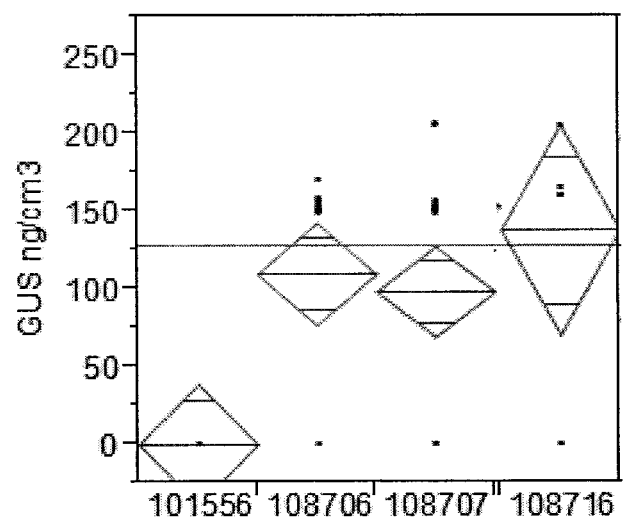
Figure 34C:
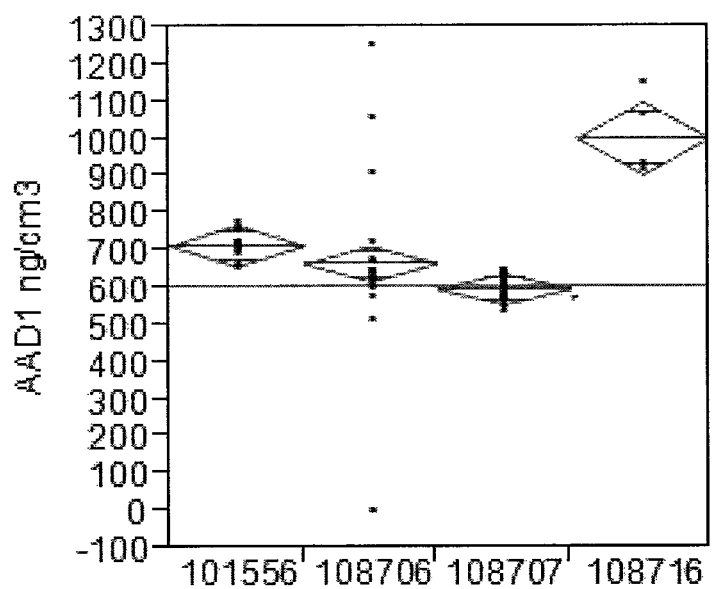

FIGS. 34A, 34B, and 34C show statistical analysis of expression results (V10) from the four constructs shown in FIG. 26 for YFP, GUS, and AAD1 protein (LCMS) in ng/cm2 respectively. The mean values for pDAB108706, pDAB108707, pDAB101556, and pDAB108716 for YFP (FIG. 34A) are 71.77, 81.81, 49.58, and 23.01 respectively. The mean values for pDAB108706, pDAB108707, pDAB101556, and pDAB108716 for GUS (FIG. 34B) are 109.63, 98.25, 0, and 138.02 respectively. The mean values for pDAB108706, pDAB108707, pDAB101556, and pDAB108716 for AAD1 (FIG. 34C) are 666.11, 597.80, 715.12, and 1002.84 respectively.

Figure 35A:
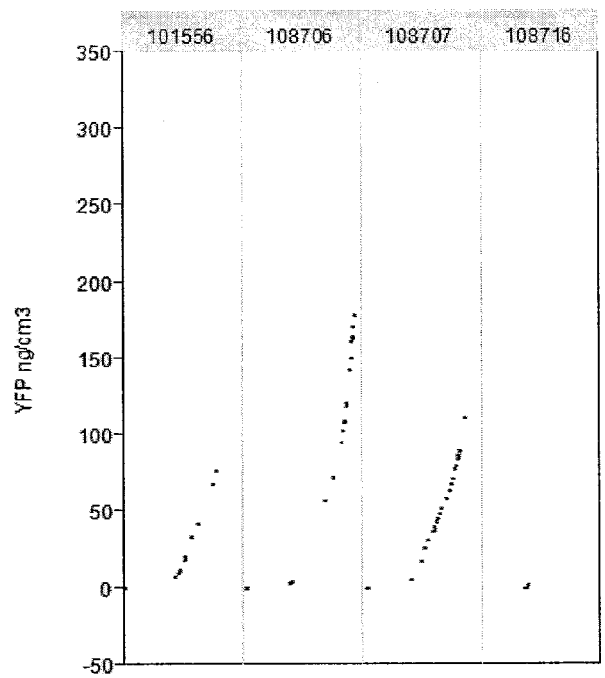
Figure 35B:
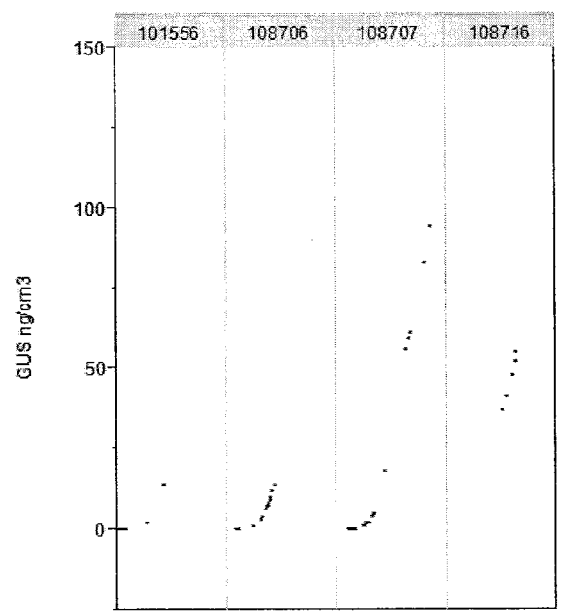
Figure 35C:
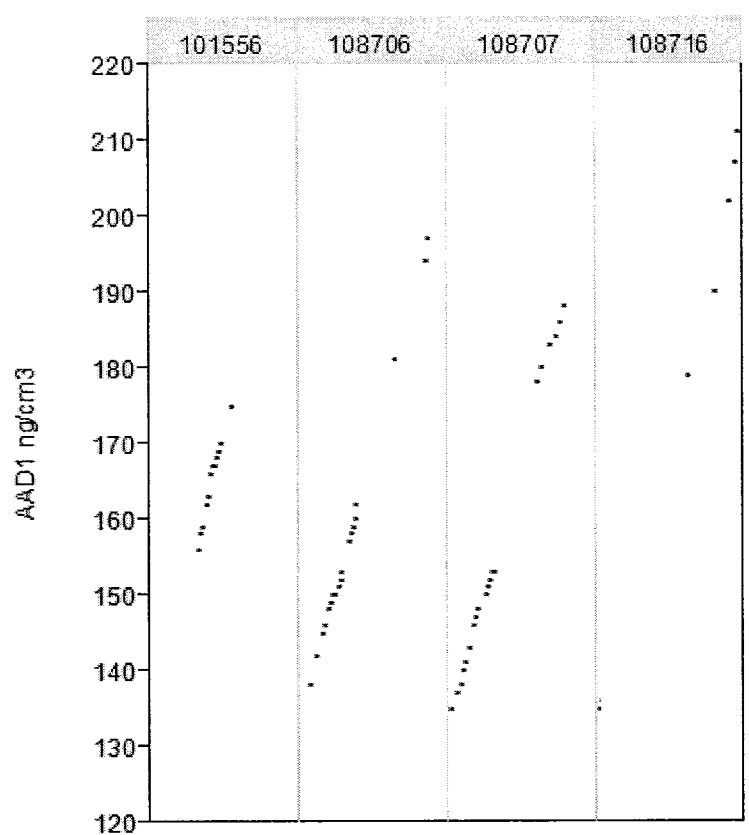

FIGS. 35A, 35B, and 35C show exemplary expression results (R3) from the four constructs shown in FIG. 26 for YFP, GUS, and AAD1 protein (LCMS) in ng/cm2 respectively.

Figure 36A:
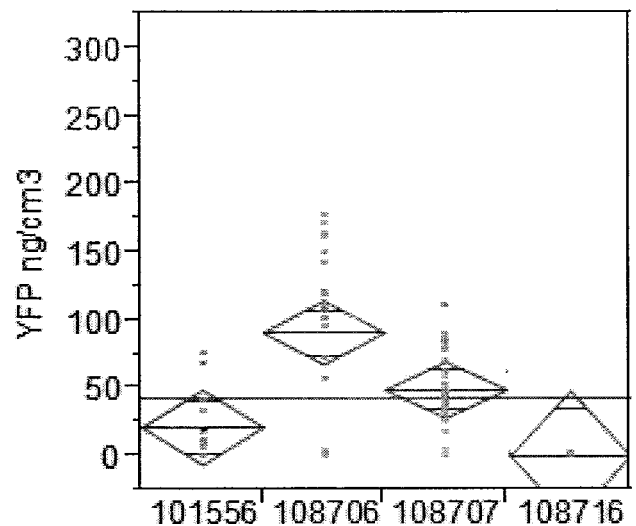
Figure 36B:
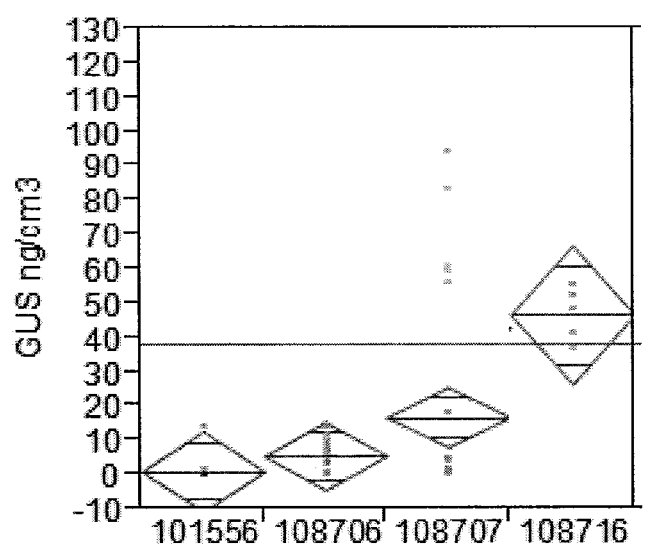
Figure 36C:
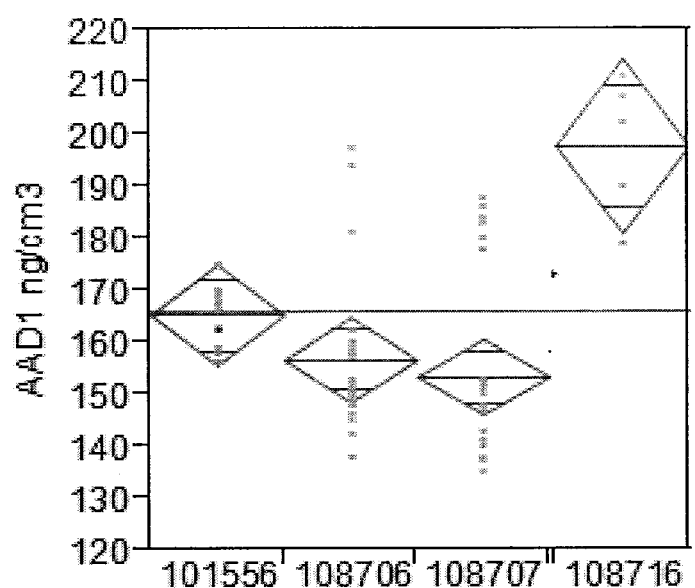

FIGS. 36A, 36B, and 36C show statistical analysis of expression results (R3) from the four constructs shown in FIG. 26 for YFP, GUS, and AAD1 protein (LCMS) in ng/cm2 respectively. The mean values for pDAB108706, pDAB108707, pDAB101556, and pDAB108716 for YFP (FIG. 36A) are 91.38, 49.49, 21.67, and 0.40 respectively. The mean values for pDAB108706, pDAB108707, pDAB101556, and pDAB108716 for GUS (FIG. 36B) are 5.52, 16.81, 1.07, and 46.60 respectively. The mean values for pDAB108706, pDAB108707, pDAB101556, and pDAB108716 for AAD1 (FIG. 36C) are 156.71, 153.44, 165.40, and 197.80 respectively.

Figure 37A:
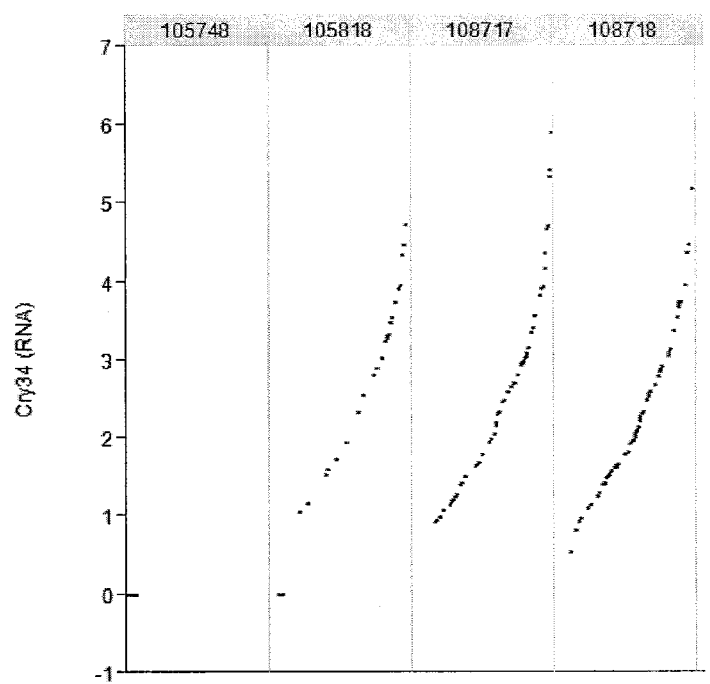
Figure 37B:
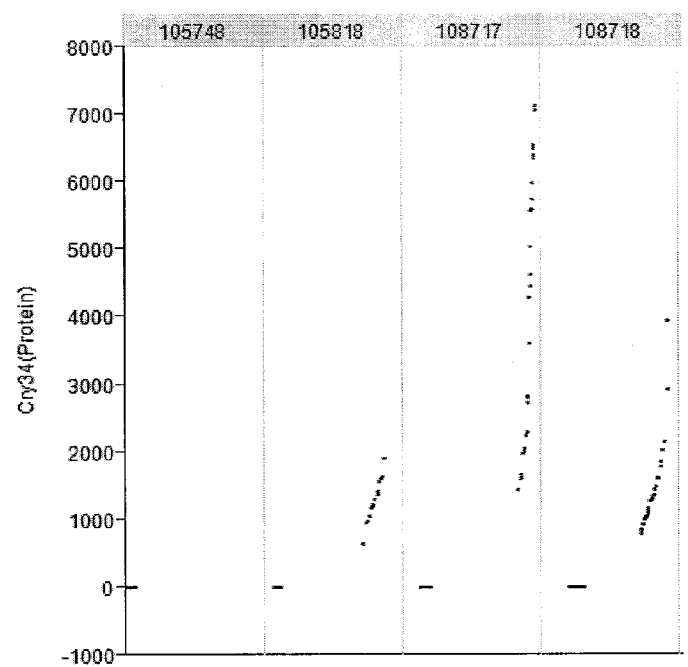

FIG. 37A shows exemplary relative expression results (V6) of Cry34 RNA from the four constructs pDAB105748 (ZMUbi1-YFP), pDAB105818 (ZMUbi1-Cry34/ZMUbi1-Cry35/ZMUbi1-AAD1), pDAB108717 (YFP/AAD-1-ZMUbi1 bidirectional-Cry34-Cry35), and pDAB108718 (AAD1/YFP-ZMUbi1 bidirectional-Cry34-Cry35). FIG. 37B shows exemplary relative expression results (V6) of Cry34 protein (LCMS) from the same four constructs pDAB105748, pDAB105818, pDAB108717, and pDAB108718.

Figure 38A:
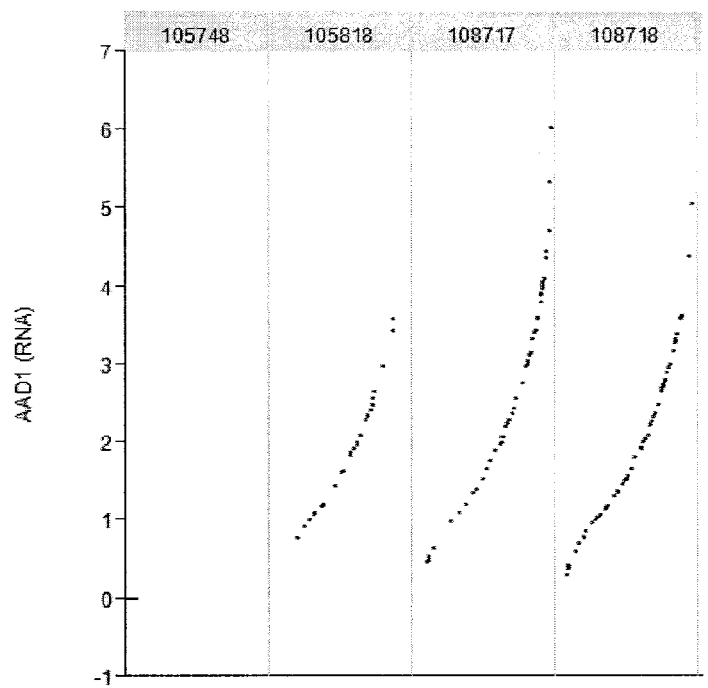
Figure 38B:
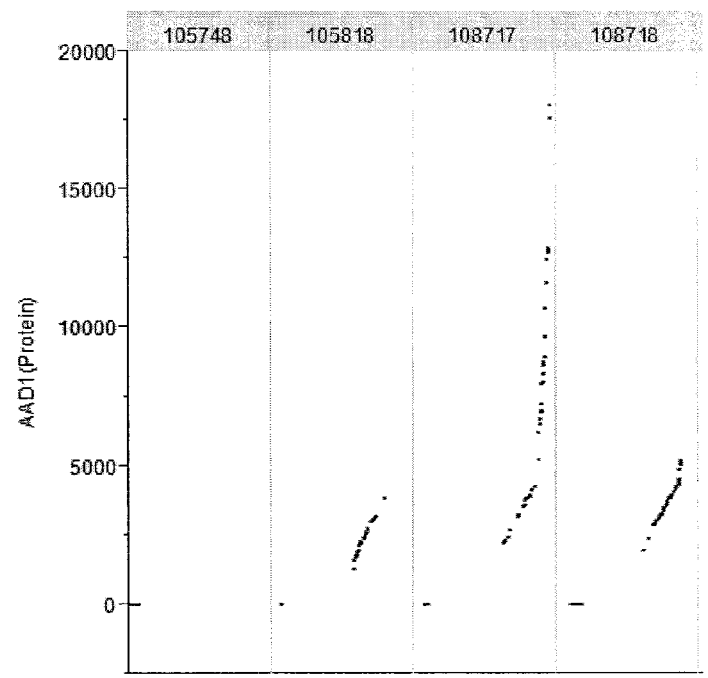

FIG. 38A shows exemplary relative expression results (V6) of AAD1 RNA from the four constructs pDAB105748, pDAB105818, pDAB108717, and pDAB108718. FIG. 38B shows exemplary relative expression results (V6) of AAD1 protein (LCMS) from the same four constructs pDAB105748, pDAB105818, pDAB108717, and pDAB108718.

Figure 39A:
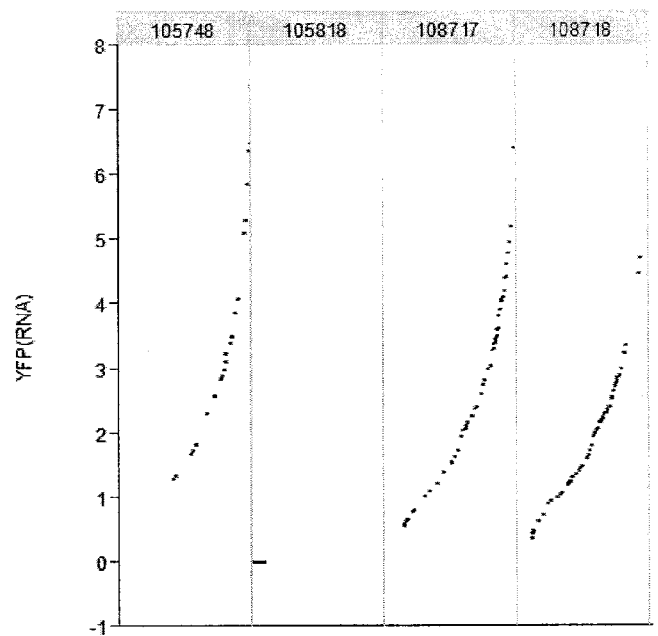
Figure 39B:
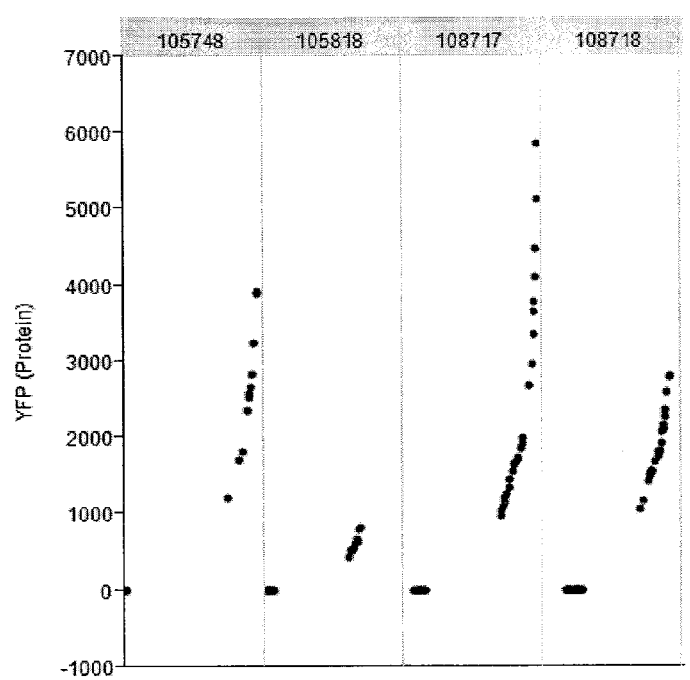

FIG. 39A shows exemplary relative expression results (V6) of YFP RNA from the four constructs pDAB105748, pDAB105818, pDAB108717, and pDAB108718. FIG. 39B shows exemplary relative expression results (V6) of YFP protein (LCMS) from the same four constructs pDAB105748, pDAB105818, pDAB108717, and pDAB108718.

Figure 40A:
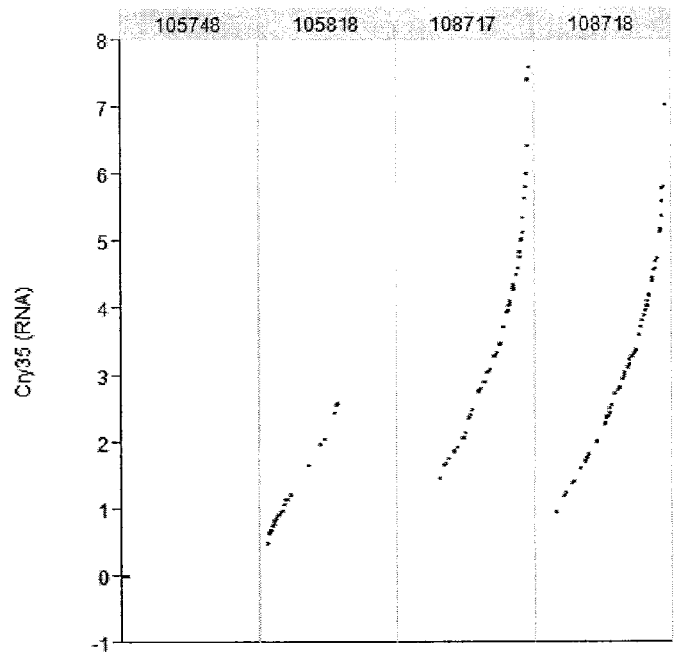
Figure 40B:
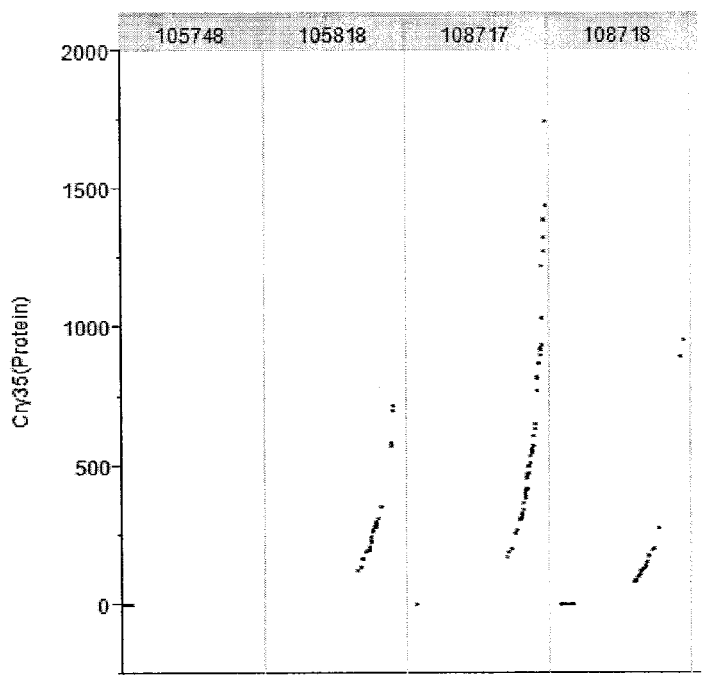

FIG. 40A shows exemplary relative expression results (V6) of Cry35 RNA from the four constructs pDAB105748, pDAB105818, pDAB108717, and pDAB108718. FIG. 40B shows exemplary relative expression results (V6) of Cry35 protein (ELISA) from the same four constructs pDAB105748, pDAB105818, pDAB108717, and pDAB108718.

Figure 41:
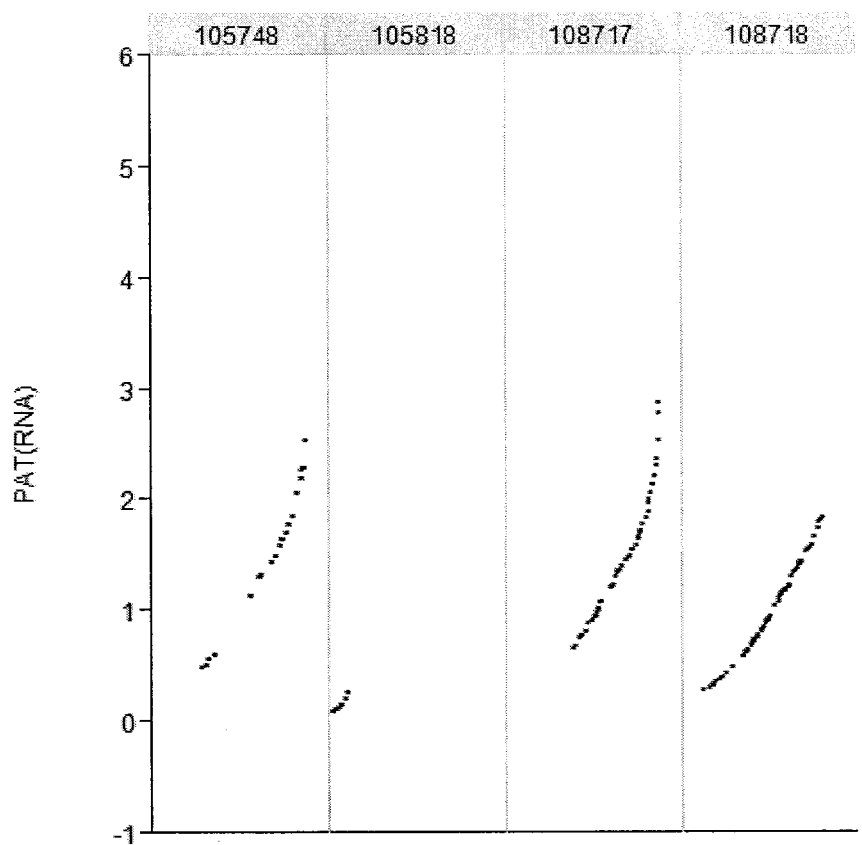

FIG. 41 shows exemplary relative expression results (V6) of PAT RNA from the four constructs pDAB105748, pDAB105818, pDAB108717, and pDAB108718.

Figure 42A:
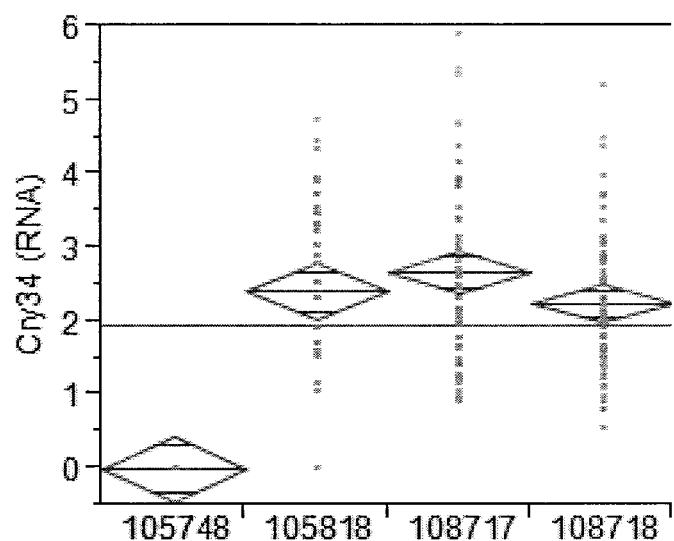
Figure 42B:
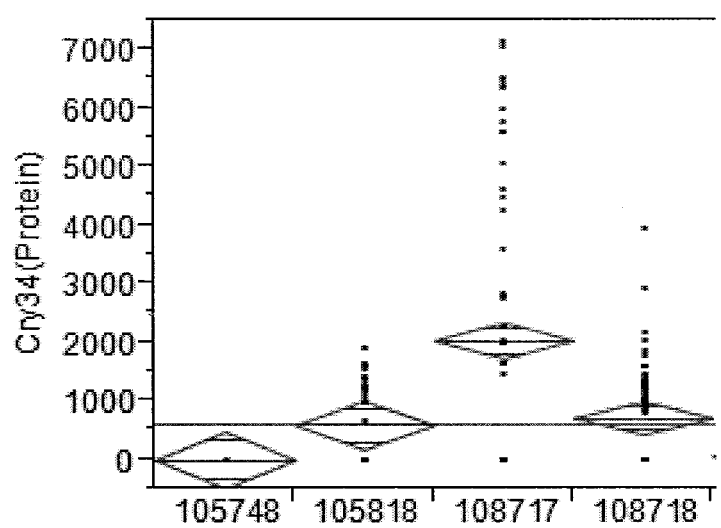

FIG. 42A shows a statistical analysis of expression results (V6) of Cry34 RNA from the four constructs pDAB105748, pDAB105818, pDAB108717, and pDAB108718 with the mean values 0, 2.42, 2.67, and 2.25 respectively. FIG. 42B shows a statistical analysis of expression results (V6) of Cry34 protein from the same four constructs pDAB105748, pDAB105818, pDAB108717, and pDAB108718 with the mean values 0, 596.94, 2044.73, and 719.18 respectively.

Figure 43A:
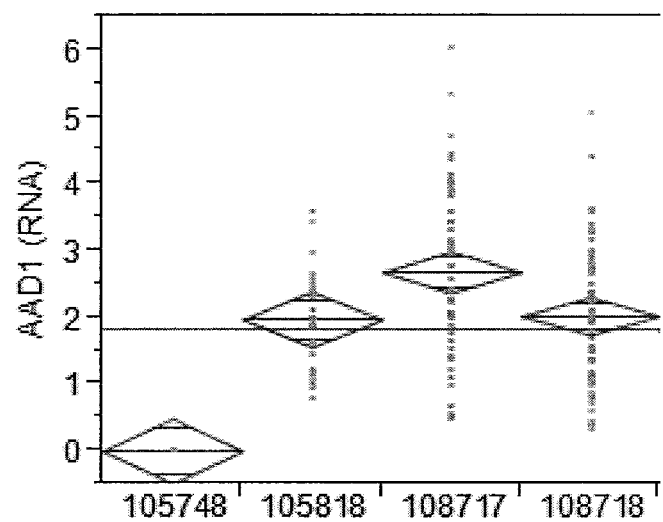
Figure 43B:
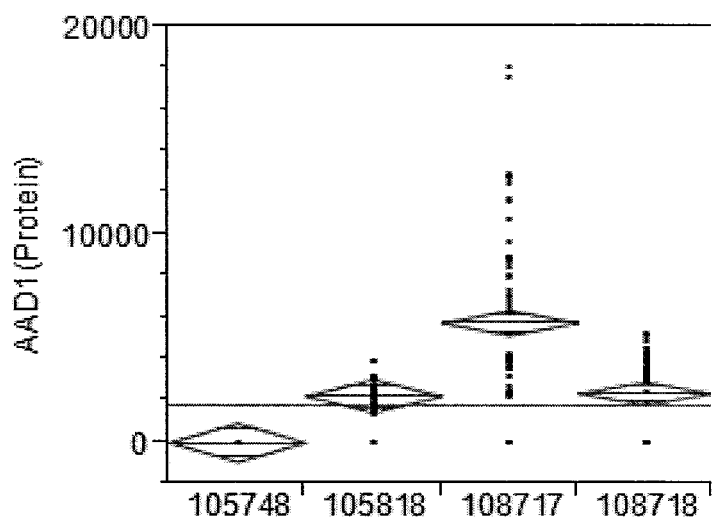

FIG. 43A shows a statistical analysis of expression results (V6) of AAD1 RNA from the four constructs pDAB105748, pDAB105818, pDAB108717, and pDAB108718 with the mean values 0, 1.98, 2.68, and 2.03 respectively. FIG. 43B shows a statistical analysis of expression results (V6) of AAD1 protein from the same four constructs pDAB105748, pDAB105818, pDAB108717, and pDAB108718 with the mean values 0, 2237.54, 5763.88, and 2379.15 respectively.

Figure 44A:
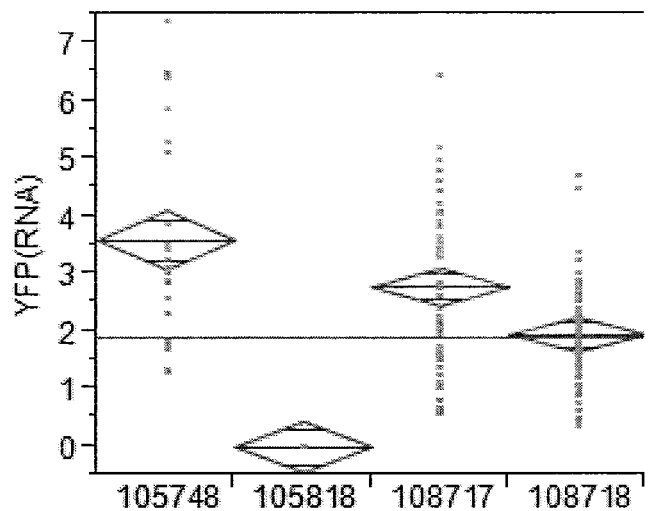
Figure 44B:
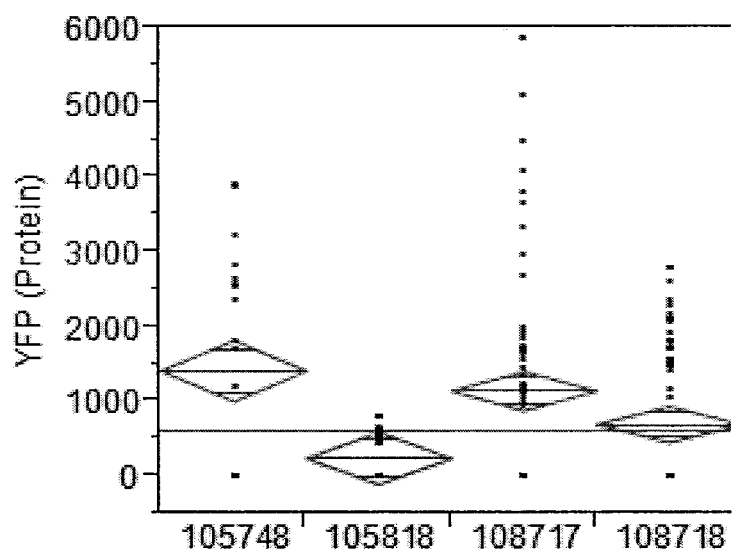

FIG. 44A shows a statistical analysis of expression results (V6) of YFP RNA from the four constructs pDAB105748, pDAB105818, pDAB108717, and pDAB108718 with the mean values 3.59, 0, 2.78, and 1.95 respectively. FIG. 44B shows a statistical analysis of expression results (V6) of YFP protein from the same four constructs pDAB105748, pDAB105818, pDAB108717, and pDAB108718 with the mean values 1420.69, 251.68, 1154.04, and 706.04 respectively.

Figure 45A:
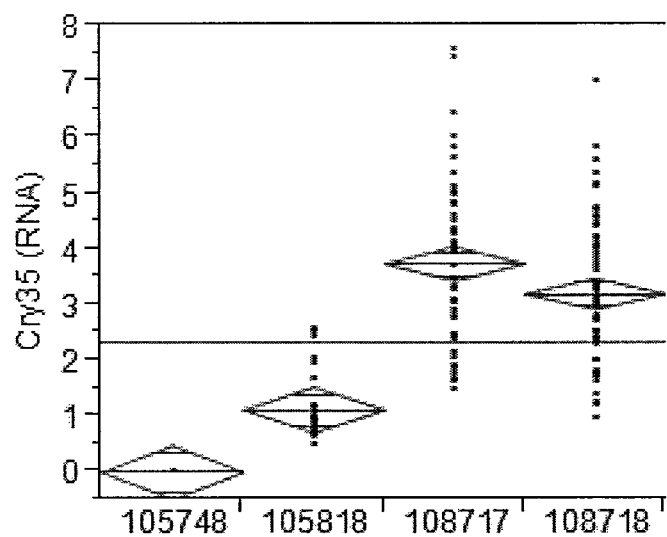
Figure 45B:
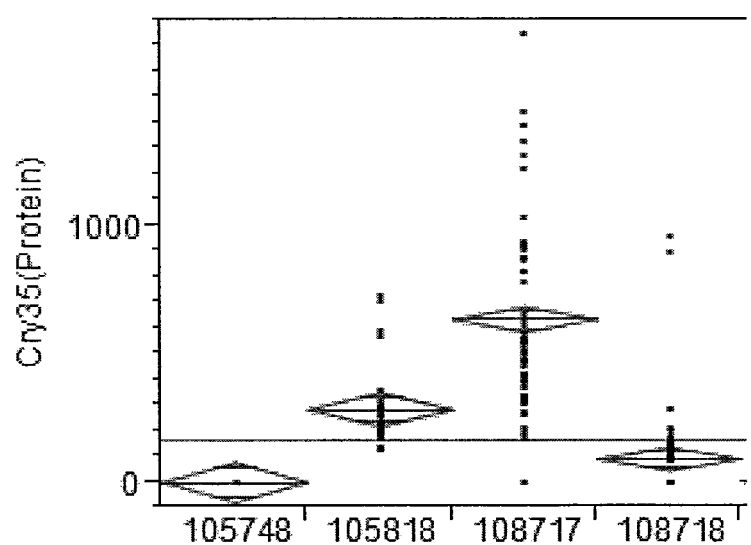

FIG. 45A shows a statistical analysis of expression results (V6) of Cry35 RNA from the four constructs pDAB105748, pDAB105818, pDAB108717, and pDAB108718 with the mean values 0, 1.12, 3.74, and 3.20 respectively. FIG. 45B shows a statistical analysis of expression results (V6) of Cry35 protein from the same four constructs pDAB105748, pDAB105818, pDAB108717, and pDAB108718 with the mean values 0, 283.54, 635.83, and 90.97 respectively.

Figure 46:
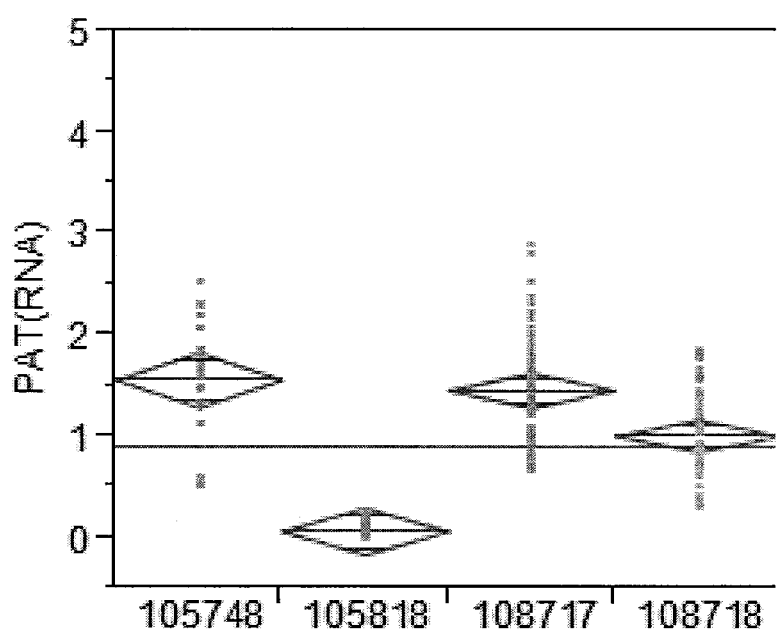
Figure 47A:
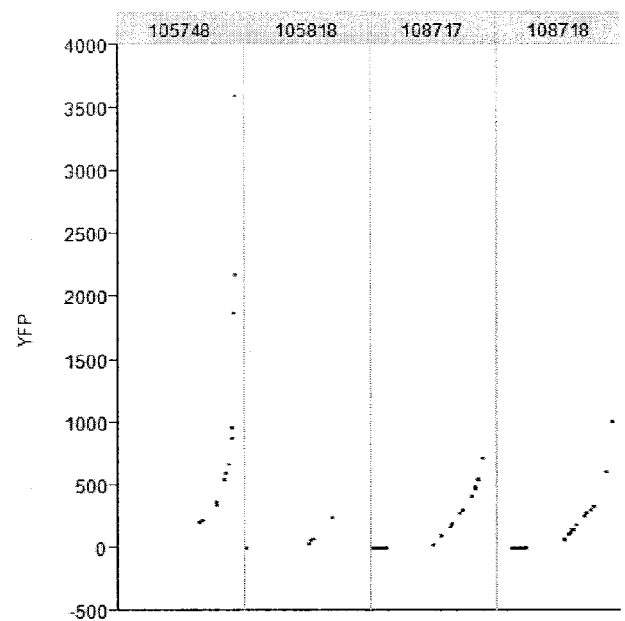
Figure 47B:
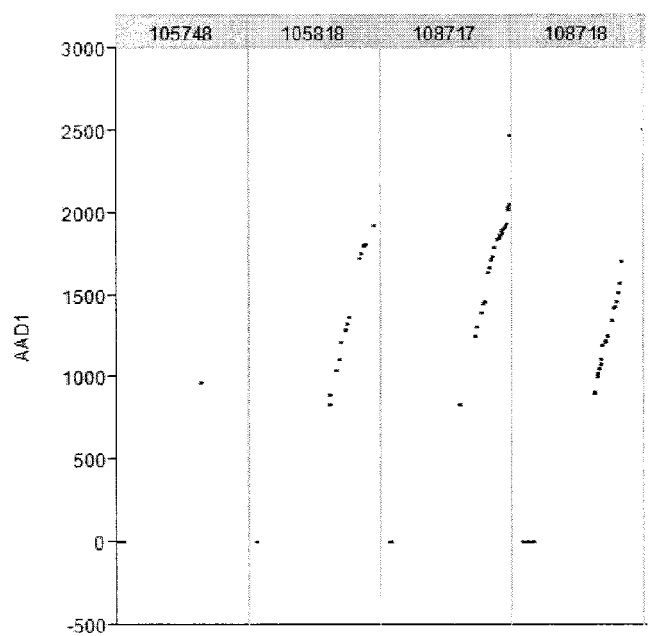
Figure 47C:
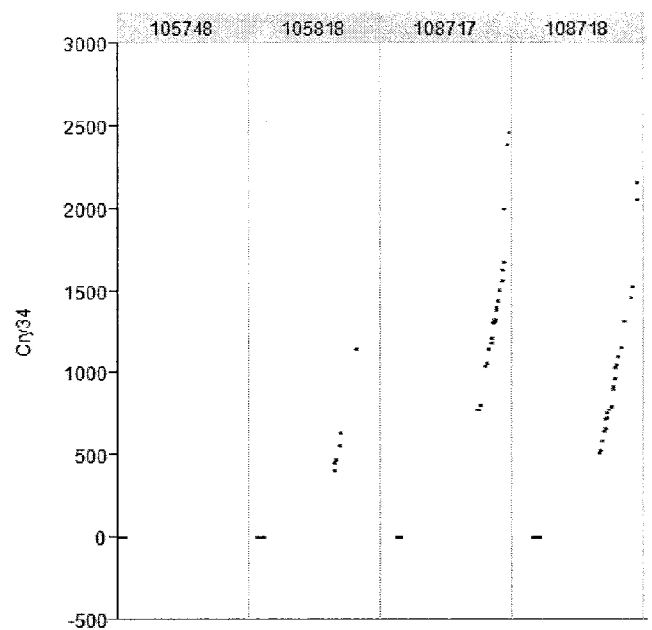
Figure 47D:
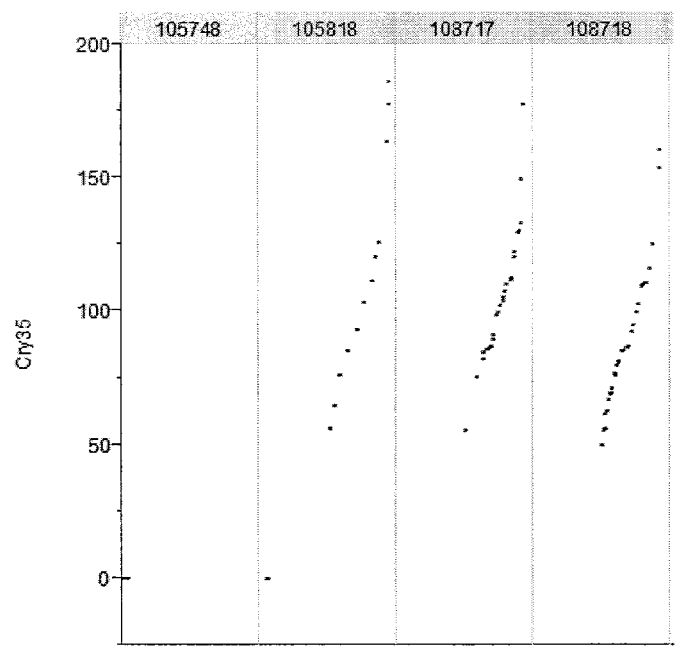
Figure 48A:
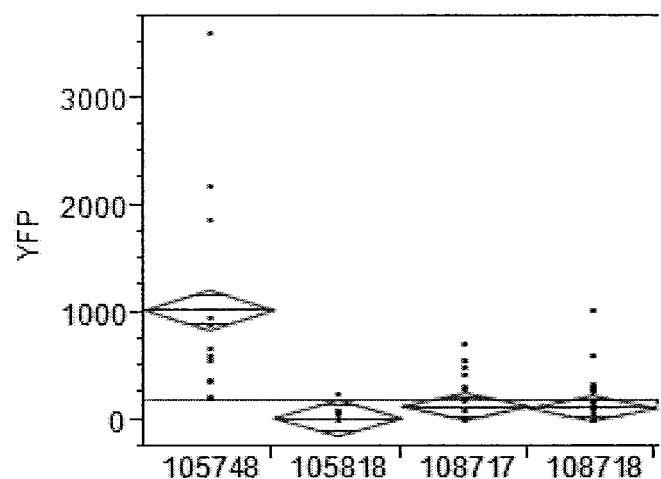
Figure 48B:
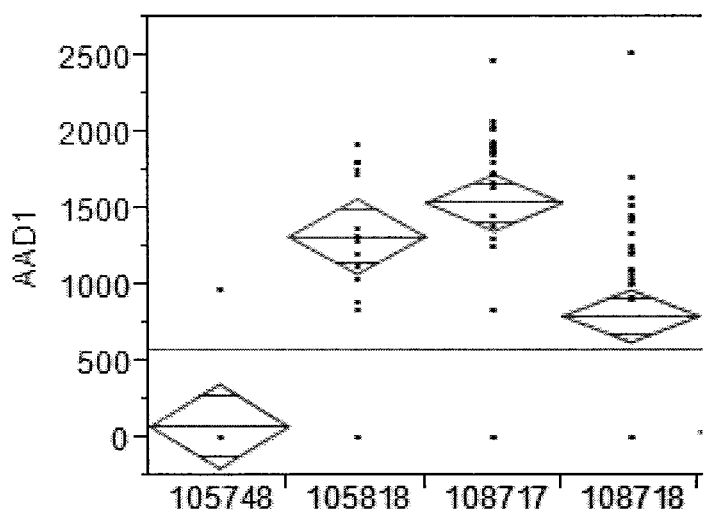
Figure 48C:
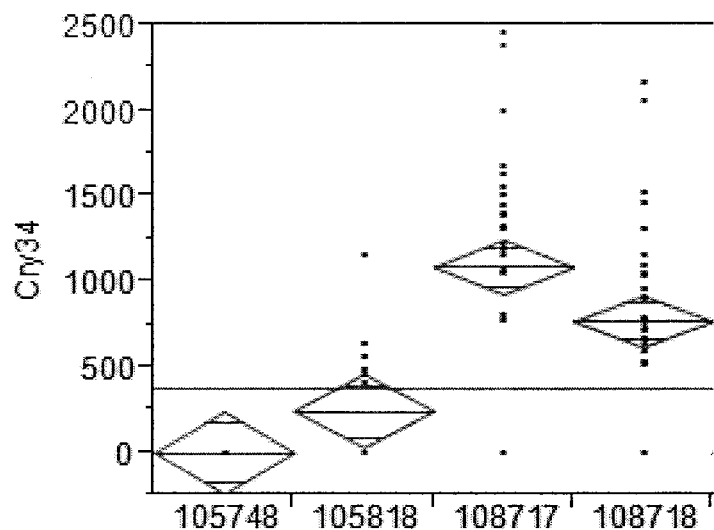
Figure 48D:
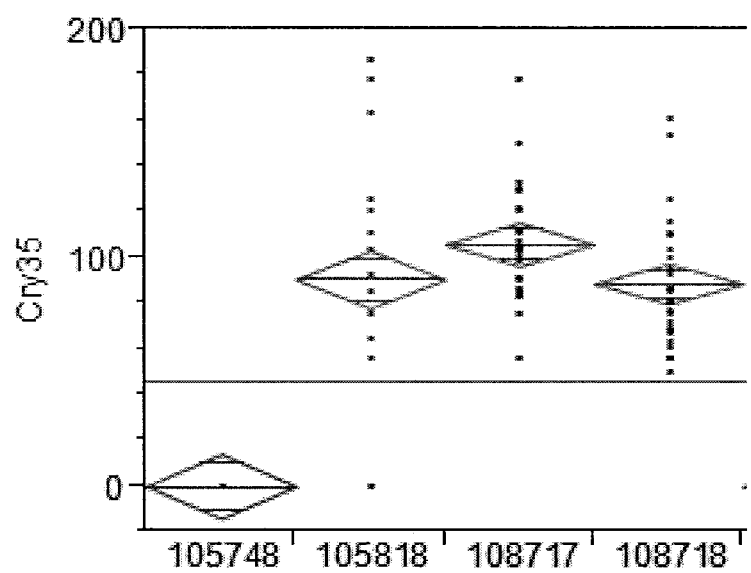
Figure 49A:
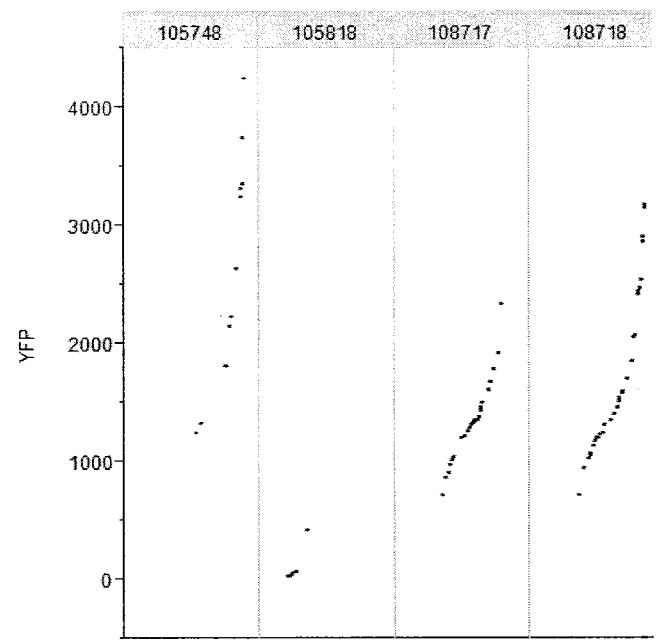
Figure 49B:
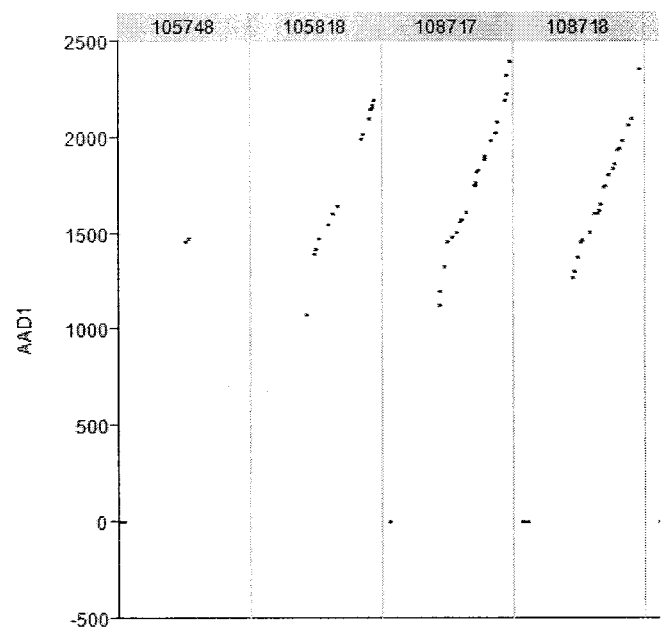
Figure 49C:
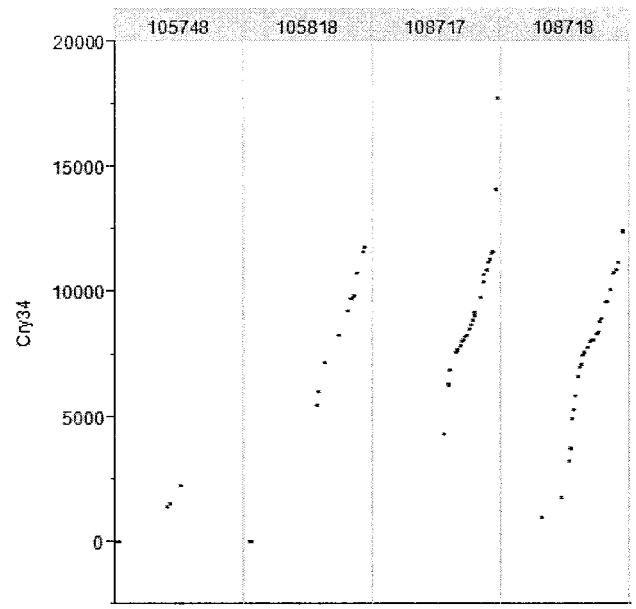
Figure 49D:
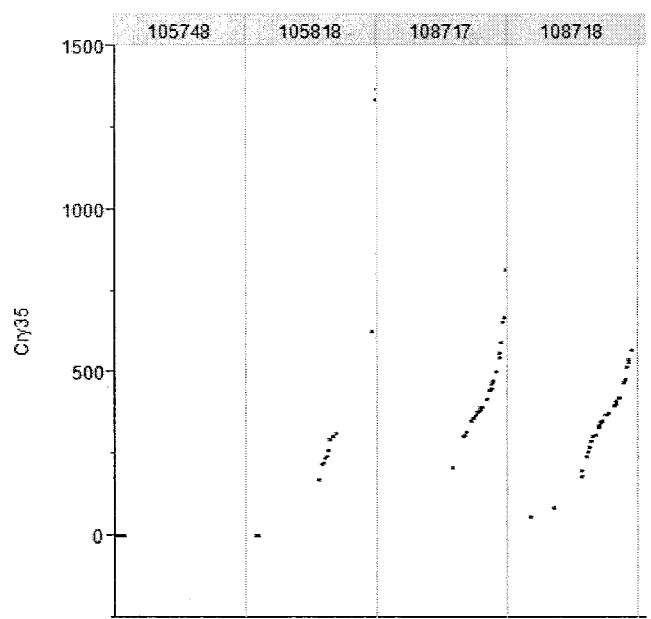
Figure 50A:
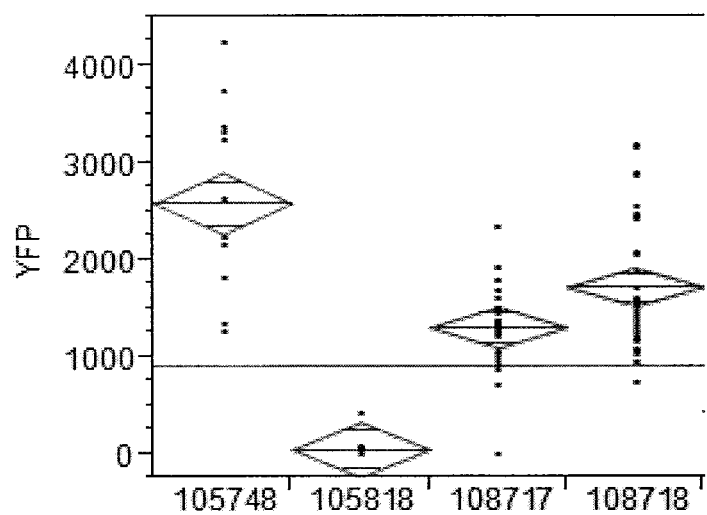
Figure 50B:
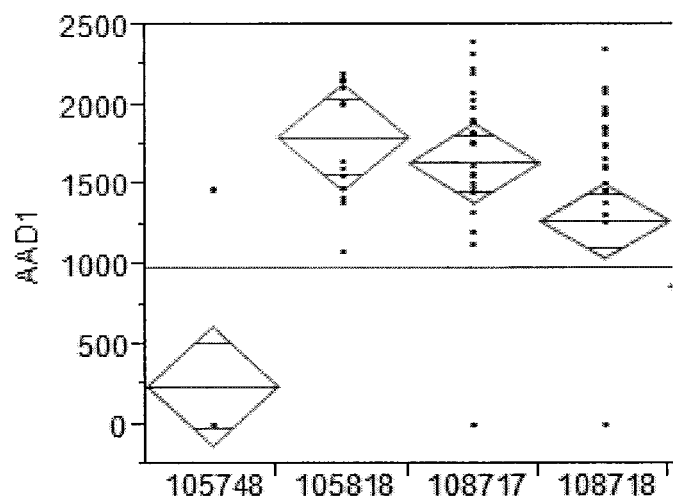
Figure 50C:
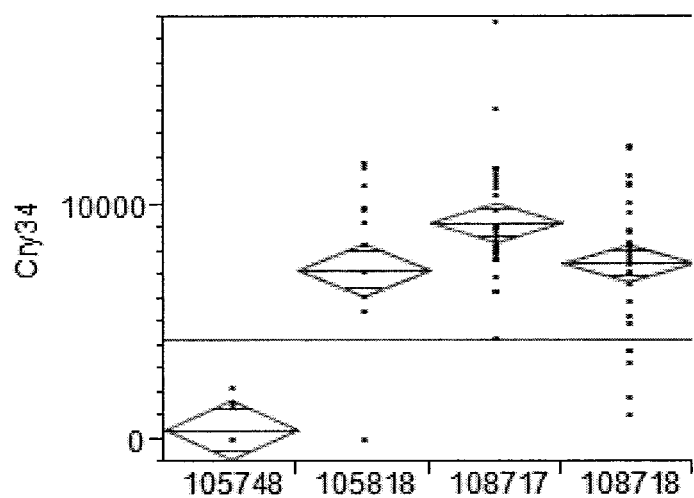
Figure 50D:
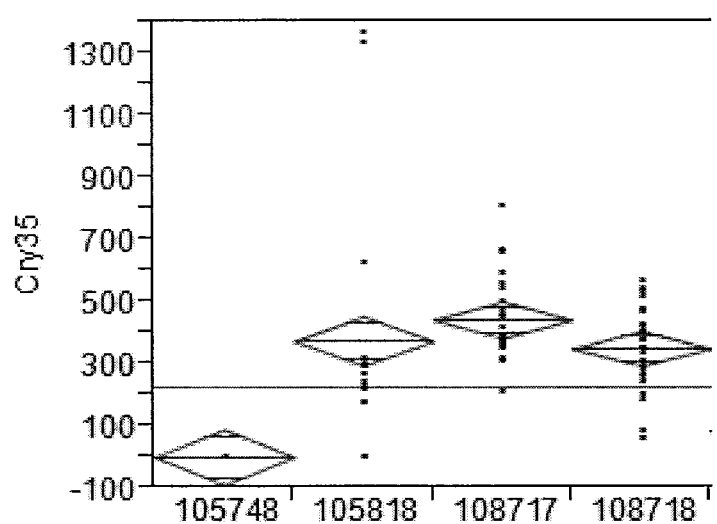

FIG. 46 shows a statistical analysis of expression results (V6) of PAT RNA from the four constructs pDAB105748, pDAB105818, pDAB108717, and pDAB108718 with mean values 1.56, 0.07, 1.46, and 1.01 respectively.

FIGS. 47A, 47B, 47C, and 47D show exemplary protein expression results (V10) of YFP, AAD1, Cry34, and Cry35 respectively from the four constructs pDAB105748, pDAB105818, pDAB108717, and pDAB108718.

FIGS. 48A, 48B, 48C, and 48D show statistical analysis of protein expression results (V10) of YFP, AAD1, Cry34, and Cry35 respectively from the four constructs pDAB105748, pDAB105818, pDAB108717, and pDAB108718. The mean values for YFP (FIG. 48A) are 1033.47, 27.51, 136.18, and 119.06 respectively. The mean values for AAD1 (FIG. 48B) are 80.89, 1323.80, 1544.69, and 802.50 respectively. The mean values for Cry34 (FIG. 48C) are 0, 246.05, 1089.18, and 769.81 respectively. The mean values for Cry35 (FIG. 48D) are 0, 90.75, 106.09, and 88.80 respectively.

FIGS. 49A, 49B, 49C, and 49D show exemplary protein expression results (R3) of YFP, AAD1, Cry34, and Cry35 respectively from the four constructs pDAB105748, pDAB105818, pDAB108717, and pDAB108718.

FIGS. 50A, 50B, 50C, and 50D show statistical analysis of protein expression results (R3) of YFP, AAD1, Cry34, and Cry35 respectively from the four constructs pDAB105748, pDAB105818, pDAB108717, and pDAB108718. The mean values for YFP (FIG. 50A) are 2589.63, 43.62, 1305.27, and 1727.96 respectively. The mean values for AAD1 (FIG. 50B) are 244.41, 1803.99, 1642.44, and 1279.17 respectively. The mean values for Cry34 (FIG. 50C) are 422.45, 7258.15, 9285.74, and 7544.75 respectively. The mean values for Cry35 (FIG. 50D) are 0, 373.35, 441.11, and 348.45 respectively.

Figure 51:
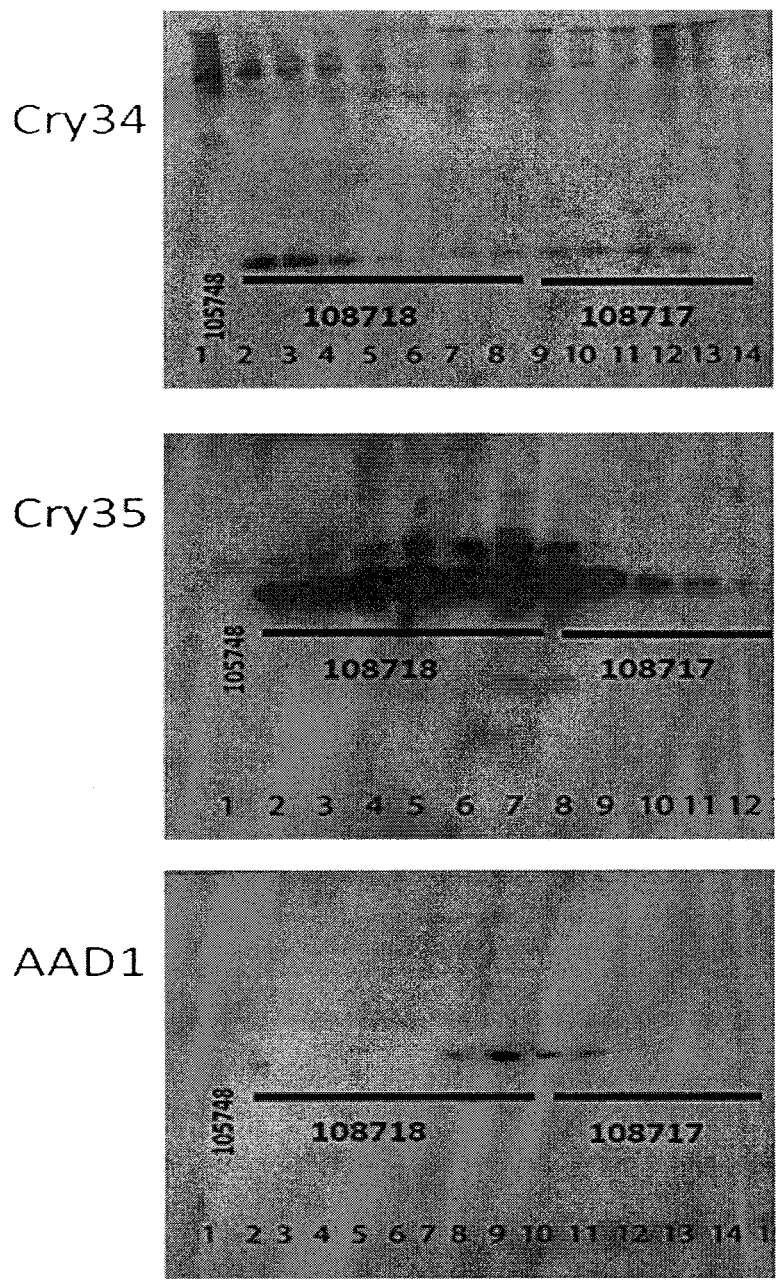

FIG. 51 shows exemplary results of Western blot for protein expression of Cry34, Cry35, and AAD1 from pDAB108718 and pDAB108717.

DETAILED DESCRIPTION OF THE INVENTION

Development of transgenic products is becoming increasingly complex, which requires pyramiding multiple transgenes into a single locus. Traditionally each transgene usually requires a unique promoter for expression, so multiple promoters are required to express different transgenes within one gene stack. In addition to increasing the size of the gene stack, this frequently leads to repeated use of the same promoter to obtain similar levels of expression patterns of different transgenes controlling the same trait. Multi-gene constructs driven by the same promoter are known to cause gene silencing, thus making transgenic products less efficacious in the field. Excess of transcription factor (TF)-binding sites due to promoter repetition can cause depletion of endogenous TFs leading to transcriptional inactivation.

Provided are constructs and methods combining the bidirectional promoter system with bicistronic organization of genes on either one or both ends of the promoter, for example with the use of a 2A sequence from Thosea asigna virus. The 2A protein, which is only 16-20 amino acids long, cleaves the polyprotein at its own carboxyl-terminus. This "self-cleavage" or "ribosome skip" property of the 2A or 2A-like peptide can be used to process artificial polyproteins produced in transgenic plants. In one embodiment, Cry34 and Cry35 genes are fused in one gene expression cassette, where YFP (or Phiyfp) and AAD1 genes are fused into another gene expression cassette (with a single open reading frame (ORF) with a copy of the 2A protein gene placed between the two genes in each combination). For example, each of these gene expression cassettes (or gene pairs) can be placed on the either end of the bidirectional promoter to drive 4 transgenes using a single promoter. Thus, the constructs and methods provided herein are useful to avoid repeated use of the same promoter and significantly reduce the size of commercial constructs. In addition, driving four or more genes with one promoter also provides ability to co-express genes controlling a single trait.

Plant promoters used for basic research or biotechnological application are generally unidirectional, directing only one gene that has been fused at its 3' end (downstream). It is often necessary to introduce multiple genes into plants for metabolic engineering and trait stacking and therefore, multiple promoters are typically required in future transgenic crops to drive the expression of multiple genes. It is desirable to design strategies that can save the number of promoters deployed and allow simultaneous co-regulated expression for gene pyramiding. In some embodiment, the bidirectional promoters provided can drive transcription of multiple transcription units, including RNAi, artificial miRNA, or hairpin-loop RNA sequences.

One approach for reducing the number of promoters deployed is the use of critical transcription-activating switches that may drive transcription in both directions. These promoters are called bidirectional promoters. Synthetic promoters can be designed to limit the level of homology among multiple promoters to be used for genetic engineering in crop plants, which may avoid homology based gene silencing. Artificially designed bidirectional promoters can be valuable tools for the development of transgenic plants. Bidirectional function of promoters in plants has been reported in some cases, including the CaMV 35S and the mannopine synthase promoter (mas) promoters. However, suitability of using such promoters has not been examined for predictable, stable and simultaneous expression of genes in the two directions.

Another method for coordinate expression of multiple genes is to encode a single open reading frame into a polyprotein precursor containing short intervening motif with self processing properties between two coding sequences. Autocatalytic processing of the polyprotein precursor leads to release of multiple independent proteins resulting into their synchronized coordinated expression. A synthetic self-hydrolyzing 2A peptide sequence has been used both in plant and animal system to express two transgenes. The 2A peptide sequence is utilized by several known viruses and consists of 16-20 amino acids. This 2A peptide sequence self-cleaves (or ribosome skip) co-translationally by modifying the activity of the ribosome to allow hydrolysis of the 2A between two proteins resulting in the release of the two protein products.

Provided are constructs and methods combining bidirectional promoter approach with polyprotein processing using intervening synthetic motifs, where expression of at least 4 transgenes using a single promoter can be readily achieved. Genes of Cry34 and Cry35, and genes of YFP (or Phiyfp) and AAD1 have been fused as gene expression cassettes or gene pairs into single open reading frames (ORF) with a copy of the 2A protein gene placed between the genes. The gene pairs can be placed on either end of the bidirectional promoter to drive four transgenes using one single promoter. The constructs and/or methods provided herein are useful to avoid repeated use of the same promoter avoiding potential transgene silencing problems. In addition, this transgene design approach can significantly reduce the size of the transgene stacks containing multiple transgenes. Driving four or more genes with one promoter also provides ability to co-express genes controlling a single trait ensuring long-term efficacy of transgenic products.

Development of transgenic plants is becoming increasingly complex, and typically requires stacking multiple transgenes into a single locus. See Xie et al. (2001) Nat. Biotechnol. 19(7):677-9. Since each transgene usually requires a unique promoter for expression, multiple promoters are required to express different transgenes within one gene stack. In addition to increasing the size of the gene stack, this frequently leads to repeated use of the same promoter to obtain similar levels of expression patterns of different transgenes. This approach is often problematic, as the expression of multiple genes driven by the same promoter may lead to gene silencing or HBGS. An excess of competing transcription factor (TF)-binding sites in repeated promoters may cause depletion of endogenous TFs and lead to transcriptional down regulation. The silencing of transgenes will likely undesirably affect the performance of a transgenic plant produced to express the transgenes. Repetitive sequences within a transgene may lead to gene intra-locus homologous recombination resulting in polynucleotide rearrangements.

Plant promoters used for basic research or biotechnological application are generally unidirectional, and regulate only one gene that has been fused at its 3' end (downstream). To produce transgenic plants with various desired traits or characteristics, it would be useful to reduce the number of promoters that are deployed to drive expression of the transgenes that encode the desired traits and characteristics. It is often necessary to introduce multiple transgenes into plants for metabolic engineering and trait stacking, thereby necessitating multiple promoters to drive the expression of multiple transgenes. By developing a single synthetic bidirectional promoter that can drive expression of two transgenes that flank the promoter, the total numbers of promoters needed for the development of transgenic crops may be reduced, thereby lessening the repeated use of the same promoter, reducing the size of transgenic constructs, and/or reducing the possibility of HBGS.

Embodiments herein utilize a process wherein a unidirectional promoter from a maize ubiquitin-1 gene (e.g., ZmUbi1) is used to design a synthetic bidirectional promoter, such that one promoter can direct the expression of two genes, one on each end of the promoter. Processes as utilized herein may comprise identification of the Ubi1 minimal core promoter element (minUbi1P) from a ZmUbi1 gene, and engineering of this element into new contexts to construct certain synthetic bidirectional promoters. Synthetic bidirectional promoters, such as may be created by a process according to some embodiments of the invention, may allow those in the art to stack transgenes in plant cells and plants while lessening the repeated use of the same promoter and reducing the size of transgenic constructs. Furthermore, regulating the expression of two genes with a single synthetic bidirectional promoter may also provide the ability to co-express the two genes under the same conditions, such as may be useful, for example, when the two genes each contribute to a single trait in the host. The use of bidirectional promoters in plants has been reported in some cases, including the CaMV 35 promoters (Barfield and Pua (1991) Plant Cell Rep. 10(6-7):308-14; Xie et al. (2001), and the mannopine synthase promoter (mas) promoters (Velten et al. (1984) EMBO J. 3(12):2723-30; Langridge et al. (1989) Proc. Natl. Acad. Sci. USA 86:3219-23).

Transcription initiation and modulation of gene expression in plant genes is directed by a variety of DNA sequence elements that are collectively arranged within the promoter. Eukaryotic promoters consist of minimal core promoter element (minP), and further upstream regulatory sequences (URSs). The core promoter element is a minimal stretch of contiguous DNA sequence that is sufficient to direct accurate initiation of transcription. Core promoters in plants also comprise canonical regions associated with the initiation of transcription, such as CAAT and TATA boxes. The TATA box element is usually located approximately 20 to 35 nucleotides upstream of the initiation site of transcription.

The activation of the minP is dependent upon the URS, to which various proteins bind and subsequently interact with the transcription initiation complex. URSs comprise DNA sequences that determine the spatiotemporal expression pattern of a promoter comprising the URS. The polarity of a promoter is often determined by the orientation of the minP, while the URS is bipolar (i.e., it functions independent of its orientation). For example, the CaMV 35S synthetic unidirectional polar promoter may be converted to a bidirectional promoter by fusing a minP at the 5' end of the promoter in the opposite orientation. See, for example, Xie et al. (2001) Nat. Biotechnol. 19(7):677-9.

Certain abbreviations disclosed are listed in Table 1.

TABLE 1

Abbreviations used in the disclosure

| Phrase | Abbreviation |
|---|---|
| bicinchoninic acid | BCA |
| cauliflower mosaic virus | CaMV |

TABLE 1-continued

Abbreviations used in the disclosure

| Phrase | Abbreviation |
|---|---|
| chloroplast transit peptide | CTP |
| homology-based gene silencing | HBGS |
| ZmUbi1 minimal core promoter | minUbi1P |
| oligo ligation amplification | OLA |
| phosphate buffered saline | PBS |
| phosphate buffered saline with 0.05% Tween 20 | PBST |
| polymerase chain reaction | PCR |
| rolling circle amplification | RCA |
| reverse transcriptase PCR | RT-PCR |
| single nucleotide primer extension | SNuPE |
| upstream regulatory sequence | URS |
| Zea mays Ubiquitin-1 gene | ZmUbi1 |

In specific examples of some embodiments, modified elements of a maize Ubi1 (ZmUbi1) promoter derived from the Z. mays inbred line, B73, are used to engineer synthetic bidirectional promoters that may function in plants to provide expression control characteristics that are unique with respect to previously available bidirectional promoters. This ZmUbi1 promoter originally derived from B73 comprises sequences located in the maize genome within about 899 bases 5' of the transcription start site, and further within about 1093 bases 3' of the transcription start site. Christensen et al. (1992) Plant Mol. Biol. 18(4):675-89 (describing a B73 ZmUbi1 gene). A modified ZmUbi1 promoter derived from B73 that is used in some examples is an approximately 2 kb promoter that contains a TATA box; two overlapping heat shock consensus elements; an 82 or 83 nucleotide (depending on the reference strand) leader sequence immediately adjacent to the transcription start site, which is referred to herein as ZmUbi1 exon; and a 1015-1016 nucleotide intron (see FIG. 1 for example). Other maize ubiquitin promoter variants derived from Zea species and Zea mays genotypes may exhibit high sequence conservation around the minP element consisting of the TATA element and the upstream heat shock consensus elements. Thus, embodiments of the invention are exemplified by the use of this short (~200 nt) highly-conserved region (e.g., SEQ ID NO: 1) of a ZmUbi1 promoter as a minimal core promoter element for constructing synthetic bidirectional plant promoters.

As used herein, the articles, "a," "an," and "the" include plural references unless the context clearly and unambiguously dictates otherwise.

As used herein, the phrase "backcrossing" refers to a process in which a breeder crosses hybrid progeny back to one of the parents, for example, a first generation hybrid $_{F1}$ with one of the parental genotypes of the F1 hybrid.

As used herein, the phrase "intron" refers to any nucleic acid sequence comprised in a gene (or expressed nucleotide sequence of interest) that is transcribed but not translated. Intron is different from 5' end untranslated leader sequence which is not considered as part of a gene. Introns include untranslated nucleic acid sequence within an expressed sequence of DNA, as well as the corresponding sequence in RNA molecules transcribed therefrom.

As used herein, the phrase "isolated" refers to biological component (including a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The phrase "isolated" also embraces nucleic acids and proteins prepared by recombinant expression in a host cell, as well as chemically-synthesized nucleic acid molecules, proteins, and peptides.

As used herein, the phrase "gene expression" refers to a process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the phrase "homology-based gene silencing" (HBGS) refers to a generic term that includes both transcriptional gene silencing and posttranscriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes. See, for example, Mourrain et al. (2007) Planta 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the phrase "nucleic acid molecule" (or "nucleic acid" or "polynucleotide") refers to a polymeric form of nucleotides, which may include both sense and antisense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the phrase "base position," refers to the location of a given base or nucleotide residue within a designated nucleic acid. The designated nucleic acid may be defined by alignment (see below) with a reference nucleic acid.

As used herein, the phrase "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the phrases "specifically hybridizable" and "specifically complementary" refers to a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989, chs. 9 and 11.

As used herein, the phrase "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:
  Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.
  High Stringency: Hybridization in 5x-6×SSC buffer at 65-70° C. for 16-20 hours; wash twice in 2×SSC buffer at room temperature for 5-20 minutes each; and wash twice in 1×SSC buffer at 55-70° C. for 30 minutes each.
  Moderate Stringency: Hybridization in 6×SSC buffer at room temperature to 55° C. for 16-20 hours; wash at least twice in 2x-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the phrase "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

As used herein, the phrase "sequence identity" or "identity," refers to a context where two nucleic acid or polypeptide sequences, may refer to the residues in the two sequences that are the same when aligned for maximum correspondence over a specified comparison window.

As used herein, the phrase "percentage of sequence identity" refers to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the phrase "operably linked" refers to a context where the first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the phrase "promoter" refers to a region of DNA that generally is located upstream (towards the 5' region of a gene) that is needed for transcription. Promoters may permit the proper activation or repression of the gene which they control. A promoter may contain specific sequences that are recognized by transcription factors. These factors may bind to the promoter DNA sequences and result in the recruitment of RNA polymerase, an enzyme that synthesizes RNA from the coding region of the gene.

As used herein, the phrase "transforms" or "transduces" refers to a process where a virus or vector transfers nucleic acid molecules into a cell. A cell is "transformed" by a nucleic acid molecule "transduced" into the cell when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; whiskers-mediated transformation; and microprojectile bombardment (Klein et al. (1987) Nature 327:70).

As used herein, the phrase "transgene" refers to an exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a nucleic acid sequence of interest is a transgene. However, in other embodiments, a nucleic acid sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the phrase "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the phrase "plant" includes plants and plant parts including but not limited to plant cells and plant tissues such as leaves, stems, roots, flowers, pollen, and seeds. The class of plants that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicotyledons plants and monocotyledons plants. Examples of dicotyledons plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the phrase "plant material" refers to leaves, stems, roots, flowers or flower parts, fruits, pollen, egg cells, zygotes, seeds, cuttings, cell or tissue cultures, or any other part or product of a plant. In some embodiment, plant material includes cotyledon and leaf.

As used herein, the phrase "translation switch" refers to a mechanism at end of a gene allowing translation of an immediate downstream gene. The mechanism of translation switch can function at nucleic acid level (for example, viral or eukaryotic internal ribosome entry site (IRES), an alternative splicing site, or a ribozyme cleavage site) or at peptide/protein level (for example, a 2A peptide, a 2A-like peptide, an intern peptide, or a protease cleavage site).

These mechanisms of translation switch at nucleic acid level or at peptide/protein level are well known in the art. See e.g., Ali, Z., H. M. Schumacher, et al. (2010) J Biotechnol 145(1): 9-16; Chen, Y., K. Perumal, et al. (2000) Gene Expr 9(3): 133-143; Dinkova, T. D., H. Zepeda, et al. (2005) Plant J 41(5): 722-731; Dorokhov, Y. L., M. V. Skulachev, et al. (2002) Proc Natl Acad Sci USA 99(8): 5301-5306; Fernandez-Miragall, 0. and C. Hernandez (2011) PLoS One 6(7): e22617; Groppelli, E., G. J. Belsham, et al. (2007) J Gen Virol 88(Pt 5): 1583-1588; Ha, S. H., Y. S. Liang, et al. (2010) Plant Biotechnol J 8(8): 928-938; Karetnikov, A. and K. Lehto (2007) J Gen Virol 88(Pt 1): 286-297; Karetnikov, A. and K. Lehto (2008) Virology 371(2): 292-308; Khan, M. A., H. Yumak, et al. (2009) J Biol Chem 284(51): 35461-35470; and Koh, D. C., S. M. Wong, et al. (2003) J Biol Chem 278(23): 20565-20573, the content of which are hereby incorporated by reference in their entireties. Multi-gene expression constructs containing modified interns have been disclosed in U.S. Pat. Nos. 7,026,526 and 7,741,530, as well as U.S. Patent application 2008/0115243, the content of which are hereby incorporated by reference in their entireties.

As used herein, the phrase "selectable marker" or "selectable marker gene" refers to a gene that is optionally used in plant transformation to, for example, protect the plant cells from a selective agent or provide resistance/tolerance to a selective agent. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include gene for neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. The phrase "marker-positive" refers to plants that have been transformed to include the selectable marker gene.

Various selectable or detectable markers can be incorporated into the chosen expression vector to allow identification and selection of transformed plants, or transformants. Many methods are available to confirm the expression of selection markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or other proteins such as reporter genes β-glucuronidase (GUS), luciferase, green fluorescent protein (GFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N. Y., 2001, the content of which is incorporated herein by reference in its entirety).

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate or has been obtained by using genes coding for the mutant target enzymes, 5-enolpyruvylshikimate-3-phosphate synthase (EPSPS). Genes and mutants for EPSPS have been disclosed in U.S. Pat. Nos. 4,940,835, 5,188,642, 5,310,667, 5,633,435, 5,633,448, and 6,566,587, the contents of which are incorporated by reference in their entireties. Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Enzymes/genes for glufosinate resistance/tolerance have been disclosed in U.S. Pat. Nos. 5,273,894, 5,276,268, 5,550, 318, and 5,561,236, the contents of which are incorporated by reference in their entireties. Enzymes/genes for 2,4-D resistance have been previously disclosed in U.S. Pat. Nos. 6,100, 446 and 6,153,401, as well as patent applications US 2009/0093366 and WO 2007/053482, the contents of which are hereby incorporated by reference in their entireties. Enzymes/genes for nitrilase has been previously disclosed in U.S. Pat. No. 4,810,648, the content of which is incorporated by reference in its entirety.

Other herbicides can inhibit the growing point or meristem, including imidazolinone or sulfonylurea, and genes for resistance/tolerance of acetohydroxyacid synthase (AHAS) and acetolactate synthase (ALS) for these herbicides have been described. Genes and mutants for AHAS and mutants have been disclosed in U.S. Pat. Nos. 4,761,373, 5,304,732, 5,331, 107, 5,853,973, and 5,928,937, the contents of which are incorporated by reference in their entireties. Genes and mutants for ALS have been disclosed in U.S. Pat. Nos. 5,013, 659 and 5,141,870, the contents of which are incorporated by reference in their entireties.

Glyphosate resistance genes include mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include glufosinate (phosphinothricin acetyl transferase (PAT) genes from Streptomyces species, including Streptomyces hygroscopicus and Streptomyces viridichromogenes), and pyridinoxy or phenoxy proprionic acids and cyclohexones (ACCase inhibitor-encoding genes). Herbicide resistance/tolerance genes of acetyl coemzyme A carboxylase (ACCas) have been described in U.S. Pat. Nos. 5,162,602 and 5,498,544, the contents of which are incorporated by reference in their entireties.

A DNA molecule encoding a mutant aroA gene can be obtained under ATCC accession number 39256, and the nucleotide sequence of the mutant gene is disclosed in U.S. Pat. No. 4,769,061 to Comai, European patent application No. 0 333 033 to Kumada et al., and U.S. Pat. No. 4,975,374 to Goodman et al., disclosing nucleotide sequences of glutamine synthetase genes which confer resistance to herbicides such as L-phosphinothricin. The nucleotide sequence of a PAT gene is provided in European application No. 0 242 246 to Leemans et al. Also DeGreef et al., Bio/Technology 7:61 (1989), describes the production of transgenic plants that express chimeric bar genes coding for PAT activity. Exemplary of genes conferring resistance to phenoxy proprionic acids and cyclohexones, including sethoxydim and haloxyfop, are the Acc1-S1, Acc1-S2 and Acc1-S3 genes described by Marshall et al., Theon. Appl. Genet. 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893.

Other herbicides can inhibit photosynthesis, including triazine (psbA and ls+ genes) or benzonitrile (nitrilase gene). Przibila et al., Plant Cell 3:169 (1991), describes the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

For purposes of the present invention, selectable marker genes include, but are not limited to genes encoding: neomycin phosphotransferase II (Fraley et al. (1986) CRC Critical Reviews in Plant Science, 4:1-25); cyanamide hydratase (Maier-Greiner et al. (1991) Proc. Natl. Acad. Sci. USA, 88:4250-4264); aspartate kinase; dihydrodipicolinate synthase (Perl et al. (1993) Bio/Technology, 11:715-718); tryptophan decarboxylase (Goddijn et al. (1993) Plant Mol. Bio., 22:907-912); dihydrodipicolinate synthase and desensitized aspartade kinase (Perl et al. (1993) Bio/Technology, 11:715-718); bar gene (Toki et al. (1992) Plant Physiol., 100:1503-1507 and Meagher et al. (1996) and Crop Sci., 36:1367); tryptophan decarboxylase (Goddijn et al. (1993) Plant Mol. Biol., 22:907-912); neomycin phosphotransferase (NEO) (Southern et al. (1982) J. Mol. Appl. Gen., 1:327; hygromycin phosphotransferase (HPT or HYG) (Shimizu et al. (1986) Mol. Cell Biol., 6:1074); dihydrofolate reductase (DHFR) (Kwok et al. (1986) PNAS USA 4552); phosphinothricin acetyltransferase (DeBlock et al. (1987) EMBO J., 6:2513); 2,2-dichloropropionic acid dehalogenase (Buchanan-Wollatron et al. (1989) J. Cell. Biochem. 13D:330); acetohydroxyacid synthase (Anderson et al., U.S. Pat. No. 4,761,373; Haughn et al. (1988) Mol. Gen. Genet. 221:266); 5-enolpyruvyl-shikimate-phosphate synthase (aroA) (Comai et al. (1985) Nature 317:741); haloarylnitrilase (Stalker et al., published PCT application WO87/04181); acetyl-coenzyme A carboxylase (Parker et al. (1990) Plant Physiol. 92:1220); dihydropteroate synthase (sul I) (Guerineau et al. (1990) Plant Mol. Biol. 15:127); and 32 kD photosystem II polypeptide (psbA) (Hirschberg et al. (1983) Science, 222:1346).

Also included are genes encoding resistance to: chloramphenicol (Herrera-Estrella et al. (1983) EMBO J., 2:987-992); methotrexate (Herrera-Estrella et al. (1983) Nature, 303:209-213; Meijer et al. (1991) Plant Mol Bio., 16:807-820 (1991); hygromycin (Waldron et al. (1985) Plant Mol. Biol., 5:103-108; Zhijian et al. (1995) Plant Science, 108:219-227 and Meijer et al. (1991) Plant Mol. Bio. 16:807-820); streptomycin (Jones et al. (1987) Mol. Gen. Genet., 210:86-91);

spectinomycin (Bretagne-Sagnard et al. (1996) Transgenic Res., 5:131-137); bleomycin (Hille et al. (1986) Plant Mol. Biol., 7:171-176); sulfonamide (Guerineau et al. (1990) Plant Mol. Bio., 15:127-136); bromoxynil (Stalker et al. (1988) Science, 242:419-423); 2,4-D (Streber et al. (1989) Bio/Technology, 7:811-816); glyphosate (Shaw et al. (1986) Science, 233:478-481); and phosphinothricin (DeBlock et al. (1987) EMBO J., 6:2513-2518). All references recited in the disclosure are hereby incorporated by reference in their entireties unless stated otherwise.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency. Methods for synthetic optimization of genes are available in the art. In fact, several genes have been optimized to increase expression of the gene product in plants.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) Proc. Natl. Acad. Sci. USA, 88:3324-3328; and Murray et al. (1989) Nucleic Acids Research, 17: 477-498; U.S. Pat. No. 5,380,831; and U.S. Pat. No. 5,436,391, herein incorporated by reference. In this manner, the nucleotide sequences can be optimized for expression in any plant. It is recognized that all or any part of the gene sequence may be optimized or synthetic. That is, fully optimized or partially optimized sequences may also be used.

Genes that Confer Resistance to an Herbicide:

A. Resistance/tolerance of acetohydroxyacid synthase (AHAS) and acetolactate synthase (ALS) against herbicides imidazolinone or sulfonylurea. Genes and mutants for AHAS and mutants have been disclosed in U.S. Pat. Nos. 4,761,373, 5,304,732, 5,331,107, 5,853,973, and 5,928,937. Genes and mutants for ALS have been disclosed in U.S. Pat. Nos. 5,013,659 and 5,141,870.

B. Resistance/tolerance genes of acetyl coemzyme A carboxylase (ACCas) against herbicides cyclohexanediones and/or aryloxyphenoxypropanoic acid (including Haloxyfop, Diclofop, Fenoxyprop, Fluazifop, Quizalopfop) have been described in U.S. Pat. Nos. 5,162,602 and 5,498,544.

C. Genes for glyphosate resistance/tolerance. Gene of 5-enolpyruvyl-3-phosphoshikimate synthase (ES3P synthase) has been described in U.S. Pat. No. 4,769,601. Genes of 5-enolpyruvylshikimate-3-phosphate synthase (EPSPS) and mutants have been described in U.S. Pat. Nos. 4,940,835, 5,188,642, 5,310,667, 5,633,435, 5,633,448, and 6,566,587.

D. Genes for glufosinate (bialaphos, phosphinothricin (PPT)) resistance/tolerance. Gene for phosphinothricin acetyltransferase (Pat) has been described in U.S. Pat. Nos. 5,273,894, 5,276,268, and 5,550,318; and gene for bialaphos resistance gene (Bar) has been described in U.S. Pat. No. 5,561,236 and U.S. Pat. Nos. 5,646,024, 5,648,477, and 7,112,665. Gene for glutamine synthetase (GS) has been described in U.S. Pat. No. 4,975,372 and European patent application EP 0333033 A1.

E. Resistance/tolerance genes of hydroxy phenyl pyruvate dioxygenase (HPPD) against herbicides isoxazole, diketonitriles, and/or triketones including sulcotrione and mesotrione have been described in U.S. Pat. Nos. 6,268,549 and 6,069,115.

F. Genes for 2,4-D resistance/tolerance. Gene of 2,4-D-monooxygenase has been described in U.S. Pat. Nos. 6,100,446 and 6,153,401. Additional genes for 2,4-D resistance/tolerance are disclosed in US 2009/0093366 and WO 2007/053482.

G. Gene of imidazoleglycerol phosphate dehydratase (IGPD) against herbicides imidazole and/or triazole has been described in U.S. Pat. No. 5,541,310. Genes of Dicamba degrading enzymes (oxygenase, ferredoxin, and reductase) against herbicide Dicamba have been disclosed in U.S. Pat. Nos. 7,022,896 and 7,105,724.

H. Genes for herbicides that inhibit photosynthesis, including triazine (psbA and ls+ genes) or a benzonitrile (nitrilase gene). See e.g., Przibila et al., Plant Cell 3:169 (1991) disclosing transformation of *Chlamydomonas* with plasmids encoding mutant psbA genes. Nucleotide sequences for nitrilase genes are disclosed in U.S. Pat. No. 4,810,648 and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

Provided are nucleic acid molecules comprising a synthetic nucleotide sequence that may function as a bidirectional promoter. In some embodiments, a synthetic bidirectional promoter may be operably linked to one or two nucleotide sequence(s) of interest. For example, a synthetic bidirectional promoter may be operably linked to one or two nucleotide sequence(s) of interest (e.g., two genes, one on each end of the promoter), so as to regulate transcription of at least one (e.g., one or both) of the nucleotide sequence(s) of interest. By incorporating a URS from a promoter in the synthetic bidirectional promoter, particular expression and regulatory patterns (e.g., such as are exhibited by genes under the control of the native promoter) may be achieved with regard to a nucleotide sequence of interest that is operably linked to the synthetic bidirectional promoter.

Some embodiments of the invention are exemplified herein by incorporating a minimal core promoter element from a unidirectional maize ubiquitin-1 gene (ZmUbi1) promoter into a molecular context different from that of the native promoter to engineer a synthetic bidirectional promoter. This minimal core promoter element is referred to herein as "minUbi1P," and is approximately 200 nt in length. Sequencing and analysis of minUbi1P elements from multiple *Zea* species and *Z. mays* genotypes has revealed that functional minUbi1P elements are highly conserved, such that a minUbi1P element may preserve its function as an initiator of transcription if it shares, for example, at least about 75%; at least about 80%; at least about 85%; at least about 90%; at least about 91%; at least about 92%; at least about 93%; at least about 94%; at least about 95%; at least about 96%; at least about 97%; at least about 98%; at least about 99%; and/or at least about 100% sequence identity to the minUbi1P element of SEQ ID NO:1. Characteristics of minUbi1P elements that may be useful in some embodiments of the invention may include, for example and without limitation, the aforementioned high conservation of nucleotide sequence; the presence of at least one TATA box; and/or the presence of at least one (e.g., two) heat shock consensus element(s). In particular minUbi1P elements, more than one heat shock consensus elements may be overlapping within the minUbi1P sequence.

The process of incorporating a minUbi1P element into a molecular context different from that of a native promoter to engineer a synthetic bidirectional promoter may comprise reversing the orientation of the minUbi1P element in a nucleic acid with respect to the remaining sequence of the promoter, including its native minimal core promoter. Thus, a synthetic bidirectional promoter may comprise a first minUbi1P element incorporated 5' of a second minimal core promoter element (e.g., a second minUbi1P element) in the promoter in the reverse orientation, such that it may be operably linked to a nucleotide sequence of interest located 5' of the first minUbi1P element. For example, the first minUbi1P element may be incorporated at the 5' end of a ZmUbi1 promoter in reverse orientation.

A synthetic bidirectional Ubi1 promoter may also comprise one or more additional sequence elements in addition to at least one minUbi1P element. In some embodiments, a synthetic bidirectional Ubi1 promoter may comprise a promoter URS; an exon (e.g., a leader or signal peptide); an intron; a spacer sequence; and or combinations of one or more of any of the foregoing. For example and without limitation, a synthetic bidirectional Ubi1 promoter may comprise a URS sequence from a Ubi1 promoter (e.g., the maize Ubi1 promoter); an exon encoding a leader peptide from a Ubi1 gene; an intron from a Ubi1 gene; and combinations of these.

In some of those examples comprising a synthetic bidirectional Ubi1 promoter comprising a promoter URS, the URS may be selected to confer particular regulatory properties on the synthetic promoter. Known promoters vary widely in the type of control they exert on operably linked genes (e.g., environmental responses, developmental cues, and spatial information), and a URS incorporated into a heterologous promoter typically maintains the type of control the URS exhibits with regard to its native promoter and operably linked gene(s). Langridge et al. (1989), supra. Examples of eukaryotic promoters that have been characterized and may contain a URS comprised within a synthetic bidirectional Ubi1 promoter according to some embodiments include, for example and without limitation: those promoters described in U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. No. 6,433,252 (maize L3 oleosin promoter); U.S. Pat. No. 6,429,357 (rice actin 2 promoter, and rice actin 2 intron); U.S. Pat. No. 5,837,848 (root-specific promoter); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter).

Additional exemplary prokaryotic promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); CaMV35S (U.S. Pat. Nos. 5,322,938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7), and the like.

In some embodiments, a synthetic bidirectional Ubi1 promoter may further comprise an exon in addition to minUbi1P element(s). For example, it may be desirable in particular embodiments to target or traffic a polypeptide encoded by a nucleotide sequence of interest operably linked to the promoter to a particular subcellular location and/or compartment. In these and other embodiments, a coding sequence (exon) may be incorporated into a nucleic acid molecule between the minUbi1P element and a nucleotide sequence encoding a polypeptide. These elements may be arranged according to the discretion of the skilled practitioner such that the synthetic bidirectional Ubi1 promoter promotes the expression of a polypeptide (or one or both of two polypeptide-encoding sequences that are operably linked to the promoter) comprising the peptide encoded by the incorporated coding sequence in a functional relationship with the remainder of the polypeptide. In particular examples, an exon encoding a leader, transit, or signal peptide (e.g., the Ubi1 leader peptide) may be incorporated.

Peptides that may be encoded by an exon incorporated into a synthetic bidirectional Ubi1 promoter include, for example and without limitation: a Ubiquitin (e.g., Ubi1) leader exon; and a chloroplast transit peptide (CTP) (e.g., the *A. thaliana* EPSPS CTP (Klee et al. (1987) Mol. Gen. Genet. 210:437-42), and the *Petunia hybrida* EPSPS CTP (della-Cioppa et al. (1986) Proc. Natl. Acad. Sci. USA 83:6873-7)), as exemplified for the chloroplast targeting of dicamba monooxygenase (DMO) in International PCT Publication No. WO 2008/105890.

Introns may also be incorporated in a synthetic bidirectional Ubi1 promoter in some embodiments of the invention, for example, between a minUbi1P element and a nucleotide sequence of interest that is operably linked to the promoter. In some examples, an intron incorporated into a synthetic bidirectional Ubi1 promoter may be, without limitation, a 5' UTR that functions as a translation leader sequence that is present in a fully processed mRNA upstream of the translation start sequence (such a translation leader sequence may affect processing of a primary transcript to mRNA, mRNA stability, and/or translation efficiency). Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtu.nos (GenBank Accession No. V00087; and Bevan et al. (1983) Nature 304:184-7).

Additional sequences that may optionally be incorporated into a synthetic bidirectional Ubi1 promoter include, for example and without limitation: 3' non-translated sequences; 3' transcription termination regions; and polyadenylation regions. These are genetic elements located downstream of a nucleotide sequence of interest (e.g., a sequence of interest that is operably linked to a synthetic bidirectional Ubi1 promoter), and include polynucleotides that provide polyadenylation signal, and/or other regulatory signals capable of affecting transcription, mRNA processing, or gene expression. A polyadenylation signal may function in plants to cause the addition of polyadenylate nucleotides to the 3' end of a mRNA precursor. The polyadenylation sequence may be derived from the natural gene, from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.R-bcS2-E9; Coruzzi et al. (1984) EMBO J. 3:1671-9) and AGR-tu.nos (GenBank Accession No. E01312).

In some embodiments, a synthetic bidirectional Ubi1 promoter comprises one or more nucleotide sequences that facilitate targeting of a nucleic acid comprising the promoter to a particular locus in the genome of a target organism. For example, one or more sequences may be included that are homologous to segments of genomic DNA sequence in the host (e.g., rare or unique genomic DNA sequences). In some examples, these homologous sequences may guide recombination and integration of a nucleic acid comprising a synthetic bidirectional Ubi1 promoter at the site of the homologous DNA in the host genome. In particular examples, a synthetic bidirectional Ubi1 promoter comprises one or more nucleotide sequences that facilitate targeting of a nucleic acid comprising the promoter to a rare or unique location in a host genome utilizing engineered nuclease enzymes that recognize sequence at the rare or unique location and facilitate integration at that rare or unique location. Such a targeted integration system employing zinc-finger endonucleases as the nuclease enzyme is described in U.S. patent application Ser. No. 13/011,735, the contents of the entirety of which are incorporated herein by this reference.

Nucleic acids comprising a synthetic bidirectional Ubi1 promoter may be produced using any technique known in the art, including for example and without limitation: RCA; PCR amplification; RT-PCR amplification; OLA; and SNuPE. These and other equivalent techniques are well known to those of skill in the art, and are further described in detail in, for example and without limitation: Sambrook et al. Molecular Cloning: A Laboratory Manual, 3$^{rd}$ Ed., Cold Spring Harbor Laboratory, 2001; and Ausubel et al. Current Protocols in Molecular Biology, John Wiley & Sons, 1998. All of the references cited above, including both of the foregoing manuals, are incorporated herein by this reference in their entirety, including any drawings, figures, and/or tables provided therein.

Delivery and/or transformation: The present disclosure also provides methods for transforming a cell with a nucleic acid molecule comprising a synthetic bidirectional Ubi1 promoter. Any of the large number of techniques known in the art for introduction of nucleic acid molecules into plants may be used to transform a plant with a nucleic acid molecule comprising a synthetic bidirectional Ubi1 promoter according to some embodiments, for example, to introduce one or more synthetic bidirectional Ubi1 promoters into the host plant genome, and/or to further introduce one or more nucleic acid molecule(s) of interest operably linked to the promoter.

Suitable methods for transformation of plants include any method by which DNA can be introduced into a cell, for example and without limitation: electroporation (see, e.g., U.S. Pat. No. 5,384,253); microprojectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184). Through the application of techniques such as the foregoing, the cells of virtually any plant species may be stably transformed, and these cells may be developed into transgenic plants by techniques known to those of skill in the art. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soya are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, the transformed cell is generally identified for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of the desired nucleic acid molecule comprising a synthetic bidirectional Ubi1 promoter in the regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

Some embodiments of the present invention also provide cells comprising a synthetic bidirectional Ubi1 promoter, for example, as may be present in a nucleic acid construct. In particular examples, a synthetic bidirectional Ubi1 promoter according to some embodiments may be utilized as a regulatory sequence to regulate the expression of transgenes in plant cells and plants. In some such examples, the use of a synthetic bidirectional Ubi1 promoter operably linked to a nucleotide sequence of interest (e.g., a transgene) may reduce the number of homologous promoters needed to regulate expression of a given number of nucleotide sequences of interest, and/or reduce the size of the nucleic acid construct(s) required to introduce a given number of nucleotide sequences of interest. Furthermore, use of a synthetic bidirectional Ubi1 promoter may allow co-expression of two operably linked nucleotide sequence of interest under the same conditions (i.e., the conditions under which the promoter is active). Such examples may be particularly useful, e.g., when the two operably linked nucleotide sequences of interest each contribute to a single trait in a transgenic host comprising the nucleotide sequences of interest, and co-expression of the nucleotide sequences of interest advantageously impacts expression of the trait in the transgenic host.

In some embodiments, a transgenic plant comprising one or more synthetic bidirectional Ubi1 promoter(s) and/or nucleotide sequence(s) of interest may have one or more desirable traits conferred (e.g., introduced, enhanced, or contributed to) by expression of the nucleotide sequence(s) of interest in the plant. Such traits may include, for example and without limitation: resistance to insects, other pests, and disease-causing agents; tolerances to herbicides; enhanced stability, yield, or shelf-life; environmental tolerances; pharmaceutical production; industrial product production; and nutritional enhancements. In some examples, a desirable trait may be conferred by transformation of a plant with a nucleic acid molecule comprising a synthetic bidirectional Ubi1 promoter operably linked to a nucleotide sequence of interest. In some examples, a desirable trait may be conferred to a plant produced as a progeny plant via breeding, which trait may be conferred by one or more nucleotide sequences of interest operably linked to a synthetic bidirectional Ubi1 promoter that is/are passed to the plant from a parent plant comprising a nucleotide sequence of interest operably linked to a synthetic bidirectional Ubi1 promoter.

A transgenic plant according to some embodiments may be any plant capable of being transformed with a nucleic acid molecule of the invention, or of being bred with a plant transformed with a nucleic acid molecule of the invention. Accordingly, the plant may be a dicot or monocot. Non-limiting examples of dicotyledonous plants for use in some examples include: alfalfa; beans; broccoli; canola, cabbage; carrot; cauliflower; celery; Chinese cabbage; cotton; cucumber; eggplant; lettuce; melon; pea; pepper; peanut; potato; pumpkin; radish; rapeseed; spinach; soybean; squash; sugarbeet; sunflower; tobacco; tomato; and watermelon. Non-limiting examples of monocotyledonous plants for use in some examples include: corn; onion; rice; sorghum; wheat; rye; millet; sugarcane; oat; triticale; switchgrass; and turfgrass.

In some embodiments, a transgenic plant may be used or cultivated in any manner, wherein presence a synthetic bidirectional Ubi1 promoter and/or operably linked nucleotide sequence of interest is desirable. Accordingly, such transgenic plants may be engineered to, inter alia, have one or more desired traits, by being transformed with nucleic acid molecules according to the invention, and may be cropped and/or cultivated by any method known to those of skill in the art.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

The following examples are provided to illustrate certain particular features and/or embodiments. The examples should not be construed to limit the disclosure to the particular features or embodiments exemplified.

EXAMPLES

Example 1

Transformation and Expression

Transformation of *Agrobacterium tumefaciens*: The pDAB108706 binary vector was transformed into *Agrobacterium tumefaciens* strain DAt13192 ternary (U.S. Prov. Pat. No. 61/368,965). Bacterial colonies were isolated and binary plasmid DNA was isolated and confirmed via restriction enzyme digestion.

Corn Transformation: Ear Sterilization and Embryo Isolation. To obtain maize immature embryos, plants of *Zea mays* (c.v. B104) were grown in the greenhouse and self or sib-pollinated to produce ears. The ears were harvested approximately 9-12 days post-pollination. On the day of the experiment, ears were surface-sterilized by immersion in a 20% solution of household bleach, which contained 5% sodium hypochlorite, and shaken for 20-30 minutes, followed by three rinses in sterile water. After sterilization, immature zygotic embryos (1.5-2.2 mm) were aseptically dissected from each ear and randomly distributed into micro-centrifuge tubes containing liquid infection media (LS Basal Medium, 4.43 gm/L; N6 Vitamin Solution [1000×], 1.00 mL/L; L-proline, 700.0 mg/L; sucrose, 68.5 gm/L; glucose, 36.0 gm/L; 2,4-D, 1.50 mg/L. For a given set of experiments, pooled embryos from 2-3 ears were used for each treatment.

*Agrobacterium* Culture Initiation: Glycerol stocks of *Agrobacterium* containing the binary vectors described above were streaked on AB minimal medium plates containing appropriate antibiotics and were grown at 20° C. for 3-4 days. A single colony was picked and streaked onto YEP plates containing the same antibiotics and was incubated at 28° C. for 1-2 days.

*Agrobacterium* Culture and Co-cultivation: On the day of the experiment, *Agrobacterium* colonies were taken from the YEP plate, suspended in 10 mL of infection medium in a 50 mL disposable tube, and the cell density was adjusted to OD600=0.2-0.4 nm using a spectrophotometer. The *Agrobacterium* cultures were placed on a rotary shaker at 100 rpm, room temperature, while embryo dissection was performed. Immature zygotic embryos between 1.5-2.2 mm in size were isolated from the sterilized maize kernels and placed in 1 mL of the infection medium and washed once in the same medium. The *Agrobacterium* suspension (2 mL) was added to each tube and the tubes were inverted for about 20 times then shaken for 10-15 minutes. The embryos were transferred onto co-cultivation media (MS Salts, 4.33 gm/L; L-proline, 700.0 mg/L; myo-inositol, 100.0 mg/L; casein enzymatic hydrolysate 100.0 mg/L; Dicamba—3.30 mg/L; sucrose, 30.0 gm/L; Gelzan™, 3.00 gm/L; modified MS-Vitamin [1000×], 1.00 ml/L, AgNo$_3$, 15.0 mg/L; Acetosyringone, 100 μM), oriented with the scutellum facing up, and incubated for 3-4 days in the light at 25° C.

GUS and YFP/Phiyfp Transient expression: Transient YFP/Phiyfp and GUS expression was observed in transformed embryos and after 3 days of co-cultivation with *Agrobacterium*. The embryos were observed under a stereomicroscope (Leica Microsystems, Buffalo Grove, Ill.) using YFP filter and 500 nm light source. Embryos showing YFP/Phiyfp expression were selected for GUS histochemical assay. GUS staining solution was prepared as described in Maniatis et al. (1989) and embryos were incubated in 1 mL solution for 24 hours at 37° C. The embryos were observed for GUS transient expression under the microscope.

Callus Selection and Regeneration of Putative Events: Following the co-cultivation period, embryos were transferred to resting media (MS salts, 4.33 gm/L; L-proline, 700.0 mg/L; myo-inositol, 100.0 mg/L; MES [(2-(n-morpholino)-ethanesulfonic acid), free acid] 500.0 mg/L; casein enzymatic hydrolysate 100.0 mg/L; Dicamba, 3.30 mg/L; sucrose, 30.0 gm/L; Gelzan 2.30 gm/L; modified MS-Vitamin [1000×], 1.00 ml/L; AgNo$_3$, 15.0 mg/L; Carbenicillin, 250.0 mg/L) without selective agent and incubated in 24 hours light with light intensity of 50 μmol m$^{-2}$s$^{-1}$ for 7 days at 28° C. Embryos were transferred onto selection 1 media (MS salts, 4.33 gm/L; L-proline, 700.0 mg/L; myo-inositol, 100.0 mg/L; MES [(2-(n-morpholino)-ethanesulfonic acid), free acid] 500.0 mg/L; casein enzymatic hydrolysate 100.0 mg/L; Dicamba, 3.30 mg/L; sucrose, 30.0 gm/L; Gelzan™ 2.30 gm/L; modified MS-Vitamin [1000×], 1.00 ml/L; AgNo$_3$, 15.0 mg/L; Carbenicillin, 250.0 mg/L) containing 100 nM haloxyfop and incubated in 24 hours light with light intensity of 50 μmol m$^{-2}$s$^{-1}$ for 7 days at 28° C.

Embryos with proliferating embryogenic calli were transferred onto selection 2 media (MS salts, 4.33 gm/L; myo-inositol, 100.0 mg/L; L-proline, 700.0 mg/L; MES [(2-(n-morpholino)-ethanesulfonic acid), free acid] 500.0 mg/L; casein enzymatic hydrolysate 100.0 mg/L; Dicamba, 3.30 mg/L; sucrose, 30.0 gm/L; Gelzan™ 2.30 gm/L; modified MS-Vitamin [1000×], 1.00 ml/L; AgNo$_3$, 15.0 mg/L; Carbenicillin, 250.0 mg/L) containing 500 nM haloxyfop and were incubated in 24 hours light with light intensity of 50 μmol m$^{-2}$s$^{-1}$ for another 14 days at 28° C. This selection step allowed transgenic callus to further proliferate and differentiate. The callus selection period lasted for three weeks. Proliferating, embryogenic calli were transferred onto regeneration 1 media (MS salts, 4.33 gm/L; myo-inositol, 100.0 mg/L; L-proline, 350.0 mg/L; MES [(2-(n-morpholino)-ethanesulfonic acid), free acid] 250.0 mg/L; casein enzymatic hydrolysate 50.0 mg/L; NAA 0.500 mg/L; ABA 2.50 mg/L; BA 1.00 mg/L; sucrose, 45.0 gm/L; Gelzan™ 2.50 gm/L; modified MS-Vitamin [1000×], 1.00 ml/L; AgNo$_3$, 1.00 mg/L; Carbenicillin, 250.0 mg/L) containing 500 nM haloxyfop and cultured in 24 hours light with light intensity of 50 μmol m$^{-2}$s$^{-1}$ for 7 days at 28° C. Embryogenic calli with shoot/buds were transferred onto regeneration 2 media (MS salts, 4.33 gm/L; modified MS-Vitamin [1000×], 1.00 ml/L; myo-inositol, 100.0 mg/L; sucrose, 60.0 gm/L; Gellan Gum G434™ 3.00 gm/L; Carbenicillin, 250.0 mg/L) containing 500 nM haloxyfop. The cultures were incubated under 24 hours light with light intensity of 50 μmol m$^{-2}$s$^{-1}$ for 7-10 days at 28° C. Small shoots with primary roots were transferred to shoot elongation and rooting media (MS salts, 4.33 gm/L; modified MS-Vitamin [1000×], 1.00 ml/L; myo-inositol, 100.0 mg/L; sucrose, 60.0 gm/L; Gellan Gum G434™ 3.00 gm/L; Carbenicillin, 250.0 mg/L) in MAGENTA™ boxes (Sigma-Aldrich, St. Louis, Mo.), and were incubated under 16/8 hours light/dark for 7 days at 28° C. Putative transgenic plantlets were analyzed for transgene copy number and transferred to the greenhouse.

Example 2

Construction of Synthetic Bidirectional Ubi1 Promoter and pDAB108706 Vector

Figure 1:
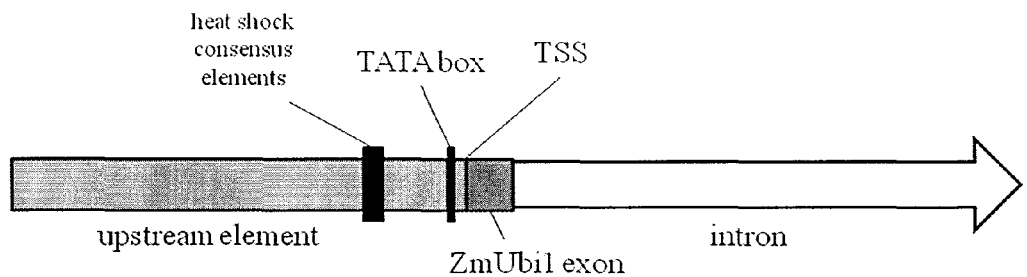
Figure 2:
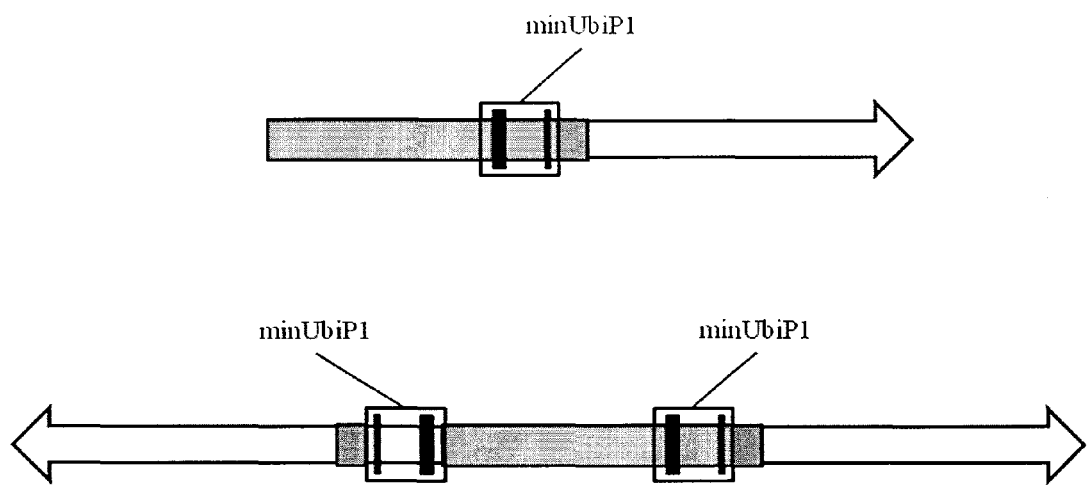
FIG. 2 shows an exemplary embodiment of the synthetic Ubi1 bidirectional promoter provided, which includes a minUbi1P minimal core element cloned upstream (in the reverse complementary orientation) of a ZmUbi1 promoter.
Figure 5:
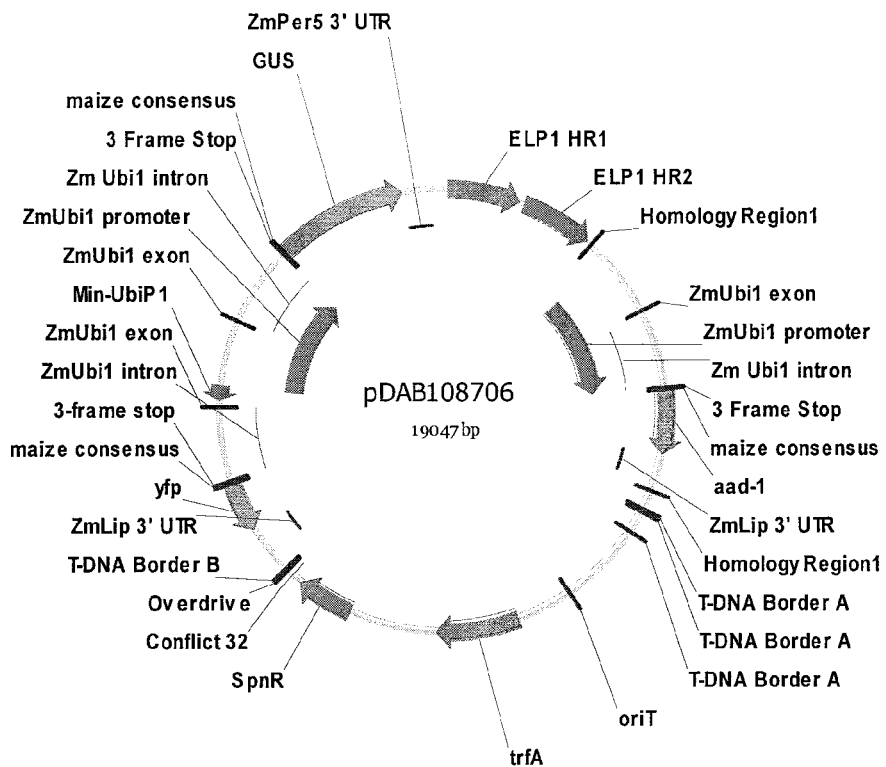
FIG. 5 shows a representative plasmid map of pDAB108706.
Figure 6:
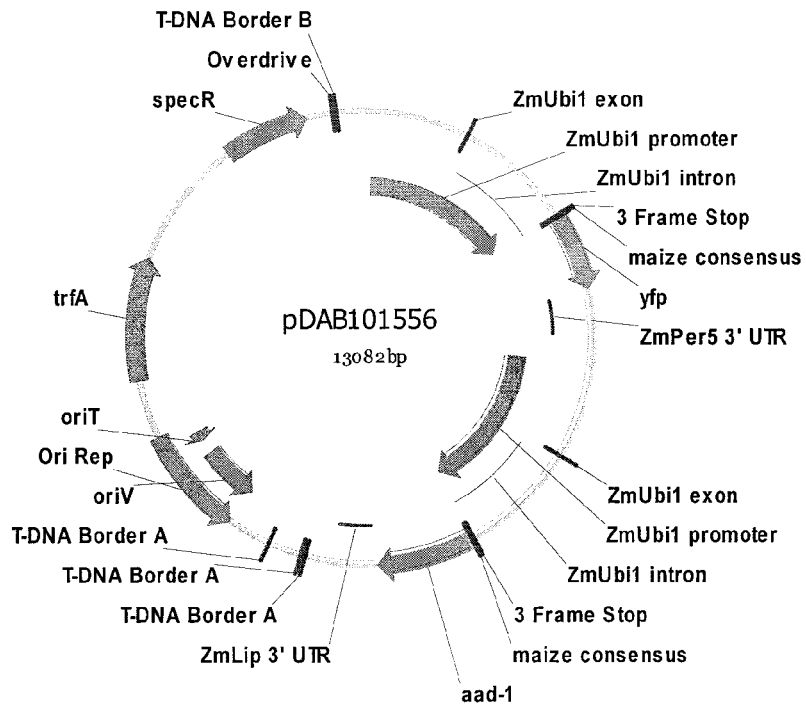
FIG. 6 shows a representative plasmid map of pDAB101556.

An exemplary schematic drawing of the maize Ubiquitin-1 promoter (Ubi1) is shown in FIG. 1. An Ubi1 promoter is cloned from maize. A plasmid containing the Ubi1 promoter was PCR amplified using a high-fidelity PCR amplification system. An approximately 200 nt region of the maize Ubi1 promoter was identified as a *Zea mays* Ubi1 minimal core promoter (minUbi1P) (SEQ ID NO: 1). The minUbi1P of SEQ ID NO: 1 was then added to a polynucleotide (SEQ ID NO: 2) comprising a *Zea mays* Ubiquitin-1 exon (ZmUbi1 exon) and *Zea mays* Ubiquitin-1 intron (ZmUbi1 intron) using cloning methods commonly known in the art to produce the polynucleotide of SEQ ID NO: 3. The resulting polynucleotide was then cloned upstream in reverse orientation of a nucleic acid comprising the maize Ubi1 promoter (including the Ubi1 upstream regulatory sequence (URS)); SEQ ID NO: 4) to produce the synthetic bidirectional Ubi1 promoter of SEQ ID NO: 5 (see FIG. 5 for example).

Figure 3:
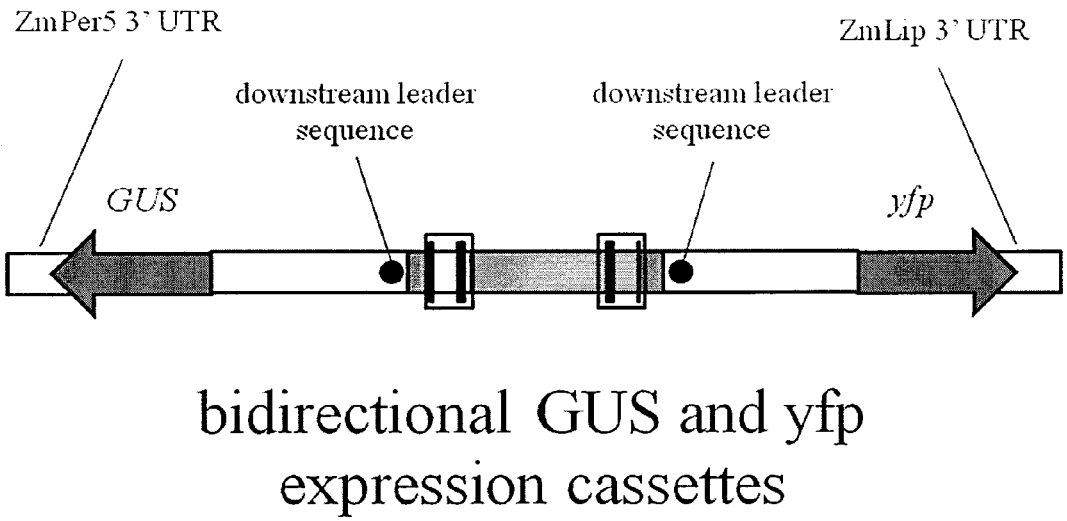
FIG. 3 shows an exemplary schematic drawing of yfp and GUS gene expression cassettes, which are each operably linked to a synthetic Ubi1 bidirectional promoter.
Figure 4:
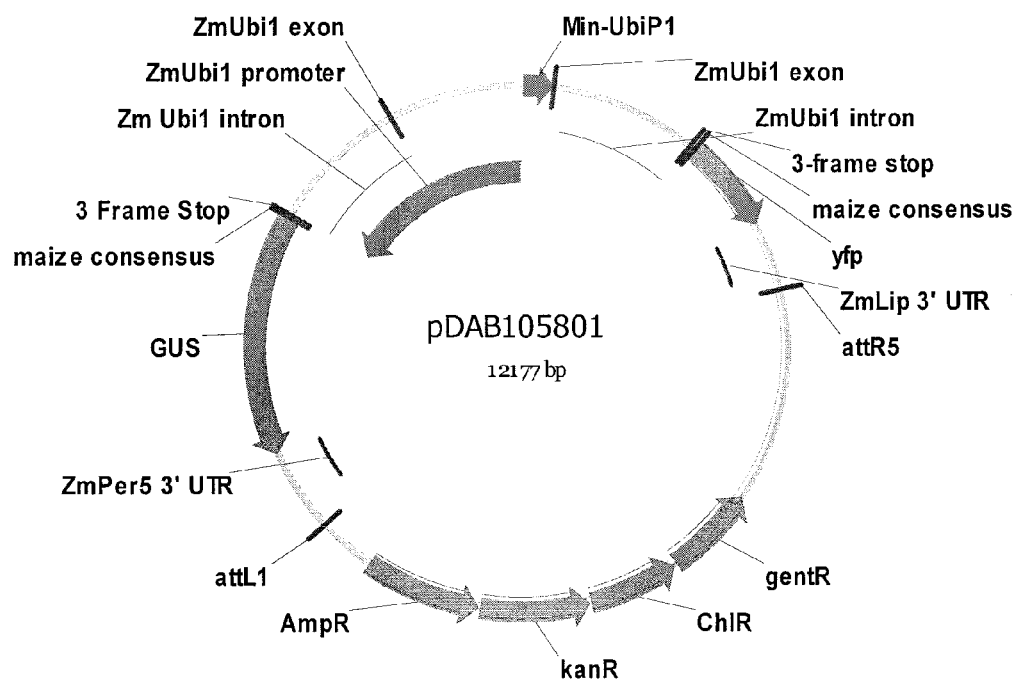
FIG. 4 shows a representative plasmid map of pDAB105801.

Reporter gene coding sequences were cloned downstream of each end of the synthetic bidirectional Ubi1 promoter. A yellow fluorescence protein (yfp) coding sequence was inserted downstream of the polynucleotide fragment that contains the minUbi1P, ZmUbi1 exon, and ZmUbi1 intron promoter elements. In addition, a downstream leader sequence containing a 3-frame stop polynucleotide sequence and the maize consensus polynucleotide (Kozak) sequence was added to the minUbi1P, ZmUbi1, exon and ZmUbi1 intron promoter elements fragment. A uidA (GUS) coding sequence was inserted downstream of the synthetic bidirectional Ubi1 promoter in reverse orientation with respect to the yfp sequence (SEQ ID NO: 6; see FIG. 3 for example). The resulting polynucleotide comprising the synthetic bidirectional Ubi1 promoter operably linked to the yfp and GUS genes was cloned into plasmid pDAB105801.

A binary vector that contained the GUS and yfp gene expression cassettes from plasmid pDAB105801 was completed via a GATEWAY™ L-R CLONASE™ reaction (Invitrogen, Carlsbad, Calif.). The resulting vector, pDAB108706, contained the GUS, yfp, and aad-1 gene expression cassettes within the T-strand region (see FIG. 5 for example).

Example 3

Transient Expression of Genes Operably-Linked to a Synthetic Bidirectional Ubiquitin 1 Promoter Representative examples of YFP and GUS transient expression in *Zea mays* embryos transformed with pDAB108706 were imaged. Both sides of the bidirectional ZmUbi1 promoter drove robust expression of the operably linked yfp and GUS coding sequences. The YFP expression levels were comparable to the GUS expression levels. These observations confirmed that both sides of the bidirectional ZmUbi1 promoter are biologically functional. Moreover, the minUbi1P element of the synthetic bidirectional Ubi1 promoter expressed YFP at similar expression levels as compared to *Zea mays* callus transformed with a binary plasmid (pDAB101556) that contained a unidirectional ZmUbi1 promoter driving the yfp coding sequence. Expression of YFP or GUS was not detected in negative control immature embryos that were not transformed with a binary construct, and did not contain the yfp or GUS coding sequences.

Example 4

Stable Expression of Genes Operably-Linked to a Synthetic Bidirectional Ubiquitin 1 Promoter Images of *Zea mays* callus cells that were stably transformed with the pDAB108706 binary vector, which contained the yfp coding sequence, were observed. These cells were obtained from *Z. mays* embryos that had been propagating on selection 2 medium. The bidirectional ZmUbi1 promoter drove robust expression of the yfp coding sequences. These results confirmed that the Min-UbiP1 minimal promoter element of the bidirectional ZmUbi1 promoter is capable of expressing a reporter gene in stably-transformed *Z. mays* callus cells. The levels of expression of the YFP protein were similar as compared to YFP expression in *Z. mays* callus transformed with a control binary vector that contained the unidirectional ZmUbi1 promoter driving the yfp coding sequence (pDAB101556). Expression of YFP or GUS was not detected in the negative control callus that was not transformed with a binary construct and did not contain a yfp or GUS coding sequence.

Example 5

Transgene Copy Number Estimation Using Real Time TaqMan® PCR

*Zea mays* embryos were transformed with a binary vector containing a bidirectional ZmUbi1 promoter, pDAB108706, and other plants were transformed with a control binary vector, pDAB101556. The presence of yfp transgenes within the genome of both set of *Z. mays* plants was confirmed via a hydrolysis probe assay. Stably-transformed transgenic *Z. mays* plantlets that developed from the callus were obtained and analyzed to identify events that contained a low copy number (1-2 copies) of full-length T-strand inserts from the pDAB108706 binary vector and pDAB101556 control binary vector. Identified plantlets were advanced to the green house and grown.

The Roche Light Cycler480™ system was used to determine the transgene copy number for events that were transformed with the pDAB108706 binary vector, and for control events that were transformed with the pDAB101556 binary vector. The method utilized a biplex TaqMan® reaction that employs oligonucleotides specific to the yfp gene and to the endogenous *Z. mays* reference gene, invertase (Genbank Accession No: U16123.1), in a single assay. Copy number and zygosity were determined by measuring the intensity of yfp-specific fluorescence, relative to the invertase-specific fluorescence, as compared to known copy number standards.

In *Z. mays* transformed with the pDAB108706 binary vector, a yfp gene-specific DNA fragment was amplified with one TaqMan® primer/probe set containing a probe labeled with FAM fluorescent dye, and invertase was amplified with a second TaqMan® primer/probe set containing a probe labeled with HEX fluorescence (Table 2). The PCR reaction mixture was prepared as set forth in Table 3, and the gene-specific DNA fragments were amplified according to the conditions set forth in Table 4. Copy number and zygosity of the samples were determined by measuring the relative intensity of fluorescence specific for the reporter gene, yfp, to fluorescence specific for the reference gene, invertase, as compared to known copy number standards.

TABLE 2

Forward and reverse nucleotide primer and fluorescent probes (synthesized by Integrated DNA Technologies, Coralville, IA).

| Primer Name | SEQ ID NO: | Primer Sequence |
|---|---|---|
| YFP Forward Primer | SEQ ID NO: 7 | GATGCCTCAGTGGGAAAGG |
| YFP Reverse Primer | SEQ ID NO: 8 | CCATAGGTGAGAGTGGTGACAA |
| YFP Probe | — | ROCHE UPL Probe #125 CTTGGAGC Cat # 04693604001 (Roche, Indianapolis, IN) |

TABLE 2-continued

Forward and reverse nucleotide primer and fluorescent probes (synthesized by Integrated DNA Technologies, Coralville, IA).

| Primer Name | SEQ ID NO: | Primer Sequence |
|---|---|---|
| Invertase Forward Primer | SEQ ID NO: 9 | TGGCGGACGACGACTTGT |
| Invertase Reverse Primer | SEQ ID NO: 10 | AAAGTTTGGAGGCTGCCGT |
| Invertase Probe | SEQ ID NO: 11 | 5'HEX/CGAGCAGACCGCCGTGTACTTCTACC/3BHQ_1/3' |
| AAD1 Forward Primer | SEQ ID NO: 12 | TGTTCGGTTCCCTCTACCAA |
| AAD1 Reverse Primer | SEQ ID NO: 13 | CAACATCCATCACCTTGACTGA |
| AAD1 Probe | SEQ ID NO: 14 | CACAGAACCGTCGCTTCAGCAACA |

Standards were created by diluting the vector, pDAB108706, into *Z. mays* B104 genomic DNA (gDNA) to obtain standards with a known relationship of pDAB108706: gDNA. One and two copy dilutions of the pDAB108706 mixed with the *Z. mays* B104 gDNA standard were validated against a control *Z. mays* event that was known to be hemizygous, and a control *Z. mays* event that was known to be homozygous (*Z. mays* event 278; see PCT International Patent Publication No. WO 2011/022469 A2). A TaqMan® biplex assay that utilizes oligonucleotides specific to the AAD1 gene and oligonucleotides specific to the endogenous *Z. mays* reference gene, invertase, was performed by amplifying and detecting a gene-specific DNA fragment for AAD1 with one TaqMan® primer/probe set containing a probe labeled with FAM fluorescent dye, and by amplifying and detecting a gene-specific DNA fragment for invertase with a second TaqMan® primer/probe set containing a probe labeled with HEX fluorescence (Table 2). The AAD1 TaqMan® reaction mixture was prepared as set forth in Table 3 and the specific fragments were amplified according to the conditions set forth in Table 4.

TABLE 3

Taqman® PCR reaction mixture.

| Number of Reactions | µl each | Final Concentration |
|---|---|---|
| H$_2$O | 0.5 µL | — |
| PVP (10%) | 0.1 µL | 0.1% |
| ROCHE 2X Master Mix | 5 µL | 1X |
| Gene Forward Primer (10 µM) | 0.4 µL | 0.4 µM |
| Gene Reverse Primer (10 µM) | 0.4 µL | 0.4 µM |
| Gene Probe UPL#125 (5 µM) | 0.4 µL | 0.2 µM |
| Invertase Forward Primer (10 µM) | 0.4 µL | 0.4 µM |
| Invertase Reverse Primer (10 µM) | 0.4 µL | 0.4 µM |
| Invertase Probe (5 µM) | 0.4 µL | 0.2 µM |
| DNA Template | 2.0 µL | — |
| Total reaction volume | 10 µL | — |

The level of fluorescence that was generated for each reaction was analyzed using the Roche LightCycler 480™ Thermocycler according to the manufacturer's directions. The FAM fluorescent moiety was excited at an optical density of 465/510 nm, and the HEX fluorescent moiety was excited at an optical density of 533/580 nm. The copy number was determined by comparison of Target/Reference values for unknown samples (output by the LightCycler 480™) to Target/Reference values of four known copy number standards (Null, 1-Copy (hemi), 2-Copy (homo) and 4-Copy).

TABLE 4

Thermocycler conditions for PCR amplification.

| PCR Steps | Temp (° C.) | Time | No. of cycles |
|---|---|---|---|
| Step-1 | 95 | 10 minutes | 1 |
| Step-2 | 95 | 10 seconds | 40 |
|  | 59 | 35 seconds |  |
|  | 72 | 1 second |  |
| Step-3 | 40 | 10 seconds | 1 |

Results from the transgene copy number analysis of transgenic plants obtained via transformation with a bidirectional ZmUbi1 promoter construct (pDAB108706), and of transgenic plants obtained via transformation with a control unidirectional ZmUbi1 promoter YFP construct (pDAB101556) is shown in Table 5. Only plants with 1-2 copies of the yfp transgene were transferred to the greenhouse for further expression analyses.

TABLE 5

Transgene copy number estimation of the transgenic plants obtained from bidirectional promoter construct and control construct.

| Construct | Number of Embryos Transformed | Number of Positive Events | 1-2 Copies of yfp |
|---|---|---|---|
| pDAB101566 | 100 | 31 | 13 |
| pDAB108706 | 110 | 29 | 12 |

Example 6

Whole Plant Stable Expression of Genes Operably-Linked to a Synthetic Bidirectional Ubiquitin1 Promoter Whole plants that contained a low copy T-DNA number of the binary plasmid pDAB108706, and plants that contained a low copy number of the control binary plasmid pDAB101556, were grown in a greenhouse. Representative examples of stable expression of YFP in leaf and root tissue of transgenic T$_0$ maize plants obtained from *Z. mays* embryos transformed with pDAB108706 were analyzed. The bidirectional ZmUbi1 promoter drove robust expression of the yfp coding sequences both in leaf tissues and root tissues. The microscopy analysis also confirmed that the Min-UbiP1 minimal promoter element in the bidirectional ZmUbi1 promoter can drive a control binary plasmid (pDAB101556) that contains an unidirectional ZmUbi1 promoter driving expression of the yfp coding sequence. These control plants also showed stable YFP expression in leaf tissues and root tissues.

Example 7

Western Blot Analysis of Genes Operably-Linked to a Synthetic Bidirectional Ubiquitin1 Promoter Total Soluble Protein: Transformed $T_0$ maize plants were sampled at the V6 developmental stage. A total of four leaf punches from the youngest unfolded leaf were sampled into a matrix tube and placed into a matrix box. As a negative control, four leaf punches of two untransformed B104 maize plants at the V6 developmental stage were sampled into a matrix tube. A steel bead was placed into the matrix tubes with the samples, and then 400 µL PBST was added to each tube. The tubes were capped, and protein was extracted via bead beating at 1500 rpm for 5 minutes in a Kleco™ tissue grinder. Debris was pelleted via centrifugation.

A 5 µL sample from each tube was diluted to 25 µL with PBST in a 96-well microtiter plate. These samples were analyzed for total soluble protein using a BCA protein assay kit (Thermo Scientific Pierce, Rockford, Ill.) according to the manufacturer's directions. Bovine serum albumin (BSA) standards provided in the kit were analyzed in duplicate, and the average of the values was used to generate a standard curve that was subsequently used to calculate total soluble protein for each sample. The total soluble protein for each sample was then normalized to mg/µL.

TABLE 6

Western blot protocol.

| Step | Condition | Time |
| --- | --- | --- |
| First Wash | PBST | 5 min. |
| Primary Hybridization | 2 µg/mL rabbit anti-PhiYFP (Axxora, San Diego, CA) in StartingBlock ™ T20 (Thermo Fisher Scientific Inc., Waltham, MA) | 60 min. |
| Rinse | PBST | 3 × 5 min. |
| Secondary Hybridization | horse radish peroxidase (HRP)-conjugated goat anti-rabbit IgG | 30 min. |
| Second Wash | PBST | 3 × 5 min. |
| Rinse | PBS | 3 × 2 min. |

YFP/Phiyfp Western Blot Analysis: In the 96-well microtiter plate, each 5 µL sample of extracted protein was diluted with 5 µL 2× Laemmli Buffer+2-β-mercaptoethanol. Control samples of purified YFP/Phiyfp in HEPES buffer (50 mM HEPES, 200 mM KCl, 10% glycerol) were purchased from Axxora (San Diego, Calif.). The samples were prepared in the same plate by diluting 1:1 with Laemmli buffer to produce a standard curve of the following concentrations: 0.5 ng/µL, 0.25 ng/µL, and 0.125 ng/µL. Samples were heated in a Thermocycler at 95° C. for 30 minutes, and then cooled to 4° C. A Bio-Rad Criterion Gel™ was then assembled using MES/SDS buffer. The samples were allowed to warm to room temperature, and 10 µL of sample were loaded into each well of two gels. In addition, samples of purified YFP/Phiyfp used for a standard curve, and protein ladder marker, were loaded into wells of the gel. The gels were electrophoretically run at 150 V and 150 mA for 90 min. After the run, the gel casings were opened and the proteins were transferred to a nitrocellulose membrane using the iBlot System™ (Invitrogen). Protein was transferred from the gel to the membrane by running a current of 20 V for 10 minutes. The nitrocellulose membrane was removed and placed in StartingBlock T20™ blocking buffer overnight at 4° C. The blocking buffer was then discarded, and the membrane was processed using the protocol set forth in Table 6.

Antibody binding was detected using the Amersham ECL™ plus chemiluminescent detection system following the manufacturer's directions. Film was exposed at 10 minutes and 30 minutes. The 10 minute exposed film was used to quantify protein, and the 30 minute overexposure film was used to confirm the absence of protein in B104 and other control samples. The membrane was taped to the back of the exposed film, and protein was quantified via pixel density analysis. The pixel density of the purified protein standards was first used to generate a standard curve that was used to quantify protein in the samples. Though membrane shows bands for a PhiYFP monomer and dimer even in the purified standard, only the PhiYFP monomer was used to quantify protein expression. Values for the protein were then normalized to ng/µL. The ratio of normalized total soluble protein (TSP) to PhiYFP was calculated to the units of ng YFP/mg TSP, or alternatively, parts per million (ppm).

GUS Western Blot Analysis: Expression of GUS protein was quantified in a similar manner to PhiYFP, with the following exception: a 10 µL sample of extract was diluted 1:1 with 2× Laemmli+2-β-mercaptoethanol, denatured at 95° C. for 30 minutes, and then 15 µL was loaded into the gel. Processed membranes with film (1 minute exposure) were overlayed with the membrane for pixel density analysis.

Results of a Western blot analysis of 12 transgenic $T_0$ maize plants obtained from Z. mays embryos transformed with the binary vector, pDAB108706, are shown in FIG. 11. The bidirectional ZmUbi1 promoter drove robust expression of the yfp and GUS coding sequences from leaf tissue. These observations confirmed that the Min-UbiP1 minimal promoter element of the bidirectional ZmUbi1 promoter expressed YFP at similar expression levels as compared to Z. mays callus transformed with a binary plasmid containing a unidirectional ZmUbi1 promoter driving the yfp coding sequence (pDAB101556; see FIG. 12).

Example 8

Construct of a Four-Gene Cassette Stack

A plasmid pDAB105803 construct was used as the starting plasmid to generate a four-gene cassette stack (aad1-2a-Phiyfp and cry34-2a-cry35) driven by single Zea mays Ubiquitin-1 bidirectional promoter. A representative map of plasmid pDAB105803 is shown in FIG. 16, which contains a Zea mays Ubiquitin-1 bidirectional promoter.

The aad1-2a-Phiyfp fragment derived from plasmid pDAB105841 was cloned into the BamHI and SacI cut vector backbone of the plasmid pDAB105803 using cloning methods commonly known in the art. This resulted in the intermediate plasmid pDAB105842 (FIG. 17). A NotI/XbaI digested cry34(8V6)-2a-cry35 fragment obtained from the plasmid pDAB105840 was cloned between NotI/SpeI sites of plasmid pDAB105842 to construct plasmid pDAB105843. The plasmid pDAB105843 contains cry34(8V6)-2a-cry35 and aad1-2a-Phiyfp gene cassettes on each side of ZmUbi1 bidirectional promoter (FIG. 18).

A binary vector containing the ZmUbi1 bidirectional promoter, and gene expression cassettes cry34(8V6)-2a-cry35 and Phiyfp-2a-aad1 from plasmid pDAB105842 was generated via a GATEWAY L-R CLONASE reaction (Invitrogen, Carlsbad, Calif.) with a destination plasmid pDAB101917. The resulting vector, pDAB108717, contained the cry34 (8V6)-2a-cry35, aad1-2a-Phiyfp, and PAT gene expression cassettes within the T-DNA borders (FIG. 19).

Example 9

Construct of a Second Four-Gene Cassette Stack

A plasmid pDAB105803 construct was used to generate a second four-gene cassette stack (Phiyfp-2a-aad1 and cry34-2a-cry35) driven by single Zea mays Ubiquitin-1 bidirectional promoter. A Phiyfp-2a-aad1 fragment derived from plasmid pDAB105844 was cloned into the BamHI and SacI cut vector backbone of the plasmid pDAB105803 using cloning methods commonly known in the art. This resulted in the intermediate plasmid pDAB105845 (FIG. 20). A NotI/XbaI digested cry34(8V6)-2a-cry35 fragment obtained from the plasmid pDAB105840 was cloned between NotI/SpeI sites of plasmid pDAB105845 to construct plasmid pDAB105846 (FIG. 21). The plasmid pDAB105846 contained cry34(8V6)-2a-cry35 and Phiyfp-2a-aad1 gene cassettes on each side of the ZmUbi1 bidirectional promoter.

A binary vector containing the ZmUbi1 bidirectional promoter, and gene cassettes cry34(8V6)-2a-cry35 and Phiyfp-2a-aad1 from plasmid pDAB105846 was generated via a GATEWAY L-R CLONASE reaction (Invitrogen, Carlsbad, Calif.) with a destination plasmid pDAB101917. The resulting vector, pDAB108718, contained the cry34(8V6)-2a-cry35, Phiyfp-2a-aad1, and PAT gene expression cassettes within the T-DNA borders (FIG. 21).

Example 10

Transformation of *Agrobacterium tumefaciens* Strain DAt13192

The pDAB108717 and pDAB108718 binary vectors were transformed into *Agrobacterium tumefaciens* ternary strain DAt13192 (see U.S. Prov. Pat. App. No. 61/368,965, the content of which is hereby incorporated by reference in its entirety). Bacterial colonies were isolated and binary plasmid DNA was extracted and verified via restriction enzyme digestions.

Example 11

Transformation into Maize

Ear Sterilization and Embryo Isolation: To obtain maize immature embryos, plants of Zea mays (c.v. B104) were grown in the greenhouse and self or sib-pollinated to produce ears. The ears were harvested approximately 9-12 days post-pollination. On the day of the experiment, ears were surface-sterilized by immersion in a 20% solution of household bleach, which contained 5% sodium hypochlorite, and shaken for 20-30 minutes, followed by three rinses in sterile water. After sterilization, immature zygotic embryos (1.5-2.2 mm) were aseptically dissected from each ear and randomly distributed into micro-centrifuge tubes containing liquid infection media (LS Basal Medium, 4.43 g/L; N6 Vitamin Solution [1000×], 1.00 mL/L; L-proline, 700.0 mg/L; sucrose, 68.5 g/L; glucose, 36.0 g/L; 2,4-D, 1.50 mg/L. For a given set of experiments, pooled embryos from 2-3 ears were used for each treatment.

*Agrobacterium* Culture Initiation: Glycerol stocks of *Agrobacterium* strains containing the binary vectors described above were streaked on AB minimal medium plates containing appropriate antibiotics and were grown at 20° C. for 3-4 days. A single colony was picked and streaked onto YEP plates containing the same antibiotics and was incubated at 28° C. for 1-2 days.

*Agrobacterium* Culture and Co-cultivation: On the day of the experiment, *Agrobacterium* colonies were picked from the YEP plate, suspended in 10 mL of infection medium in a 50 mL disposable tube, and the cell density was adjusted to $OD_{600}$=0.2-0.4 nm using a spectrophotometer. The *Agrobacterium* cultures were placed on a rotary shaker at 115 rpm, room temperature, while embryo dissection was performed. Immature zygotic embryos between 1.5-2.2 mm in size were isolated from the sterilized maize kernels and placed in 1 mL of the infection medium and washed once in the same medium. The *Agrobacterium* suspension (2 mL) was added to each tube and the tubes were inverted for about 20 times then shaken for 10-15 minutes. The embryos were transferred onto co-cultivation media (MS Salts, 4.33 g/L; L-proline, 700.0 mg/L; myo-inositol, 100.0 mg/L; casein enzymatic hydrolysate 100.0 mg/L; Dicamba 3.30 mg/L; sucrose, 30.0 g/L; Gelzan™, 3.00 g/L; modified MS-Vitamin [1000×], 1.00 ml/L; $AgNo_3$, 15.0 mg/L; Acetosyringone, 100.0 µM), oriented with the scutellum facing up, and incubated for 3-4 days in the light at 25° C.

YFP/Phiyfp Transient expression: Transient YFP/Phiyfp expression was observed in transformed embryos after 3 days of co-cultivation with *Agrobacterium*. The embryos were observed under a stereomicroscope (Leica Microsystems, Buffalo Grove, Ill.) using YFP filter and 500 nm light source.

Callus Selection and Regeneration of Putative Events: Following the co-cultivation period, embryos were transferred to resting media (MS salts, 4.33 g/L; L-proline, 700.0 mg/L; myo-inositol, 100.0 mg/L; MES [(2-(n-morpholino)-ethanesulfonic acid), free acid], 500.0 mg/L; casein enzymatic hydrolysate, 100.0 mg/L; Dicamba, 3.30 mg/L; sucrose, 30.0 g/L; Gelzan™, 2.30 g/L; modified MS-Vitamin [1000×], 1.00 ml/L; $AgNO_3$, 15.0 mg/L; Carbenicillin, 250.0 mg/L) without selective agent and incubated in 24 hours light with light intensity of 50 µmol $m^{-2}s^{-1}$ for 7 days at 28° C. Embryos were transferred onto selection 1 media (MS salts, 4.33 g/L; L-proline, 700.0 mg/L; myo-inositol, 100.0 mg/L; MES [(2-(n-morpholino)-ethanesulfonic acid), free acid], 500.0 mg/L; casein enzymatic hydrolysate, 100.0 mg/L; Dicamba, 3.30 mg/L; sucrose, 30.0 g/L; Gelzan™, 2.30 g/L; modified MS-Vitamin [1000×], 1.00 ml/L; $AgNO_3$, 15.0 mg/L; Carbenicillin, 250.0 mg/L), containing 3 mg/L Bialaphos and incubated in 24 hours light with light intensity of 50 µmol $m^{-2}s^{-1}$ for 7 days at 28° C.

Embryos with proliferating embryogenic calli were transferred onto selection 2 media (MS salts, 4.33 g/L; myo-inositol, 100.0 mg/L; L-proline, 700.0 mg/L; MES [(2-(n-morpholino)-ethanesulfonic acid), free acid], 500.0 mg/L; casein enzymatic hydrolysate, 100.0 mg/L; Dicamba, 3.30 mg/L; sucrose, 30.0 g/L; Gelzan™ 2.30 g/L; modified MS-Vitamin [1000×], 1.00 ml/L; $AgNo_3$, 15.0 mg/L; Carbenicillin, 250.0 mg/L), containing 5 mg/L Bialaphos and were incubated in 24 hours light with light intensity of 50 µmol $m^{-2}s^{-1}$ for another 14 days at 28° C. This selection step allowed transgenic callus to further proliferate and differentiate. The callus selection period lasted for up to three weeks. Proliferating, embryogenic calli were transferred onto regeneration 1 media (MS salts, 4.33 g/L; myo-inositol, 100.0 mg/L; L-proline, 350.0 mg/L; MES [(2-(n-morpholino)-ethanesulfonic acid), free acid], 250.0 mg/L; casein enzymatic hydrolysate, 50.0 mg/L; NAA, 0.500 mg/L; ABA, 2.50 mg/L; BA, 1.00 mg/L; sucrose, 45.0 g/L; Gelzan™ 2.50 g/L; modified MS-Vitamin [1000×], 1.00 ml/L; AgNO$_3$, 1.00 mg/L; Carbenicillin, 250.0 mg/L), containing 3 mg/L Bialaphos and cultured in 24 hours light with light intensity of 50 µmol m$^{-2}$S$^1$ for 7 days at 28° C.

Embryogenic calli with shoot/buds were transferred onto regeneration 2 media (MS salts, 4.33 g/L; modified MS-Vitamin [1000×], 1.00 ml/L; myo-inositol, 100.0 mg/L; sucrose, 60.0 g/L; Gellan Gum G434™, 3.00 g/L; Carbenicillin, 250.0 mg/L), containing 3 mg/L Bialaphos. The cultures were incubated under 24 hours light with light intensity of 50 µmol m$^{-2}$s$^{-1}$ for 7-10 days at 28° C. Small shoots with primary roots were transferred to shoot elongation and rooting media (MS salts, 4.33 g/L; N6 Vitamin Solution [1000×], 1.00 mL/L; myo-inositol, 100.0 mg/L; sucrose, 30.0 g/L; agar 5.50 g/L; in phytatrays and were incubated under 16/8 hours light/dark at 90 µmol m$^{-2}$s$^{-1}$ for 7 days at 28° C. Healthy putative transgenic plantlets were selected then incubated in 16/8 hours light/dark at 200 µmol m$^{-2}$s$^{-1}$ for another 2-5 days at 25° C. and were analyzed for transgene copy number and transferred to the greenhouse.

Example 12

Transient Phiyfp Expression

Transient expression of Phiyfp from *Zea mays* embryos transformed with pDAB108717 was performed. The bidirectional ZmUbi1 promoter expressed Phiyfp from an aad1-2a-Phiyfp gene expression cassette, where non-transformed embryos did not show any Phiyfp fluorescence. Similar levels of Phiyfp expression were observed from *Zea mays* embryos transformed with a binary plasmid pDAB105748 (FIG. 15) containing a unidirectional *Zea mays* (Zm) Ubi1 promoter driving a single Phiyfp coding sequence. Transient expression of Phiyfp was observed from *Zea mays* embryos transformed with pDAB108718, where the bidirectional Zm Ubi1 promoter expressed Phiyfp from the Phiyfp-2a-aad1 gene expression cassette.

Example 13

Phiyfp Expression in Stably Transformed Maize

Phiyfp Expression in Stably Transformed *Zea mays* Callus Driven by a Bidirectional Zm Ubi1 Promoter: *Zea mays* embryos transformed with the pDAB108717 binary vector containing the aad1-2a-Phiyfp gene expression cassette showed good Phiyfp expression. The bidirectional Zm Ubi1 promoter drove robust expression of Phiyfp. These results confirmed that the Min-UbiP1 minimal promoter element of the bidirectional Zm Ubi1 promoter is capable of expressing a reporter gene, for example Phiyfp or YFP. The levels of expression of the Phiyfp protein were similar as compared to *Zea mays* callus transformed with a control binary vector that contained the unidirectional Zm Ubi1 promoter driving the Phiyfp coding sequence (pDAB105748). Expression of Phiyfp was not detected in the negative control callus that was not transformed with a binary construct and did not contain the Phiyfp coding sequences.

*Zea mays* embryos transformed with the pDAB108718 binary vector that contains the Phiyfp-2a-aad1 gene expression cassette showed good Phiyfp expression. The bidirectional Zm Ubi1 promoter drove robust expression of Phiyfp. These results confirmed that the Min-UbiP1 minimal promoter element of the bidirectional Zm Ubi1 promoter is capable of expressing a reporter gene, for example Phiyfp or YFP.

Example 14

Estimation of Transgene Copy Number

Transgene Copy Number Estimation Using Real Time TaqMan™ PCR: *Zea mays* plants were transformed with binary vectors containing a bidirectional Zm Ubi1 promoter, pDAB108717 and pDAB108718, and other plants were transformed with a control binary vector, pDAB105748. The presence of coding sequence (Phiyfp, aad1, cry34, cry35, Pat) within the genome of *Z. mays* plants transgenic to pDAB108717 and pDAB108718 was confirmed via a TaqMan hydrolysis probe assay. The plants transgenic to control vector pDAB105748 were analyzed for the presence of Phiyfp sequence. Stably-transformed transgenic *Z. mays* plantlets that developed from the callus were obtained and analyzed to identify events that contained a low copy number (1-2 copies) of full-length T-strand inserts from the pDAB108717 and pDAB108718 binary vectors, and pDAB105748 control binary vector. Confirmed plantlets were advanced to the green house and grown.

The Roche Light Cycler480™ system was used to determine the transgene copy number for events that were transformed with the pDAB108717 and pDAB108718 binary vector. The method utilized a biplex TaqMan® reaction that employed oligonucleotides specific to the coding sequence and to the endogenous *Z. mays* reference gene, invertase (Genbank Accession No: U16123.1), in a single assay. Copy number and zygosity were determined by measuring the intensity of coding sequence-specific fluorescence, relative to the invertase-specific fluorescence, as compared to known copy number standards.

Table 7. Forward and Reverse Nucleotide Primer and Fluorescent Probes (Synthesized by Integrated DNA Technologies, Coralville, Iowa).

TABLE 7

Forward and reverse nucleotide primer and fluorescent probes (synthesized by Integrated DNA Technologies, Coralville, IA).

| Primer Name | Primer Sequence |
| --- | --- |
| YFP Forward Primer | GATGCCTCAGTGGGAAAGG (SEQ ID NO: 7) |
| YFP Reverse Primer | CCATAGGTGAGAGTGGTGACAA (SEQ ID NO: 8) |

TABLE 7-continued

Forward and reverse nucleotide primer and fluorescent probes (synthesized by Integrated DNA Technologies, Coralville, IA).

| Primer Name | Primer Sequence |
|---|---|
| YFP Probe | ROCHE UPL Probe #125 CTTGGAGC (SEQ ID NO: 40) Cat # 04693604001 (Roche, Indianapolis, IN) |
| Invertase Forward Primer | TGGCGGACGACGACTTGT (SEQ ID NO: 9) |
| Invertase Reverse Primer | AAAGTTTGGAGGCTGCCGT (SEQ ID NO: 10) |
| Invertase Probe | 5'HEX/CGAGCAGACCGCCGTGTACTTCTACC/3BHQ1/3' (SEQ ID NO: 11) |
| AAD1 Forward Primer | TGTTCGGTTCCCTCTACCAA (SEQ ID NO: 12) |
| AAD1 Reverse Primer | CAACATCCATCACCTTGACTGA (SEQ ID NO: 13) |
| AAD1 Probe | CACAGAACCGTCGCTTCAGCAACA (SEQ ID NO: 14) |
| Cry34 Forward Primer | GCCAACGACCAGATCAAGAC (SEQ ID NO: 41) |
| Cry34 Reverse Primer | GCCGTTGATGGAGTAGTAGATGG (SEQ ID NO: 42) |
| Cry34 Probe | CCGAATCCAACGGCTTCA (SEQ ID NO: 43) |
| Cry35 Forward Primer | CCTCATCCGCCTCACCG (SEQ ID NO: 44) |
| Cry35 Reverse Primer | GGTAGTCCTTGAGCTTGGTGTC (SEQ ID NO: 45) |
| Cry35 Probe | CAGCAATGGAACCTGACGT (SEQ ID NO: 46) |
| PAT Forward Primer | ACAAGAGTGGATTGATGATCTAGAGAGGT (SEQ ID NO: 47) |
| PAT Reverse Primer | CTTTGATGCCTATGTGACACGTAAACAGT (SEQ ID NO: 48) |
| PAT Probe | GGTGTTGTGGCTGGTATTGCTTACGCTGG (SEQ ID NO: 49) |

For *Z. mays* samples transformed with the pDAB108717 and pDAB108718 binary vectors, a coding sequence-specific DNA fragment was amplified with one TaqMan® primer/probe set containing a probe labeled with FAM fluorescent dye, and invertase was amplified with a second TaqMan® primer/probe set containing a probe labeled with HEX fluorescence (Table 7). The PCR reaction mixture was prepared as set forth in Table 8, and the gene-specific DNA fragments were amplified according to the conditions set forth in Table 9. Copy number and zygosity of the samples were determined by measuring the relative intensity of fluorescence specific for the coding sequence to fluorescence specific for the reference gene, invertase, as compared to known copy number standards.

Standards were created by diluting the vector (pDAB108717 and pDAB108717) into *Z. mays* B104 genomic DNA (gDNA) to obtain standards with a known relationship of vector:gDNA. For example, samples having one, two, and four cop(ies) of vector DNA per one copy of the *Z. mays* B104 gDNA were prepared. One and two copy dilutions of the vector mixed with the *Z. mays* B104 gDNA standard were validated against a control *Z. mays* event that was known to be hemizygous, and a control *Z. mays* event that was known to be homozygous (*Z. mays* event 278; See PCT International Patent Publication No. WO 2011/022469 A2, the content of which is hereby incorporated by reference in its entirety). A TaqMan® biplex assay that utilizes oligonucleotides specific to the coding sequence gene and oligonucleotides specific to the endogenous *Z. mays* reference gene, invertase, was performed by amplifying and detecting a gene-specific DNA fragment for the coding sequence with one TaqMan® primer/probe set containing a probe labeled with FAM fluorescent dye, and by amplifying and detecting a gene-specific DNA fragment for invertase with a second TaqMan® primer/probe set containing a probe labeled with HEX fluorescence. According to Table 7, the coding sequence TaqMan® reaction mixture was prepared as set forth in Table 8 and the specific fragments were amplified according to the conditions set forth in Table 9.

TABLE 8

Taqman ® PCR reaction mixture.

| Number of Reactions | μl each | Final Concentration |
|---|---|---|
| H₂O | 0.5 μL | — |
| PVP (10%) | 0.1 μL | 0.1% |
| ROCHE 2X Master Mix | 5.0 μL | 1X |
| Coding sequence Forward Primer (10 μM) | 0.4 μL | 0.4 μM |
| Coding sequence Reverse Primer (10 μM) | 0.4 μL | 0.4 μM |
| Coding sequence Probe UPL#125 (5 μM) | 0.4 μL | 0.2 μM |
| Invertase Forward Primer (10 μM) | 0.4 μL | 0.4 μM |
| Invertase Reverse Primer (10 μM) | 0.4 μL | 0.4 μM |
| Invertase Probe (5 μM) | 0.4 μL | 0.2 μM |
| Template DNA | 2.0 μL | — |
| Total reaction volume | 10 μL | — |

The level of fluorescence generated for each reaction was analyzed using the Roche LightCycler 480™ Thermocycler according to the manufacturer's directions. The FAM fluorescent moiety was excited at an optical density of 465/510 nm, and the HEX fluorescent moiety was excited at an optical density of 533/580 nm. The copy number could be determined by comparison of Target/Reference values for unknown samples (output by the LightCycler 480™) to Target/Reference values of four known copy number standards (for example, Null, 1-Copy (hemi), 2-Copy (homo), and 4-Copy).

TABLE 9

Thermocycler conditions for PCR amplification.

| PCR Steps | Temp (° C.) | Time | No. of cycles |
|---|---|---|---|
| Step-1 | 95 | 10 minutes | 1 |
| Step-2 | 95 | 10 seconds | 40 |
|  | 59 | 35 seconds |  |
|  | 72 | 1 second |  |
| Step-3 | 40 | 10 seconds | 1 |

Results from the transgene copy number analysis of transgenic plants obtained via transformation with a bidirectional ZmUbi1 promoter constructs (pDAB108717 and pDAB108718), and of transgenic plants obtained via transformation with a control unidirectional ZmUbi1 promoter Phiyfp construct (pDAB105748) are summarized in Table 10. Only plants with 1-2 copies of the all transgenes were transferred to the greenhouse for further expression analyses.

TABLE 10

Transgene copy number estimation of the transgenic plants obtained from bidirectional promoter and control constructs.

| Construct | Number of Embryos Transformed | Number of Positive Events | 1-2 Copies of all genes |
|---|---|---|---|
| pDAB108717 | 314 | 66 | 14 |
| pDAB108718 | 252 | 63 | 10 |
| pDAB105748 | 32 | 8 | 2 |

Example 15

Stable Phiyfp Expression in Maize T0 Plants

Stable Phiyfp Expression in *Zea mays* T₀ Plants Driven by bidirectional Zm Ubi1 Promoter: *Zea mays* embryos transformed with the pDAB108717 binary vector containing the aad1-2a-Phiyfp gene expression cassette were observed. The bidirectional Zm Ubi1 promoter drove robust expression of the Phiyfp both in shoot and root tissues. The results confirmed that the Min-UbiP1 minimal promoter element of the bidirectional Zm Ubi1 promoter could express a reporter gene, for example Phiyfp or YFP that is bicistronically fused with aad1 using a 2A sequence. The levels of expression of the Phiyfp protein was similar to *Z. mays* embryos transformed with a control binary vector that contains the unidirectional Zm Ubi1 promoter driving the Phiyfp coding sequence (pDAB105748). Expression of Phiyfp was not detected in the negative control plants that were not transformed with a binary construct and did not contain the Phiyfp coding sequences.

Phiyfp expression in leaf and root tissues of *Zea mays* T0 plants transgenic to pDAB108718 binary vector that contains the Phiyfp-2a-aad1 gene expression cassette was observed. The bidirectional Zm Ubi1 promoter drove robust expression of Phiyfp. The results confirmed that the Min-UbiP1 minimal promoter element of the bidirectional Zm Ubi1 promoter is capable of expressing a reporter gene, for example Phiyfp or YFP fused to aad-1 with a 2A sequence.

Example 16

Cry34, Cry35, and AAD1 Protein Analysis

Plants were sampled into columns 1-10 of a matrix box in 1.5 mL conical tubes, to which 1 steel bead was added, followed by PBST+0.5% BSA (0.6 mL). The box was then bead beated for sample grinding in a Geno Grinder for 5 minutes at 1500 rpm then centrifuged at 3700 rpm for 7 minutes at 4° C.

Cry34/35 ELISA assay: In a separate, 96 deep well plate, a sample of the extract was diluted 1:200 in PBST+1% blotto. Two volumes of 25 μl of the diluted sample were then transferred to separate 96-well plates that had been arrayed with anti-Cry34 and anti-Cry35 (Meso Scale Discovery). In the 11 and 12 columns of each plate, standard concentrations of Cry34 and Cry35 in PBST+1% blotto were added (25 μL). The plates were then incubated while shaking at room temperature for one hour. The plates were then washed with PBST (3×300 μL). Then 25 μl of a solution of SulfoTAG conjugated anti-Cry34 and anti-Cry35 was added to each well and incubated with shaking at room temperature for one hour. The plates were then washed with PBST (3×300 μL). A volume of 150 μL Read Buffer T (Meso Scale Discovery) was then added and the plate was immediately read on a SECTOR® 6000 reader. Concentrations of proteins in the sample were calculated using the standard curve for the respective protein generated from the same plate.

AAD-1 ELISA assay: In a separate, 96 deep well plate, a sample of the extract was diluted 1:20 in PBST+0.5% BSA. Two volumes of 200 μL of the diluted sample were then transferred to separate 96 well plates that had been coated with anti-AAD1 (provided by Acadia Bioscience LLC). In the 11 and 12 columns of each plate, standard concentrations of AAD1 in PBST+0.5% BSA were added (200 μL). A volume of 50 μL of biotinylated anti-AAD1 was then added to each well, and the plates were incubated while shaking at room temperature for one hour. The plates were then washed with PBST (5×300 μL). Then, 100 μL of a steptavidin-alkaline phosphate conjugate solution was added to each well and incubated with shaking at room temperature for 30 minutes. The plates were then washed with PBST (5×300 μL). A volume of 100 μL substrate (p-nitrophenylphosphate, PNPP)

was then added and incubated with shaking at room temperature for 45 minutes. The plates were then read at A405 on a SpectraMax M5 plate reader (Molecular Devices). Concentrations of proteins in the sample were calculated using the standard curve generated from the same plate.

Example 17

Protein Analysis of Maize T0 Plants

Protein analysis of maize T0 plants driven by the bidirectional Zea mays Ubiquitin1 Promoter construct (pDAB108717): Representative ELISA analysis of 11 transgenic T0 maize plants obtained from Zea mays embryos transformed with pDAB108717 that contains cry34-2a-cry35 and aad1-2a-Phiyfp is summarized in Table 11. Bidirectional Zm Ubi1 promoter showed robust expression of both Cry34 and Cry35 coding sequences in leaf. Surprisingly, the protein data demonstrated up to 4-fold higher expression of Cry34 from bidirectional construct pDAB108717, compared to unidirectional Zm Ubi1-driven construct. A similar 8-10 fold higher expression of Cry35 and AAD1 proteins was also unexpectedly observed from bidirectional construct pDAB108717 compared to unidirectional Zm Ubi1-driven construct. These observations showed that the single ZmUbiquitin1 bidirectional promoter in construct pDAB108717 could express multiple genes (e.g., Cry34, Cry35, and AAD1) at unexpectedly higher levels, as compared to Zea mays plants transformed with a binary plasmid which contains unidirectional Zm Ubi1 promoter driving the same genes, where each coding sequence is driven by an independent Zm Ubi1 promoter.

Cry34 and Cry35 expression correlation of maize T0 plants driven by the bidirectional Zea mays Ubiquitin1 Promoter construct (pDAB108717): The correlation analysis between Cry34 and Cry35 proteins in 11 transgenic T0 maize plants obtained from Zea mays embryos transformed with pDAB108717 that contained cry34-2a-cry35 is shown in FIG. 23A. A very high correlation (R Square=0.98) demonstrated strong expression co-regulation between Cry34 and Cry 35 from the cry34-2a-cry35 gene expression cassette driven by the bidirectional Zm Ubi1 promoter.

TABLE 11

Cry34/Cry35/AAD1 expression in T0 maize pDAB108717 transgenic plants

| Plant ID | Cry34 ng/cm$^2$ | Cry35 ng/cm$^2$ | AAD1 ng/cm$^2$ |
|---|---|---|---|
| 108717[1]-032.001 | 277 | 294 | 137 |
| 108717[3]-067.001 | 85 | 93 | 130 |
| 108717[2]-137.001 | 427 | 467 | 6 |
| 108717[1]-027.001 | 484 | 563 | 185 |
| 108717[1]-036.001 | 0 | 0 | −7 |
| 108717[2]-107.001 | 219 | 296 | 112 |
| 108717[2]-113.001 | 0 | 0 | −12 |
| 108717[2]-115.001 | 160 | 175 | 68 |
| 108717[2]-118.001 | 196 | 179 | −5 |
| 108717[2]-125.001 | 318 | 335 | 193 |
| 108717[2]-127.001 | 115 | 127 | 101 |
| Zm Ubi-Cry34/Cry35 | 110 | 67 | 18 |

Protein analysis of maize T0 plants driven by the bidirectional Zea mays Ubiquitin1 Promoter construct (pDAB108718): Representative ELISA analyses of 11 transgenic T0 maize plants obtained from Zea mays embryos transformed with pDAB108718 that contains cry34-2a-cry35 is summarized in Table 12. Bidirectional ZmUbi1 promoter showed robust expression of both Cry34 and Cry35 coding sequences in leaf. The protein data demonstrate several fold higher expression of Cry34, Cry35 and AAD1 proteins from the bidirectional construct pDAB108718, as compared to the unidirectional Zm Ubi1-driven construct. These observations confirmed that the Zea mays Ubiquitin1 bidirectional promoter in construct pDAB108718 expressed multiple genes (e.g., Cry34, Cry35, and AAD1) at unexpectedly higher levels, as compared to Zea mays plants transformed with a binary plasmid which contains unidirectional Zm Ubi1 promoter driving the same genes, where each coding sequence is driven by an independent Zm Ubi1 promoter.

Cry34 and Cry35 expression correlation of maize T0 plants driven by the bidirectional Zea mays Ubiquitin1 Promoter construct (pDAB108718): The correlation analysis between Cry34 and Cry35 proteins in 11 transgenic T0 maize plants obtained from Zea mays embryos transformed with pDAB108718 that contains cry34-2a-cry35 is shown in FIG. 23B. A very high correlation (R Square=0.98) demonstrated strong expression co-regulation between Cry34 and Cry 35 from the cry34-2a-cry35 gene expression cassette driven by the bidirectional Zm Ubi1 promoter.

TABLE 12

Cry34/Cry35/AAD1 expression in T0 maize pDAB108718 transgenic plants
Table 12. Cry34/Cry35/AAD1 expression in T0 maize pDAB108718 transgenic plants

| Plant ID | Cry34 ng/cm$^2$ | Cry35 ng/cm$^2$ | AAD1 ng/cm$^2$ |
|---|---|---|---|
| 108718[3]-060.001 | 0 | 0 | −9 |
| 108718[3]-048.001 | 129 | 155 | 72 |
| 108718[2]-106.001 | 0 | 0 | −8 |
| 108718[3]-061.001 | 78 | 109 | 0 |
| 108718[3]-049.001 | 28 | 11 | −5 |
| 108718[3]-053.001 | 128 | 175 | 2 |
| 108718[1]-024.001 | 157 | 186 | 0 |
| 108718[2]-083.001 | 177 | 205 | 42 |
| 108718[2]-085.001 | 642 | 642 | 32 |
| 108718[2]-089.001 | 127 | 139 | 50 |
| 108718[2]-091.001 | 175 | 168 | 58 |
| 108718[2]-100.001 | 181 | 188 | 104 |
| Zm Ubi-Cry34/Cry35 | 110 | 67 | 18 |

Example 18

Transgene Stacking: Synthetic Bidirectional Promoters (T1 Data)

Gene expression of T1 plants driven by the bidirectional Zea mays Ubiquitin1 Promoter constructs: ten to twelve single copy events per construct were selected for analysis, except that the control construct pDAB108716 has only one event. Five plants/events for the V6 stage were tested and three plants/events for the V10-12 and/R3 stages were tested. Protein assays were performed using LCMS or ELISA.

The constructs used in this example are shown in FIG. 26. pDAB108706 (ZMUbi bidirectional (−200)) and pDAB108707 (ZMUbi bidirectional (−90)) are constructs with representative bidirectional promoter of the present invention; pDAB101556 (ZmUbi1-YFP control) and pDAB108716 (ZMUbi1 without minimal promoter) served as control constructs with unidirectional promoters.

Exemplary expression results (V6) from the four constructs for YFP protein (LCMS) in ng/cm2 are shown in FIG. 27A, and exemplary relative expression results (V6) from the four constructs for YFP RNA are shown in FIG. 27B.

Exemplary expression results (V6) from the four constructs for GUS protein (LCMS) in ng/cm2 are shown in FIG. 28A, and exemplary relative expression results (V6) from the four constructs for GUS RNA are shown in FIG. 28B.

Exemplary expression results (V6) from the four constructs for AAD1 protein (LCMS) in ng/cm2 are shown in FIG. 29A, and exemplary relative expression results (V6) from the four constructs for AAD1 RNA are shown in FIG. 29B.

A statistical analysis of expression results (V6) from the four constructs for YFP protein (LCMS) in ng/cm2 is shown in FIG. 30A, and the mean values for pDAB108707, pDAB108706, pDAB101556, and pDAB108716 are 57.63, 52.66, 49.75, and 0 respectively. A statistical analysis of relative expression results (V6) from the four constructs for YFP RNA is shown in FIG. 30B, and the mean values for pDAB108706, pDAB108707, pDAB101556, and pDAB108716 were 9.96, 8.07, 6.95, and 1.01, respectively.

A statistical analysis of expression results (V6) from the four constructs for GUS protein (LCMS) in ng/cm2 is shown in FIG. 31A, and the mean values for pDAB108706, pDAB108707, pDAB101556, and pDAB108716 were 151.27, 143.22, 0, and 213.17, respectively. A statistical analysis of relative expression results (V6) from the four constructs for GUS RNA is shown in FIG. 31B, and the mean values for pDAB108706, pDAB108707, pDAB101556, and pDAB108716 were 0.65, 0.78, 0, and 3.03, respectively.

A statistical analysis of expression results (V6) from the four constructs for AAD1 protein (LCMS) in ng/cm2 is shown in FIG. 32A, and the mean values for pDAB108706, pDAB108707, pDAB101556, and pDAB108716 were 710.88, 1417.01, 856.58, and 1795.43 respectively. A statistical analysis of relative expression results (V6) from the four constructs for AAD1 RNA is shown in FIG. 32B, and the mean values for pDAB108706, pDAB108707, pDAB101556, and pDAB108716 were 1.33, 1.37, 1.93, and 2.93, respectively.

FIGS. 33A, 33B, and 33C show exemplary expression results (V10) from the four constructs for YFP, AAD1, and GUS protein (LCMS) in ng/cm2, respectively.

FIGS. 34A, 34B, and 34C show statistical analysis of expression results (V10) from the four constructs for YFP, GUS, and AAD1 protein (LCMS) in ng/cm2, respectively. The mean values for pDAB108706, pDAB108707, pDAB101556, and pDAB108716 for YFP (FIG. 34A) were 71.77, 81.81, 49.58, and 23.01, respectively. The mean values for pDAB108706, pDAB108707, pDAB101556, and pDAB108716 for GUS (FIG. 34B) were 109.63, 98.25, 0, and 138.02, respectively. The mean values for pDAB108706, pDAB108707, pDAB101556, and pDAB108716 for AAD1 (FIG. 34C) were 666.11, 597.80, 715.12, and 1002.84, respectively.

FIGS. 35A, 35B, and 35C show exemplary expression results (R3) from the four constructs for YFP, GUS, and AAD1 protein (LCMS) in ng/cm2, respectively.

FIGS. 36A, 36B, and 36C show statistical analysis of expression results (R3) from the four constructs for YFP, GUS, and AAD1 protein (LCMS) in ng/cm2, respectively. The mean values for pDAB108706, pDAB108707, pDAB101556, and pDAB108716 for YFP (FIG. 36A) were 91.38, 49.49, 21.67, and 0.40, respectively. The mean values for pDAB108706, pDAB108707, pDAB101556, and pDAB108716 for GUS (FIG. 36B) were 5.52, 16.81, 1.07, and 46.60, respectively. The mean values for pDAB108706, pDAB108707, pDAB101556, and pDAB108716 for AAD1 (FIG. 36C) were 156.71, 153.44, 165.40, and 197.80, respectively.

The results showed that maize Ubi1 bidirectional promoters of the present invention can drive robust expression of GUS and YFP, where the YFP expression from Maize Ubi1 bidirectional promoter was similar to unidirectional maize Ubi1 driven YFP. The results also suggested that bidirectional transcription has non-significant effect on GUS expression (GUS expression compared to the constructs lacking minimal promoter without YFP expression).

Example 19

A Combination of Bidirectional Promoter and 2a Bicistronic Sequence to Drive Four Transgenes from One Single Promoter (T1 Data)

Gene expression of T1 plants driven by the bidirectional *Zea mays* Ubiquitin1 Promoter constructs: ten to twelve single copy events per construct were selected for analysis, except that the control constructs had four or five events per construct. Five plants/events for the V6 stage were tested and three plants/events for the V10-12 and/R3 stages were tested. Protein assays were performed using LCMS or ELISA.

FIG. 37A shows exemplary relative expression results (V6) of Cry34 RNA from the four constructs pDAB105748 (ZMUbi1-YFP), pDAB105818 (ZMUbi1-Cry34/ZMUbi1-Cry35/ZMUbi1-AAD1), pDAB108717 (YFP/AAD-1-ZMUbi1 bidirectional-Cry34-Cry35), and pDAB108718 (AAD1/YFP-ZMUbi1 bidirectional-Cry34-Cry35). FIG. 37B shows exemplary relative expression results (V6) of Cry34 protein (LCMS) from the same four constructs pDAB105748, pDAB105818, pDAB108717, and pDAB108718.

FIG. 38A shows exemplary relative expression results (V6) of AAD1 RNA from the four constructs pDAB105748, pDAB105818, pDAB108717, and pDAB108718. FIG. 38B shows exemplary relative expression results (V6) of AAD1 protein (LCMS) from the same four constructs pDAB105748, pDAB105818, pDAB108717, and pDAB108718.

FIG. 39A shows exemplary relative expression results (V6) of YFP RNA from the four constructs pDAB105748, pDAB105818, pDAB108717, and pDAB108718. FIG. 39B shows exemplary relative expression results (V6) of YFP protein (LCMS) from the same four constructs pDAB105748, pDAB105818, pDAB108717, and pDAB108718.

FIG. 40A shows exemplary relative expression results (V6) of Cry35 RNA from the four constructs pDAB105748, pDAB105818, pDAB108717, and pDAB108718. FIG. 40B shows exemplary relative expression results (V6) of Cry35 protein (ELISA) from the same four constructs pDAB105748, pDAB105818, pDAB108717, and pDAB108718.

FIG. 41 shows exemplary relative expression results (V6) of PAT RNA from the four constructs pDAB105748, pDAB105818, pDAB108717, and pDAB108718.

FIG. 42A shows a statistical analysis of expression results (V6) of Cry34 RNA from the four constructs pDAB105748, pDAB105818, pDAB108717, and pDAB108718 with the mean values 0, 2.42, 2.67, and 2.25, respectively. FIG. 42B shows a statistical analysis of expression results (V6) of Cry34 protein from the same four constructs pDAB105748, pDAB105818, pDAB108717, and pDAB108718, for which the mean values were 0, 596.94, 2044.73, and 719.18, respectively.

FIG. 43A shows a statistical analysis of expression results (V6) of AAD1 RNA from the four constructs pDAB105748, pDAB105818, pDAB108717, and pDAB108718, for which the mean values were 0, 1.98, 2.68, and 2.03, respectively.

FIG. 43B shows a statistical analysis of expression results (V6) of AAD1 protein from the same four constructs pDAB105748, pDAB105818, pDAB108717, and pDAB108718, for which the mean values were 0, 2237.54, 5763.88, and 2379.15, respectively.

FIG. 44A shows a statistical analysis of expression results (V6) of YFP RNA from the four constructs pDAB105748, pDAB105818, pDAB108717, and pDAB108718, for which the mean values were 3.59, 0, 2.78, and 1.95, respectively.

FIG. 44B shows a statistical analysis of expression results (V6) of YFP protein from the same four constructs pDAB105748, pDAB105818, pDAB108717, and pDAB108718, for which the mean values were 1420.69, 251.68, 1154.04, and 706.04, respectively.

FIG. 45A shows a statistical analysis of expression results (V6) of Cry35 RNA from the four constructs pDAB105748, pDAB105818, pDAB108717, and pDAB108718 with the mean values 0, 1.12, 3.74, and 3.20 respectively. FIG. 45B shows a statistical analysis of expression results (V6) of Cry35 protein from the same four constructs pDAB105748, pDAB105818, pDAB108717, and pDAB108718 with the mean values 0, 283.54, 635.83, and 90.97 respectively.

FIG. 46 shows a statistical analysis of expression results (V6) of PAT RNA from the four constructs pDAB105748, pDAB105818, pDAB108717, and pDAB108718, for which the mean values were 1.56, 0.07, 1.46, and 1.01, respectively.

FIGS. 47A, 47B, 47C, and 47D show exemplary protein expression results (V10) of YFP, AAD1, Cry34, and Cry35, respectively, from the four constructs pDAB105748, pDAB105818, pDAB108717, and pDAB108718.

FIGS. 48A, 48B, 48C, and 48D show statistical analysis of protein expression results (V10) of YFP, AAD1, Cry34, and Cry35, respectively, from the four constructs pDAB105748, pDAB105818, pDAB108717, and pDAB108718.

FIGS. 49A, 49B, 49C, and 49D show exemplary protein expression results (R3) of YFP, AAD1, Cry34, and Cry35, respectively, from the four constructs pDAB105748, pDAB105818, pDAB108717, and pDAB108718.

FIGS. 50A, 50B, 50C, and 50D show statistical analysis of protein expression results (R3) of YFP, AAD1, Cry34, and Cry35, respectively, from the four constructs pDAB105748, pDAB105818, pDAB108717, and pDAB108718.

FIG. 51 shows exemplary results of Western blot for protein expression of Cry34, Cry35, and AAD1 from pDAB108718 and pDAB108717.

The results show that all four transgenes in the single promoter-driven constructs were functional with good expression levels. Three genes (Cry34/Cry35/AAD1) in a Ubi1 bidirectional stack showed robust expression levels, similar to expression levels provided by the single Ubi1-driven gene stack (DExT).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A synthetic polynucleotide comprising a bidirectional promoter, comprising:

a minimal core promoter element from an Ubiquitin 1 gene of *Zea mays* or *Zea luxurians*, and a second minimal core promoter element from an Ubiquitin 1 gene of *Zea mays* or *Zea luxurians*, wherein the two minimal core promoter elements are in reverse complementary orientation with respect to each other in the synthetic polynucleotide; and a heterologous nucleotide sequence of interest operably linked to the bidirectional promoter, wherein the bidirectional promoter consists of the polynucleotide of SEQ ID NO:5.

* * * * *

SEQUENCE LISTING

```
<160> NUMBER OF SEQ ID NOS: 52

<210> SEQ ID NO 1
<211> LENGTH: 215
<212> TYPE: DNA
<213> ORGANISM: Zea mays

<400> SEQUENCE: 1
ctggacccct ctcgagagtt ccgctccacc gttggacttg ctccgctgtc ggcatccaga      60
aattgcgtgg cggagcggca gacgtgagcc ggcacggcag gcggcctcct cctcctctca     120
cggcaccggc agctacgggg gattcctttc ccaccgctcc ttcgctttcc cttcctcgcc     180
cgccgtaata aatagacacc ccctccacac cctct                                215

<210> SEQ ID NO 2
<211> LENGTH: 1102
<212> TYPE: DNA
<213> ORGANISM: Zea mays

<400> SEQUENCE: 2
gtacctcccc aacctcgtgt tgttcggagc gcacacacac acaaccagat ctcccccaaa      60
tccacccgtc ggcacctccg cttcaaggta cgccgctcgt cctcccccc ccccccctct     120 ctaccttctc tagatcggcg ttccggtcca tgcatggtta gggcccggta gttctacttc     180
tgttcatgtt tgtgttagat ccgtgtttgt gttagatccg tgctgctagc gttcgtacac     240
ggatgcgacc tgtacgtcag acacgttctg attgctaact tgccagtgtt tctctttggg     300
gaatcctggg atggctctag ccgttccgca gacgggatcg atttcatgat tttttttgtt     360
tcgttgcata gggtttggtt tgcccttttc ctttatttca atatatgccg tgcacttgtt     420
```

```
tgtcgggtca tcttttcatg ctttttttg tcttggttgt gatgatgtgg tctggttggg      480
cggtcgttct agatcggagt agaattctgt ttcaaactac ctggtggatt tattaatttt      540
ggatctgtat gtgtgtgcca tacatattca tagttacgaa ttgaagatga tggatggaaa      600
tatcgatcta ggataggtat acatgttgat gcgggtttta ctgatgcata tacagagatg      660 cttttttgttc gcttggttgt gatgatgtgg tgtggttggg cggtcgttca ttcgttctag     720
```

```
atcggagtag aatactgttt caaactacct ggtgtattta ttaattttgg aactgtatgt      780
gtgtgtcata catcttcata gttacgagtt taagatggat ggaaatatcg atctaggata      840
ggtatacatg ttgatgtggg ttttactgat gcatatacat gatggcatat gcagcatcta      900
ttcatatgct ctaaccttga gtacctatct attataataa acaagtatgt tttataatta      960
tttcgatctt gatatacttg gatgatggca tatgcagcag ctatatgtgg atttttttag     1020
ccctgccttc atacgctatt tatttgcttg gtactgtttc ttttgtcgat gctcaccctg     1080
ttgtttggtg ttacttctgc ag                                              1102
```

<210> SEQ ID NO 3
<211> LENGTH: 1319
<212> TYPE: DNA
<213> ORGANISM: Artificial sequence
<220> FEATURE:
<223> OTHER INFORMATION: Reverse complement of polynucleotide comprising Z. mays minUbi1P minimal core promoter; Z. mays Ubi1 leader; and Z mays Ubi1 intron
<220> FEATURE:
<221> NAME/KEY: misc_feature
<222> LOCATION: (1)..(1015)
<223> OTHER INFORMATION: UbiI-Intron
<220> FEATURE:
<221> NAME/KEY: misc_feature
<222> LOCATION: (1016)..(1097)
<223> OTHER INFORMATION: Ubi1-leader
<220> FEATURE:
<221> NAME/KEY: misc_feature
<222> LOCATION: (1098)..(1319)
<223> OTHER INFORMATION: minUbi1P-min_core_promoter

<400> SEQUENCE: 3

```
ctgcagaagt aacaccaaac aacagggtga gcatcgacaa agaaacagt accaagcaaa        60 taaatagcgt atgaaggcag ggctaaaaaa atccacatat agctgctgca tatgccatca      120
tccaagtata tcaagatcga aataattata aaacatactt gtttattata atagataggt      180
actcaaggtt agagcatatg aatagatgct gcatatgcca tcatgtatat gcatcagtaa      240
aacccacatc aacatgtata cctatcctag atcgatattt ccatccatct aaactcgta       300 actatgaaga tgtatgacac acacatacag ttccaaaatt aataaataca ccaggtagtt      360
tgaaacagta ttctactccg atctagaacg aatgaacgac cgcccaacca caccacatca      420
tcacaaccaa gcgaacaaaa agcatctctg tatatgcatc agtaaaaccc gcatcaacat      480
gtatacctat cctagatcga tatttccatc catcatcttc aattcgtaac tatgaatatg      540
tatggcacac acatacagat ccaaaattaa taaatccacc aggtagtttg aaacagaatt      600
ctactccgat ctagaacgac cgcccaacca gaccacatca tcacaaccaa gacaaaaaaa      660
agcatgaaaa gatgacccga caaacaagtg cacggcatat attgaaataa aggaaagggg      720
caaaccaaac cctatgcaac gaaacaaaaa aaatcatgaa atcgatcccg tctgcggaac      780
ggctagagcc atcccaggat tccccaaaga gaaacactgg caagttagca atcagaacgt      840
gtctgacgta caggtcgcat ccgtgtacga acgctagcag cacggatcta acacaaacac      900
ggatctaaca caaacatgaa cagaagtaga actaccgggc cctaaccatg catggaccgg      960
```

```
aacgccgatc tagagaaggt agagaggggg gggggggga ggacgagcgg cgtaccttga    1020
agcggaggtg ccgacgggtg gatttggggg agatctggtt tgtgtgtgt gcgctccgaa    1080 caacacgagg ttggggaggt accaagaggg tgtggagggg gtgtctattt attacggcgg   1140
gcgaggaagg gaaagcgaag gagcggtggg aaaggaatcc cccgtagctg ccggtgccgt   1200
gagaggagga ggaggccgcc tgccgtgccg gctcacgtct gccgctccgc cacgcaattt   1260
ctggatgccg acagcggagc aagtccaacg gtggagcgga actctcgaga ggggtccag    1319
```

```
<210> SEQ ID NO 4
<211> LENGTH: 680
<212> TYPE: DNA
<213> ORGANISM: Zea mays

<400> SEQUENCE: 4
```

```
gtgcagcgtg acccggtcgt gcccctctct agagataatg agcattgcat gtctaagtta    60
taaaaaatta ccacatattt tttttgtcac acttgtttga agtgcagttt atctatcttt   120
atacatatat ttaaacttta ctctacgaat aatataatct atagtactac aataatatca   180
gtgttttaga gaatcatata aatgaacagt tagacatggt ctaaaggaca attgagtatt   240
ttgacaacag gactctacag ttttatcttt ttagtgtgca tgtgttctcc ttttttttg    300 caaatagctt cacctatata atacttcatc cattttatta gtacatccat ttagggttta   360
gggttaatgg ttttttataga ctaatttttt tagtacatct atttttattct attttagcct  420 ctaaattaag aaaactaaaa ctctatttta gttttttttat ttaatagttt agatataaaa   480
tagaataaaa taaagtgact aaaaattaaa caaatacctt ttaagaaatt aaaaaaacta   540
aggaaacatt tttcttgttt cgagtagata atgccagcct gttaaacgcc gtcgacgagt   600
ctaacggaca ccaaccagcg aaccagcagc gtcgcgtcgg gccaagcgaa gcagacggca   660
cggcatctct gtcgctgcct                                               680
```

```
<210> SEQ ID NO 5
<211> LENGTH: 3322
<212> TYPE: DNA
<213> ORGANISM: Artificial sequence
<220> FEATURE:
<223> OTHER INFORMATION: Exemplary synthetic Ubi1 bidirectional promoter
<220> FEATURE:
<221> NAME/KEY: misc_feature
<222> LOCATION: (1105)..(1319)
<223> OTHER INFORMATION: First_minUbi1P-reverse_complement
<220> FEATURE:
<221> NAME/KEY: misc_feature
<222> LOCATION: (2009)..(2244)
<223> OTHER INFORMATION: Second_minUbi1P-reverse_complement

<400> SEQUENCE: 5
```

```
ctgcagaagt aacaccaaac aacagggtga gcatcgacaa agaaacagt accaagcaaa     60 taaatagcgt atgaaggcag ggctaaaaaa atccacatat agctgctgca tatgccatca   120
tccaagtata tcaagatcga ataattata aaacatactt gttattata atagataggt    180 actcaaggtt agagcatatg aatagatgct gcatatgcca tcatgtatat gcatcagtaa   240
aacccacatc aacatgtata cctatcctag atcgatattt ccatccatct taaactcgta   300
actatgaaga tgtatgacac acacatacag ttccaaaatt aataaataca ccaggtagtt   360
tgaaacagta ttctactccg atctagaacg aatgaacgac cgcccaacca caccacatca   420
tcacaaccaa gcgaacaaaa agcatctctg tatatgcatc agtaaaaccc gcatcaacat   480
```

```
gtatacctat cctagatcga tatttccatc catcatcttc aattcgtaac tatgaatatg      540
tatggcacac acatacagat ccaaaattaa taaatccacc aggtagtttg aaacagaatt      600
ctactccgat ctagaacgac cgcccaacca gaccacatca tcacaaccaa gacaaaaaaa      660
agcatgaaaa gatgacccga caaacaagtg cacggcatat attgaaataa aggaaaaggg      720
caaaccaaac cctatgcaac gaaacaaaaa aaatcatgaa atcgatcccg tctgcggaac      780
ggctagagcc atcccaggat tccccaaaga gaaacactgg caagttagca atcagaacgt      840
gtctgacgta caggtcgcat ccgtgtacga acgctagcag cacggatcta acacaaacac      900
ggatctaaca caaacatgaa cagaagtaga actaccgggc cctaaccatg catggaccgg      960
aacgccgatc tagagaaggt agagaggggg ggggggggga ggacgagcgg cgtaccttga     1020
agcggaggtg ccgacgggtg gatttggggg agatctggtt gtgtgtgtgt gcgctccgaa     1080
caacacgagg ttggggaggt accaagaggg tgtggagggg gtgtctattt attacggcgg     1140
gcgaggaagg gaaagcgaag gagcggtggg aaaggaatcc cccgtagctg ccggtgccgt     1200
gagaggagga ggaggccgcc tgccgtgccg gctcacgtct gccgctccgc cacgcaattt     1260
ctggatgccg acagcggagc aagtccaacg gtggagcgga actctcgaga ggggtccagc     1320
cgcggagtgt gcagcgtgac ccggtcgtgc ccctctctag agataatgag cattgcatgt     1380
ctaagttata aaaaattacc acatattttt tttgtcacac ttgtttgaag tgcagtttat     1440
ctatctttat acatatattt aaactttact ctacgaataa tataatctat agtactacaa     1500
taatatcagt gttttagaga atcatataaa tgaacagtta gacatggtct aaaggacaat     1560
tgagtatttt gacaacagga ctctacagtt ttatcttttt agtgtgcatg tgttctcctt     1620 ttttttttgca aatagcttca cctatataat acttcatcca ttttattagt acatccattt     1680
agggtttagg gttaatggtt tttatagact aattttttta gtacatctat tttattctat     1740
tttagcctct aaattaagaa aactaaaact ctattttagt ttttttattt aatagtttag     1800
atataaaata gaataaaata aagtgactaa aaattaaaca aatacccttt aagaaattaa     1860
aaaaactaag gaaacatttt tcttgtttcg agtagataat gccagcctgt taaacgccgt     1920
cgacgagtct aacggacacc aaccagcgaa ccagcagcgt cgcgtcgggc caagcgaagc     1980
agacggcacg gcatctctgt cgctgcctct ggacccctct cgagagttcc gctccaccgt     2040
tggacttgct ccgctgtcgg catccagaaa ttgcgtggcg gagcggcaga cgtgagccgg     2100
cacggcaggc ggcctcctcc tcctctcacg gcaccggcag ctacggggga ttcctttccc     2160
accgctcctt cgctttccct tcctcgcccg ccgtaataaa tagacacccc ctccacaccc     2220
tctttcccca acctcgtgtt gttcggagcg cacacacaca caaccagatc tcccccaaat     2280
ccacccgtcg gcacctccgc ttcaaggtac gccgctcgtc ctcccccccc cccccctct     2340 ctaccttctc tagatcggcg ttccggtcca tgcatggtta gggcccggta gttctacttc     2400
tgttcatgtt tgtgttagat ccgtgttttgt gttagatccg tgctgctagc gttcgtacac     2460
ggatgcgacc tgtacgtcag acacgttctg attgctaact tgccagtgtt tctctttggg     2520
gaatcctggg atggctctag ccgttccgca gacgggatcg atttcatgat tttttttgtt     2580
tcgttgcata gggtttggtt tgcccttttc ctttatttca atatatgccg tgcacttgtt     2640
tgtcgggtca tcttttcatg cttttttttg tcttggttgt gatgatgtgg tctggttggg     2700
cggtcgttct agatcggagt agaattctgt ttcaaactac ctggtggatt tattaatttt     2760
ggatctgtat gtgtgtgcca tacatattca tagttacgaa ttgaagatga tggatggaaa     2820
tatcgatcta ggataggtat acatgttgat gcgggtttta ctgatgcata tacagagatg     2880
```

| | |
|---|---|
| cttttttgttc gcttggttgt gatgatgtgg tgtggttggg cggtcgttca ttcgttctag | 2940 |
| atcggagtag aatactgttt caaactacct ggtgtattta ttaattttgg aactgtatgt | 3000 |
| gtgtgtcata catcttcata gttacgagtt taagatggat ggaaatatcg atctaggata | 3060 |
| ggtatacatg ttgatgtggg ttttactgat gcatatacat gatggcatat gcagcatcta | 3120 |
| ttcatatgct ctaaccttga gtacctatct attataataa acaagtatgt tttataatta | 3180 |
| tttcgatctt gatatacttg gatgatgca tatgcagcag ctatatgtgg attttttag | 3240 |
| ccctgccttc atacgctatt tatttgcttg gtactgtttc ttttgtcgat gctcaccctg | 3300 |
| ttgtttggtg ttacttctgc ag | 3322 |

<210> SEQ ID NO 6
<211> LENGTH: 6698
<212> TYPE: DNA
<213> ORGANISM: Artificial sequence
<220> FEATURE:
<223> OTHER INFORMATION: Exemplary nucleic acid comprising yfp and GUS
      expression cassettes driven by a synthetic Ubi1 bidirectional
      promoter

<400> SEQUENCE: 6

| | |
|---|---|
| agcacttaaa gatctttaga agaaagcaaa gcatttatta atacataaca atgtccaggt | 60 |
| agcccagctg aattacaata cgcaactgct cataataatt caacaaaccc aagtagtaca | 120 |
| caacatccag aagcaaataa agcccatacg taccaaagcc tacacaagca gcaacactca | 180 |
| ctgccagtgc cggtgggtct ttaaagcaca cgggccttga ccacgcgatc caccttgaaa | 240 |
| caaacttggt aaaattaaag caaaccagaa gcacacacac gccaacgcaa cgcttctgat | 300 |
| cgcgcgccca aggcccggcc ggccagaacg tacgacggac acgcacacgc tgcgaccgag | 360 |
| ctctaggtga ttaagctaac tactcaaagg taggtcttgc gacagtcaac agctctgaca | 420 |
| gtttctttca aggacatgtt gtctctgtgg tctgtcacat cttttggaaag tttcacatgg | 480 |
| taagacatgt gatgatactc tggaacatga actggacctc caccaatggg agtgttcatc | 540 |
| tgggtgtggt cagccactat gaagtcgcct ttgctgccag taatctcatg acagatcttg | 600 |
| aaggctgact tgagaccgtg gttggcttgg tcaccccaga tgtagaggca gtggggagtg | 660 |
| aagttgaact ccaagttctt tcccaacaca tgaccatctt tcttgaagcc ttgaccattg | 720 |
| agtttgaccc tattgtagac agacccattc tcaaaggtga cttcagccct agtcttgaag | 780 |
| ttgccatctc cttcaaaggt gattgtgcgc tcttgcacat agccatctgg catacaggac | 840 |
| ttgtagaagt ccttcaactc tggaccatac ttggcaaagc actgtgctcc ataggtgaga | 900 |
| gtggtgacaa gtgtgctcca aggcacagga acatccaccag ttgtgcagat gaactgtgca | 960 |
| tcaaccttc ccactgaggc atctccgtag cctttcccac gtatgctaaa ggtgtggcca | 1020 |
| tcaacattcc cttccatctc cacaacgtaa ggaatcttcc catgaaagag aagtgctcca | 1080 |
| gatgccatgg tgtcgtgtgg atccggtaca cgtgcctaa ggaccggttc aactaactac | 1140 |
| tgcagaagta acaccaaaca acagggtgag catcgacaaa agaaacagta ccaagcaaat | 1200 |
| aaatagcgta tgaaggcagg gctaaaaaaa tccacatata gctgctgcat atgccatcat | 1260 |
| ccaagtatat caagatcgaa ataattataa aacatacttg tttattataa tagataggta | 1320 |
| ctcaaggtta gagcatatga atagatgctg catatgccat catgtatatg catcagtaaa | 1380 |
| acccacatca acatgtatac ctatcctaga tcgatatttc catccatctt aaactcgtaa | 1440 |
| ctatgaagat gtatgcacaca cacatacagt tccaaaatta ataaatacac caggtagttt | 1500 |

```
gaaacagtat tctactccga tctagaacga atgaacgacc gcccaaccac accacatcat    1560
cacaaccaag cgaacaaaaa gcatctctgt atatgcatca gtaaaacccg catcaacatg    1620
tatacctatc ctagatcgat atttccatcc atcatcttca attcgtaact atgaatatgt    1680
atggcacaca catacagatc caaaattaat aaatccacca ggtagtttga aacagaattc    1740
tactccgatc tagaacgacc gcccaaccag accacatcat cacaaccaag acaaaaaaaa    1800
gcatgaaaag atgacccgac aaacaagtgc acggcatata ttgaaataaa ggaaaagggc    1860
aaaccaaacc ctatgcaacg aaacaaaaaa aatcatgaaa tcgatcccgt ctgcggaacg    1920
gctagagcca tcccaggatt ccccaaagag aaacactggc aagttagcaa tcagaacgtg    1980
tctgacgtac aggtcgcatc cgtgtacgaa cgctagcagc acggatctaa cacaaacacg    2040
gatctaacac aaacatgaac agaagtagaa ctaccgggcc ctaaccatgc atggaccgga    2100
acgccgatct agagaaggta gagaggggggg gggggggggag gacgagcggc gtaccttgaa    2160
gcggaggtgc cgacgggtgg atttggggga gatctggttg tgtgtgtgtg cgctccgaac    2220
aacacgaggt tggggaggta ccaagagggt gtggaggggg tgtctattta ttacggcggg    2280
cgaggaaggg aaagcgaagg agcggtggga aaggaatccc ccgtagctgc cggtgccgtg    2340
agaggaggag gaggccgcct gccgtgccgg ctcacgtctg ccgctccgcc acgcaatttc    2400
tggatgccga cagcggagca agtccaacgg tggagcggaa ctctcgagag gggtccagcc    2460
gcggagtgtg cagcgtgacc cggtcgtgcc cctctctaga gataatgagc attgcatgtc    2520
taagttataa aaattacca catatttttt ttgtcacact tgtttgaagt gcagtttatc    2580
tatctttata catatattta aactttactc tacgaataat ataatctata gtactacaat    2640
aatatcagtg ttttagagaa tcatataaat gaacagttag acatggtcta aaggacaatt    2700
gagtattttg acaacaggac tctacagttt tatcttttta gtgtgcatgt gttctccttt    2760
ttttttgcaa atagcttcac ctatataata cttcatccat tttattagta catccattta    2820
gggtttaggg ttaatggttt ttatagacta atttttttag tacatctatt ttattctatt    2880
ttagcctcta aattaagaaa actaaaactc tattttagtt tttttattta atagtttaga    2940
tataaaatag aataaaataa agtgactaaa aattaaacaa ataccttta agaaattaaa     3000 aaaactaagg aaacattttt cttgtttcga gtagataatg ccagcctgtt aaacgccgtc    3060
gacgagtcta acggacacca accagcgaac cagcagcgtc cgtcgggcc aagcgaagca     3120 gacggcacgg catctctgtc gctgcctctg dacccctctc gagagttccg ctccaccgtt    3180
ggacttgctc cgctgtcggc atccagaaat tgcgtggcgg agcggcagac gtgagccggc    3240
acggcaggcg gcctcctcct cctctcacgg caccggcagc tacggggat tccttccca      3300 ccgctccttc gctttcccctt cctcgcccgc cgtaataaat agacacccc tccacaccct    3360 ctttccccaa cctcgtgttg ttcggagcgc acacacacac aaccagatct cccccaaatc    3420
cacccgtcgg cacctccgct tcaaggtacg ccgctcgtcc tccccccccc cccccctctc    3480
taccttctct agatcggcgt tccggtccat gcatggttag ggcccggtag ttctacttct    3540
gttcatgttt gtgttagatc cgtgtttgtg ttagatccgt gctgctagcg ttcgtacacg    3600
gatgcgacct gtacgtcaga cacgttctga ttgctaactt gccagtgttt ctctttgggg    3660
aatcctggga tggctctagc cgttccgcag acgggatcga tttcatgatt ttttttgttt    3720
cgttgcatag ggtttggttt gccctttttcc tttatttcaa tatatgccgt gcacttgttt    3780
gtcgggtcat ctttttcatgc ttttttttgt cttggttgtg atgatgtggt ctggttgggc    3840
ggtcgttcta gatcggagta gaattctgtt tcaaactacc tggtggattt attaattttg    3900
```

```
gatctgtatg tgtgtgccat acatattcat agttacgaat tgaagatgat ggatggaaat    3960
atcgatctag gataggtata catgttgatg cgggttttac tgatgcatat acagagatgc    4020
tttttgttcg cttggttgtg atgatgtggt gtggttgggc ggtcgttcat tcgttctaga    4080
tcggagtaga atactgtttc aaactacctg gtgtatttat taattttgga actgtatgtg    4140
tgtgtcatac atcttcatag ttacgagttt aagatggatg gaaatatcga tctaggatag    4200
gtatacatgt tgatgtgggt tttactgatg catatacatg atggcatatg cagcatctat    4260
tcatatgctc taaccttgag tacctatcta ttataataaa caagtatgtt ttataattat    4320
ttcgatcttg atatacttgg atgatggcat atgcagcagc tatatgtgga ttttttttagc    4380
cctgccttca tacgctattt atttgcttgg tactgtttct tttgtcgatg ctcaccctgt    4440
tgtttggtgt tacttctgca ggtacagtag ttagttgagg tacagcggcc gcagggcacc    4500
atggtccgtc ctgtagaaac cccaacccgt gaaatcaaaa aactcgacgg cctgtgggca    4560
ttcagtctgg atcgcgaaaa ctgtggaatt gatcagcgtt ggtgggaaag cgcgttacaa    4620
gaaagccggg caattgctgt gccaggcagt tttaacgatc agttcgccga tgcagatatt    4680
cgtaattatg cggcaacgt ctggtatcag cgcgaagtct ttataccgaa aggttgggca    4740
ggccagcgta tcgtgctgcg tttcgatgcg gtcactcatt acggcaaagt gtgggtcaat    4800
aatcaggaag tgatggagca tcagggcggc tatacgccat ttgaagccga tgtcacgccg    4860
tatgttattg ccgggaaaag tgtacgtatc accgtttgtg tgaacaacga actgaactgg    4920
cagactatcc cgccgggaat ggtgattacc gacgaaaacg gcaagaaaaa gcagtcttac    4980
ttccatgatt tctttaacta tgccggaatc catcgcagcg taatgctcta caccacgccg    5040
aacacctggg tggacgatat caccgtggtg acgcatgtcg cgcaagactg taaccacgcg    5100
tctgttgact ggcaggtggt ggccaatggt gatgtcagcg ttgaactgcg tgatgcggat    5160
caacaggtgg ttgcaactgg acaaggcact agcgggactt gcaagtggt gaatccgcac    5220
ctctggcaac cgggtgaagg ttatctctat gaactgtgcg tcacagccaa aagccagaca    5280
gagtgtgata tctacccgct tcgcgtcggc atccggtcag tggcagtgaa gggcgaacag    5340
ttcctgatta accacaaacc gttctacttt actggctttg gtcgtcatga agatgcggac    5400
ttgcgtggca aaggattcga taacgtgctg atggtgcacg accacgcatt aatggactgg    5460
attgggccca actcctaccg tacctcgcat tacccttacg ctgaagagat gctcgactgg    5520
gcagatgaac atggcatcgt ggtgattgat gaaactgctg ctgtcggctt taacctctct    5580
ttaggcattg gtttcgaagc gggcaacaag ccgaaagaac tgtacagcga agaggcagtc    5640
aacggggaaa ctcagcaagc gcacttacag gcgattaaag agctgatagc gcgtgacaaa    5700
aaccacccaa gcgtggtgat gtggagtatt gccaacgaac cggatacccg tccgcaaggt    5760
gcacgggaat atttcgcgcc actggcggaa gcaacgcgta aactcgaccc gacgcgtccg    5820
atcacctgcg tcaatgtaat gttctgcgac gctcacaccg ataccatcag cgatctcttt    5880
gatgtgctgt gcctgaaccg ttattacgga tggtatgtcc aaagcggcga tttggaaacg    5940
gcagagaagg tactggaaaa agaacttctg gcctggcagg agaaactgca tcagccgatt    6000
atcatcaccg aatacggcgt ggatacgtta gccgggctgc actcaatgta caccgacatg    6060
tggagtgaag agtatcagtg tgcatggctg gatatgtatc accgcgtctt tgatcgcgtc    6120
agcgccgtcg tcggtgaaca ggtatggaat ttcgccgatt ttgcgacctc gcaaggcata    6180
ttgcgcgttg gcggtaacaa gaaagggatc ttcactcgcg accgcaaacc gaagtcggcg    6240
```

```
gcttttctgc tgcaaaaacg ctggactggc atgaacttcg gtgaaaaacc gcagcaggga    6300
ggcaaacaat gagacgtccg gtaacctta aactgagggc actgaagtcg cttgatgtgc     6360
tgaattgttt gtgatgttgg tggcgtattt tgtttaaata agtaagcatg gctgtgattt    6420
tatcatatga tcgatctttg gggttttatt taacacattg taaaatgtgt atctattaat    6480
aactcaatgt ataagatgtg ttcattcttc ggttgccata gatctgctta tttgacctgt    6540
gatgttttga ctccaaaaac caaaatcaca actcaataaa ctcatggaat atgtccacct    6600
gtttcttgaa gagttcatct accattccag ttggcattta tcagtgttgc agcggcgctg    6660
tgctttgtaa cataacaatt gttacggcat atatccaa                            6698

<210> SEQ ID NO 7
<211> LENGTH: 19
<212> TYPE: DNA
<213> ORGANISM: Artificial sequence
<220> FEATURE:
<223> OTHER INFORMATION: YFP Forward primer

<400> SEQUENCE: 7
gatgcctcag tgggaaagg                                                 19

<210> SEQ ID NO 8
<211> LENGTH: 22
<212> TYPE: DNA
<213> ORGANISM: Artificial sequence
<220> FEATURE:
<223> OTHER INFORMATION: YFP Reverse primer

<400> SEQUENCE: 8
ccataggtga gagtggtgac aa                                             22

<210> SEQ ID NO 9
<211> LENGTH: 18
<212> TYPE: DNA
<213> ORGANISM: Artificial sequence
<220> FEATURE:
<223> OTHER INFORMATION: Invertase forward primer

<400> SEQUENCE: 9
tggcggacga cgacttgt                                                  18

<210> SEQ ID NO 10
<211> LENGTH: 19
<212> TYPE: DNA
<213> ORGANISM: Artificial sequence
<220> FEATURE:
<223> OTHER INFORMATION: Invertase Reverse primer

<400> SEQUENCE: 10
aaagtttgga ggctgccgt                                                 19

<210> SEQ ID NO 11
<211> LENGTH: 26
<212> TYPE: DNA
<213> ORGANISM: Artificial sequence
<220> FEATURE:
<223> OTHER INFORMATION: Invertase probe

<400> SEQUENCE: 11
cgagcagacc gccgtgtact tctacc                                         26

<210> SEQ ID NO 12
<211> LENGTH: 20
```

```
<212> TYPE: DNA
<213> ORGANISM: Artificial sequence
<220> FEATURE:
<223> OTHER INFORMATION: AAD1 Forward primer

<400> SEQUENCE: 12
tgttcggttc cctctaccaa                                              20

<210> SEQ ID NO 13
<211> LENGTH: 22
<212> TYPE: DNA
<213> ORGANISM: Artificial sequence
<220> FEATURE:
<223> OTHER INFORMATION: AAD1 Reverse primer

<400> SEQUENCE: 13
caacatccat caccttgact ga                                           22

<210> SEQ ID NO 14
<211> LENGTH: 24
<212> TYPE: DNA
<213> ORGANISM: Artificial sequence
<220> FEATURE:
<223> OTHER INFORMATION: AAD1 probe

<400> SEQUENCE: 14
cacagaaccg tcgcttcagc aaca                                         24

<210> SEQ ID NO 15
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter

<400> SEQUENCE: 15
ctggacccct ctcgagtgtt ccgcttcacc gttggacttg ctacgctgtc agcatcgaga    60
tgttgcgtgg cggagcggca gacttgagcc gtcacggcag gcggcctcct cctcctctca   120
cggcatctgt agctacgggg gattcctttc gcaccgctcg ttcgctttcc cttcctcgtc   180
tgccgaaata atgttacacc ccctccacag cctct                             215

<210> SEQ ID NO 16
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 2

<400> SEQUENCE: 16
ctggacccct ctcgagagtt ccgctccacc gttggactag ctctgctgtc ggcatccaga    60
aaatgcttgg cagtgcggca gacgtgagcc ggcacggcag ggggcctcct cctgctctca   120
cggcacatga agctacgggt gatagcttgc ccaccgctcc aacgctttcc cttactctca   180
cgccgtaata aatagacacc ccttccacaa cctct                             215

<210> SEQ ID NO 17
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 3

<400> SEQUENCE: 17
```

```
ctggacctct ctcgagagtt gcgctccacc gatggacttg ctccgctgtc ggcgtccata    60
atttgcgtgg cggagcggca gacgggagcc ggcacggcag ggagcctcgt cctcctctca   120
cggcacctgc aactacgggg gattcctatc ccaccgctcc ttcgctttca cttcttcgcc   180
ctccttaata agtagacacc ccatccgagc cctct                              215
```

<210> SEQ ID NO 18
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 4

<400> SEQUENCE: 18

```
caagacccct ctcgagagtt ccgcaccacc gttggacgtg ctccgctatc tgcatccaga    60
aattgcgtgg cggaacggta aacgtgagcc gtcacggcag gcggcctcct cctcctctca   120
cgacaccggc agctacgggg gatacctgtc acacagctcc ttcgcttttc tttcctcgcc   180
cgccgtaata tgtatacact ccctccgcac cctct                              215
```

<210> SEQ ID NO 19
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 5

<400> SEQUENCE: 19

```
ctggacccct ctcgagggtt ccgttccacc gttggtcttg gtccgctgtc gggatccaga    60
aatagcgtgg cggagcggca gacgtgatcc ggcacggcat gcggcctcct agtcctatca   120
cagcaccggc agctatggga gattccattc ccaccgctcc tgcgctttca ctggctggcc   180
cgccgtgata gatagacacc ccctccacac cctct                              215
```

<210> SEQ ID NO 20
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 6

<400> SEQUENCE: 20

```
gttggcttct cttgtgagtt ctgcttcacg gatggacttg gtcaacggac ggcatccaga    60
atttgcgtgg cgtagcggcg gacgtgatcc ggcgcggcag gcggcttcct cctcctctca   120
cttaagcgac agctacaggg gattcctttc ccaccgctcc ttcgcttgcc gtacctcgcc   180
cgccgtaata aatagacacc ccttccactc cctct                              215
```

<210> SEQ ID NO 21
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 7

<400> SEQUENCE: 21

```
ctggatccct ctcgagagtg cggctccgac gttggacttg ctccgaagtc ggcatccaaa    60
aattgcgtgg tggagaggca gacttgagcc ggcacggcag gaggcctcgt cctactcgca   120
cggtatcggc agcaacggga gaatccttgc actctgctcc ttcgctgtac cttcctcgcc   180
cgctgatatt gatagacacc ccctgcatac cctct                              215
```

```
<210> SEQ ID NO 22
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 8

<400> SEQUENCE: 22 atggacccctt ctcgagtgtt cggctccacc gttagacttg ctccacgatc gacatcaaga      60
aattgcgaga cggagctaca aacgtaagaa atctcggtag ggggcctcct cctcctctca     120
cggcaccggc agctacgggg gattcctgtc ccacctctcc ttcacgttcc ctacctcgcc     180
cgccataatt aataagcacc ccctccgcac cctct                                215

<210> SEQ ID NO 23
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 9

<400> SEQUENCE: 23 ctggaccccct ctaaagagtt ccacgccacc gttataatgg ctccgctgtc ggcatccaga      60
aattacttgg cggatcagca gacgtgagcc agcatggctg gcggcctcct cctcctctca     120
cgatgccgtc agctacgggg gattcctttc ccaacgctcc ttcgctttcc tatgcgcgcc     180
tgccggatta aataggcagc ttctcgtcac cctct                                215

<210> SEQ ID NO 24
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
        10

<400> SEQUENCE: 24
caagacacct ctcgattgtt ccgcttcacc gttggacttt ctcctcagtc ggcatacaga      60
aattgcttgg cgaagcggca gacatgagcc ggcacgacat gcgtcctcat tctcctctca     120
tggcaccggc agttactggt gaatcctatc gcaccgctcc ttcgctgtcc cttaatcgcc     180
cgccgaaaat aattgacacc ccatccacac cctct                                215

<210> SEQ ID NO 25
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
        11

<400> SEQUENCE: 25 gaggaccccct ctcgtgtgta tcgctccacc tttggagttg gtccactatc ggcgtacaga      60
aaattcgttg cgaagcggca gacgtgagcc tacacggcag tcggcctcta cctcctgaca     120
aggcacgtgc agctacagat gatgcctttc ccaccactcc ttcgcgttcc tttcctcgcc     180
atcagtaatg aatggacacg tcctccagac tctct                                215

<210> SEQ ID NO 26
<211> LENGTH: 215
<212> TYPE: DNA
```

<213> ORGANISM: Artificial sequence
<220> FEATURE:
<223> OTHER INFORMATION: min-Ubi1P or Ubi1-min P Minimal core promoter 12

<400> SEQUENCE: 26

```
ctgaacccat ctcgagtatg ccgcacgatc gattgacatg ctccactggc agcatccaga      60
aattgcattg gggagcatca ggcgtgagcc tgcacggcag gcggactatt cctcctcgcg     120
cggcaccggc aactacgggg gatgcttgac cgaccgctcc atcgatttcc caatctcgct     180
tgccgtatta aatagataac cccttcacac cctct                                215
```

<210> SEQ ID NO 27
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 13

<400> SEQUENCE: 27

```
ctggactcct tacgggagat ccgctccacc gttggactag ctccgttttc ggcttcaata      60
aagggcgtgg gggagcggca gtcggggggca ggcacggcag tggtcctcat ccatatctca    120
cggggccggc agttgagggg gattcctgtc ccacctcacc tactctttcc ctacctcgtc     180
tgccatatta aatagtcacc ccctccacaa ccttt                                215
```

<210> SEQ ID NO 28
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 14

<400> SEQUENCE: 28

```
ttggacccct ctcgaaagtt aggctccgcc gttggactgg tttcgcggtc atcaatcagg      60
aattgcgggg cggagggtca gacgtgtgcc ggcacagcag gtggcctcct catcgtcaca     120
aggcactggc aactacgggt gattcatttc cttcagcacc tacgcttacc ctgccacgcc     180
ctccgtatta taatgacacc ccctccacac cttat                                215
```

<210> SEQ ID NO 29
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 15

<400> SEQUENCE: 29

```
ctggacccca cgcggggttt tcgttcctcc gttgggatag ctccggtgtc agcatacaga      60
gaatatatgt cggagcggaa gacgtgagcc gacacggcgg gctgccgcct cctcctgtca     120
cgacaccggc aggtacgggg gattccgttc ccgccgcaca gtcactttcg cttccttgcc     180
ggtcgtatta aatagacacc gtgtccacag cctct                                215
```

<210> SEQ ID NO 30
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter

16

<400> SEQUENCE: 30

```
cttgagccca ctctagagtt ccgtttcacc gaatgactag ctccgctgtc ggtatccatt      60
aagtgggagg cagaacgtca tatgagagtc ggcacgggag gcgttcgcca cgtccgcgca     120
ctacagcggg agctgcggaa tatacctgtc ccaatgctgc tacgctttcc cttccgcgcc     180
caccgtagaa aaatgacagt cccttcacac cctct                                215
```

<210> SEQ ID NO 31
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 17

<400> SEQUENCE: 31

```
taggaggcct ctcgaaaggt ccggaactcc gtaggacgtg ctccgctgac agcatccagg      60
aatatcatgg gggagctgca gacgagagcc tggacgacaa ggggtcacct cggccgctga     120
cagctgcggc agcaacggag tatgcttttc tcaccgctcc ggcgctttcc cttcgacgca     180
ggccagaata agtagacatc agcgccacac cctct                                215
```

<210> SEQ ID NO 32
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 18

<400> SEQUENCE: 32

```
cttgtctcca ctctgatgtt ccgctccaac atttgatttg ctcctctgta ggcatacagt      60
tattggggga ctgatcggca gacgtgagcc agcactgcaa acggccaact cctcctctct     120
cgactaaggg attaattaag gataccttac ccgcggctcc ttctctttcc ctacctagcc     180
cgccttatta aatagagacc gcctccacag ccgct                                215
```

<210> SEQ ID NO 33
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 19

<400> SEQUENCE: 33

```
ctgtacccctt cacaagggtt acacgctacc gatggacttg caccactgtg gggttccaat     60
aattgcgtgg ctgggcgtca gacatattcc ggcatggcaa gcggcctgct cctcctctgg    120
gagcaccggc aacaatgggg gattccaagc ccgcaggtcc ttcgttttac cgtcctcgcc    180
cgccgtagta tgtaggcatc ccagagacta cctct                               215
```

<210> SEQ ID NO 34
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 20

<400> SEQUENCE: 34

```
caggaaccct aacgagggtt ccgcacgacc aaatgacttg atcttctgtc ggcatccaga      60 aatgggtgt cagagcggca tgcgtgagcc ggcggggcgt gcggcctcat gctgctctcg      120
cgggactagg agttacgggg gatacctgta ttgccgctcc gacactgtac catcctctcc     180
cgccggagta tagagacacc ccctcgacgc catat                                215
```

<210> SEQ ID NO 35
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 21

<400> SEQUENCE: 35

```
ctgtgctcct gtatggggtt caactccacc gtgaaatttg cgcctctgtc gtcatccaga     60
aattgcgtgg ttgatctgct gacgttaaag ggctctgcag gcggcttcct tcggctatga   120
aggtactggc gtctgcaagt gatgcttttg ctaactcgcc ttcgatgtcc cttcctcgcg   180
tgctttaata ggttgtcagc cgctccagac cattt                               215
```

<210> SEQ ID NO 36
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 22

<400> SEQUENCE: 36

```
ctggtcccat cgctagtggt acgctccacc ggtggagtag ctcagatgtc tgaagggtgg    60
aatttagagg tggagagaca gacgtgagct agagcggcat gggacctggt ccaccgctcg   120
aggcaatggc aacgactgtt gaaaccttgc ccaccactcc tgcaattttc catcctcacc   180
ggccggaatg aattaaaacc cacgtcacaa cctct                               215
```

<210> SEQ ID NO 37
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 23

<400> SEQUENCE: 37

```
cgtgacaggg ctcgggtgtt cggctccatc gtagtgcatg cgccgatgta agtatacaag    60
aagtacgtgg cttggcgtct gacgagggcc gtcaaggcag gcggcctcct tctaagctta   120
cggcgccggc aggttcgtag gttaccttac actcaactca tagtctatct attactcgta   180
ctgcgttata aattgtcacc ccctccacac cctct                               215
```

<210> SEQ ID NO 38
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 24

<400> SEQUENCE: 38

```
aggaacgctt ctcgatggtt gcgcacatag gagggacttg atagtcggtg gaaatctaag    60
```

```
aattgcatat cagatctgca gacgttagcc gacatggcta gcagactact ccgcttcaca    120
cgtcagcgaa agcgacggag gatttcttgc caacggcgcc ttcgcgaacc cttcctcgcc    180
cgtcggaaga aagatactcc ccttgcacac cctct                              215
```

```
<210> SEQ ID NO 39
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
      25

<400> SEQUENCE: 39
```

```
cttgacttgg ctcgagagtt ctgcgcttcc attgtagttg cagcgatgtc ggagtccgag    60
ggttgcgtgg cggtgcggca gacgtgggca gatacgactg tatgccagca cctaaacata   120
cggtaccaga agctgcggtg gataccttc ccgacgcata tacgttttcc gtgcctctca    180
cgccgtagta aataaactcc ccctcctgtt cctttt                             215
```

```
<210> SEQ ID NO 40
<211> LENGTH: 8
<212> TYPE: DNA
<213> ORGANISM: Artificial sequence
<220> FEATURE:
<223> OTHER INFORMATION: YFP probe

<400> SEQUENCE: 40
```

```
cttggagc                                                              8
```

```
<210> SEQ ID NO 41
<211> LENGTH: 20
<212> TYPE: DNA
<213> ORGANISM: Artificial sequence
<220> FEATURE:
<223> OTHER INFORMATION: Cry34 Forward Primer

<400> SEQUENCE: 41
```

```
gccaacgacc agatcaagac                                                20
```

```
<210> SEQ ID NO 42
<211> LENGTH: 23
<212> TYPE: DNA
<213> ORGANISM: Artificial sequence
<220> FEATURE:
<223> OTHER INFORMATION: Cry34 Reverse Primer

<400> SEQUENCE: 42
```

```
gccgttgatg gagtagtaga tgg                                            23
```

```
<210> SEQ ID NO 43
<211> LENGTH: 18
<212> TYPE: DNA
<213> ORGANISM: Artificial sequence
<220> FEATURE:
<223> OTHER INFORMATION: Cry34 Probe

<400> SEQUENCE: 43
```

```
ccgaatccaa cggcttca                                                  18
```

```
<210> SEQ ID NO 44
<211> LENGTH: 17
<212> TYPE: DNA
<213> ORGANISM: Artificial sequence
<220> FEATURE:
```

<210> SEQ ID NO 44
<211> LENGTH: 17
<212> TYPE: DNA
<213> ORGANISM: Artificial sequence
<220> FEATURE:
<223> OTHER INFORMATION: Cry35 Forward Primer

<400> SEQUENCE: 44
cctcatccgc ctcaccg                                              17

<210> SEQ ID NO 45
<211> LENGTH: 22
<212> TYPE: DNA
<213> ORGANISM: Artificial sequence
<220> FEATURE:
<223> OTHER INFORMATION: Cry35 Reverse Primer

<400> SEQUENCE: 45
ggtagtcctt gagcttggtg tc                                        22

<210> SEQ ID NO 46
<211> LENGTH: 19
<212> TYPE: DNA
<213> ORGANISM: Artificial sequence
<220> FEATURE:
<223> OTHER INFORMATION: Cry35 Probe

<400> SEQUENCE: 46
cagcaatgga acctgacgt                                            19

<210> SEQ ID NO 47
<211> LENGTH: 29
<212> TYPE: DNA
<213> ORGANISM: Artificial sequence
<220> FEATURE:
<223> OTHER INFORMATION: PAT Forward Primer

<400> SEQUENCE: 47
acaagagtgg attgatgatc tagagaggt                                 29

<210> SEQ ID NO 48
<211> LENGTH: 29
<212> TYPE: DNA
<213> ORGANISM: Artificial sequence
<220> FEATURE:
<223> OTHER INFORMATION: PAT Reverse Primer

<400> SEQUENCE: 48
ctttgatgcc tatgtgacac gtaaacagt                                 29

<210> SEQ ID NO 49
<211> LENGTH: 29
<212> TYPE: DNA
<213> ORGANISM: Artificial sequence
<220> FEATURE:
<223> OTHER INFORMATION: PAT Probe

<400> SEQUENCE: 49
ggtgttgtgg ctggtattgc ttacgctgg                                 29

<210> SEQ ID NO 50
<211> LENGTH: 234
<212> TYPE: PRT
<213> ORGANISM: Phialidium sp.

<400> SEQUENCE: 50

Met Ser Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
            20                  25                  30

Gly Tyr Gly Asp Ala Ser Val Gly Lys Val Asp Ala Gln Phe Ile Cys
            35                  40                  45

Thr Thr Gly Asp Val Pro Val Pro Trp Ser Thr Leu Val Thr Thr Leu
 50                  55                  60

Thr Tyr Gly Ala Gln Cys Phe Ala Lys Tyr Gly Pro Glu Leu Lys Asp
 65                  70                  75                  80

Phe Tyr Lys Ser Cys Met Pro Glu Gly Tyr Val Gln Glu Arg Thr Ile
                 85                  90                  95

Thr Phe Glu Gly Asp Gly Val Phe Lys Thr Arg Ala Glu Val Thr Phe
                100                 105                 110

Glu Asn Gly Ser Val Tyr Asn Arg Val Lys Leu Asn Gly Gln Gly Phe
            115                 120                 125

Lys Lys Asp Gly His Val Leu Gly Lys Asn Leu Glu Phe Asn Phe Thr
130                 135                 140

Pro His Cys Leu Tyr Ile Trp Gly Asp Gln Ala Asn His Gly Leu Lys
145                 150                 155                 160

Ser Ala Phe Lys Ile Met His Glu Ile Thr Gly Ser Lys Glu Asp Phe
                165                 170                 175

Ile Val Ala Asp His Thr Gln Met Asn Thr Pro Ile Gly Gly Gly Pro
                180                 185                 190

Val His Val Pro Glu Tyr His His Ile Thr Tyr His Val Thr Leu Ser
            195                 200                 205

Lys Asp Val Thr Asp His Arg Asp Asn Met Ser Leu Val Glu Thr Val
210                 215                 220

Arg Ala Val Asp Cys Arg Lys Thr Tyr Leu
225                 230

<210> SEQ ID NO 51
<211> LENGTH: 234
<212> TYPE: PRT
<213> ORGANISM: Phialidium sp.

<400> SEQUENCE: 51

Met Ser Ser Gly Ala Leu Leu Phe His Gly Lys Ile Pro Tyr Val Val
 1               5                  10                  15

Glu Met Glu Gly Asn Val Asp Gly His Thr Phe Ser Ile Arg Gly Lys
             20                  25                  30

Gly Tyr Gly Asp Ala Ser Val Gly Lys Val Asp Ala Gln Phe Ile Cys
            35                  40                  45

Thr Thr Gly Asp Val Pro Val Pro Trp Ser Thr Leu Val Thr Thr Leu
 50                  55                  60

Thr Tyr Gly Ala Gln Cys Phe Ala Lys Tyr Gly Pro Glu Leu Lys Asp
 65                  70                  75                  80

Phe Tyr Lys Ser Cys Met Pro Asp Gly Tyr Val Gln Glu Arg Thr Ile
                 85                  90                  95

Thr Phe Glu Gly Asp Gly Asn Phe Lys Thr Arg Ala Glu Val Thr Phe
                100                 105                 110

Glu Asn Gly Ser Val Tyr Asn Arg Val Lys Leu Asn Gly Gln Gly Phe
            115                 120                 125

Lys Lys Asp Gly His Val Leu Gly Lys Asn Leu Glu Phe Asn Phe Thr
130                 135                 140

Pro His Cys Leu Tyr Ile Trp Gly Asp Gln Ala Asn His Gly Leu Lys
145                 150                 155                 160

Ser Ala Phe Lys Ile Cys His Glu Ile Thr Gly Ser Lys Gly Asp Phe

```
                165                 170                 175
Ile Val Ala Asp His Thr Gln Met Asn Thr Pro Ile Gly Gly Pro
            180                 185                 190

Val His Val Pro Glu Tyr His His Met Ser Tyr His Val Lys Leu Ser
        195                 200                 205

Lys Asp Val Thr Asp His Arg Asp Asn Met Ser Leu Lys Glu Thr Val
210                 215                 220

Arg Ala Val Asp Cys Arg Lys Thr Tyr Leu
225                 230

<210> SEQ ID NO 52
<211> LENGTH: 11522
<212> TYPE: DNA
<213> ORGANISM: Artificial
<220> FEATURE:
<223> OTHER INFORMATION: pDAB108717 gene expression cassette sequence

<400> SEQUENCE: 52 aattcaacg gtatatatcc tgccagtcag catcatcaca ccaaaagtta ggcccgaata    60
gtttgaaatt agaaagctcg caattgaggt ctacaggcca aattcgctct tagccgtaca   120
atattactca ccagatccta accggtgtga tcatgggccg cgattaaaaa tctcaattat   180
atttggtcta atttagtttg gtattgagta aaacaaattc ggcgccatgc ccgggcaagc   240
ggccgcacaa gtttgtacaa aaaagcaggc tgagtattca ctacagtagt gcatcgatgg   300
agtcatcacg cagactatct cagcatgtgc gtagcacgtc tagacctagg taggttaatt   360
aagcttgcat gccggaggaa atatgaattc agcacttaaa gatctttaga agaaagcaaa   420
gcatttatta atacataaca atgtccaggt agcccagctg aattacaata cgcaactgct   480
cataataatt caacaaaccc aagtagtaca acatccag aagcaaataa agcccatacg     540
taccaaagcc tacacaagca gcaacactca ctgccagtgc cggtgggtct ttaaagcaca   600
cgggccttga ccacgcgatc caccttgaaa caaacttggt aaaattaaag caaaccagaa   660
gcacacacac gccaacgcaa cgcttctgat cgcgcgccca aggcccggcc ggccagaacg   720
tacgacggac acgcacacgc tgcgaccgag ctctcaaagg taggtcttgc gacagtcaac   780
agctctgaca gtttctttca agctcatgtt gtctctgtgg tctgtcacat ctttggaaag   840
tttcacatgg taagacatat gatgatactc tggaacatga actggacctc caccaatggg   900
agtgttcatc tgggtgtggt cagccactat gaagtcgcct ttgctgccag taatctcatg   960
acatatcttg aaggctgact tgagaccgtg gttggcttgg tctccccaga tgtagaggca  1020
gtggggagtg aagttgaact ccaagttctt tcccaacacg tgaccatctt tcttgaagcc  1080
ttgaccattg agtttgaccc tattgtagac agacccattc tcaaaggtga cttcagccct  1140
agtcttgaag ttgccatctc cttcaaaggt gattgtgcgc tcttgcacat agccatctgg  1200
catacaggac ttgtagaagt ccttcaactc tggaccatac ttggcaaagc actgtgctcc  1260
ataggtgaga gtggtgacaa gtgtgctcca aggcacagga acatctccgg tagtacagat  1320
gaattgtgca tcaacctgca catcaccatg ttttggtcat atattagaaa agttataaat  1380
taaaatatac acacttataa actacagaaa agcaatagct atatactaca ttctttttatt 1440 ttgaaaaaaa tacttgaaat actatattac tactaattag tgataattat tatatatata  1500
tcaaaggtag aagcagaaac ataccttttcc cactgaggca tctccgtagc ctttcccacg  1560
tatgctaaag gtgtggccat caacattccc ttccatctcc acaacgtaag gaatcttccc  1620
atgaaagaga agtgctccag atgacatagg gccgggattc tcctccacgt caccgcatgt  1680
```

```
tagaagactt cctctgccct cgcgggcagg cctaactcca ccaactgtgg tgcgagtcaa    1740
gtatctgaac ttgccagcat agtcaggaac agcacggtgc atggtgcaca agttgtccca    1800
gacaaggact tggtctttct tccacctcac acggcaagtg aagtcaaatc tggtggcatg    1860
ctcatagagg aactgaagca atggctttga ttctgcatct gtcatgccct caattctctg    1920
acagtagact tgattcacat aaaggccttt ccttccagag ccaggatgag tcacaaccaa    1980
gggatggact gtctctctgt caccagcatc aacatccatc accttgactg aggtgttgct    2040
gaagcgacgg ttctgtgctt ggtagaggga accgaacaca cgtgtggcag agtgcacaac    2100
gttgagccct cgatggtgg cttgcatggt tggagacaag gtctcccaag ctgtgtacat     2160
tgaaaggaac ccagtgtctc cgccatgctc aggaacatct atggccctca tcacaacagc    2220
agctggaggt gcatcaagga aagtggagtc tgtgtgccag tcatcaccaa tcacccttcc    2280
agactcattg gcttctctgc ggatcatctg aacctctgga tagccttcaa tgctcttgag    2340
aagaggcact ggatcaactg gtccaaacct tcttgagaat gcaatgtgct gctcattggt    2400
gattgcttgg ccaggaaagt agatgacttg gtaagtgtgg aaggcatcca atatctcatt    2460
ccaggtgctg tcatcaagtg gttccctcaa gtccactcca gtgatctcag caccaaggac    2520
accagtgagt ggctggacag ctattctctc aaagcgttgg gagagagggc tgagggcagc    2580
atgagccatg gtgtcgtgtg gatccggtac acacgtgcct aggaccggtt caactaacta    2640
ctgcagaagt aacaccaaac aacagggtga gcatcgacaa agaaacagt accaagcaaa     2700 taaatagcgt atgaaggcag ggctaaaaaa atccacatat agctgctgca tatgccatca    2760
tccaagtata tcaagatcga ataattata aaacatactt gtttattata atagataggt      2820
actcaaggtt agagcatatg aatagatgct gcatatgcca tcatgtatat gcatcagtaa    2880
aacccacatc aacatgtata cctatcctag atcgatattt ccatccatct taaactcgta    2940
actatgaaga tgtatgacac acacatacag ttccaaaatt aataaataca ccaggtagtt    3000
tgaaacagta ttctactccg atctagaacg aatgaacgac cgcccaacca caccacatca    3060
tcacaaccaa gcgaacaaaa agcatctctg tatatgcatc agtaaaaccc gcatcaacat    3120 gtataccat cctagatcga tatttccatc catcatcttc aattcgtaac tatgaatatg      3180
tatggcacac acatacagat ccaaaattaa taaatccacc aggtagtttg aaacagaatt    3240
ctactccgat ctagaacgac cgcccaacca gaccacatca tcacaaccaa gacaaaaaaa    3300
agcatgaaaa gatgacccga caaacaagtg cacggcatat attgaaataa aggaaaaggg    3360
caaaccaaac cctatgcaac gaaacaaaaa aaatcatgaa atcgatcccg tctgcggaac    3420
ggctagagcc atcccaggat tccccaaaga gaaacactgg caagttagca atcagaacgt    3480
gtctgacgta caggtcgcat ccgtgtacga acgctagcag cacggatcta acacaaacac    3540
ggatctaaca caaacatgaa cagaagtaga actaccgggc cctaaccatg catggaccgg    3600
aacgccgatc tagagaaggt agagaggggg gggggggga ggacgagcgg cgtaccttga     3660
agcggaggtg ccgacgggtg gatttgggg agatctggtt gtgtgtgtgt gcgctccgaa     3720
caacacgagg ttggggaggt accaagaggg tgtggagggg gtgtctattt attacggcgg    3780
gcgaggaagg gaaagcgaag gagcggtggg aaaggaatcc cccgtagctg ccggtgccgt    3840
gagaggagga ggaggccgcc tgccgtgccg gctcacgtct gccgctccgc cacgcaattt    3900
ctggatgccg acagcggagc aagtccaacg gtggagcgga actctcgaga ggggtccagc    3960
cgcggagtgt gcagcgtgac ccggtcgtgc ccctctctag agataatgag cattgcatgt    4020
```

```
ctaagttata aaaaattacc acatatttt  tttgtcacac ttgtttgaag tgcagtttat   4080
ctatctttat acatatattt aaactttact ctacgaataa tataatctat agtactacaa   4140
taatatcagt gttttagaga atcatataaa tgaacagtta gacatggtct aaaggacaat   4200
tgagtatttt gacaacagga ctctacagtt ttatctttt  agtgtgcatg tgttctcctt   4260
ttttttttgca aatagcttca cctatataat acttcatcca ttttattagt acatccattt   4320
agggttttagg gttaatggtt tttatagact aatttttta  gtacatctat tttattctat   4380
tttagcctct aaattaagaa aactaaaact ctatttttagt ttttttattt aatagtttag  4440
atataaaata gaataaaata aagtgactaa aaattaaaca aatacccttt aagaaattaa   4500
aaaaactaag gaaacatttt tcttgtttcg agtagataat gccagcctgt aaacgccgt    4560
cgacgagtct aacggacacc aaccagcgaa ccagcagcgt cgcgtcgggc caagcgaagc   4620
agacggcacg gcatctctgt cgctgcctct ggacccctct cgagagttcc gctccaccgt   4680
tggacttgct ccgctgtcgg catccagaaa ttgcgtggcg agcggcaga  cgtgagccgg   4740
cacggcaggc ggcctcctcc tcctctcacg gcaccggcag ctacggggga ttcctttccc   4800
accgctcctt cgcttttccct tcctcgcccg ccgtaataaa tagacacccc ctccacaccc  4860
tctttcccca acctcgtgtt gttcggagcg cacacacaca caaccagatc tccccccaaat  4920
ccacccgtcg gcacctccgc ttcaaggtac gccgctcgtc ctcccccccc cccccctct    4980
ctaccttctc tagatcggcg ttccggtcca tgcatggtta gggcccggta gttctacttc   5040
tgttcatgtt tgtgttagat ccgtgtttgt gttagatccg tgctgctagc gttcgtacac   5100
ggatgcgacc tgtacgtcag acacgttctg attgctaact tgccagtgtt tctctttggg   5160
gaatcctggg atggctctag ccgttccgca gacgggatcg atttcatgat tttttttgtt   5220
tcgttgcata gggtttggtt tgcccttttc ctttatttca atatatgccg tgcacttgtt   5280
tgtcgggtca tcttttcatg cttttttttg tcttggttgt gatgatgtgg tctggttggg   5340
cggtcgttct agatcggagt agaattctgt ttcaaactac ctggtggatt tattaatttt   5400
ggatctgtat gtgtgtgcca tacatattca tagttacgaa ttgaagatga tggatggaaa   5460
tatcgatcta ggataggtat acatgttgat gcgggtttta ctgatgcata tacagagatg   5520
cttttttgttc gcttggttgt gatgatgtgg tgtggttggg cggtcgttca ttcgttctag   5580
atcggagtag aatactgttt caaactacct ggtgtattta ttaattttgg aactgtatgt   5640
gtgtgtcata catcttcata gttacgagtt taagatggat ggaaatatcg atctaggata   5700
ggtatacatg ttgatgtggg ttttactgat gcatatacat gatggcatat gcagcatcta   5760
ttcatatgct ctaaccttga gtacctatct attataataa acaagtatgt tttataatta   5820
tttcgatctt gatatacttg gatgatggca tatgcagcag ctatatgtgg attttttttag  5880
ccctgccttc atacgctatt tatttgcttg gtactgtttc ttttgtcgat gctcaccctg   5940
ttgtttggtg ttacttctgc aggtacagta gttagttgag gtacagcggc cgcacacgac   6000
accatgtccg cccgcgaggt gcacatcgac gtgaacaaca agaccggcca cccctccag    6060
ctggaggaca agaccaagct cgacggcggc aggtggcgca cctccccgac caacgtggcc   6120
aacgaccaga tcaagacctt cgtggccgaa tccaacggct tcatgaccgg caccgagggc   6180
accatctact actccatcaa cggcgaggcc gagatcagcc tctacttcga caacccgttc   6240
gccggctcca acaaatacga cggccactcc aacaagtccc agtacgagat catcacccag   6300
ggcggctccg gcaaccagtc ccacgtgacc tacaccatcc agaccacctc ctcccgctac   6360
ggccacaagt ccgagggcag aggaagtctt ctaacatgcg gtgacgtgga ggagaatccc   6420
```

```
ggccctatgc tcgacaccaa caaggtgtac gagatcagca accacgccaa cggcctctac    6480
gccgccacct acctctccct cgacgactcc ggcgtgtccc tcatgaacaa gaacgacgac    6540
gacatcgacg actacaacct caagtggttc ctcttcccga tcgacgacga ccagtacatc    6600
atcacctcct acgccgccaa caactgcaag gtgtggaacg tgaacaacga caagatcaac    6660
gtgtccacct actcctccac caactccatc cagaagtggc agatcaaggc caacggctcc    6720
tcctacgtga tccagtccga caacggcaag gtgctcaccg ccggcaccgg ccaggccctc    6780
ggcctcatcc gcctcaccga cgagtcctcc aacaacccga accagcagtg aacctgacg    6840
tccgtgcaga ccatccagct cccgcagaag ccgatcatcg acaccaagct caaggactac    6900
ccgaagtact ccccgaccgg caacatcgac aacggcacct ccccgcagct catgggctgg    6960
accctcgtgc cgtgcatcat ggtgaacgac ccgaacatcg acaagaacac ccagatcaag    7020
accaccccgt actacatcct caagaagtac cagtactggc agagggccgt gggctccaac    7080
gtcgcgctcc gcccgcacga gaagaagtcc tacacctacg agtgggggcac cgagatcgac    7140
cagaagacca ccatcatcaa caccctcggc ttccagatca catcgacag cggcatgaag    7200
ttcgacatcc cggaggtggg cggcggtacc gacgagatca agacccagct caacgaggag    7260
ctcaagatcg agtactccca cgagacgaag atcatggaga agtaccagga gcagtccgag    7320
atcgacaacc cgaccgacca gtccatgaac tccatcggct tcctcaccat cacctccctg    7380
gagctctacc gctacaacgg ctccgagatc cgcatcatgc agatccagac ctccgacaac    7440
gacacctaca acgtgacctc ctacccgaac caccagcagg ccctgctgtg agtagttagc    7500
ttaatcacct agaacctaga cttgtccatc ttctggattg gccaacttaa ttaatgtatg    7560
aaataaaagg atgcacacat agtgacatgc taatcactat aatgtgggca tcaaagttgt    7620
gtgttatgtg taattactag ttatctgaat aaaagagaaa gagatcatcc atatttctta    7680
tcctaaatga atgtcacgtg tctttataat tctttgatga accagatgca tttcattaac    7740
caaatccata tacatataaa tattaatcat atataattaa tatcaattgg gttagcaaaa    7800
caaatctagt ctaggtgtgt tttgctctag tgctagcctc gaggtcgact ctgatcatgg    7860
atgctacgtc acggcagtac aggactatca tcttgaaagt cgattgagca tcgaaaccca    7920
gctttcttgt acaaagtggt tgcggccgct taattaaatt taaatgtttg gggatcctct    7980
agagtcgacc tgcagtgcag cgtgacccgg tcgtgcccct ctctagagat aatgagcatt    8040
gcatgtctaa gttataaaaa attaccacat attttttttg tcacacttgt ttgaagtgca    8100
gtttatctat ctttatacat atatttaaac tttactctac gaataatata atctatagta    8160
ctacaataat atcagtgttt tagagaatca tataaatgaa cagttagaca tggtctaaag    8220
gacaattgag tattttgaca acaggactct acagttttat cttttttagtg tgcatgtgtt    8280
ctccttttt tttgcaaata gcttcaccta tataatactt catccatttt attagtacat    8340
ccatttaggg tttagggtta atggttttta tagactaatt ttttagtac atctattta    8400
ttctatttta gcctctaaat taagaaaact aaaactctat tttagttttt ttatttaata    8460
gtttagatat aaaatagaat aaaataaagt gactaaaaat taaacaaata ccctttaaga    8520
aattaaaaaa actaaggaaa cattttttctt gtttcgagta gataatgcca gcctgttaaa    8580
cgccgtcgac gagtctaacg gacaccaacc agcgaaccag cagcgtcgcg tcgggccaag    8640
cgaagcagac ggcacggcat ctctgtcgct gcctctggac ccctctcgag agttccgctc    8700
caccgttgga cttgctccgc tgtcggcatc cagaaattgc gtggcggagc ggcagacgtg    8760
```

```
agccggcacg gcaggcggcc tcctcctcct ctcacggcac cggcagctac gggggattcc    8820
tttcccaccg ctccttcgct ttcccttcct cgcccgccgt aataaataga caccccctcc    8880
acaccctctt tccccaacct cgtgttgttc ggagcgcaca cacacacaac cagatctccc    8940
ccaaatccac ccgtcggcac ctccgcttca aggtacgccg ctcgtcctcc ccccccccc     9000 ccctctctac cttctctaga tcggcgttcc ggtccatgca tggttagggc ccggtagttc    9060
tacttctgtt catgtttgtg ttagatccgt gtttgtgtta gatccgtgct gctagcgttc    9120
gtacacggat gcgacctgta cgtcagacac gttctgattg ctaacttgcc agtgtttctc    9180
tttggggaat cctgggatgg ctctagccgt tccgcagacg ggatcgattt catgattttt    9240
tttgtttcgt tgcatagggt ttggtttgcc cttttccttt atttcaatat atgccgtgca    9300
cttgtttgtc gggtcatctt ttcatgcttt tttttgtctt ggttgtgatg atgtggtctg    9360
gttgggcggt cgttctagat cggagtagaa ttctgtttca aactacctgg tggatttatt    9420
aattttggat ctgtatgtgt gtgccataca tattcatagt tacgaattga agatgatgga    9480
tggaaatatc gatctaggat aggtatacat gttgatgcgg gttttactga tgcatataca    9540
gagatgcttt tgttcgctt ggttgtgatg atgtggtgtg gttgggcggt cgttcattcg     9600
ttctagatcg gagtagaata ctgtttcaaa ctacctggtg tatttattaa ttttggaact    9660
gtatgtgtgt gtcatacatc ttcatagtta cgagtttaag atggatggaa atatcgatct    9720
aggataggta tacatgttga tgtgggtttt actgatgcat atacatgatg gcatatgcag    9780
catctattca tatgctctaa ccttgagtac ctatctatta aataaacaa gtatgtttta     9840 taattatttc gatcttgata tacttggatg atggcatatg cagcagctat atgtggattt    9900
ttttagccct gccttcatac gctatttatt tgcttggtac tgtttctttt gtcgatgctc    9960
accctgttgt ttggtgttac ttctgcaggg tacagtagtt agttgacacg acaccatgtc   10020
tccggagagg agaccagttg agattaggcc agctacagca gctgatatgg ccgcggtttg   10080
tgatatcgtt aaccattaca ttgagacgtc tacagtgaac tttaggacag agccacaaac   10140
accacaagag tggattgatg atctagagag gttgcaagat agatacccctt ggttggttgc   10200 tgaggttgag ggtgttgtgg ctggtattgc ttacgctggg ccctggaagg ctaggaacgc   10260
ttacgattgg acagttgaga gtactgttta cgtgtcacat aggcatcaaa ggtttgggcct  10320 aggatccaca ttgtacacac attttgcttaa gtctatggag gcgcaaggtt ttaagtctgt   10380
ggttgctgtt ataggccttc caaacgatcc atctgttagg ttgcatgagg ctttgggata   10440
cacagcccgt ggtacattgc gcgcagctgg atacaagcat ggtggatggc atgatgttgg   10500
tttttggcaa agggattttg agttgccagc tcctccaagg ccagttaggc cagttaccca   10560
gatctgactg agcttgagct tatgagctta tgagcttaga gctcggtcgc agcgtgtgcg   10620
tgtccgtcgt acgttctggc cggccgggcc ttgggcgcgc gatcagaagc gttgcgttgg   10680
cgtgtgtgtg cttctggttt gctttaattt taccaagttt gtttcaaggt ggatcgcgtg   10740
gtcaaggccc gtgtgcttta agacccacc ggcactggca gtgagtgttg ctgcttgtgt   10800
aggctttggt acgtatgggc tttatttgct tctggatgtt gtgtactact tgggtttgtt   10860
gaattattat gagcagttgc gtattgtaat tcagctgggc tacctggaca ttgttatgta   10920
ttaataaatg ctttgctttc ttctaaagat ctttaagtgc ttctagagca tgcacataga   10980
cacacacatc atctcattga tgcttggtaa taattgtcat tagattgttt ttatgcatag   11040
atgcactcga aatcagccaa ttttagacaa gtatcaaacg gatgtgactt cagtacatta   11100
aaaacgtccg caatgtgtta ttaagttgtc taagcgtcaa tttgatttac aattgaatat   11160
```

-continued

```
atcctgcccc agccagccaa cagctcgatt tacaattgaa tatatcctgc cggccggccc   11220
acgcgtgtcg aggaattctg atctggcccc catttggacg tgaatgtaga cacgtcgaaa   11280
taaagatttc cgaattagaa taatttgttt attgctttcg cctataaata cgacggatcg   11340
taatttgtcg ttttatcaaa atgtactttc attttataat aacgctgcgg acatctacat   11400
ttttgaattg aaaaaaaatt ggtaattact ctttcttttt ctccatattg accatcatac   11460
tcattgctga tccatgtaga tttcccggac atgaagccat ttacaattga atatatcctg   11520
cc                                                                 11522
```